US007611718B1

(12) United States Patent
Kemble et al.

(10) Patent No.: US 7,611,718 B1
(45) Date of Patent: Nov. 3, 2009

(54) ATTENUATION OF CYTOMEGALOVIRUS VIRULENCE

(75) Inventors: George Kemble, Saratoga, CA (US); Gregory M. Duke, Redwood City, CA (US); Richard Spaete, Emerald Hills, CA (US)

(73) Assignee: MedImmune, LLC, Gaithersburg, MD (US)

( * ) Notice: Subject to any disclaimer, the term of this patent is extended or adjusted under 35 U.S.C. 154(b) by 250 days.

(21) Appl. No.: 11/614,035

(22) Filed: Dec. 20, 2006

Related U.S. Application Data

(62) Division of application No. 09/724,935, filed on Nov. 28, 2000, now Pat. No. 7,204,990.

(51) Int. Cl.
*A61K 39/12* (2006.01)
*A61K 39/245* (2006.01)
*C12Q 1/70* (2006.01)

(52) U.S. Cl. .............. 424/204.1; 424/205.1; 424/230.1; 435/5

(58) Field of Classification Search ........................ None
See application file for complete search history.

(56) References Cited

U.S. PATENT DOCUMENTS

| 5,721,354 | A | 2/1998 | Spaete |
|---|---|---|---|
| 2007/0292455 | A1 | 12/2007 | Kemble |
| 2008/0019945 | A1 | 1/2008 | Kemble |

OTHER PUBLICATIONS

Beisel, 2000, "Cytomegalovirus Vaccine Development," Jordan Reprt, 105-110.
Cha et al., Human Cytomegalovirus Clinical Isolates Carry at Least 19 Genes Not Found in Laboratory Strains, 1996, J Virol 70:78-83.
Chee et al., Analysis of the Protein-Coding Content of the Sequence of Human Cytomegalovirus Strain AD169, 1990, Curr Top Microbiol Immunol. 154, 125-169.
Cihlar et al., Characterization of Drug Resistance-Associated Mutations in the Human Cytomegalovirus DNA Polymerase Gene by Using Recombinant . . . 1998, J Virol 72:5927-36.
Haberland et al., Variation Within the Glycoprotein B Gene of Human Cytomegalovirus is Due to Homologous Recombination, 1999, J Gen Virol 80:1495-1500.
Kemble et al., 1996, "A New Generation of Live, Attenuated Cytomegalovirus (CMV) Vaccine Strains," Interscience Conf. Antimicrob. Agents and Chem, H88.
Kemble et al., 1996, "Genetic Determinanats of CMV Virulence," 21st Herpesvirus Workshop; 315.
Kemble et al., 1997, "Derivation of Novel, Recombinant, Live, Attenuated CMV Vaccine Strains," 6th Int. Cytomegalovirus Workshop, A-25(49).
Kemble et al., Jul. 1999, "Development of Live, Attenuated Human Cytomegalovirus Vaccine Candidates," 24th Inter. Herpesvirus Workshop; 13.007.
Kemble et al., Apr. 1999, "Towne/Toledo Vaccine Development," 7th Intl. Cytomegalovirus Workshop, Brighton, U.K.
Mocarski et al., a Deletion Mutant in the Human Cytomegalovirus Gene Encoding IE1-491aa is Replication Defective Due to a Failure in Autoregulation, 1996, PNAS 93:11321-11326.
Pande et al., Cloning and Physical Mapping of a Gene Fragment Coding for a 64-kilodalton Major Late Antigen of Human Cytomegalovirus, 1984, PNAS 54:817-24.
Plotkin, Apr. 1999, "Vaccination Against Cytomegalovirus, The Changeling Demon," Pediatr Infect Dis J., 18:313-326.
Spaete et al., 1997, Progress in Developing a CMV Vaccine, Virology Seminar; Max-von-Pettenkofer Institute und Genz, Munchen,Germany;1-13.
Spaete et al., "Controling CMV through Vaccination," Mar. 20-22, 1998, Science Symposium; Tucson AZ.
Spaete et al., 1998, "Progress in Developing a CMV Vaccine," Virology Seminar; University of California —Irvine.
Spector et al., Cleavage Maps for Human Cytomegalovirus DNA Strain AD169 for Restriction Endonucleases EcoRI, BgIII, and HindIII, 1982, J Virol 42:558-82.

*Primary Examiner*—Stacy B Chen

(57) ABSTRACT

A method is provided for attenuating a cytomegalovirus comprising functionally disrupting an open reading frame of a Toledo genome region or its homolog and making chimeric CMV virus genomes.

6 Claims, 36 Drawing Sheets

```
           10         20         30         40         50         60
    CGCTGTAGGG ATAAATAGTG CGATGGCGTT TGTGGGAGAA CGCAGTAGCG ATGGGTTGCG
    GCGACATCCC TATTTATCAC GCTACCGCAA ACACCCTCTT GCGTCATCGC TACCCAACGC 100        80         90         100        110        120
    ACGTGCACGA TCCTTCGTGG CAATGCCAAT GGGGCGTTCC CACGATTATC GTGGCCTGGA
    TGCACGTGCT AGGAAGCACC GTTACGGTTA CCCCGCAAGG GTGCTAATAG CACCGGACCT 130        140        150        160        170        180
    TAACATGCGC GGCTTTAGGA ATTTGGTGTT TGGCGGGATC GTCGGCGGAT GTCTCTTCGG
    ATTGTACGCG CCGAAATCCT TAAACCACAA ACCGCCCTAG CAGCCGCCTA CAGAGAAGCC 190        200        210        220        230        240
    GACCCGGCAT CGCAGCCGTA GTCGGCTGTT CTGTTTTCAT GATTTTCCTC TGCGCGTATC
    CTGGGCCGTA GCGTCGGCAT CAGCCGACAA GACAAAGTA CTAAAAGGAG ACGCGCATAG 250        260        270        280        290        300
    TCATCCGTTA CCGGGAATTC TTCAAAGACT CCGTAATCGA CCTCCTTACC TGCCGATGGG
    AGTAGGCAAT GGCCCTTAAG AAGTTTCTGA GGCATTAGCT GGAGGAATGG ACGGCTACCC 310        320        330        340        350        360
    TTCGCTACTG CAGCTGCAGC TGTAAGTGCA GCTGCAAATG CATCTCGGGC CCCTGTAGCC
    AAGCGATGAC GTCGACGTCG ACATTCACGT CGACGTTTAC GTAGAGCCCG GGGACATCGG 370        380        390        400        410        420
    GCTGCTGTTC AGCGTGTTAC AAGGAGACGA TGATTTACGA CATGGTCCAA TACGGTCATC
    CGACGACAAG TCGCACAATG TTCCTCTGCT ACTAAATGCT GTACCAGGTT ATGCCAGTAG 430        440        450        460        470        480
    GACGGCGTCC CGGACACGGC GACGATCCCG ACAGGGTGAT CTGCGAGATA GTCGAGAGTC
    CTGCCGCAGG GCCTGTGCCG CTGCTAGGGC TGTCCCACTA GACGCTCTAT CAGCTCTCAG 490        500        510        520        530        540
    CCCCGGTTTC GGCGCCGACG GTGTCCGTCC CCCCGCCGTC GGAGGAGTCC CACCAGCCCG
    GGGGCCAAAG CCGCGGCTGC CACAGGCAGG GGGGCGGCAG CCTCCTCAGG GTGGTCGGGC 550        560        570        580        590        600
    TCATCCCACC GCAGCCGCCA GCACCGACAT CGGAACCCAA ACCGAAGAAA GGTAGGGCGA
    AGTAGGGTGG CGTCGGCGGT CGTGGCTGTA GCCTTGGGTT TGGCTTCTTT CCATCCCGCT 610        620        630        640        650        660
    AAGATAAACC GAAGGGTAGA CCGAAAGACA AACCTCCGTG CGAACCGACG GTGAGTTCAC
    TTCTATTTGG CTTCCCATCT GGCTTTCTGT TTGGAGGCAC GCTTGGCTGC CACTCAAGTG 670        680        690        700        710        720
    AACCACCGTC GCAGCCGACG GCAATGCCCG GCGGTCCGCC CGACGCGCCT CCCCCCGCCA
    TTGGTGGCAG CGTCGGCTGC CGTTACGGGC CGCCAGGCGG GCTGCGCGGA GGGGGGCGGT 730        740        750        760        770        780
    TGCCGCAGAT GCCACCCGGC GTGGCCGAGG CGGTACAAGC TGCCGTGCAG GCGGCCGTGG
    ACGGCGTCTA CGGTGGGCCG CACCGGCTCC GCCATGTTCG ACGGCACGTC CGCCGGCACC 790        800        810        820        830        840
    CCGCGGCTCT ACAACAACAG CAGCAGCATC AGACCGGAAC GTAACCCGCC CCCGGTGCGA
    GGCGCCGAGA TGTTGTTGTC GTCGTCGTAG TCTGGCCTTG CATTGGGCGG GGGCCACGCT 850        860        870        880        890        900
    TAAGGAATTT TCCGACTTGG CGCACATCTC CTTCCTCAAT GTTTGGACAA TAAACACATT
    ATTCCTTAAA AGGCTGAACC GCGTGTAGAG GAAGGAGTTA CAAACCTGTT ATTTGTGTAA 910        920        930        940        950        960
    CCTTGCCAAA AAATGACGTT TCCAGAAATC CAAGGCATAA ATGTCCGTAC ACCGGCCCTT
    GGAACGGTTT TTTACTGCAA AGGTCTTTAG GTTCCGTATT TACAGGCATG TGGCCGGGAA 970        980        990        1000       1010       1020
    CCCAACACGG AGTTTGAGAT TCCAAGCAGG AGAGAAGATC ATGGTGTGGA TATGGCTCGG
    GGGTTGTGCC TCAAACTCTA AGGTTCGTCC TCTCTTCTAG TACCACACCT ATACCGAGCC
```

Fig. 1A (SEQ ID NO: 1)

```
              1030       1040       1050       1060       1070       1080
         CATCGGGCTC CTCGGCGGTA CCGGACTGGC TTCCCTGGTC CTGGCCATTT CCTTATTTAC
         GTAGCCCGAG GAGCCGCCAT GGCCTGACCG AAGGGACCAG GACCGGTAAA GGAATAAATG
              1090       1100       1110       1120       1130       1140
         CCAGCGCCGA GGCCGCAAGC GATCCGACGA GACTTCGTCG CGAGGCCGGC TCCCGGGTGC
         GGTCGCGGCT CCGGCGTTCG CTAGGCTGCT CTGAAGCAGC GCTCCGGCCG AGGGCCCACG
              1150       1160       1170       1180       1190       1200
         TGCTTCTGAT AAGCGTGGTG CCTGCGCGTG CTGCTATCGA AATCCGAAAG AAGACGTCGT
         ACGAAGACTA TTCGCACCAC GGACGCGCAC GACGATAGCT TTAGGCTTTC TTCTGCAGCA
              1210       1220       1230       1240       1250       1260
         CGAGCCGCTG GATCTGGAAC TGGGGCTCAT GCGGGTGGAC ACCCACCCGC CGACGCCGCA
         GCTCGGCGAC CTAGACCTTG ACCCCGAGTA CGCCCACCTG TGGGTGGGCG GCTGCGGCGT
              1270       1280       1290       1300       1310       1320
         GGTGCCGCGG TGTACGTCGC TCTACATAGG AGAGGATGGT CTGCCGATAG ATAAACCCGA
         CCACGGCGCC ACATGCAGCG AGATGTATCC TCTCCTACCA GACGGCTATC TATTTGGGCT
              1330       1340       1350       1360       1370       1380
         GTTTCCTCCG GCGCGGTTCG AGATCCCCGA CGTATCCACG CCGGGAACGC CGACCAGCAT
         CAAAGGAGGC CGCGCCAAGC TCTAGGGGCT GCATAGGTGC GGCCCTTGCG GCTGGTCGTA
              1390       1400       1410       1420       1430       1440
         CGGCCGATCT CCGTCGCATT GCTCCTCGTC GAGCTCTTTG TCGTCCTCGA CCAGCGTCGA
         GCCGGCTAGA GGCAGCGTAA CGAGGAGCAG CTCGAGAAAC AGCAGGAGCT GGTCGCAGCT
              1450       1460       1470       1480       1490       1500
         CACGGTGCTG TATCAGCCGC CGCCATCCTG GAAGCCACCT CCGCCGCCCG GGCGCAAGAA
         GTGCCACGAC ATAGTCGGCG GCGGTAGGAC CTTCGGTGGA GGCGGCGGGC CCGCGTTCTT
              1510       1520       1530       1540       1550       1560
         GCGGCCGCCT ACGCCGCCGG TCCGGGCCCC CACCACGCGG CTGTCGTCGC ACAGACCCCC
         CGCCGGCGGA TGCGGCGGCC AGGCCCGGGG GTGGTGCGCC GACAGCAGCG TGTCTGGGGG
              1570       1580       1590       1600       1610       1620
         GACGCCGATA CCCGCGCCGC GTAAGAACCT GAGCACGCCG CCCACCAAGA AAACGCCGCC
         CTGCGGCTAT GGGCGCGGCG CATTCTTGGA CTCGTGCGGC GGGTGGTTCT TTTGCGGCGG
              1630       1640       1650       1660       1670       1680
         GCCCACGAAA CCCAAGCCGG TCGGCTGGAC ACCGCCGGTG ACACCCAGGC CCTTCCCGAA
         CGGGTGCTTT GGGTTCGGCC AGCCGACCTG TGGCGGCCAC TGTGGGTCCG GGAAGGGCTT
              1690       1700       1710       1720       1730       1740
         AACGCCGACG CCACAAAAGC CGCCGCGGAA TCCGAGACTA CCGCGCACCG TCGGTCTGGA
         TTGCGGCTGC GGTGTTTTCG GCGGCGCCTT AGGCTCTGAT GGCGCGTGGC AGCCAGACCT
              1750       1760       1770       1780       1790       1800
         GAATCTCTCG AAGGTGGGAC TCTCGTGTCC CTGTCCCCGA CCCCGCACGC CGACGGAGCC
         CTTAGAGAGC TTCCACCCTG AGAGCACAGG GACAGGGGCT GGGGCGTGCG GCTGCCTCGG
              1810       1820       1830       1840       1850       1860
         GACCACGCTG CCTATCGTGT CGGTTTCCGA GCTAGCCCCG CCTCCTCGAT GGTCGGACAT
         CTGGTGCGAC GGATAGCACA GCCAAAGGCT CGATCGGGGC GGAGGAGCTA CCAGCCTGTA
              1870       1880       1890       1900       1910       1920
         CGAGGAACTC TTGGAACAGG CGGTGCAGAG CGTCATGAAG GACGCCGAGT CGATGCAGAT
         GCTCCTTGAG AACCTTGTCC GCCACGTCTC GCAGTACTTC CTGCGGCTCA GCTACGTCTA
              1930       1940       1950       1960       1970       1980
         GACCTGAGAC CGAAAGAGCG AGCGCGTCCG TTGTACAGTT GTATAGCAGC ACACGCCTTC
         CTGGACTCTG GCTTTCTCGC TCGCGCAGGC AACATGTCAA CATATCGTCG TGTGCGGAAG
              1990       2000       2010       2020       2030       2040
         CCTCTTTTTC ACCGCAGCTA AGAGAGAGAA AGAGAGTATG TCAGTCAAGG GCGTGGAGAT
         GGAGAAAAAG TGGCGTCGAT TCTCTCTCTT TCTCTCATAC AGTCAGTTCC CGCACCTCTA
```

Fig. 1B (SEQ ID NO: 1)

```
            2050       2060       2070       2080       2090       2100
       GCCAGAAATG ACGTGGGACT TGGACGTTAG AAATAAATGG CGGCGTCGAA AGGCCCTGAG
       CGGTCTTTAC TGCACCCTGA ACCTGCAATC TTTATTTACC GCCGCAGCTT TCCGGGACTC
            2110       2120       2130       2140       2150       2160
       TCGCATTCAC CGGTTCTGGG AATGTCGGCT ACGGGTGTGG TGGCTGAGTG ACGCCGGCGT
       AGCGTAAGTG GCCAAGACCC TTACAGCCGA TGCCCACACC ACCGACTCAC TGCGGCCGCA
            2170       2180       2190       2200       2210       2220
       AAGAGAAACC GACCCACCGC GTCCCCGACG CCGCCCGACT TGGATGACCG CGGTGTTTCA
       TTCTCTTTGG CTGGGTGGCG CAGGGGCTGC GGCGGGCTGA ACCTACTGGC GCCACAAAGT
            2230       2240       2250       2260       2270       2280
       CGTTATCTGT GCCGTTTTGC TTACGCTTAT GATTATGGCC ATCGGCGCGC TCATCGCGTA
       GCAATAGACA CGGCAAAACG AATGCGAATA CTAATACCGG TAGCCGCGCG AGTAGCGCAT
            2290       2300       2310       2320       2330       2340
       CTTAAGATAT TACCACCAGG ACAGTTGGCG AGACATGCTC CACGATCTAT TTTGCGGCTG
       GAATTCTATA ATGGTGGTCC TGTCAACCGC TCTGTACGAG GTGCTAGATA AAACGCCGAC
            2350       2360       2370       2380       2390       2400
       TCATTATCCC GAGAAGTGCC GTCGGCACCA CGAGCGGCAG AGAAGGAGAC GGCAAGCCAT
       AGTAATAGGG CTCTTCACGG CAGCCGTGGT GCTCGCCGTC TCTTCCTCTG CCGTTCGGTA
            2410       2420       2430       2440       2450       2460
       GGATGTGCCC GACCCGGAAC TCGGCGACCC GGCCCGCCGG CCGTTGAACG GAGCTATGTA
       CCTACACGGG CTGGGCCTTG AGCCGCTGGG CCGGGCGGCC GGCAACTTGC CTCGATACAT
            2470       2480       2490       2500       2510       2520
       CTACGGCAGC GGCTGTCGCT TCGACACGGT GGAAATGGTG GACGAGACGA GACCCGCGCC
       GATGCCGTCG CCGACAGCGA AGCTGTGCCA CCTTTACCAC CTGCTCTGCT CTGGGCGCGG
            2530       2540       2550       2560       2570       2580
       GCCGGCGCTG TCATCGCCCG AAACCGGCGA CGATAGCAAC GACGACGCGG TTGCCGGCGG
       CGGCCGCGAC AGTAGCGGGC TTTGGCCGCT GCTATCGTTG CTGCTGCGCC AACGGCCGCC
            2590       2600       2610       2620       2630       2640
       AGGTGCTGGC GGGGTAACAT CACCCGCGAC TCGTACGACG TCGCCGAACG CACTGCTGCC
       TCCACGACCG CCCCATTGTA GTGGGCGCTG AGCATGCTGC AGCGGCTTGC GTGACGACGG
            2650       2660       2670       2680       2690       2700
       AGAATGGATG GATGCGGTGC ATGTGGCGGT CCAAGCCGCC GTTCAAGCGA CCGTGCAAGT
       TCTTACCTAC CTACGCCACG TACACCGCCA GGTTCGGCGG CAAGTTCGCT GGCACGTTCA
            2710       2720       2730       2740       2750       2760
       AAGTGGCCCG CGGGAGAACG CCGTATCTCC CGCTACGTAA GAGGGTTGAG GGGGCCGTTC
       TTCACCGGGC GCCCTCTTGC GGCATAGAGG GCGATGCATT CTCCCAACTC CCCCGGCAAG
            2770       2780       2790       2800       2810       2820
       CCGCGCGAGT GCTGTACAAA AGAGAGAGAC TGGGACGTAG ATCCGGACAG AGGACGGTCA
       GGCGCGCTCA CGACATGTTT TCTCTCTCTG ACCCTGCATC TAGGCCTGTC TCCTGCCAGT
            2830       2840       2850       2860       2870       2880
       CCATGGACGA TCTGCCGCTG AATGTCGGGT TACCCATCAT CGGCGTGATG CTCGTGCTGA
       GGTACCTGCT AGACGGCGAC TTACAGCCCA ATGGGTAGTA GCCGCACTAC GAGCACGACT
            2890       2900       2910       2920       2930       2940
       TCGTGGCCAT CCTCTGCTAT CTGGCTTACC ACTGGCACGA CACCTTCAAA CTGGTGCGCA
       AGCACCGGTA GGAGACGATA GACCGAATGG TGACCGTGCT GTGGAAGTTT GACCACGCGT
            2950       2960       2970       2980       2990       3000
       TGTTTCTGAG CTACCGCTGG CTGATCCGCT GTTGCGAGCT GTACGGGAG TACGAGCGCC
       ACAAAGACTC GATGGCGACC GACTAGGCGA CAACGCTCGA CATGCCCCTC ATGCTCGCGG
            3010       3020       3030       3040       3050       3060
       GGTTCGCGGA CCTGTCGTCT CTGGGCCTCG GCGCCGTACG GCGGGAGTCG ACAGACGAT
       CCAAGCGCCT GGACAGCAGA GACCCGGAGC CGCGGCATGC CGCCCTCAGC CTGTCTGCTA
```

Fig. 1C (SEQ ID NO: 1)

```
       3070       3080       3090       3100       3110       3120
 ACCGTTTCTC CGAACGGCCC GACGAGATCT TGGTCCGTTG GGAGGAAGTG TCTTCCCAGT
 TGGCAAAGAG GCTTGCCGGG CTGCTCTAGA ACCAGGCAAC CCTCCTTCAC AGAAGGGTCA 3130       3140       3150       3160       3170       3180
 GCAGCTACGC GTCGTCGCGG ATAACAGACC GCCGTGTGGG TTCATCGTCT TCGTCGTCGG
 CGTCGATGCG CAGCAGCGCC TATTGTCTGG CGGCACACCC AAGTAGCAGA AGCAGCAGCC 3190       3200       3210       3220       3230       3240
 TCCACGTCGC TAGCCAGAGA AACAGCGTGC CTCCGCCGGA CATGGCGGTG ACGGCGCCGC
 AGGTGCAGCG ATCGGTCTCT TTGTCGCACG GAGGCGGCCT GTACCGCCAC TGCCGCGGCG 3250       3260       3270       3280       3290       3300
 TGACCGACGT CGATCTGTTG AAACCCGTGA CGGGATCCGC GACGCAGTTC ACCACCGTAG
 ACTGGCTGCA GCTAGACAAC TTTGGGCACT GCCCTAGGCG CTGCGTCAAG TGGTGGCATC 3310       3320       3330       3340       3350       3360
 CCATGGTACA TTATCATCAA GAGTACACGT GAATGAGAAA AAGAAAAAAG AGGGGAGCGG
 GGTACCATGT AATAGTAGTT CTCATGTGCA CTTACTCTTT TTCTTTTTTC TCCCCTCGCC 3370       3380       3390       3400       3410       3420
 ATCGCGATAA TGTCGCTTTG ACATTCTCTG CTCGATCTAC TCAGCGTCTG CACGAAACGG
 TAGCGCTATT ACAGCGAAAC TGTAAGAGAC GAGCTAGATG AGTCGCAGAC GTGCTTTGCC 3430       3440       3450       3460       3470       3480
 CATCCGCACG GAGGCGAGCC CAAGCGTATC TGCAGCAAGC GGTTCTTTCC CTCGGTGATG
 GTAGGCGTGC CTCCGCTCGG GTTCGCATAG ACGTCGTTCG CCAAGAAAGG GAGCCACTAC 3490       3500       3510       3520       3530       3540
 GTGGCAGCAT CGGTGGCGGG AGCTTGTTCG GACGATGGAC GGTGAGGAGT CCCTGGCGAT
 CACCGTCGTA GCCACCGCCC TCGAACAAGC CTGCTACCTG CCACTCCTCA GGGACCGCTA 3550       3560       3570       3580       3590       3600
 CAGGCGGCTC CCGGGTGTGG AGTTCAACGG GTGGTAATGG TGGCGGTGAT CGGTGTTAGA
 GTCCGCCGAG GGCCCACACC TCAAGTTGCC CACCATTACC ACCGCCACTA GCCACAATCT 3610       3620       3630       3640       3650       3660
 AAACGGTGGC CCTGGCAAAC ATATATCTAC TGTAAACCCT CTGCTCTGTT AATAAAAAGC
 TTTGCCACCG GGACCGTTTG TATATAGATG ACATTTGGGA GACGAGACAA TTATTTTTCG 3670       3680       3690       3700       3710       3720
 ACACTTTTCA CATGAGTTCG TAATTTTATT GTGTAGTGGA AATTTTTACG TCATTGGGAA
 TGTGAAAAGT GTACTCAAGC ATTAAAATAA CACATCACCT TTAAAAATGC AGTAACCCTT 3730       3740       3750       3760       3770       3780
 ACCCCAGAAT GAAAGAGTAT AATGTGCATA TCACCGGGGG TTCCCTGTCA GTACGAATGT
 TGGGGTCTTA CTTTCTCATA TTACACGTAT AGTGGCCCCC AAGGGACAGT CATGCTTACA 3790       3800       3810       3820       3830       3840
 ACACAACGCG GGTTACATTA CGATAAACTT TCCGGTAAAA CGATGCCGAT ACAGCGTGTA
 TGTGTTGCGC CCAATGTAAT GCTATTTGAA AGGCCATTTT GCTACGGCTA TGTCGCACAT 3850       3860       3870       3880       3890       3900
 TAACGCTGAT TGTTACGACA AACGAGTTGG TATATCCATT ATATAGTAAC GAACATGCTG
 ATTGCGACTA ACAATGCTGT TTGCTCAACC ATATAGGTAA TATATCATTG CTTGTACGAC 3910       3920       3930       3940       3950       3960
 TGGATATTAG TTTTATTTGC ACTCGCCGCA TCGGCGAGTG AAACCACTAC AGGTACCAGC
 ACCTATAATC AAAATAAACG TGAGCGGCGT AGCCGCTCAC TTTGGTGATG TCCATGGTCG 3970       3980       3990       4000       4010       4020
 TCTAATTCCA GTCAATCTAC TAGTGCTACC GCCAACACGA CCGTATCGAC ATGTATTAAT
 AGATTAAGGT CAGTTAGATG ATCACGATGG CGGTTGTGCT GGCATAGCTG TACATAATTA 4030       4040       4050       4060       4070       4080
 GCCTCTAACG GCAGTAGCTG GACAGTACCA CAGCTCGCGC TGCTTGCCGC TAGCGGCTGG
 CGGAGATTGC CGTCATCGAC CTGTCATGGT GTCGAGCGCG ACGAACGGCG ATCGCCGACC
```

Fig. 1D (SEQ ID NO: 1)

```
       4090       4100       4110       4120       4130       4140
ACATTATCTG GACTCCTTCT CTTATTTACC TGCTGCTTTT GCTGCTTTTG GCTAGTACGT
TGTAATAGAC CTGAGGAAGA GAATAAATGG ACGACGAAAA CGACGAAAAC CGATCATGCA
       4150       4160       4170       4180       4190       4200
AAAATCTGCA GCTGCTGCGG CAACTCCTCC GAGTCAGAGA GCAAAACAAC CCACGCGTAC
TTTTAGACGT CGACGACGCC GTTGAGGAGG CTCAGTCTCT CGTTTTGTTG GGTGCGCATG
       4210       4220       4230       4240       4250       4260
ACCAATGCCG CATTCACTTC TTCCGACGCA ACGTTACCCA TGGGCACTAC AGGGTCGTAC
TGGTTACGGC GTAAGTGAAG AAGGCTGCGT TGCAATGGGT ACCCGTGATG TCCCAGCATG
       4270       4280       4290       4300       4310       4320
ACTCCCCCAC AGGACGGCTC ATTTCCACCT CCGCCTCGGT GACGTAGGCT AAACCGAAAC
TGAGGGGGTG TCCTGCCGAG TAAAGGTGGA GGCGGAGCCA CTGCATCCGA TTTGGCTTTG
       4330       4340       4350       4360       4370       4380
CCACGTTGAA CCTAACGCGG TTTCGGAAGG CCTGAGACGT CACTTTCACA ATGACGTCCG
GGTGCAACTT GGATTGCGCC AAAGCCTTCC GGACTCTGCA GTGAAAGTGT TACTGCAGGC
       4390       4400       4410       4420       4430       4440
TATACACGTT CATCATAAAA CACCGTAGAG GCTAAGGCTT CGGTAGGGAG AGACCTCAAC
ATATGTGCAA GTAGTATTTT GTGGCATCTC CGATTCCGAA GCCATCCCTC TCTGGAGTTG
       4450       4460       4470       4480       4490       4500
TGTTCCTGAT GAGCACCCGT GCTCTCATCT CTTCAGACTT GTCATGACCC CCGCTCAGAC
ACAAGGACTA CTCGTGGGCA CGAGAGTAGA GAAGTCTGAA CAGTACTGGG GGCGAGTCTG
       4510       4520       4530       4540       4550       4560
TAACGCGACT ACCACCGTGC ACCCGCACGA CGCAAAAAAC GGCAGCGGCG GTAGTGCCCT
ATTGCGCTGA TGGTGGCACG TGGGCGTGCT GCGTTTTTTG CCGTCGCCGC CATCACGGGA
       4570       4580       4590       4600       4610       4620
GCCGACCCTC GTCGTTTTCG GCTTTATCGT TACGCTACTT TTCTTTCTCT TTATGCTCTA
CGGCTGGGAG CAGCAAAAGC CGAAATAGCA ATGCGATGAA AAGAAAGAGA AATACGAGAT
       4630       4640       4650       4660       4670       4680
CTTTTGGAAC AACGACGTGT TCCGTAAGCT GCTCCGTGCG CTTGGATCCA GCGCTGTTGC
GAAAACCTTG TTGCTGCACA AGGCATTCGA CGAGGCACGC GAACCTAGGT CGCGACAACG
       4690       4700       4710       4720       4730       4740
GACCGCTTCG ACGCGTGGCA AGACGAGGTC ATCTACCGTC GTCCATCACG TCGTTCCCAG
CTGGCGAAGC TGCGCACCGT TCTGCTCCAG TAGATGGCAG CAGGTAGTGC AGCAAGGGTC
       4750       4760       4770       4780       4790       4800
AGCGACGACG AGAGTCGTAC TAACAGCGTG TCATCGTACG TTCTTTTATC ACCCGCGTCC
TCGCTGCTGC TCTCAGCATG ATTGTCGCAC AGTAGCATGC AAGAAAATAG TGGGCGCAGG
       4810       4820       4830       4840       4850       4860
GATGGCGGTT TTGACAACCC GGCACTGACA GAGGCCGTCG ACAGCGTGGA CGACTGGGCG
CTACCGCCAA AACTGTTGGG CCGTGACTGT CTCCGGCAGC TGTCGCACCT GCTGACCCGC
       4870       4880       4890       4900       4910       4920
ACCACCTCGG TTTTCTACGC CACGTCCGAC GAAACGGCGG ACGCCGAGCG CCGAGACTCG
TGGTGGAGCC AAAAGATGCG GTGCAGGCTG CTTTGCCGCC TGCGGCTCGC GGCTCTGAGC
       4930       4940       4950       4960       4970       4980
CAGCAACTGC TCATCGAGCT TCCGCCGGAG CCGCTCCCGC CCGACGTGGG GCGGCCATG
GTCGTTGACG AGTAGCTCGA AGGCGGCCTC GGCGAGGGCG GGCTGCACCA CCGCCGGTAC
       4990       5000       5010       5020       5030       5040
CAGAAAGCAG TGAAACGCGC TGTACAGAAC GCACTACGAC ACAGCCACGA CTCTTGGCAG
GTCTTTCGTC ACTTTGCGCG ACATGTCTTG CGTGATGCTG TGTCGGTGCT GAGAACCGTC
       5050       5060       5070       5080       5090       5100
CTTCATCAGA CCCTGTGACG CCAGATGAAC GTTCCTTCTT AAACATCCGA GGTAGCAATG
GAAGTAGTCT GGGACACTGC GGTCTACTTG CAAGGAAGAA TTTGTAGGCT CCATCGTTAC
```

Fig. 1E (SEQ ID NO: 1)

```
          5110       5120       5130       5140       5150       5160
     AGACAGGTCG CGTACCGCCG GCGACGCGAG AGTTCCTGCG CGGTGCTGGT CCACCACGTC
     TCTGTCCAGC GCATGGCGGC CGCTGCGCTC TCAAGGACGC GCCACGACCA GGTGGTGCAG 5170       5180       5190       5200       5210       5220
     GGCCGCGACG GCGACGGCGA GGGGGAGGCA GCAAAAAAGA CCTGCAAAAA AACCGGACGC
     CCGGCGCTGC CGCTGCCGCT CCCCCTCCGT CGTTTTTTCT GGACGTTTTT TTGGCCTGCG 5230       5240       5250       5260       5270       5280
     TCAGTTGCGG GCATCCCGGG CGAGAAGCTG CGTCGCACGG TGGTCACCAC CACGCCGGCC
     AGTCAACGCC CGTAGGGCCC GCTCTTCGAC GCAGCGTGCC ACCAGTGGTG GTGCGGCCGG 5290       5300       5310       5320       5330       5340
     CGACGTTTGA GCGGCCGACA CACGGAGCAG GAGCAGGCGG GCATGCGTCT CTGTGAAAAA
     GCTGCAAACT CGCCGGCTGT GTGCCTCGTC CTCGTCCGCC CGTACGCAGA GACACTTTTT 5350       5360       5370       5380       5390       5400
     GGGAAGAAAA GAATCATCAT GTGCCGCCGG GAGTCGCTCC GAACTCTGCC GTGGCTGTTC
     CCCTTCTTTT CTTAGTAGTA CACGGCGGCC CTCAGCGAGG CTTGAGACGG CACCGACAAG 5410       5420       5430       5440       5450       5460
     TGGGTGCTGT TGAGCTGCCC GCGACTCCTC GAATATTCTT CCTCTTCGTT CCCCTTCGCC
     ACCCACGACA ACTCGACGGG CGCTGAGGAG CTTATAAGAA GGAGAAGCAA GGGGAAGCGG 5470       5480       5490       5500       5510       5520
     ACCGCTGACA TTGCCGAAAA GATGTGGGCC GAGAATTATG AGACCACGTC GCCGGCGCCG
     TGGCGACTGT AACGGCTTTT CTACACCCGG CTCTTAATAC TCTGGTGCAG CGGCCGCGGC 5530       5540       5550       5560       5570       5580
     GTGTTGGTCG CCGAGGGAGA GCAAGTTACC ATCCCCTGCA CGGTCATGAC ACACTCCTGG
     CACAACCAGC GGCTCCCTCT CGTTCAATGG TAGGGGACGT GCCAGTACTG TGTGAGGACC 5590       5600       5610       5620       5630       5640
     CCCATGGTCT CCATTCGCGC ACGTTTCTGT CGTTCCCACG ACGGCAGCGA CGAGCTCATC
     GGGTACCAGA GGTAAGCGCG TGCAAAGACA GCAAGGGTGC TGCCGTCGCT GCTCGAGTAG 5650       5660       5670       5680       5690       5700
     CTGGACGCCG TCAAAGGCCA TCGGCTGATG AACGGACTCC AGTACCGCCT GCCGTACGCC
     GACCTGCGGC AGTTTCCGGT AGCCGACTAC TTGCCTGAGG TCATGGCGGA CGGCATGCGG 5710       5720       5730       5740       5750       5760
     ACTTGGAATT TCTCGCAATT GCATCTCGGC CAAATATTCT CGCTTACTTT TAACGTATCG
     TGAACCTTAA AGAGCGTTAA CGTAGAGCCG GTTTATAAGA GCGAATGAAA ATTGCATAGC 5770       5780       5790       5800       5810       5820
     ATGGACACAG CCGGCATGTA CGAATGCGTG CTACGCAACT ACAGCCACGG CCTCATCATG
     TACCTGTGTC GGCCGTACAT GCTTACGCAC GATGCGTTGA TGTCGGTGCC GGAGTAGTAC 5830       5840       5850       5860       5870       5880
     CAACGCTTCG TAATTCTCAC GCAGCTGGAG ACGCTCAGCC GGCCCGACGA ACCTTGCTGC
     GTTGCGAAGC ATTAAGAGTG CGTCGACCTC TGCGAGTCGG CCGGGCTGCT TGGAACGACG 5890       5900       5910       5920       5930       5940
     ACACCGGCGT TAGGTCGCTA CTCGCTGGGA GACCAGATCT GGTCGCCGAC GCCCTGGCGT
     TGTGGCCGCA ATCCAGCGAT GAGCGACCCT CTGGTCTAGA CCAGCGGCTG CGGGACCGCA 5950       5960       5970       5980       5990       6000
     CTACGGAATC ACGACTGCGG AACGTACCGC GGCTTTCAAC GCAACTACTT CTATATCGGC
     GATGCCTTAG TGCTGACGCC TTGCATGGCG CCGAAAGTTG CGTTGATGAA GATATAGCCG 6010       6020       6030       6040       6050       6060
     CGCGCCGACG CCGAGGATTG CTGGAAACCC GCATGTCCGG ACGAGGAACC CGACCGCTGT
     GCGCGGCTGC GGCTCCTAAC GACCTTTGGG CGTACAGGCC TGCTCCTTGG GCTGGCGACA 6070       6080       6090       6100       6110       6120
     TGGACAGTGA TACAGCGTTA CCGGCTCCCC GGCGACTGCT ACCGTTCGCA GCCACACCCG
     ACCTGTCACT ATGTCGCAAT GGCCGAGGGG CCGCTGACGA TGGCAAGCGT CGGTGTGGGC
```

Fig. 1F (SEQ ID NO: 1)

```
            6130       6140       6150       6160       6170       6180
       CCGAAATTTT TACCGGTGAC GCCAGCACCG CCGGCCGACA TAGACACCGG GATGTCTCCC
       GGCTTTAAAA ATGGCCACTG CGGTCGTGGC GGCCGGCTGT ATCTGTGGCC CTACAGAGGG
            6190       6200       6210       6220       6230       6240
       TGGGCCACTC GGGGAATCGC GGCGTTTTTG GGGTTTTGGA GTATTTTTAC CGTATGTTTC
       ACCCGGTGAG CCCCTTAGCG CCGCAAAAAC CCCAAAACCT CATAAAAATG GCATACAAAG
            6250       6260       6270       6280       6290       6300
       CTATGCTACC TGTGTTATCT GCAGTGTTGT GGACGCTGGT GTCCCACGCC GGGAAGGGGA
       GATACGATGG ACACAATAGA CGTCACAACA CCTGCGACCA CAGGGTGCGG CCCTTCCCCT
            6310       6320       6330       6340       6350       6360
       CGACGAGGCG GTGAGGGCTA TCGACGCCTA CCGACTTACG ATAGTTACCC CGGTGTTAGA
       GCTGCTCCGC CACTCCCGAT AGCTGCGGAT GGCTGAATGC TATCAATGGG GCCACAATCT
            6370       6380       6390       6400       6410       6420
       AAGATGAAGA GGTGAGAACA CGTATAAAAT AAAAAAATAA TATGTTAAAA AATGCAGTGT
       TTCTACTTCT CCACTCTTGT GCATATTTTA TTTTTTTATT ATACAATTTT TTACGTCACA
            6430       6440       6450       6460       6470       6480
       GTGAAGTGTG AATAGTGTGA TTAAAATATG CGGATTGAAT GGGTGTGGTG GTTATTCGGA
       CACTTCACAC TTATCACACT AATTTTATAC GCCTAACTTA CCCACACCAC CAATAAGCCT
            6490       6500       6510       6520       6530       6540
       TACTTTGTGT CATCCGTTGG GAGCGAACGG TCATTATCCT ATCGTTACCA CTTGGAATCT
       ATGAAACACA GTAGGCAACC CTCGCTTGCC AGTAATAGGA TAGCAATGGT GAACCTTAGA
            6550       6560       6570       6580       6590       6600
       AATTCATCTA CCAACGTGGT TGCAACGGA AACATTTCCG TGTTTGTAAA CGGCACCCTA
       TTAAGTAGAT GGTTGCACCA AACGTTGCCT TTGTAAAGGC ACAAACATTT GCCGTGGGAT
            6610       6620       6630       6640       6650       6660
       GGTGTGCGGT ATAACATTAC GGTAGGAATC AGTTCGTCTT TATTAATAGG ACACCTTACT
       CCACACGCCA TATTGTAATG CCATCCTTAG TCAAGCAGAA ATAATTATCC TGTGGAATGA
            6670       6680       6690       6700       6710       6720
       ATACAAGTAT TGGAATCATG GTTCACACCC TGGGTCCAAA ATAAAGTTA CAACAAACAA
       TATGTTCATA ACCTTAGTAC CAAGTGTGGG ACCCAGGTTT TATTTTCAAT GTTGTTTGTT
            6730       6740       6750       6760       6770       6780
       CCCCTAGGTG ACACTGAAAC GCTTTATAAT ATAGATAGCG AAAACATTCA TCGCGTATCT
       GGGGATCCAC TGTGACTTTG CGAAATATTA TATCTATCGC TTTTGTAAGT AGCGCATAGA
            6790       6800       6810       6820       6830       6840
       CAATATTTTC ACACAAGATG GATAAAATCT CTGCAAGAGA ATCACACTTG CGACCTCACA
       GTTATAAAAG TGTGTTCTAC CTATTTTAGA GACGTTCTCT TAGTGTGAAC GCTGGAGTGT
            6850       6860       6870       6880       6890       6900
       AACAGTACAC CTACCTATAC ATATCAAGTA AACGTGAACA ACACGAATTA CCTAACACTA
       TTGTCATGTG GATGGATATG TATAGTTCAT TTGCACTTGT TGTGCTTAAT GGATTGTGAT
            6910       6920       6930       6940       6950       6960
       ACATCCTCGG GATGGCAAGA CCGTCTAAAT TACACCGTCA TAAATAGTAC ACACTTTAAC
       TGTAGGAGCC CTACCGTTCT GGCAGATTTA ATGTGGCAGT ATTTATCATG TGTGAAATTG
            6970       6980       6990       7000       7010       7020
       CTCACAGAAT CGAACATAAC CAGCATTCAA AAATATCTCA ACACTACCTG CATAGAAAGA
       GAGTGTCTTA GCTTGTATTG GTCGTAAGTT TTTATAGAGT TGTGATGGAC GTATCTTTCT
            7030       7040       7050       7060       7070       7080
       CTCCGTAACT ACACCTTGGA GTCCGTATAC ACCACAACTG TGCCTCAAAA CATAACAACA
       GAGGCATTGA TGTGGAACCT CAGGCATATG TGGTGTTGAC ACGGAGTTTT GTATTGTTGT
            7090       7100       7110       7120       7130       7140
       TCTCAACACG CAACAACCAC TATGCACACA ATACCTCCAA ATACAATAAC AATTCAAAAT
       AGAGTTGTGC GTTGTTGGTG ATACGTGTGT TATGGAGGTT TATGTTATTG TTAAGTTTTA
```

Fig. 1G (SEQ ID NO: 1)

```
                7150       7160       7170       7180       7190       7200
           ACAACTCAAA GCCATACTGT ACAGACGCCG TCTTTTAACG ACACACATAA CGTGACGAAA
           TGTTGAGTTT CGGTATGACA TGTCTGCGGC AGAAAATTGC TGTGTGTATT GCACTGCTTT 7210       7220       7230       7240       7250       7260
           CACACGTTAA ACATAAGCTA CGTTTTATCA CAAAAAACGA ATAACACAAC ATCACCGTGG
           GTGTGCAATT TGTATTCGAT GCAAAATAGT GTTTTTTGCT TATTGTGTTG TAGTGGCACC 7270       7280       7290       7300       7310       7320
           ATATATGCCA TACCTATGGG CGCTACAGCC ACAATAGGCG CCGGTTTATA TATCGGGAAA
           TATATACGGT ATGGATACCC GCGATGTCGG TGTTATCCGC GGCCAAATAT ATAGCCCTTT 7330       7340       7350       7360       7370       7380
           CACTTTACGC CGGTTAAGTT CGTATACGAG GTATGGCGCG GTCAGTAAAG ACGATTCGGA
           GTGAAATGCG GCCAATTCAA GCATATGCTC CATACCGCGC CAGTCATTTC TGCTAAGCCT 7390       7400       7410       7420       7430       7440
           TTCAACACAT ATACTCCCCA CGATCCTCGA ACACCTTACA GCATATGAGC AAAAAACAAG
           AAGTTGTGTA TATGAGGGGT GCTAGGAGCT TGTGGAATGT CGTATACTCG TTTTTTGTTC 7450       7460       7470       7480       7490       7500
           AAAGTATAGC CACAATCACA TTTGGGCGAA TAACATGCTG TCATCCACTA GCGTCTATTA
           TTTCATATCG GTGTTAGTGT AAACCCGCTT ATTGTACGAC AGTAGGTGAT CGCAGATAAT 7510       7520       7530       7540       7550       7560
           ATCTAATGTT TAACGGGAGC TGTACTGTCA CCGTTAAAAT ATCCATGGGA ATCAACGGGT
           TAGATTACAA ATTGCCCTCG ACATGACAGT GGCAATTTTA TAGGTACCCT TAGTTGCCCA 7570       7580       7590       7600       7610       7620
           CAACCAACGT CCATCAGCTT GTGATTGTGC TCCATCTGGG TAACCGCTGT CAGCCTTGGC
           GTTGGTTGCA GGTAGTCGAA CACTAACACG AGGTAGACCC ATTGGCGACA GTCGGAACCG 7630       7640       7650       7660       7670       7680
           GACAGGTGTA ATCACAGCTG TCACATAACT CACGAAGCCT CCAATCACAG CAGCACACAT
           CTGTCCACAT TAGTGTCGAC AGTGTATTGA GTGCTTCGGA GGTTAGTGTC GTCGTGTGTA 7690       7700       7710       7720       7730       7740
           AGTCCTAACG CCATTGGCGT GTATAAAAGT TCGGAAAACT TGACGGTTGT ACGGCACGAC
           TCAGGATTGC GGTAACCGCA CATATTTTCA AGCCTTTTGA ACTGCCAACA TGCCGTGCTG 7750       7760       7770       7780       7790       7800
           AAATCGATGT AGTGGTATGT TTTTCCAGCA GAGACCGTGT GCGGTCTCTT AGGTTCGCTA
           TTTAGCTACA TCACCATACA AAAAGGTCGT CTCTGGCACA CGCCAGAGAA TCCAAGCGAT 7810       7820       7830       7840       7850       7860
           TACTGTGGCT GGAAACTGGT TACCTGTGAA GATGGCTAAC TATCCTGTTC TGTCCTGGAA
           ATGACACCGA CCTTTGACCA ATGGACACTT CTACCGATTG ATAGGACAAG ACAGGACCTT 7870       7880       7890       7900       7910       7920
           AAACTTTTGG CGTCGTAGGT GGACTTTGCA GTATGCGGGT TAGTGAAGTT ATGTCATTTA
           TTTGAAAACC GCAGCATCCA CCTGAAACGT CATACGCCCA ATCACTTCAA TACAGTAAAT 7930       7940       7950       7960       7970       7980
           TTTACGTTTA CGATCTCGTA TTACAAACCG CGGAGAGGAT GATACCGTTC GGCCCCATGA
           AAATGCAAAT GCTAGAGCAT AATGTTTGGC GCCTCTCCTA CTATGGCAAG CCGGGGTACT 7990       8000       8010       8020       8030       8040
           GTTATTTTTA TTCTTCCGGT AGGAGGCATG AAGCCTCTGA TAATGCTCAT CTGCTTTGCT
           CAATAAAAAT AAGAAGGCCA TCCTCCGTAC TTCGGAGACT ATTACGAGTA GACGAAACGA 8050       8060       8070       8080       8090       8100
           GTGATATTAT TGCAGCTTGG AGTGACTAAA GTGTGTCAGC ATAATGAAGT GCAACTGGGC
           CACTATAATA ACGTCGAACC TCACTGATTT CACACAGTCG TATTACTTCA CGTTGACCCG 8110       8120       8130       8140       8150       8160
           AATGAGTGCT GCCCTCCGTG TGGTTCGGGA CAAAGAGTTA CTAAAGTATG CACGGATTAT
           TTACTCACGA CGGGAGGCAC ACCAAGCCCT GTTTCTCAAT GATTTCATAC GTGCCTAATA
```

Fig. 1H (SEQ ID NO: 1)

```
           8170       8180       8190       8200       8210       8220
      ACCAGTGTAA CGTGTACCCC TTGCCCCAAC GGCACGTATG TATCGGGACT TTACAACTGT
      TGGTCACATT GCACATGGGG AACGGGGTTG CCGTGCATAC ATAGCCCTGA AATGTTGACA 8230       8240       8250       8260       8270       8280
      ACCGATTGCA CTCAATGTAA CGTCACTCAG GTCATGATTC GTAACTGCAC TTCCACCAAT
      TGGCTAACGT GAGTTACATT GCAGTGAGTC CAGTACTAAG CATTGACGTG AAGGTGGTTA 8290       8300       8310       8320       8330       8340
      AATACCGTAT GCGCACCTAA GAACCATACG TACTTTTCCA CTCCAGGCGT CCAACATCAC
      TTATGGCATA CGCGTGGATT CTTGGTATGC ATGAAAAGGT GAGGTCCGCA GGTTGTAGTG 8350       8360       8370       8380       8390       8400
      AAACAACGAC AGCAAAATCA TACCGCACAT ATAACCGTCA AACAAGGAAA AAGCGGTCGT
      TTTGTTGCTG TCGTTTTAGT ATGGCGTGTA TATTGGCAGT TTGTTCCTTT TTCGCCAGCA 8410       8420       8430       8440       8450       8460
      CATACTCTAG CCTGGTTGTC TCTCTTTATC TTTCTTGTGG GTATCATACT TTTAATTCTC
      GTATGAGATC GGACCAACAG AGAGAAATAG AAAGAACACC CATAGTATGA AAATTAAGAG 8470       8480       8490       8500       8510       8520
      TATCTTATAG CCGCCTATCG GAGTGAGAGA TGCCAACAGT GTTGCTCAAT CGGCAAAATT
      ATAGAATATC GGCGGATAGC CTCACTCTCT ACGGTTGTCA CAACGAGTTA GCCGTTTTAA 8530       8540       8550       8560       8570       8580
      TTCTACCGCA CCCTGTAAGC TTCCTGTTGT TGTTTTTACA TCACGGTACG ATGAAGTCAC
      AAGATGGCGT GGGACATTCG AAGGACAACA ACAAAAATGT AGTGCCATGC TACTTCAGTG 8590       8600       8610       8620       8630       8640
      ACAGATAATT ACAGATGAGC TGTTCATATT TTTTATTATT TTTTCCAATT CCTGCACTAA
      TGTCTATTAA TGTCTACTCG ACAAGTATAA AAAATAATAA AAAAGGTTAA GGACGTGATT 8650       8660       8670       8680       8690       8700
      AAAAAGAAGC ACTTTACGGA ACCGTGTCTG AGTATCTGTG GGGAATTTAG GTACTTTTTG
      TTTTTCTTCG TGAAATGCCT TGGCACAGAC TCATAGACAC CCCTTAAATC CATGAAAAAC 8710       8720       8730       8740       8750       8760
      CCGACGTCAG GAAAAATAAG TGTCGCCTAC ATAAGAGCCC GGTGCTATCG TGCTGTCACT
      GGCTGCAGTC CTTTTTATTC ACAGCGGATG TATTCTCGGG CCACGATAGC ACGACAGTGA 8770       8780       8790       8800       8810       8820
      CTTTCTTGTT GCCTTCGATG TACGGCGTCC TGGCTCATTA CTACTCCTTC ATCAGTAGCC
      GAAAGAACAA CGGAAGCTAC ATGCCGCAGG ACCGAGTAAT GATGAGGAAG TAGTCATCGG 8830       8840       8850       8860       8870       8880
      CCAGCGTTAT GGTTAATTTT AAGCATCATA ACGCCGTGCA GCTGTTATGT GCACGGACCC
      GGTCGCAATA CCAATTAAAA TTCGTAGTAT TGCGGCACGT CGACAATACA CGTGCCTGGG 8890       8900       8910       8920       8930       8940
      GAGACGCACT GCCGGATGGG AACGTTTAAC CCATCATGCG TCGTATCACG CGAACTACGG
      CTCTGCGTGA CGGCCTACCC TTGCAAATTG GGTAGTACGC AGCATAGTGC GCTTGATGCC 8950       8960       8970       8980       8990       9000
      GGCATACGCC GTGTTGATGG CTACATCGCA AAGAAAGTCC CTAGTGTTAC ATCGATACAG
      CCGTATGCGG CACAACTACC GATGTAGCGT TTCTTTCAGG GATCACAATG TAGCTATGTC 9010       9020       9030       9040       9050       9060
      TGCCGTGACA GCCGTGGCCC TGCAGCTCAT GCCTGTTGAG ATCGTCCGCA AGCTAGATCA
      ACGGCACTGT CGGCACCGGG ACGTCGAGTA CGGACAACTC TAGCAGGCGT TCGATCTAGT 9070       9080       9090       9100       9110       9120
      GTCGGACTGG GTGCGGGGTG CCTGGATCGT GTCAGAGACT TTTCCAACTA GCGACCCCAA
      CAGCCTGACC CACGCCCCAC GGACCTAGCA CAGTCTCTGA AAAGGTTGAT CGCTGGGGTT 9130       9140       9150       9160       9170       9180
      AGGAGTTTGG AGCGACGATG ACTCCTCGAT GGGTGGAAGT GATGATTGAT GATGAGAACC
      TCCTCAAACC TCGCTGCTAC TGAGGAGCTA CCCACCTTCA CTACTAACTA CTACTCTTGG
```

Fig. 1I (SEQ ID NO: 1)

```
           9190       9200       9210       9220       9230       9240
      TGACAAGAAA GACGAGAGAG AAATTTAGAG CTGTCATTGT AGAATTAGTC TAGATTCCTG
      ACTGTTCTTT CTGCTCTCTC TTTAAATCTC GACAGTAACA TCTTAATCAG ATCTAAGGAC
           9250       9260       9270       9280       9290       9300
      ATAATAAACA GTATCGATTT TGAAACCTAA TTGACGTGTG ATCGATTTTT AAACCTCTGT
      TATTATTTGT CATAGCTAAA ACTTTGGATT AACTGCACAC TAGCTAAAAA TTTGGAGACA
           9310       9320       9330       9340       9350       9360
      GTTGTGTGAT TGATTGGTAT GTGGGGGGAT CCGATTTCAA AGGGGGGTAC TTATCGGGAA
      CAACACACTA ACTAACCATA CACCCCCCTA GGCTAAAGTT TCCCCCCATG AATAGCCCTT
           9370       9380       9390       9400       9410       9420
      TTGATGTGTC ATGGACGCAG TTTTGAGCGA TTTTCCGGGA ATACCGGATA TTACGAATTA
      AACTACACAG TACCTGCGTC AAAACTCGCT AAAAGGCCCT TATGGCCTAT AATGCTTAAT
           9430       9440       9450       9460       9470       9480
      CTGGTAGTGA CGTAGATAAT AAAATTATAA TGCGATTAAT TTTTGGTGCG TTGATTATTT
      GACCATCACT GCATCTATTA TTTTAATATT ACGCTAATTA AAAACCACGC AACTAATAAA
           9490       9500       9510       9520       9530       9540
      TTTTAGCATA TGTGTATCAT TATGAGGTGA ATGGAACAGA ATTACGCTGC AGATGTCTTC
      AAAATCGTAT ACACATAGTA ATACTCCACT TACCTTGTCT TAATGCGACG TCTACAGAAG
           9550       9560       9570       9580       9590       9600
      ATAGAAAATG GCCGCCTAAT AAAATTATAT TGGGTAATTA TTGGCTTCAT CGCGATCCCA
      TATCTTTTAC CGGCGGATTA TTTTAATATA ACCCATTAAT AACCGAAGTA GCGCTAGGGT
           9610       9620       9630       9640       9650       9660
      GAGGGCCCGG ATGCGATAAA AATGAACATT TATTGTATCC AGACGGAAGG AAACCGCCTG
      CTCCCGGGCC TACGCTATTT TTACTTGTAA ATAACATAGG TCTGCCTTCC TTTGGCGGAC
           9670       9680       9690       9700       9710       9720
      GACCTGGAGT ATGTTTATCG CCCGATCACC TCTTCTCAAA ATGGTTAGAC AAACACAACG
      CTGGACCTCA TACAAATAGC GGGCTAGTGG AGAAGAGTTT TACCAATCTG TTTGTGTTGC
           9730       9740       9750       9760       9770       9780
      ATAATAGGTG GTATAATGTT AACATAACGA AATCACCAGG ACCGAGACGA ATAAATATAA
      TATTATCCAC CATATTACAA TTGTATTGCT TTAGTGGTCC TGGCTCTGCT TATTTATATT
           9790       9800       9810       9820       9830       9840
      CCTTGATAGG TGTTAGAGGA TAATATTTAA TGTATGTTTT CAAACAGACA AGTTCGTTAA
      GGAACTATCC ACAATCTCCT ATTATAAATT ACATACAAAA GTTTGTCTGT TCAAGCAATT
           9850       9860       9870       9880       9890       9900
      AACAAAATAT TACAGTATGT GTTTAATATG GTGCTAACAT GGTTGCACCA TCCGGTTTCA
      TTGTTTTATA ATGTCATACA CAAATTATAC CACGATTGTA CCAACGTGGT AGGCCAAAGT
           9910       9920       9930       9940       9950       9960
      AACTCGCATA TCAATCTGTT ATCGGTACGA CACCTGTCAT TAATCGCATA TATGTTACTT
      TTGAGCGTAT AGTTAGACAA TAGCCATGCT GTGGACAGTA ATTAGCGTAT ATACAATGAA
           9970       9980       9990      10000      10010      10020
      ACCATATGTC CCCTAGCCGT CCATGTTTTA GAACTAGAAG ATTACGACAG GCGCTGCCGT
      TGGTATACAG GGGATCGGCA GGTACAAAAT CTTGATCTTC TAATGCTGTC CGCGACGGCA
          10030      10040      10050      10060      10070      10080
      TGCAACAACC AAATTCTGTT GAATACCCTG CCGGTCGGAA CCGAATTGCT TAAGCCAATC
      ACGTTGTTGG TTTAAGACAA CTTATGGGAC GGCCAGCCTT GGCTTAACGA ATTCGGTTAG
          10090      10100      10110      10120      10130      10140
      GCAGCGAGCG AAAGCTGCAA TCGTCAGGAA GTGCTGGCTA TTTTAAAGGA CAAGGGAACC
      CGTCGCTCGC TTTCGACGTT AGCAGTCCTT CACGACCGAT AAAATTTCCT GTTCCCTTGG
          10150      10160      10170      10180      10190      10200
      AAGTGTCTCA ATCCTAACGC GCAAGCCGTG CGTCGTCACA TCAACCGGCT ATTTTTTCGG
      TTCACAGAGT TAGGATTGCG CGTTCGGCAC GCAGCAGTGT AGTTGGCCGA TAAAAAAGCC
```

Fig. 1J (SEQ ID NO: 1)

```
         10210      10220      10230      10240      10250      10260
   TTAATCTTAG ACGAGGAACA ACGCATTTAC GACGTAGTGT CTACCAATAT TGAGTTCGGT
   AATTAGAATC TGCTCCTTGT TGCGTAAATG CTGCATCACA GATGGTTATA ACTCAAGCCA
         10270      10280      10290      10300      10310      10320
   GCCTGGCCAG TCCCTACGGC CTACAAAGCC TTTCTTTGGA AATACGCCAA GAGACTGAAC
   CGGACCGGTC AGGGATGCCG GATGTTTCGG AAAGAAACCT TTATGCGGTT CTCTGACTTG
         10330      10340      10350      10360      10370      10380
   TACCACCACT TCAGACTGCG CTGGTGATCA TGTCCCTATT TTACCGTGCG GTAGCTCTGG
   ATGGTGGTGA AGTCTGACGC GACCACTAGT ACAGGGATAA AATGGCACGC CATCGAGACC
         10390      10400      10410      10420      10430      10440
   GCACGCTAAG CGCTTTGGTG TGGTACAGCA CTAGCATCCT CGCAGAGATT AACGAAAATT
   CGTGCGATTC GCGAAACCAC ACCATGTCGT GATCGTAGGA GCGTCTCTAA TTGCTTTTAA
         10450      10460      10470      10480      10490      10500
   CCTGCTCCTC ATCTTCTGCG GATCACGAAG ACTGCGAGGA ACCGGACGAG ATCGTTCGCG
   GGACGAGGAG TAGAAGACGC CTAGTGCTTC TGACGCTCCT TGGCCTGCTC TAGCAAGCGC
         10510      10520      10530      10540      10550      10560
   AAGAGCAAGA CTATCGGGCT CTGCTGGCCT TTTCCCTAGT GATTTGCGGT ACGCTCCTCG
   TTCTCGTTCT GATAGCCCGA GACGACCGGA AAAGGGATCA CTAAACGCCA TGCGAGGAGC
         10570      10580      10590      10600      10610      10620
   TCACTTGTGT GATCTGAGAC GTCATGCTGG TAGCGTTTAT GAGTCGGGCG GTGGCCGACA
   AGTGAACACA CTAGACTCTG CAGTACGACC ATCGCAAATA CTCAGCCCGC CACCGGCTGT
         10630      10640      10650      10660      10670      10680
   CGCCGCATTT CCTAACCCGC GCAGCATGTT GCGCTTGCTG TTCACGCTCG TCCTGCTGGC
   GCGGCGTAAA GGATTGGGCG CGTCGTACAA CGCGAACGAC AAGTGCGAGC AGGACGACCG
         10690      10700      10710      10720      10730      10740
   CCTCCACGGG CAGTCTGTCG GCGCTAGCCG CGACTATGTG CATGTTCGGC TACTGAGCTA
   GGAGGTGCCC GTCAGACAGC CGCGATCGGC GCTGATACAC GTACAAGCCG ATGACTCGAT
         10750      10760      10770      10780      10790      10800
   CCGAGGCGAC CCCCTGGTCT TCAAGCACAC TTTCTCGGGT GTGCGTCGAC CCTTCACCGA
   GGCTCCGCTG GGGGACCAGA AGTTCGTGTG AAAGAGCCCA CACGCAGCTG GGAAGTGGCT
         10810      10820      10830      10840      10850      10860
   GCTAGGCTGG GCTGCGTGTC GCGACTGGGA CAGTATGCAT TGCACACCCT TCTGGTCTAC
   CGATCCGACC CGACGCACAG CGCTGACCCT GTCATACGTA ACGTGTGGGA AGACCAGATG
         10870      10880      10890      10900      10910      10920
   CGATCTGGAG CAGATGACCG ACTCGGTGCG GCGTTACAGC ACGGTGAGCC CCGGCAAGGA
   GCTAGACCTC GTCTACTGGC TGAGCCACGC CGCAATGTCG TGCCACTCGG GGCCGTTCCT
         10930      10940      10950      10960      10970      10980
   AGTGACGCTT CAGCTTCACG GGAACCAAAC CGTACAGCCG TCGTTTCTAA GCTTTACGTG
   TCACTGCGAA GTCGAAGTGC CCTTGGTTTG GCATGTCGGC AGCAAAGATT CGAAATGCAC
         10990      11000      11010      11020      11030      11040
   CCGCCTGCAG CTAGAACCCG TGGTGGAAAA TGTTGGCCTC TACGTGGCCT ACGTGGTCAA
   GGCGGACGTC GATCTTGGGC ACCACCTTTT ACAACCGGAG ATGCACCGGA TGCACCAGTT
         11050      11060      11070      11080      11090      11100
   CGACGGCGAA CGCCCACAAC AGTTTTTTAC ACCGCAGGTA GACGTGGTAC GCTTTGCTCT
   GCTGCCGCTT GCGGGTGTTG TCAAAAAATG TGGCGTCCAT CTGCACCATG CGAAACGAGA
         11110      11120      11130      11140      11150      11160
   ATATCTAGAA ACACTCTCCC GGATCGTGGA ACCGTTAGAA TCAGGTCGCC TGGCAGTGGA
   TATAGATCTT TGTGAGAGGG CCTAGCACCT TGGCAATCTT AGTCCAGCGG ACCGTCACCT
         11170      11180      11190      11200      11210      11220
   ATTTGATACG CCTGACCTAG CTCTGGCGCC CGATTTAGTA AGCAGCCTCT TCGTGGCCGG
   TAAACTATGC GGACTGGATC GAGACCGCGG GCTAAATCAT TCGTCGGAGA AGCACCGGCC
```

Fig. 1K (SEQ ID NO: 1)

```
            11230        11240        11250        11260        11270        11280
       ACACGGCGAG   ACCGACTTTT   ACATGAACTG   GACGCTGCGT   CGCAGTCAGA   CCCACTACCT
       TGTGCCGCTC   TGGCTGAAAA   TGTACTTGAC   CTGCGACGCA   GCGTCAGTCT   GGGTGATGGA
            11290        11300        11310        11320        11330        11340
       GGAGGAGATG   GCCTTACAGG   TGGAGATTCT   AAAACCCCGC   GGCGTACGTC   ACCGCGCTAT
       CCTCCTCTAC   CGGAATGTCC   ACCTCTAAGA   TTTTGGGGCG   CCGCATGCAG   TGGCGCGATA
            11350        11360        11370        11380        11390        11400
       TATCCACCAT   CCGAAGCTAC   AGCCGGGCGT   TGGCCTGTGG   ATAGATTTCT   GCGTGTACCG
       ATAGGTGGTA   GGCTTCGATG   TCGGCCCGCA   ACCGGACACC   TATCTAAAGA   CGCACATGGC
            11410        11420        11430        11440        11450        11460
       CTACAACGCG   CGCCTGACCC   GCGGCTACGT   ACGATACACC   CTGTCACCGA   AAGCGCGCTT
       GATGTTGCGC   GCGGACTGGG   CGCCGATGCA   TGCTATGTGG   GACAGTGGCT   TTCGCGCGAA
            11470        11480        11490        11500        11510        11520
       GCCCGCAAAA   GCAGAGGGTT   GGCTGGTGTC   ACTAGACAGA   TTCATCGTGC   AGTACCTCAA
       CGGGCGTTTT   CGTCTCCCAA   CCGACCACAG   TGATCTGTCT   AAGTAGCACG   TCATGGAGTT
            11530        11540        11550        11560        11570        11580
       CACATTGCTG   ATTACAATGA   TGGCGGCGAT   ATGGGCTCGC   GTTTTGATAA   CCTACCTGGT
       GTGTAACGAC   TAATGTTACT   ACCGCCGCTA   TACCCGAGCG   CAAAACTATT   GGATGGACCA
            11590        11600        11610        11620        11630        11640
       GTCGCGGCGT   CGGTAGAGGC   TTGCGGAAAC   CACGTCCTCG   TCACACGTCG   TTCGCGGACA
       CAGCGCCGCA   GCCATCTCCG   AACGCCTTTG   GTGCAGGAGC   AGTGTGCAGC   AAGCGCCTGT
            11650        11660        11670        11680        11690        11700
       TAGCAAGAAA   TCCACGTCGC   CACATCTCGA   GAATGCCGGC   CTTGCGGGGT   CCCCTTCGCG
       ATCGTTCTTT   AGGTGCAGCG   GTGTAGAGCT   CTTACGGCCG   GAACGCCCCA   GGGGAAGCGC
            11710        11720        11730        11740        11750        11760
       CAACATTCCT   GGCCCTGGTC   GCGTTCGGGT   TGCTGCTTCA   GATAGACCTC   AGCGACGCTA
       GTTGTAAGGA   CCGGGACCAG   CGCAAGCCCA   ACGACGAAGT   CTATCTGGAG   TCGCTGCGAT
            11770        11780        11790        11800        11810        11820
       CGAATGTGAC   CAGCAGCACA   AAAGTCCCTA   CTAGCACCAG   CAACAGAAAT   AACGTCGACA
       GCTTACACTG   GTCGTCGTGT   TTTCAGGGAT   GATCGTGGTC   GTTGTCTTTA   TTGCAGCTGT
            11830        11840        11850        11860        11870        11880
       ACGCCACGAG   TAGCGGACCC   ACAACCGGGA   TCAACATGAC   CACCACCCAC   GAGTCTTCCG
       TGCGGTGCTC   ATCGCCTGGG   TGTTGGCCCT   AGTTGTACTG   GTGGTGGGTG   CTCAGAAGGC
            11890        11900        11910        11920        11930        11940
       TTCACAACGT   GCGCAATAAC   GAGATCATGA   AAGTGCTGGC   TATCCTCTTC   TACATCGTGA
       AAGTGTTGCA   CGCGTTATTG   CTCTAGTACT   TTCACGACCG   ATAGGAGAAG   ATGTAGCACT
            11950        11960        11970        11980        11990        12000
       CAGGCACCTC   CATTTTCAGC   TTCATAGCGG   TACTGATCGC   GGTAGTTTAC   TCCTCGTGTT
       GTCCGTGGAG   GTAAAAGTCG   AAGTATCGCC   ATGACTAGCG   CCATCAAATG   AGGAGCACAA
            12010        12020        12030        12040        12050        12060
       GCAAGCACCC   GGGCCGCTTT   CGTTTCGCCG   ACGAAGAGGC   CGTCAACCTG   TTGGACGACA
       CGTTCGTGGG   CCCGGCGAAA   GCAAAGCGGC   TGCTTCTCCG   GCAGTTGGAC   AACCTGCTGT
            12070        12080        12090        12100        12110        12120
       CGGACGACAG   TGGCGGCAGC   AGCCCGTTTG   GCAGCGGTTC   CCGACGAGGT   TCTCAGATCC
       GCCTGCTGTC   ACCGCCGTCG   TCGGGCAAAC   CGTCGCCAAG   GGCTGCTCCA   AGAGTCTAGG
            12130        12140        12150        12160        12170        12180
       CCGCCGGATT   TTGTTCCTCG   AGCCCTTATC   AGCGGTTGGA   AACTCGGGAC   TGGGACGAGG
       GGCGGCCTAA   AACAAGGAGC   TCGGGAATAG   TCGCCAACCT   TTGAGCCCTG   ACCCTGCTCC
            12190        12200        12210        12220        12230        12240
       AGGAGGAGGC   GTCCGCGGCC   CGCGAGCGCA   TGAAACATGA   TCCTGAGAAC   GTCATCTATT
       TCCTCCTCCG   CAGGCGCCGG   GCGCTCGCGT   ACTTTGTACT   AGGACTCTTG   CAGTAGATAA
```

Fig. 1L (SEQ ID NO: 1)

```
           12250      12260      12270      12280      12290      12300
       TCAGAAAGGA TGGCAACTTG GACACGTCGT TCGTGAATCC CAATTATGGG AGAGGCTCGC
       AGTCTTTCCT ACCGTTGAAC CTGTGCAGCA AGCACTTAGG GTTAATACCC TCTCCGAGCG 12310      12320      12330      12340      12350      12360
       CTTTGACCAT CGAATCTCAC CTCTCGGACA ATGAGGAGGA CCCCATCAGG TACTACGTTT
       GAAACTGGTA GCTTAGAGTG GAGAGCCTGT TACTCCTCCT GGGGTAGTCC ATGATGCAAA 12370      12380      12390      12400      12410      12420
       CGGTGTACGA TGAACTGACC GCCTCGGAAA TGGAAGAACC TTCGAACAGC ACCAGCTGGC
       GCCACATGCT ACTTGACTGG CGGAGCCTTT ACCTTCTTGG AAGCTTGTCG TGGTCGACCG 12430      12440      12450      12460      12470      12480
       AGATTCCCAA ACTAATGAAA GTTGCCATGC AACCCGTCTC GCTCAGAGAT CCCGAGTACG
       TCTAAGGGTT TGATTACTTT CAACGGTACG TTGGGCAGAG CGAGTCTCTA GGGCTCATGC 12490      12500      12510      12520      12530      12540
       ACTAGGCTTT TTTTTTTGTC TTTCGGTTCC AACTCTTTCC CCGCCCCATC ACCTCGCCTG
       TGATCCGAAA AAAAAAACAG AAAGCCAAGG TTGAGAAAGG GGCGGGGTAG TGGAGCGGAC 12550      12560      12570      12580      12590      12600
       TACTATGTGT ATGATGTCTC ATAATAAAGC TTTCTTTCTC AGTCTGCAAC ATGCAGCTGT
       ATGATACACA TACTACAGAG TATTATTTCG AAAGAAAGAG TCAGACGTTG TACGTCGACA 12610      12620      12630      12640      12650      12660
       GTCGGGTGTG GCTGTCTGTT TGTCTGTGCG CCGTGGTGCT GGGTCAGTGC CAGCGGGAAA
       CAGCCCACAC CGACAGACAA ACAGACACGC GGCACCACGA CCCAGTCACG GTCGCCCTTT 12670      12680      12690      12700      12710      12720
       CCGCGGAAAA AAACGATTAT TACCGAGTAC CGCATTACTG GGACGCGTGC TCTCGCGCGC
       GGCGCCTTTT TTTGCTAATA ATGGCTCATG GCGTAATGAC CCTGCGCACG AGAGCGCGCG 12730      12740      12750      12760      12770      12780
       TGCCCGACCA AACCCGTTAC AAGTATGTGG AACAGCTCGT GGACCTCACG TTGAACTACC
       ACGGGCTGGT TTGGGCAATG TTCATACACC TTGTCGAGCA CCTGGAGTGC AACTTGATGG 12790      12800      12810      12820      12830      12840
       ACTACGATGC GAGCCACGGC TTGGACAACT TTGACGTGCT CAAGAGGTGA GGGTACGCGC
       TGATGCTACG CTCGGTGCCG AACCTGTTGA AACTGCACGA GTTCTCCACT CCCATGCGCG 12850      12860      12870      12880      12890      12900
       TAAAGGTGCA TGACAACGGG AAGGTAAGGG CGAACGGGTA ACGGCTAAGT AACCGCATGG
       ATTTCCACGT ACTGTTGCCC TTCCATTCCC GCTTGCCCAT TGCCGATTCA TTGGCGTACC 12910      12920      12930      12940      12950      12960
       GGTATGAAAT GACGTTTGGA ACCTGTGCTT GCAGAATCAA CGTGACCGAG GTGTCGTTGC
       CCATACTTTA CTGCAAACCT TGGACACGAA CGTCTTAGTT GCACTGGCTC CACAGCAACG 12970      12980      12990      13000      13010      13020
       TCATCAGCGA CTTTAGACGT CAGAACCGTC GCGGCGGCAC CAACAAAAGG ACCACGTTCA
       AGTAGTCGCT GAAATCTGCA GTCTTGGCAG CGCCGCCGTG GTTGTTTTCC TGGTGCAAGT 13030      13040      13050      13060      13070      13080
       ACGCCGCCGG TTCGCTGGCG CCACACGCCC GGAGCCTCGA GTTCAGCGTG CGGCTCTTTG
       TGCGGCGGCC AAGCGACCGC GGTGTGCGGG CCTCGGAGCT CAAGTCGCAC GCCGAGAAAC 13090      13100      13110      13120      13130      13140
       CCAACTAGCC TGCGTCACGG GAAATAATAT GCTGCGGCTT CTGCTTCGTC ACCACTTTCA
       GGTTGATCGG ACGCAGTGCC CTTTATTATA CGACGCCGAA GACGAAGCAG TGGTGAAAGT 13150      13160      13170      13180      13190      13200
       CTGCCTGCTT CTGTGCGCGG TTTGGGCAAC GCCCTGTCTG GCGTCTCCGT GGTCGACGCT
       GACGGACGAA GACACGCGCC AAACCCGTTG CGGGACAGAC CGCAGAGGCA CCAGCTGCGA 13210      13220      13230      13240      13250      13260
       AACGGCAAAC CAGAATCCGT CCCCGCCATG GTCTAAACTG ACGTATTCCA AACCGCATGA
       TTGCCGTTTG GTCTTAGGCA GGGGCGGTAC CAGATTTGAC TGCATAAGGT TTGGCGTACT
```

Fig. 1M (SEQ ID NO: 1)

```
       13270      13280      13290      13300      13310      13320
   CGCGGCGACG TTTTTACTGTC CTTTTCTCTA TCCCTCGCCC CCACGGTCCC CCTTGCAATT
   GCGCCGCTGC AAAATGACAG GAAAAGAGAT AGGGAGCGGG GGTGCCAGGG GGAACGTTAA 13330      13340      13350      13360      13370      13380
   CTCGGGGTTC CAGCAGGTAT CAACGGGTCC CGAGTGTCGC AACGAGACCC TGTATCTGCT
   GAGCCCCAAG GTCGTCCATA GTTGCCCAGG GCTCACAGCG TTGCTCTGGG ACATAGACGA 13390      13400      13410      13420      13430      13440
   GTACAACCGG GAAGGCCAGA CCTTGGTGGA GAGAAGCTCC ACCTGGGTGA AAAAGGTGAT
   CATGTTGGCC CTTCCGGTCT GGAACCACCT CTCTTCGAGG TGGACCCACT TTTTCCACTA 13450      13460      13470      13480      13490      13500
   CTGGTATCTG AGCGGTCGCA ACCAGACCAT CCTCCAACGG ATGCCCCAAA CGGCTTCGAA
   GACCATAGAC TCGCCAGCGT TGGTCTGGTA GGAGGTTGCC TACGGGGTTT GCCGAAGCTT 13510      13520      13530      13540      13550      13560
   ACCGAGCGAC GGAAACGTGC AGATCAGCGT GGAAGACGCC AAGATTTTTG GAGCGCACAT
   TGGCTCGCTG CCTTTGCACG TCTAGTCGCA CCTTCTGCGG TTCTAAAAAC CTCGCGTGTA 13570      13580      13590      13600      13610      13620
   GGTGCCCAAG CAGACCAAGC TGCTACGCTT CGTCGTCAAC GATGGCACGC GTTATCAGAT
   CCACGGGTTC GTCTGGTTCG ACGATGCGAA GCAGCAGTTG CTACCGTGCG CAATAGTCTA 13630      13640      13650      13660      13670      13680
   GTGTGTGATG AAGCTGGAGA GCTGGGCCCA CGTCTTCCGG GACTACAGCG TGTCTTTTCA
   CACACACTAC TTCGACCTCT CGACCCGGGT GCAGAAGGCC CTGATGTCGC ACAGAAAAGT 13690      13700      13710      13720      13730      13740
   GGTGCGATTG ACGTTCACCG AGGCCAATAA CCAGACTTAC ACCTTCTGTA CCCATCCCAA
   CCACGCTAAC TGCAAGTGGC TCCGGTTATT GGTCTGAATG TGGAAGACAT GGGTAGGGTT 13750      13760      13770      13780      13790      13800
   TCTCATCATT TGAGCCCGTC GCGCGCGCAG GGAATTTTGA AAACCGCGCG TCATGAGTCC
   AGAGTAGTAA ACTCGGGCAG CGCGCGCGTC CCTTAAAACT TTTGGCGCGC AGTACTCAGG 13810      13820      13830      13840      13850      13860
   CAAAGACCTG ACGCCGTTCT TGACGACGTT GTGGCTGCTA TTGGGTCACA GCCGCGTGCC
   GTTTCTGGAC TGCGGCAAGA ACTGCTGCAA CACCGACGAT AACCCAGTGT CGGCGCACGG 13870      13880      13890      13900      13910      13920
   GCGGGTGCGC GCAGAAGAAT GTTGCGAATT CATAAACGTC AACCACCCGC CGGAACGCTG
   CGCCCACGCG CGTCTTCTTA CAACGCTTAA GTATTTGCAG TTGGTGGGCG GCCTTGCGAC 13930      13940      13950      13960      13970      13980
   TTACGATTTC AAAATGTGCA ATCGCTTCAC CGTCGCGTAC GTATTTTCAT GATTGTCTGC
   AATGCTAAAG TTTTACACGT TAGCGAAGTG GCAGCGCATG CATAAAAGTA CTAACAGACG 13990      14000      14010      14020      14030      14040
   GTTCTGTGGT GCGTCTGGAT TTGTCTCTCG ACGTTTCTGA TAGCCATGTT CCATCGACGA
   CAAGACACCA CGCAGACCTA AACAGAGAGC TGCAAAGACT ATCGGTACAA GGTAGCTGCT 14050      14060      14070      14080      14090      14100
   TCCTCGGGAA TGCCAGAGTA GATTTTCATG AATCCACAGG CTGCGGTGTC CGGACGGCGA
   AGGAGCCCTT ACGGTCTCAT CTAAAAGTAC TTAGGTGTCC GACGCCACAG GCCTGCCGCT 14110      14120      14130      14140      14150      14160
   AGTCTGCTAC AGTCCCGAGA AAACGGCTGA GATTCGCGGG ATCGTCACCA CCATGACCCA
   TCAGACGATG TCAGGGCTCT TTTGCCGACT CTAAGCGCCC TAGCAGTGGT GGTACTGGGT 14170      14180      14190      14200      14210      14220
   TTCATTGACA CGCCAGGTCG TACACAACAA ACTGACGAGC TGCAACTACA ATCCGTAAGT
   AAGTAACTGT GCGGTCCAGC ATGTGTTGTT TGACTGCTCG ACGTTGATGT TAGGCATTCA 14230      14240      14250      14260      14270      14280
   CTCTTCCTCG AGGGCCTTAC AGCCTATGGG AGAGTAAGAC AGAGAGGGAC AAAACATCAT
   GAGAAGGAGC TCCCGGAATG TCGGATACCC TCTCATTCTG TCTCTCCCTG TTTTGTAGTA
```

Fig. 1N (SEQ ID NO: 1)

```
            14290      14300      14310      14320      14330      14340
       TAAAAAAAAA AGTCTAATTT CACGTTTTGT ACCCCCCTTC CCCTCCGTGT TGTAGCCCAT
       ATTTTTTTTT TCAGATTAAA GTGCAAAACA TGGGGGGAAG GGGAGGCACA ACATCGGGTA
            14350      14360      14370      14380      14390      14400
       CGGCCGCGGC GATCTCCTAG TAACACTCGT CCGACACTTC CACCATCTCC AGCTCGGCCG
       GCCGGCGCCG CTAGAGGATC ATTGTGAGCA GGCTGTGAAG GTGGTAGAGG TCGAGCCGGC
            14410      14420      14430      14440      14450      14460
       GCGGTTCGGC ATCCTCTACC AGCGGCGTCG TCTCATCTTT GCCGCAGCAG CGGACGCACA
       CGCCAAGCCG TAGGAGATGG TCGCCGCAGC AGAGTAGAAA CGGCGTCGTC GCCTGCGTGT
            14470      14480      14490      14500      14510      14520
       CCTTCTCCAG GCAGAACGCC ACCAGCTGCC GCCGAACGTA CCACAGGTAC ACGTGCAGAC
       GGAAGAGGTC CGTCTTGCGG TGGTCGACGG CGGCTTGCAT GGTGTCCATG TGCACGTCTG
            14530      14540      14550      14560      14570      14580
       CTGCGAACAG GACTACGGAG GTCATGACCA CCACGACGCA CACGGGAATC CAGGGATCGA
       GACGCTTGTC CTGATGCCTC CAGTACTGGT GGTGCTGCGT GTGCCCTTAG GTCCCTAGCT
            14590      14600      14610      14620      14630      14640
       GATTGTTGCT GGAACTCATG GCTATCGCCA CCGACGTGCC CGCGTCTGTC TCACCGCCGC
       CTAACAACGA CCTTGAGTAC CGATAGCGGT GGCTGCACGG GCGCAGACAG AGTGGCGGCG
            14650      14660      14670      14680      14690      14700
       TCGCCCGATG TCGCGCGGCT TGTTATACGC TAGCCCGTCG CCGCCTCGGG GCACGGTGCC
       AGCGGGCTAC AGCGCGCCGA ACAATATGCG ATCGGGCAGC GGCGGAGCCC CGTGCCACGG
            14710      14720      14730      14740      14750      14760
       CTCCTACCCA CGTAACTTCC TCCGTGACTT AAAGTCGCGT GTGGTAGATC TCCTGCTCCG
       GAGGATGGGT GCATTGAAGG AGGCACTGAA TTTCAGCGCA CACCATCTAG AGGACGAGGC
            14770      14780      14790      14800      14810      14820
       TGGACGAACC GTCCGGCAGG ATAGCGGTTA AGGATTCGGT GCTAAGGCCG TGTCGCCAAC
       ACCTGCTTGG CAGGCCGTCC TATCGCCAAT TCCTAAGCCA CGATTCCGGC ACAGCGGTTG
            14830      14840      14850      14860      14870      14880
       GTCGAATGCT ACGTTGCAAC AGCTTCGACG GACGGCCATC CCCTCTCTCA TCGCAATAAT
       CAGCTTACGA TGCAACGTTG TCGAAGCTGC CTGCCGGTAG GGGAGAGAGT AGCGTTATTA
            14890      14900      14910      14920      14930      14940
       AAAACACCAG CAGCGCGCAC GACGCGATCA CGGTGACACC CATGATTAGA CCCACGCAGA
       TTTTGTGGTC GTCGCGCGTG CTGCGCTAGT GCCACTGTGG GTACTAATCT GGGTGCGTCT
            14950      14960      14970      14980      14990      15000
       TAGCCAGCCC CGCTAGCGTA TCTAGCGCCA TCCCGTTCGC TCCCGTTGTC TCCTGAGCGA
       ATCGGTCGGG GCGATCGCAT AGATCGCGGT AGGGCAAGCG AGGGCAACAG AGGACTCGCT
            15010      15020      15030      15040      15050      15060
       AGCAACTTCT CGGTCCCCGT TTTCAACAGT TTTTGTTTCC TTCTCCGCGA CTAGATGTTA
       TCGTTGAAGA GCCAGGGGCA AAAGTTGTCA AAAACAAAGG AAGAGGCGCT GATCTACAAT
            15070      15080      15090      15100      15110      15120
       ACGCCCGCGG TCTTTCCGGC CGTGCTCTAC CTCCTGGCGC TTGTCGTCTG GGTTGAGATG
       TGCGGGCGCC AGAAAGGCCG GCACGAGATG GAGGACCGCG AACAGCAGAC CCAACTCTAC
            15130      15140      15150      15160      15170      15180
       TTCTGCCTCG TCGCCGTAGC CGTCGTCGAG CGCGAGATCG CCTGGGCGCT GCTGCTGCGG
       AAGACGGAGC AGCGGCATCG GCAGCAGCTC GCGCTCTAGC GGACCCGCGA CGACGACGCC
            15190      15200      15210      15220      15230      15240
       ATGCTGGTCG TTGGCCTGAT GGTGGAAGTC GGCGCCGCCG CCGCTTGGAC CTTCGTGCGT
       TACGACCAGC AACCGGACTA CCACCTTCAG CCGCGGCGGC GGCGAACCTG GAAGCACGCA
            15250      15260      15270      15280      15290      15300
       TGTCTTGCCT ATCAGCGCTC CTTCCCCGTG CTTACGGCCT TCCCCTGAAA CCCACGTTAA
       ACAGAACGGA TAGTCGCGAG GAAGGGGCAC GAATGCCGGA AGGGGACTTT GGGTGCAATT
```

Fig. 1O (SEQ ID NO: 1)

```
           15310      15320      15330      15340      15350      15360
      CCGACCGTCC CAAAAACGCC GGTGTTAACA CAGGAAAAAA AGAAACCACG CAGGAACCGC
      GGCTGGCAGG GTTTTTGCGG CCACAATTGT GTCCTTTTTT TCTTTGGTGC GTCCTTGGCG
           15370      15380      15390      15400      15410      15420
      GCAGGAACCA CGCGGAACAT GGGACACTAT CTGGAAATCC TGTTCAACGT CATCGTCTTC
      CGTCCTTGGT GCGCCTTGTA CCCTGTGATA GACCTTTAGG ACAAGTTGCA GTAGCAGAAG
           15430      15440      15450      15460      15470      15480
      ACTCTGCTGC TCGGCGTCAT GGTCAGTATC GTCGCTTGGT ACTTCACGTG AACCACCGTC
      TGAGACGACG AGCCGCAGTA CCAGTCATAG CAGCGAACCA TGAAGTGCAC TTGGTGGCAG
           15490      15500      15510      15520      15530      15540
      GTCCCGGTTT AAAAACCATC ATCGACGGCC GTTATAAAGC CACCCGGACA CGCGCCGCGG
      CAGGGCCAAA TTTTTGGTAG TAGCTGCCGG CAATATTTCG GTGGGCCTGT GCGCGGCGCC
           15550      15560      15570      15580      15590      15600
      CACTTGCCTA CGGCGCTGCT TCAGGGAAAC TCCTCTTCCT TCTGCTCTTC CTCCTTCACC
      GTGAACGGAT GCCGCGACGA AGTCCCTTTG AGGAGAAGGA AGACGAGAAG GAGGAAGTGG
           15610      15620      15630      15640      15650      15660
      GCAGGGATCG TTTCCCTCGA CCAGGGACTC GCCGAAGCAA CCGCCGGAGC AACCTGGAGG
      CGTCCCTAGC AAAGGGAGCT GGTCCCTGAG CGGCTTCGTT GGCGGCCTCG TTGGACCTCC
           15670      15680      15690      15700      15710      15720
      AGTCGCGGCA TGACGGCGCC CAAGTGTGTC ACCACCAGTA CTTATCTGGT CAAGACCAAG
      TCAGCGCCGT ACTGCCGCGG GTTCACACAG TGGTGGTCAT GAATAGACCA GTTCTGGTTC
           15730      15740      15750      15760      15770      15780
      GAACAGCCCT GGTGGCCCGA CAACGCCATC AGGAGATGGT GGATCAGTGT TGCTATCGTC
      CTTGTCGGGA CCACCGGGCT GTTGCGGTAG TCCTCTACCA CCTAGTCACA ACGATAGCAG
           15790      15800      15810      15820      15830      15840
      ATCTTCATCG GAGTCTGTCT GGTGGCCCTG ATGTACTTTA CGCAGCAGCA GGCACGCAGC
      TAGAAGTAGC CTCAGACAGA CCACCGGGAC TACATGAAAT GCGTCGTCGT CCGTGCGTCG
           15850      15860      15870      15880      15890      15900
      GGGAGCAGCA GCGGCTAGAC AAGTCTCTGG CGGCTACAGC TCCAAGCGCC GTAGCCGGGC
      CCCTCGTCGT CGCCGATCTG TTCAGAGACC GCCGATGTCG AGGTTCGCGG CATCGGCCCG
           15910      15920      15930      15940      15950      15960
      CGCCTGCCGA TCGCGACGTC GTGGACCATC GAACAGAGAC TCACGCGTAC GAGACCCCGA
      GCGGACGGCT AGCGCTGCAG CACCTGGTAG CTTGTCTCTG AGTGCGCATG CTCTGGGGCT
           15970      15980      15990      16000      16010      16020
      GGTACGCCAC GCGGTGCCTA ACGCGGTATA CCACACCCGT ACGGTCTGCA GTGCGGCGTA
      CCATGCGGTG CGCCACGGAT TGCGCCATAT GGTGTGGGCA TGCCAGACGT CACGCCGCAT
           16030      16040      16050      16060      16070      16080
      CAACGTGTGG AAAACGCGTT GCGTCGCAGA GTCCGCCACG TTCCTGTCTT GTCGCTCCCC
      GTTGCACACC TTTTGCGCAA CGCAGCGTCT CAGGCGGTGC AAGGACAGAA CAGCGAGGGG
           16090      16100      16110      16120      16130      16140
      AATCGTCTCC CGCACACCCC CCGCGACACC CAGAGGGCGG GTGAGCCAAG TATTCTTAAG
      TTAGCAGAGG GCGTGTGGGG GGCGCTGTGG GTCTCCCGCC CACTCGGTTC ATAAGAATTC
           16150      16160      16170      16180      16190      16200
      GCCGTTCTTT GTTCCATAGC CCATAAATTG TTGATTCCGG AGCTCGTTGG CGCGGAAATA
      CGGCAAGAAA CAAGGTATCG GGTATTTAAC AACTAAGGCC TCGAGCAACC GCGCCTTTAT
           16210      16220      16230      16240      16250      16260
      GCCGGATAAG GGGAGCAACA ACCGTTGGCG AAAGCCGTCC CGCTCATTCA GTCCGGGTTT
      CGGCCTATTC CCCTCGTTGT TGGCAACCGC TTTCGGCAGG GCGAGTAAGT CAGGCCCAAA
           16270      16280      16290      16300      16310      16320
      CGCGTCCAGT CGGACGTGTG ACCGTTGGGC AACGGAACGG CGTTTCACTG CCAAAATCGT
      GCGCAGGTCA GCCTGCACAC TGGCAACCCG TTGCCTTGCC GCAAAGTGAC GGTTTTAGCA
```

Fig. 1P (SEQ ID NO: 1)

```
       16330      16340      16350      16360      16370      16380
  ATCGGGTAGT GTACGAGACG TCGGCGGTGC AGAATGCGAC TCGCGGCGTA GCTCGCCGTC
  TAGCCCATCA CATGCTCTGC AGCCGCCACG TCTTACGCTG AGCGCCGCAT CGAGCGGCAG
       16390      16400      16410      16420      16430      16440
  GCTATGCGGC TCGTCGCCGT GTGGCGCGGC CTGGCCGGCT GTCTGCGTCC AGATCTGTTG
  CGATACGCCG AGCAGCGGCA CACCGCGCCG GACCGGCCGA CAGACGCAGG TCTAGACAAC
       16450      16460      16470      16480      16490      16500
  GCCTTTTGGT TCCTCTGGCT GCTGCTGCGT GTGTGCTTTG GTAGACGCGG TGGCAGTTTG
  CGGAAAACCA AGGAGACCGA CGACGACGCA CACACGAAAC CATCTGCGCC ACCGTCAAAC
       16510      16520      16530      16540      16550      16560
  CGGTCTGCGG TAAGTGAGGA TGTCGCCGAG CAAACGCACT TGCGGCGCGT GGGCGGCACG
  GCCAGACGCC ATTCACTCCT ACAGCGGCTC GTTTGCGTGA ACGCCGCGCA CCCGCCGTGC
       16570      16580      16590      16600      16610      16620
  CGTGTCATTG TAGGTTCGTT GCCAGATGGC AAGTGCTGTC AACAGCAGGC GTTGTGGGCG
  GCACAGTAAC ATCCAAGCAA CGGTCTACCG TTCACGACAG TTGTCGTCCG CAACACCCGC
       16630      16640      16650      16660      16670      16680
  GTCGGTGTAT TTTTGTGGGT TGCGGTGAGA GTCGGCACTC GGTGTTTTGT GAGTCATCTC
  CAGCCACATA AAAACACCCA ACGCCACTCT CAGCCGTGAG CCACAAAACA CTCAGTAGAG
       16690      16700      16710      16720      16730      16740
  AACTATCTGT GTTGCTTTGA GCAGCGTCCA GAACAGCGAC GCGACTTTGG GGATGGCCTC
  TTGATAGACA CAACGAAACT CGTCGCAGGT CTTGTCGCTG CGCTGAAACC CCTACCGGAG
       16750      16760      16770      16780      16790      16800
  GTGCTCACCT CCGCGGAGAG CGCCGCCGGA CCTGCTCGTC AGCAGCGAGC TACGCAGACG
  CACGAGTGGA GGCGCCTCTC GCGGCGGCCT GGACGAGCAG TCGTCGCTCG ATGCGTCTGC
       16810      16820      16830      16840      16850      16860
  GAATATCTGG AGGAGAGTTA CGTGTGTCAC AGGAGAGCGC GGGTCTCCGG CGGTAACGAC
  CTTATAGACC TCCTCTCAAT GCACACAGTG TCCTCTCGCG CCCAGAGGCC GCCATTGCTG
       16870      16880      16890      16900      16910      16920
  GGCGGTGTCG TCGACACGTG TGCGGCCTGT TGTGCTCTGC GGAAAAGTGC CGGTCTCGGA
  CCGCCACAGC AGCTGTGCAC ACGCCGGACA ACACGAGACG CCTTTTCACG GCCAGAGCCT
       16930      16940      16950      16960      16970      16980
  GACCGTGGAC GAAAAAGAGA ACGCAGCAGC TACCGCTGGC GGCGGCGGCG TTAATGCAGC
  CTGGCACCTG CTTTTTCTCT TGCGTCGTCG ATGGCGACCG CCGCCGCCGC AATTACGTCG
       16990      17000      17010      17020      17030      17040
  CGTTGATGTT CGACGTTGTG AGCACTCGGA AACAGCGGTG AGGCAGAAGG TCGATTCTCC
  GCAACTACAA GCTGCAACAC TCGTGAGCCT TTGTCGCCAC TCCGTCTTCC AGCTAAGAGG
       17050      17060      17070      17080      17090      17100
  AGGGAACGAC AGTCGATGCG TGGTAGCCGC AGCAGGTGAG GTTGGGGCGG ACAACGTGTT
  TCCCTTGCTG TCAGCTACGC ACCATCGGCG TCGTCCACTC CAACCCCGCC TGTTGCACAA
       17110      17120      17130      17140      17150      17160
  GCGGATTGTG GCGAGAACGT CGTCCTCCCC TTCTTCACCG CCCCACCCAC CCTCGGTTGG
  CGCCTAACAC CGCTCTTGCA GCAGGAGGGG AAGAAGTGGC GGGGTGGGTG GGAGCCAACC
       17170      17180      17190      17200      17210      17220
  TGTTTCTTTT TTCTTGTGTC CTGCAGATAG TTCCACGGAC AGCGACGGCA AGTCCATAAT
  ACAAAGAAAA AAGAACACAG GACGTCTATC AAGGTGCCTG TCGCTGCCGT TCAGGTATTA
       17230      17240      17250      17260      17270      17280
  CAGCGGTGTG CAAGTGGTGG AACACGACGA AGATATCATC GCGCCGCAGA GTTTGTGGTG
  GTCGCCACAC GTTCACCACC TTGTGCTGCT TCTATAGTAG CGCGGCGTCT CAAACACCAC
       17290      17300      17310      17320      17330      17340
  CACGGCGTTC AAGGAAGCCC TCTGGGATGT GGCTCTGTTG GAAGTGCCGC GTTGGGCGTG
  GTGCCGCAAG TTCCTTCGGG AGACCCTACA CCGAGACAAC CTTCACGGCG CAACCCGCAC
```

Fig. 1Q (SEQ ID NO: 1)

```
          17350      17360      17370      17380      17390      17400
     GCAGGGCTGG AAGAGGTGGC GCAACAGCGA GGCCGGGCGT CGATGGAGTG CTGGGTCTGC
     CGTCCCGACC TTCTCCACCG CGTTGTCGCT CCGGCCCGCA GCTACCTCAC GACCCAGACG 17410      17420      17430      17440      17450      17460
     GTCGGCTTCC AGCTTGTCTG ACTTGGCGGG CGAGGCCGTT GGAGAATTGG TGGGATCGGT
     CAGCCGAAGG TCGAACAGAC TGAACCGCCC GCTCCGGCAA CCTCTTAACC ACCCTAGCCA 17470      17480      17490      17500      17510      17520
     CGTCGCGTAC GTGATCCTTG AACGTCTGTG GTTGGCAGCC AGAGGTTGGG TGTGCGAAAC
     GCAGCGCATG CACTAGGAAC TTGCAGACAC CAACCGTCGG TCTCCAACCC ACACGCTTTG 17530      17540      17550      17560      17570      17580
     AGGTGTGGAA GCCGAGGAGG CCATGTCGCG GCGGCGACAG CGCATGCTGT GGCGTATTGT
     TCCACACCTT CGGCTCCTCC GGTACAGCGC CGCCGCTGTC GCGTACGACA CCGCATAACA 17590      17600      17610      17620      17630      17640
     TCTCTCGTGG AGGCGACGGC GAATGCAGCA GACGGTGTTC GATGGAGATG GCGTGCGGGG
     AGAGAGCACC TCCGCTGCCG CTTACGTCGT CTGCCACAAG CTACCTCTAC CGCACGCCCC 17650      17660      17670      17680      17690      17700
     AAGAAAGCGC CGTGTTGTGA GCAGACGACG TAGGATGCGG GACGTCGGAG CACATGGGCC
     TTCTTTCGCG GCACAACACT CGTCTGCTGC ATCCTACGCC CTGCAGCCTC GTGTACCCGG 17710      17720      17730      17740      17750      17760
     ATGTGTGGTG GCAGATGGCG GTGTCCGCTG GTGTCTGCTG CGGCAGTGCA TAGACGAAGC
     TACACACCAC CGTCTACCGC CACAGGCGAC CACAGACGAC GCCGTCACGT ATCTGCTTCG 17770      17780      17790      17800      17810      17820
     AACATGTCGC TGTGAAGAGA TAGAGTGTGA GCATAGCTGC ATGCAGCGTT GCGTGTATAA
     TTGTACAGCG ACACTTCTCT ATCTCACACT CGTATCGACG TACGTCGCAA CGCACATATT 17830      17840      17850      17860      17870      17880
     GCGGGGGGGA TTAAGACGTT AATAAAGAAT AGCGGCGGTT CTGATAGGGC GACCGCTGAA
     CGCCCCCCCT AATTCTGCAA TTATTTCTTA TCGCCGCCAA GACTATCCCG CTGGCGACTT 17890      17900      17910      17920      17930      17940
     GTGAGCTGCG TGTGCGTGTG GTTTGTGGAG TCCCCGCCGC CCCCGGTCCC GTGTCCGCCG
     CACTCGACGC ACACGCACAC CAAACACCTC AGGGGCGGCG GGGGCCAGGG CACAGGCGGC 17950      17960      17970      17980      17990      18000
     GCAAAGCCCC CCGGNTCCGC ACACTCCTGG CCGCGCAACC CTCGTCGCTG CAAAAGCCCC
     CGTTTCGGGG GGCCNAGGCG TGTGAGGACC GGCGCGTTGG GAGCAGCGAC GTTTTCGGGG 18010      18020      18030      18040      18050      18060
     CCGTCCCCGC ACACCCCCGC GACCGCCGGT CCCGCGAGTC CCCGTCCCCG CCGCAAAAGG
     GGCAGGGGCG TGTGGGGGCG CTGGCGGCCA GGGCGCTCAG GGGCAGGGC GGCGTTTTCC 18070      18080      18090      18100      18110      18120
     CCCCCGTCCT CGCCGCAAAC ACCCCCGTCA CCCCCGTCCC TCAGNCCGGG TCCGCGAGTC
     GGGGGCAGGA GCGGCGTTTG TGGGGCAGT GGGGGCAGGG AGTCNGGCCC AGGCGCTCAG 18130      18140      18150      18160      18170      18180
     CCCGTTCCCA GCGTAATCCC CGTACCCGCA ACGNCCCGGN CCCACCGTCG TCCCGCACAC
     GGGCAAGGGT CGCATTAGGG GCATGGGCGT TGCNGGGCCN GGGTGGCAGC AGGGCGTGTG 18190      18200      18210      18220      18230      18240
     CCCCCGTCCC CCAGCCCGGT GCCCAGCGTG CGAAAAAAGC TCCGTCCCTC ACACCCGCAG
     GGGGGCAGGG GGTCGGGCCA CGGGTCGCAC GCTTTTTTCG AGGCAGGGAG TGTGGGCGTC 18250      18260      18270      18280      18290      18300
     AAAGATCCCT CAGCGCGGTG AAACCCCGTC CCCAGCGCCG TGCCGCTGAC AAAGACCATG
     TTTCTAGGGA GTCGCGCCAC TTTGGGGCAG GGGTCGCGGC ACGGCGACTG TTTCTGGTAC 18310      18320      18330      18340      18350      18360
     GGACGACACG CACAGGCA.. .......... .......... .......... ..........
     CCTGCTGTGC GTGTCCGT.. .......... .......... .......... ..........
```

Fig. 1R (SEQ ID NO: 1)

Toledo UL130 (SEQ ID NO. 2)

```
         10         20         30         40         50         60
MLRLLLRHHF HCLLLCAVWA TPCLASPWST LTANQNPSPP WSKLTYSKPH DAATFYCPFL 70         80         90        100        110        120
YPSPPRSPLQ FSGFQQVSTG PECRNETLYL LYNREGQTLV ERSSTWVKKV IWYLSGRNQT 130        140        150        160        170        180
ILQRMPQTAS KPSDGNVQIS VEDAKIFGAH MVPKQTKLLR FVVNDGTRYQ MCVMKLESWA 190        200        210        220        230        240
HVFRDYSVSF QVRLTFTEAN NQTYTFCTHP NLII*..... .......... ..........
```

Toledo UL132 (SEQ ID NO. 3)

```
         10         20         30         40         50         60
MPALRGPLRA TFLALVAFGL LLQIDLSDAT NVTSSTKVPT STSNRNNVDN ATSSGPTTGI 70         80         90        100        110        120
NMTTTHESSV HNVRNNEIMK VLAILFYIVT GTSIFSFIAV LIAVVYSSCC KHPGRFRFAD 130        140        150        160        170        180
EEAVNLLDDT DDSGGSSPFG SGSRRGSQIP AGFCSSSPYQ RLETRDWDEE EEASAARERM 190        200        210        220        230        240
KHDPENVIYF RKDGNLDTSF VNPNYGRGSP LTIESHLSDN EEDPIRYYVS VYDELTASEM 250        260        270        280        290        300
EEPSNSTSWQ IPKLMKVAMQ PVSLRDPEYD *......... .......... ..........
```

Toledo UL133 (SEQ ID NO. 4)

```
         10         20         30         40         50         60
MGCDVHDPSW QCQWGVPTII VAWITCAALG IWCLAGSSAD VSSGPGIAAV VGCSVFMIFL 70         80         90        100        110        120
CAYLIRYREF FKDSVIDLLT CRWVRYCSCS CKCSCKCISG PCSRCCSACY KETMIYDMVQ 130        140        150        160        170        180
YGHRRRPGHG DDPDRVICEI VESPPVSAPT VSVPPPSEES HQPVIPPQPP APTSEPKPKK 190        200        210        220        230        240
GRAKDKPKGR PKDKPPCEPT VSSQPPSQPT AMPGGPPDAP PPAMPQMPPG VAEAVQAAVQ 250        260        270        280        290        300
AAVAAALQQQ QQHQTGT*.. .......... .......... .......... ..........
```

Fig 2A

Toledo UL134 (SEQ ID NO. 5)

```
          10         20         30         40         50         60
  MARTREASPV PPRSPMPSHI HTMIFSPAWN LKLRVGKGRC TDIYALDFWK RHFLARNVFI 70         80         90        100        110        120
  VQTLRKEMCA KSENSLSHRG RVTFRSDAAA VVVEPRPRPP ARQLVPPRPR RVASAAWRGE 130        140        150        160        170        180
  ARRADRRALP SAATVVVNSP SVRTEVCLSV YPSVYLSPYL SSVWVPMSVL AAAVG*.....
```

Toledo UL135 (SEQ ID NO. 6)

```
          10         20         30         40         50         60
  MSVHRPFPTR SLRFQAGEKI MVWIWLGIGL LGGTGLASLV LAISLFTQRR GRKRSDETSS 70         80         90        100        110        120
  RGRLPGAASD KRGACACCYR NPKEDVVEPL DLELGLMRVD THPPTPQVPR CTSLYIGEDG 130        140        150        160        170        180
  LPIDKPEFPP ARFEIPDVST PGTPTSIGRS PSHCSSSSSL SSSTSVDTVL YQPPPSWKPP 190        200        210        220        230        240
  PPPGRKKRPP TPPVRAPTTR LSSHRPPTPI PAPRKNLSTP PTKKTPPPTK PKPVGWTPPV 250        260        270        280        290        300
  TPRPFPKTPT PQKPPRNPRL PRTVGLENLS KVGLSCPCPR PRTPTEPTTL PIVSVSELAP 310        320        330        340        350        360
  PPRWSDIEEL LEQAVQSVMK DAESMQMT*.. .......... .......... ..........
```

Toledo UL136 (SEQ ID NO. 7)

```
          10         20         30         40         50         60
  MSVKGVEMPE MTWDLDVRNK WRRRKALSRI HRFWECRLRV WWLSDAGVRE TDPPRPRRRP 70         80         90        100        110        120
  TWMTAVFHVI CAVLLTLMIM AIGALIAYLR YYHQDSWRDM LHDLFCGCHY PEKCRRHHER 130        140        150        160        170        180
  QRRRRQAMDV PDPELGDPAR RPLNGAMYYG SGCRFDTVEM VDETRPAPPA LSSPETGDDS 190        200        210        220        230        240
  NDDAVAGGGA GGVTSPATRT TSPNALLPEW MDAVHVAVQA AVQATVQVSG PRENAVSPAT 250        260        270        280        290        300
  *......... .......... .......... .......... .......... ..........
```

Fig 2B

Toledo UL137 (SEQ ID NO. 8)

```
         10         20         30         40         50         60
MATISTSITP MMGNPTFSGR SSMVTVLCPD LRPSLSLLYS TRAGTAPSTL LRSGRYGVLP 70         80         90        100        110        120
RATYLHGRLN GGLDRHMHRI HPFWQQCVRR RRTSRG*... .......... ..........
```

Toledo UL138 (SEQ ID NO. 9)

```
         10         20         30         40         50         60
MDDLPLNVGL PIIGVMLVLI VAILCYLAYH WHDTFKLVRM FLSYRWLIRC CELYGEYERR 70         80         90        100        110        120
FADLSSLGLG AVRRESDRRY RFSERPDEIL VRWEEVSSQC SYASSRITDR RVGSSSSSSV 130        140        150        160        170        180
HVASQRNSVP PPDMAVTAPL TDVDLLKPVT GSATQFTTVA MVHYHQEYT* ..........
```

Toledo UL139 (SEQ ID NO. 10)

```
         10         20         30         40         50         60
MLWILVLFAL AASASETTTG TSSNSSQSTS ATANTTVSTC INASNGSSWT VPQLALLAAS 70         80         90        100        110        120
GWTLSGLLLL FTCCFCCFWL VRKICSCCGN SSESESKTTH AYTNAAFTSS DATLPMGTTG 130        140        150        160        170        180
SYTPPQDGSF PPPPR*.... .......... .......... .......... ..........
```

Toledo UL140 (SEQ ID NO. 11)

```
         10         20         30         40         50         60
MTPAQTNATT TVHPHDAKNG SGGSALPTLV VFGFIVTLLF FLFMLYFWNN DVFRKLLRAL 70         80         90        100        110        120
GSSAVATAST RGKTRSSTVV HHVVPRATTR VVLTACHRTF FYHPRPMAVL TTRH*.....
```

Fig 2C

Toledo UL141 (SEQ ID NO. 12)

```
         10         20         30         40         50         60
MRQVAYRRRR ESSCAVLVHH VGRDGDGEGE AAKKTCKKTG RSVAGIPGEK LRRTVVTTTP 70         80         90        100        110        120
ARRLSGRHTE QEQAGMRLCE KGKKRIIMCR RESLRTLPWL FWVLLSCPRL LEYSSSSFPF 130        140        150        160        170        180
ATADIAEKMW AENYETTSPA PVLVAEGEQV TIPCTVMTHS WPMVSIRARF CRSHDGSDEL 190        200        210        220        230        240
ILDAVKGHRL MNGLQYRLPY ATWNFSQLHL GQIFSLTFNV SMDTAGMYEC VLRNYSHGLI 250        260        270        280        290        300
MQRFVILTQL ETLSRPDEPC CTPALGRYSL GDQIWSPTPW RLRNHDCGTY RGFQRNYFYI 310        320        330        340        350        360
GRADAEDCWK PACPDEEPDR CWTVIQRYRL PGDCYRSQPH PPKFLPVTPA PPADIDTGMS 370        380        390        400        410        420
PWATRGIAAF LGFWSIFTVC FLCYLCYLQC CGRWCPTPGR GRRGGEGYRR LPTYDSYPGV 430        440        450        460        470        480
RKMKR*.... .......... .......... .......... .......... ..........
```

Toledo UL142 (SEQ ID NO. 13)

```
         10         20         30         40         50         60
MRIEWVWWLF GYFVSSVGSE RSLSYRYHLE SNSSTNVVCN GNISVFVNGT LGVRYNITVG 70         80         90        100        110        120
ISSSLLIGHL TIQVLESWFT PWVQNKSYNK QPLGDTETLY NIDSENIHRV SQYFHTRWIK 130        140        150        160        170        180
SLQENHTCDL TNSTPTYTYQ VNVNNTNYLT LTSSGWQDRL NYTVINSTHF NLTESNITSI 190        200        210        220        230        240
QKYLNTTCIE RLRNYTLESV YTTTVPQNIT TSQHATTTMH TIPPNTITIQ NTTQSHTVQT 250        260        270        280        290        300
PSFNDTHNVT KHTLNISYVL SQKTNNTTSP WIYAIPMGAT ATIGAGLYIG KHFTPVKFVY 310        320        330        340        350        360
EVWRGQ*... .......... .......... .......... .......... ..........
```

Fig 2D

Toledo UL143 (SEQ ID NO. 14)

```
         10         20         30         40         50         60
MARSVKTIRI QHIYSPRSSN TLQHMSKKQE SIATITFGRI TCCHPLASIN LMFNGSCTVT 70         80         90        100        110        120
VKISMGINGS TNVHQLVIVL HLGNRCQPWR QV*....... .......... ..........
```

Toledo UL144 (SEQ ID NO. 15)

```
         10         20         30         40         50         60
MKPLIMLICF AVILLQLGVT KVCQHNEVQL GNECCPPCGS GQRVTKVCTD YTSVTCTPCP 70         80         90        100        110        120
NGTYVSGLYN CTDCTQCNVT QVMIRNCTST NNTVCAPKNH TYFSTPGVQH HKQRQQNHTA 130        140        150        160        170        180
HITVKQGKSG RHTLAWLSLF IFLVGIILLI LYLIAAYRSE RCQQCCSIGK IFYRTL*...
```

Toledo UL145 (SEQ ID NO. 16)

```
         10         20         30         40         50         60
MCTDPRRTAG WERLTHHASY HANYGAYAVL MATSQRKSLV LHRYSAVTAV ALQLMPVEIV 70         80         90        100        110        120
RKLDQSDWVR GAWIVSETFP TSDPKGVWSD DDSSMGGSDD *......... ..........
```

Toledo UL146 (SEQ ID NO. 17)

```
         10         20         30         40         50         60
MRLIFGALII FLAYVYHYEV NGTELRCRCL HRKWPPNKII LGNYWLHRDP RGPGCDKNEH 70         80         90        100        110        120
LLYPDGRKPP GPGVCLSPDH LFSKWLDKHN DNRWYNVNIT KSPGPRRINI TLIGVRG*..
```

Fig 2E

Toledo UL147 (SEQ ID NO. 18)

```
           10         20         30         40         50         60
   MVLTWLHHPV SNSHINLLSV RHLSLIAYML LTICPLAVHV LELEDYDRRC RCNNQILLNT 70         80         90        100        110        120
   LPVGTELLKP IAASESCNRQ EVLAILKDKG TKCLNPNAQA VRRHINRLFF RLILDEEQRI 130        140        150        160        170        180
   YDVVSTNIEF GAWPVPTAYK AFLWKYAKRL NYHHFRLRW* .......... ..........
```

Toledo UL148 (SEQ ID NO. 19)

```
           10         20         30         40         50         60
   MLRLLFTLVL LALHGQSVGA SRDYVHVRLL SYRGDPLVFK HTFSGVRRPF TELGWAACRD 70         80         90        100        110        120
   WDSMHCTPFW STDLEQMTDS VRRYSTVSPG KEVTLQLHGN QTVQPSFLSF TCRLQLEPVV 130        140        150        160        170        180
   ENVGLYVAYV VNDGERPQQF FTPQVDVVRF ALYLETLSRI VEPLESGRLA VEFDTPDLAL 190        200        210        220        230        240
   APDLVSSLFV AGHGETDFYM NWTLRRSQTH YLEEMALQVE ILKPRGVRHR AIIHHPKLQP 250        260        270        280        290        300
   GVGLWIDFCV YRYNARLTRG YVRYTLSPKA RLPAKAEGWL VSLDRFIVQY LNTLLITMMA 310        320        330        340        350        360
   AIWARVLITY LVSRRR*... .......... .......... .......... ..........
```

Toledo UL149 (SEQ ID NO. 20)

```
           10         20         30         40         50         60
   MVDQCCYRHL HRSLSGGPDV LYAAAGTQRE QQRLDKSLAA TAPSAVAGPP ADRDVVDHRT 70         80         90        100        110        120
   ETHAYETPRY ATRCLTRYTT PVRSAVRRTT CGKRVASQSP PRSCLVAPQS SPAHPPRHPE 130        140        150        160        170        180
   GG*....... .......... .......... .......... .......... ..........
```

Fig 2F

Toledo UL150 (SEQ ID NO. 21)

```
            10         20         30         40         50         60
    MQLCSHSISS QRHVASSMHC RSRHQRTPPS ATTHGPCAPT SRILRRLLTT RRFLPRTPSP 70         80         90        100        110        120
    SNTVCCIRRR LHERTIRHSM RCRRRDMASS ASTPVSHTQP LAANHRRSRI TYATTDPTNS 130        140        150        160        170        180
    PTASPAKSDK LEADADPALH RRPASLLRHL FQPCHAQRGT SNRATSQRAS LNAVHHKLCG 190        200        210        220        230        240
    AMISSSCSTT CTPLIMDLPS LSVELSAGHK KKETPTEGGW GGEEGEDDVL ATIRNTLSAP 250        260        270        280        290        300
    TSPAAATTHR LSFPGESTFC LTAVSECSQR RTSTAALTPP PPAVAAAFSF SSTVSETGTF 310        320        330        340        350        360
    PQSTTGRTRV DDTAVVTAGD PRSPVTHVTL LQIFRLRSSL LTSRSGGALR GGEHEAIPKV 370        380        390        400        410        420
    ASLFWTLLKA TQIVEMTHKT PSADSHRNPQ KYTDRPQRLL LTALAIWQRT YNDTRAAHAP 430        440        450        460        470        480
    QVRLLGDILT YRRPQTATAS TKAHTQQQPE EPKGQQIWTQ TAGQAAPHGD EPHSDGELRR 490        500        510        520        530        540
    ESHSAPPTSR TLPDTILAVK RRSVAQRSHV RLDAKPGLNE RDGFRQRLLL PLSGYFRANE 550        560        570        580        590        600
    LRNQQFMGYG TKNGLKNTWL TRPLGVAGGV RETIGERQDR NVADSATQRV FHTLYAALQT 610        620        630        640        650        660
    VRVWYTALGT AWRTSGSRTR ESLFDGPRRR DRQAARLRRL EL*....... ..........
```

Fig 2G

Toledo UL151 (SEQ ID NO. 22)

```
         10         20         30         40         50         60
MVFVSGTALG TGFHRAEGSF CGCEGRSFFR TLGTGLGDGG CAGRRWXRXV AGTGITLGTG 70         80         90        100        110        120
TRGPGLRDGG DGGVCGEDGG LLRRGRGLAG PAVAGVCGDG GLLQRRGLRG QECAXPGGFA 130        140        150        160        170        180
GGHGTGGGGD STNHTHTQLT SAVALSEPPL FFINVLIPPA YTRNAACSYA HTLSLHSDML 190        200        210        220        230        240
LRLCTAAADT SGHRHLPPHM AHVLRRPASY VVCSQHGAFF PARHLHRTPS AAFAVASTRE 250        260        270        280        290        300
QYATACAVAA ATWPPRLPHL FRTPNLWLPT TDVQGSRTRR PIPPILQRPR PPSQTSWKPT 310        320        330        340        350        360
QTQHSIDARP RCCATSSSPA TPNAALPTEP HPRGLP*... .......... ..........
```

Fig 2H

Clinical Strains of CMV
Contain Sequences
Homologous
to the Toledo $U_L/b'$ Region

Fig. 7

Previous Towne Vaccine Strains Hybridize to the Toledo U$_L$/*b'* Region

Fig. 8

Cotransfection of Cosmids Regenerates Infectious CMV

Towne•AV

Toledo

Fig. 9

The Chimeras Replicate in the SCID-hu(thy/liv) Implant

Comparison of the Towne (long) and Towne (short) Genotypes

ATTENUATION OF CYTOMEGALOVIRUS VIRULENCE

REFERENCE TO RELATED APPLICATIONS

This application is a division of U.S. application Ser. No. 09/724,935, filed on Nov. 28, 2000, now U.S. Pat. No. 7,204,990, which is hereby incorporated by reference herein in its entirety for all purposes.

TECHNICAL FIELD

The present invention is related generally to methods and compositions for treating or preventing cytomegalovirus (CMV) infections, such as congenital CMV disease, CMV retinitis, CMV mononucleosis, and the like, and methods of attenuating pathogenic cytomegalovirus isolates and strains, genetically engineered cytomegaloviruses and combinations thereof, methods for altering the phenotype of CMV viruses, attenuated viral vaccine compositions, and uses thereof. More particularly, the present invention is related to methods and compositions for prophylaxis and therapy of human cytomegalovirus infection, including the use of methods that functionally inactivate a subset of cytomegalovirus genes present in pathogenic isolates of human cytomegalovirus.

BACKGROUND

Cytomegalovirus (CMV) is a widespread herpesvirus in the human population, with between 0.2 and 2.2% of the infant population becoming infected in utero and another 8-60% becoming infected during the first six months of life (Reynolds et al. (1973) *New Engl. J. Med.* 289:1). Although CMV infections are most commonly subclinical, CMV-induced sensorineural hearing loss and fatal cytomegalovirus infections ("cytomegalic inclusion disease") are important public health problems. Moreover, CMV is one of the more common opportunistic infections associated with Acquired Immune Deficiency Syndrome ("AIDS") and frequently produces disease, with recurrent infection occurring in HIV-positive individuals, typically taking the form of retinitis or ulcerative lesions in the colon and esophagus, and occasionally producing extensive necrotization of the bowel with a grave prognosis (Rene et al. (1988) *Div. Dis. Sci.* 33:741; Meiselman et al. (1985) *Gastroenterology:*88:171). Cytomegalovirus (CMV) infection is the major infectious cause of mental retardation and congenital deafness. CMV is also responsible for a great deal of disease among the immunosuppressed, producing general and often severe systemic effects in patients with AIDS, in organ transplant recipients who have been iatrogenically immunosuppressed, and in bone marrow transplant patients.

It is clear that cytomegalovirus infections are a significant human health problem. Therefore, it is desirable to develop prophylactic and therapeutic methods and compositions to prevent cytomegalovirus infection and/or inhibit recurrent infectious outbreaks from persistent latent infections, particularly for treating CMV retinitis, CMV mononucleosis, and related CMV pathology in human patients.

One approach that has been used to treat herpesvirus infections is to inhibit CMV viral DNA replication. For example, viral DNA replication can frequently be inhibited by agents that inhibit virally-encoded DNA polymerase. The most notable examples of such inhibitors of viral DNA polymerase are acyclovir, ganciclovir, citrusine-I, and the acyclic guanosine phosphonate (R,S)-HPMPC (Terry et al. (1988) *Antiviral Res.* 10:235; Yamamoto et al. (1989) *Antiviral Res.* 12:21). However, these compounds are not completely selective for viral thymidylate synthetases or DNA polymerases and therefore can disadvantageously cause inhibition of host DNA replication at high doses. Moreover, the development of mutant viruses which are resistant to the inhibitory effects of these compounds have been reported, and appear to result from mutations in the viral DNA polymerase (Coen et al. (1982) *J. Virol.* 41:909; Coen et al. (1980) *Proc. Natl. Acad. Sci. (U.S.A)* 77:2265; Larder et al. (1987) *EMBO J.* 6:169). Thus, while CMV infections, such as CMV retinitis, can be initially treated with foscarnet and ganciclovir, after a period of time CMV replication and progression of the pathological viral infection recurs.

Passive immunization with antibodies (e.g., immune globulin) has been tested in combination with ganciclovir for therapeutic efficacy in humans. Such antibody preparations are obtained from the serum of donors, who possess a high antibody titre to the virus as a result of an earlier infection. One disadvantage of such conventional antibody preparations is the limited number of suitable donors and the poor reproducibility or quality of the various preparations, including potential contamination with pathogens and pathogenic viruses. Unfortunately, the use of intravenous immune globulin in combination with ganciclovir apparently does not produce significantly improved efficacy as compared to ganciclovir treatment alone (Jacobson et al. (1990) *Antimicrob. Agents and Chemother.* 34:176). The safety and pharmacokinetic profiles of anti-cytomegalovirus monoclonal antibodies are discussed in Aulitzky et al. (1991) *J. Infect. Dis.* 163:1344 and Drobyski et al. (1991) *Transplantation* 51:1190. However, none of the reported human anti-CMV monoclonal antibodies have been shown to possess significant therapeutic efficacy in treating CMV infections (e.g., retinitis) in humans.

Attempts to use recombinantly produced hCMV glycoproteins as a subunit vaccine to provide protective immunity against hCMV infection and pathogenesis have not proven to be effective, but remain candidates for additional evaluation.

Thus, there exists a need in the art for effective methods and compositions for inhibiting human cytomegalovirus replication, attenuating CMV virulence in vivo, neutralizing CMV virions, and for preventing and treating human cytomegalovirus infections, and especially CMV infections in preborns, newborns, and immunosuppressed patients such as AIDS patients. For example but not limitation, a suitable attenuated human CMV vaccine which elicits satisfactory immunoprotection against CMV infection is needed in the art. The present invention fulfills these and other needs.

SUMMARY OF THE INVENTION

A basis of the present invention is the surprising and unexpected finding that: (1) clinical isolates of pathogenic CMV variants contain a genomic region ("virulence region") which typically is not present in CMV strains which have undergone extensive laboratory passaging of the virus in cell culture (hereafter termed "highly passaged strain variants") and (2) functional disruption (e.g., deletion or insertional inactivation and the like) of genes in this genomic region produces a substantial attenuation of CMV virulence and/or pathogenicity in vivo. Furthermore, the virulence region of a clinical isolate of CMV is frequently deleted, rearranged, or substantially changed over the course of passaging the virus in cell culture.

In one aspect of the invention, the virulence region is obtained from an early passage Toledo strain and is conveniently termed the "Toledo genomic region" herein, although equivalent (e.g., homologous) regions or subsequences thereof are present in other clinical isolates of CMV besides the Toledo strain of CMV; the term "Toledo genomic region" encompasses these homologous regions in other clinical CMV isolates, many early passage CMV strains, and non-isolated pathogenic CMV variants.

The Toledo genomic region which is present in pathogenic CMV isolates and which is typically substantially absent in highly passaged CMV strains (e.g., AD169, high-passage Towne) has been sequenced and several open-reading frames have been identified (PCT Publication WO96/30387, U.S. Ser. No. 08/414,926, U.S. Ser. No. 08/644,543 filed 10 May 1996, each incorporated herein in their entirety by reference). Functional disruption of these open reading frames, either singly or in combination, has been unexpectedly found to substantially reduce virulence of the resultant CMV mutant(s) in vivo. Thus, in part, the invention provides methods and compositions for suppressing or inactivating expression of genes of the Toledo genomic region and its homolog regions in other CMV variants, and thereby reducing virulence and pathogenicity of clinically important CMV variants to generate a "Toledo region-attenuated CMV variant"; such Toledo region-attenuated CMV variants have altered phenotypes which generally make them candidates for use in live attenuated virus vaccines for prophylaxis and/or treatment of CMV disease. The invention is, in part, further based on the heretofore unrecognized finding that pathogenic clinical isolates of CMV have a distinct genome as compared to the commonly used laboratory-passaged strains of human CMV (e.g., AD169, highly-passaged Towne), and that the genomic region which is present in the clinical isolates and which is substantially absent in laboratory-passaged strains confers enhanced virulence in vivo. Most common approaches to development of CMV therapies and vaccines have heretofore relied on laboratory-passaged strains which typically lack all or part of the Toledo genomic region and the genes encoded therein which have been unexpectedly found to confer enhanced in vivo virulence and are believed to contribute to clinical pathology and CMV-related disease.

The invention provides a method for attenuating virulence of CMV comprising functionally inactivating at least one open reading frame in a virulence region of a CMV genome having substantial identity to at least 300 bp, typically at least 500 bp, of a 15 kb sequence present in the genome of the Toledo strain of CMV and absent from the genome of the AD169 strain of CMV and/or absent from the genome of highly-passaged Towne (i.e., more than 50-100 passages). In an aspect, the method functionally inactivates at least one open reading frame present in a genomic region of a CMV genome having substantial identity to at least 300 bp of a 13 kb sequence present in the genome of the Toledo strain of CMV and absent from the genome of the Towne strain of CMV. In an embodiment, the method functionally inactivates at least one open reading frame present in a genomic region of a CMV genome having substantial identity to at least 500 bp of the sequence shown in FIGS. 1A through 1R (SEQ ID NO: 1). In an embodiment, the method functionally inactivates at least the open reading frame corresponding to UL 148 as identified herein. In a variation, the method functionally inactivates open reading frames in the region spanning UL138 to UL148. In an embodiment, the method functionally inactivates UL138, UL139, UL140, UL141, UL142, UL143, UL144, UL145, UL146, UL147, and/or UL148. In a variation, UL148 is inactivated singly or in combination with other open reading frames of the Toledo genomic region. In a specific embodiment, UL148 is inactivated in combination with UL141 and/or UL144. Typically, such Toledo region-attenuated CMV variants comprise at least 500 bp of the Toledo genomic region or a homolog region having at least 80 percent sequence identity; frequently they comprise at least 1.0 kbp of the Toledo genomic region or homolog virulence region; often they contain at least 5.0 kbp to 8.0 kbp of the Toledo genomic region or homolog virulence region, and can comprise up to a complete Toledo genomic region or homolog virulence region. It is possible for a synthetic virulence region to be comprised of portions of two or more virulence regions (e.g., such as a chimeric virulence region comprising part of the Toledo genomic region from a first clinical isolate with a complementing portion of the Toledo genomic region of a second clinical isolate).

In an aspect, the invention provides a method for attenuating a CMV strain or isolate containing an encoding polynucleotide sequence encoding a polypeptide which is at least 80 percent sequence identical to a polypeptide encoded by UL138, UL139, UL140, UL141, UL142, UL143, UL144, UL145, UL146, UL147, and/or UL148 of the Toledo genomic region; the method comprising functionally inactivating (e.g., deleting or introducing a nonsense or missense mutation) said encoding polynucleotide sequence to produce a Toledo region-attenuated CMV variant. In a variation, all open reading frames (ORFs) in the CMV isolate that are at least 80% sequence identical to the corresponding sequence of the Toledo genomic region are functionally inactivated. In a variation, all open reading frames (ORFs) in the CMV isolate that are at least 80% sequence identical to UL138, UL139, UL140, UL141, UL142, UL143, UL144, UL145, UL146, UL147, and/or UL148 of the Toledo genomic region are functionally inactivated. In an alternate variation, only one or a subset of the open reading frames (ORFs) in the CMV isolate that are at least 80% sequence identical to the corresponding sequence(s) of the Toledo genomic region are functionally inactivated. Such Toledo region-attenuated CMV variants comprise at least 500 bp of a Toledo genomic region and can comprise up to a complete Toledo genomic region (including a chimeric Toledo genomic region composed from distinct clinical isolates or strains).

In an aspect, the invention provides a recombinant CMV virus, comprising a genome having at least 500 bp of a virulence region wherein at least one ORF has been functionally inactivated by a genetic alteration which is predetermined and/or which does not occur in known isolates or strains of CMV regardless of passage history.

In an aspect, the method of attenuating virulence comprises functional inactivation of open reading frames by predetermined structural mutation (e.g., deletion, insertion, missense or nonsense mutation, and the like) of at least one open reading frame, or a predetermined mutation of a transcriptional control sequence that controls transcription of the open reading frame, or predetermined mutation of a splicing signal sequence or the like necessary for efficient expression of the encoded gene product of the open reading frame. In an embodiment, a selectable marker gene is introduced into an open reading frame, often in the portion of the open reading frame believed to encode the amino-terminal two-thirds of the gene product, to structurally disrupt the open reading frame and result in the inactivation of the open reading frame's capacity to encode its functional gene product. In a variation, open reading frame UL148 is structurally disrupted by mutation; in one embodiment the structural disruption results from insertion of a selectable and/or screenable marker gene (e.g., gpt/lacZ). In an embodiment, a selectable marker gene is used to replace all or part of at least one open reading frame, such as by replacement of a deleted region of the Toledo genomic region with a selectable marker gene. In a variation, a region spanning open reading frame UL138 to UL148 is structurally disrupted by mutation; in one embodiment the structural disruption results from deletion of the UL138-UL148 region and replacement with a selectable and/or screenable marker gene (e.g., gpt/lacZ).

In an aspect, the functional inactivation of a Toledo genomic region gene is provided by transcriptional and/or translational suppression with an antisense polynucleotide having a sequence of at least 15 nucleotides, typically at least 25 nucleotides, that are substantially complementary to a Toledo genomic region, most usually the antisense polynucleotide is substantially complementary to an open reading frame sequence of a Toledo genomic region open reading frame. In an embodiment, the antisense polynucleotide is substantially complementary to at least 25 nucleotides of UL148. In an embodiment, the antisense polynucleotide is complementary to UL148 and further comprises additional 5' and/or 3' nucleotide(s) which are not substantially complementary to UL148. In variations, the antisense polynucleotides comprise non-natural chemical modifications, and can include, for instance, methylphosphonates, phosphorothioates, phosphoramidites, phosphorodithioates, phosphorotriesters, and boranophosphates. In a variation the antisense molecules can comprise non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, and glycinylamides. In a variation, the invention provides peptide nucleic acids (PNAs) having a nucleobase sequence which is substantially complementary to a Toledo genomic region sequence, such as an open reading frame (e.g., UL148, UL141, UL142, etc.).

The invention also provides attenuated live virus CMV vaccines wherein at least one open reading frame of a Toledo genomic region is structurally disrupted. Typically, the UL148 open reading frame is structurally disrupted, either singly or in combination with other Toledo region open reading frames (e.g., UL141, UL144, and the like). Often the disruption of the open reading frame is an insertion, deletion, or replacement mutation which confers the property of reduced virulence as determined by a suitable in vivo virulence assay (e.g., see Experimental Examples). Toledo genomic region mutants which exhibit at least one log reduction, preferably two logs or more reduction, in virulence as determined by in vivo virulence assay, or other equivalent virulence measure, are attenuated CMV vaccines. Such attenuated CMV vaccines are used to immunize individuals to confer protective immunity, typically antibody-mediated and/or cell-mediated immunity, to prevent or reduce the severity of subsequent CMV infection following a suitable immunization period.

In an aspect, the invention also provides attenuated live virus CMV vaccines wherein at least one open reading frame of a Toledo genomic region is replaced by a segment of Towne genome which is not present in AD169. The Towne genome comprises a region no present in AD169; the region contains open reading frame designated UL147, UL152, UL153, and UL154 and generally is spanned by nucleotides 178221 to 180029 of the Towne genome according to the AD169 (EMBL accession number X17403) numbering convention. An attenuated virus of the invention can, in one embodiment, comprise a Toledo genome wherein the Toledo genome region spanning open reading frames UL133 to UL151 are replaced with a Towne genome region spanning UL147, UL152, UL153, and UL154; this engineered CMV virus variant is an attenuated Toledo virus which comprises desirable features of Towne while reducing undesirable virulence of the Toledo genome region. The invention provides other variations of this basic method, whereby a segment of the Toledo genome region comprising at least one open reading frame is deleted or otherwise structurally disrupted in a CMV variant having a Toledo genome region or its homolog, and a segment of a Towne genome region comprising at least one open reading frame inserted in the CMV variant. In an embodiment, the engineered CMV variant comprises: (1) Toledo DNA (DNA substantially identical to a Toledo strain, preferably identical to it) from about nucleotides 1 to about 168,000 corresponding to (i.e., according to) the AD169 (EMBL accession number X17403) nucleotide numbering convention, operably linked to (2) Towne DNA (DNA substantially identical to a Towne strain, preferably identical to it) from about nucleotides 143,824 to 189,466 according to the AD169 (EMBL accession number X17403) nucleotide numbering convention, operably linked to (3) Toledo DNA (DNA substantially identical to a Toledo strain, preferably identical to it) from about nucleotides 189,466 to about 209,514 corresponding to (i.e., according to) the AD169 (EMBL accession number X17403) nucleotide numbering convention, operably linked to (4) Towne DNA (DNA substantially identical to a Towne strain, preferably identical to it) from about nucleotides 200,080 to 229,354 according to the AD169 (EMBL accession number X17403) nucleotide numbering convention. The invention also provides vaccine compositions and formulations of such attenuated CMV viruses, which can include adjuvants, delivery vehicles, liposomal formulations, and the like. The invention also provides the use of such attenuated CMV variants for prevention of CMV disease and infection; in one aspect this use includes administration of such vaccine to human subjects.

In a variation, the functional inactivation of a Toledo genomic region gene is provided by suppressing function of a gene product encoded by a Toledo region open reading frame by contacting or administering an antibody which is specifically reactive with said gene product. In an embodiment, the Toledo genomic region gene is UL148, UL141, and/or UL144, typically at least UL148, although other Toledo open reading frames can be used. The antibody binds to a gene product encoded by a Toledo region open reading frame with an affinity of at least about $1 \times 10^7$ M.$^{-1}$, typically at least about $1 \times 10^8$ M.$^{-1}$, frequently at least $1 \times 10^9$ M.$^{-1}$ to $1 \times 10^{10}$ M.$^{-1}$ or more. In some aspects, the antibody is substantially monospecific. In an embodiment, the antibody is a human antibody raised by immunizing an individual with an immunogenic dose of a gene product of a Toledo region open reading frame. In an embodiment, the human antibody is a monoclonal antibody, or collection of human monoclonal antibodies which bind to the Toledo region gene product(s). In an embodiment, the antibody is a humanized antibody comprising complementarity-determining regions substantially obtained from a non-human species immunoglobulin reactive with the Toledo region gene product, and further comprising substantially human sequence framework and constant regions. The invention also comprises pharmaceutical formulations of such antibodies and the use of such antibodies to treat or prevent CMV diseases, such as by passive immunization or the like.

In an aspect, the invention provides a composite CMV variant comprising a highly-passaged Towne genome and at least one open reading frame of a Toledo genome region, typically present in or adjacent to the $U_L$/b' region of the composite CMV. In an aspect, the composite CMV is a highly-passaged Towne genome further comprising a Toledo UL148, UL141, and/or UL144. In an embodiment, the composite CMV is a highly-passaged Towne genome with a complete Toledo genome region; in a variation said Toledo genome region has at least one open reading frame functionally inactivated to further attenuate the virulence of the composite CMV. In a variation, a low passage Towne genome (i.e, less than 40 passages in culture) is used in place of a highly-passaged Towne genome. In an alternate variation, a virulence region from a low-passage Towne genome is emplaced in a Toledo genome so as to thereby replace at least 1 kbp of the virulence region of the Toledo genome with at least 500 bp, typically approximately the same length, of a corresponding region (e.g., substantial sequence identity) of low-passage Towne.

In an aspect, the invention provides a chimeric CMV virus, comprising a genome having a plurality of polynucleotide sequences, linked in conventional phosphodiester linkage, wherein at least two of said polynucleotide sequences are derived from different clinical isolates or strains of CMV. Said chimeric CMV virus can comprise a genome having a plurality of polynucleotide sequences, linked in conventional phosphodiester linkage, wherein a first CMV genome sequence of at least 500 bp and less than a complete CMV genome length (e.g., less than 250 kbp) is at least 98 percent sequence identical to a first CMV isolate or strain, and at least one additional CMV sequence of at least 500 bp and less than a complete CMV genome length (e.g., less than 250 kbp) is at least 98 percent sequence identical to a second CMV isolate or strain which has a genome having a polynucleotide sequence of at least 500 bp which is less than 60 percent sequence identical to any portion of the genome of said first CMV isolate or strain and/or which is absent or substantially absent in the genome of said first CMV isolate or strain. Said chimeric CMV virus comprises a genome having sufficient genetic information to replicate as a virus, typically as an infectious virus, in suitable host cells or a suitable host organism or replication system (e.g., SCID/hu thy/liv mice, human lung fibroblasts, and other systems known in the art). Generally, said chimeric CMV virus has a genome that comprises genetic information which is substantially sequence identical, generally at least 80 percent sequence identical, usually at least 95 percent sequence identical or more, to a high-passage Towne genome; said chimeric CMV virus genome typically further comprises genetic information which is substantially sequence identical, generally at least 80 percent sequence identical, usually at least 95 percent sequence identical or more, to at least 1 kbp of a virulence region of a clinical isolate of CMV or a low-passage strain of CMV other than low-passage Towne; in an embodiment, a complete virulence region (e.g., Toledo genome region) of a clinical isolate or low-passage CMV strain is present.

In an aspect, the invention provides a chimeric CMV virus, comprising a chimeric genome comprising a polynucleotide having a first CMV sequence of at least 500 bp having at least 97 percent sequence identity with a genome of a first CMV isolate or CMV strain and a second CMV sequence of at least 500 bp having at least 97 percent sequence identity with a genome of a second CMV isolate or CMV strain, and wherein said chimeric genome comprises genetic information having substantial identity (e.g., at least 80 percent sequence identity, preferably at least 95 percent sequence identity) spanning at least about the complete low-passage Towne genome. Typically, the chimeric genome comprises at least 500 bp containing at least one ORF having at least 95 to preferably 100 percent sequence identity to a virulence region (e.g., Toledo genome region) of a clinical isolate or low-passage strain of CMV other than low-passage Towne.

In an aspect, the invention provides a chimeric CMV virus, comprising a chimeric genome comprising a polynucleotide having a first CMV sequence of at least 500 bp having at least 97 percent sequence identity with a genome of a first CMV isolate or CMV strain and a second CMV sequence of at least 500 bp having at least 97 percent sequence identity with a genome of a second CMV isolate or CMV strain, and wherein said chimeric genome comprises genetic information having substantial identity (e.g., at least 80 percent sequence identity, preferably at least 95 percent sequence identity) spanning at least about the complete Toledo genome excepting at least 1 kbp of the virulence determining region of Toledo (Toledo genome region), and preferably excepting at least 5 kbp to the entire approximately 15 kbp virulence-determining Toledo genome region. Typically, the chimeric genome comprises at least 500 bp containing at least one ORF having at least 95 to preferably 100 percent sequence identity to a virulence region of low-passage Towne.

In specific embodiments, the invention provides exemplary CMV chimeric viruses composed of genome portions of high-passage Towne and genome portions of Toledo; the exemplary CMV chimeric viruses are designated herein as Chimera I, Chimera II, Chimera III, Chimera IV, and Towne/Tol 11. In an aspect, the invention encompasses these specific embodiments and variants of each exemplified Chimera wherein the boundaries (splice junctions/recombination joints) between the various Towne and Toledo genome portions vary from the specific exemplified Chimeras by less than 20 kbp, typically less than 10 kbp, usually by less than 5 kbp, and in many embodiments by less than 1 kbp from the specific examples provided herein.

In a variation, the invention provides a diagnostic method for identifying a virulent CMV strain in a sample by detecting the presence of unique Toledo genome region polynucleotide sequences and/or by detecting the presence of a polypeptide encoded by an open reading frame of the Toledo genomic region. Detection of polynucleotide sequences can be by any suitable method, including but not limited to PCR amplification using suitable primers, LCR, hybridization of a labeled polynucleotide probe, and the like. Detection of polypeptide species is typically done by immunoassay using a specific antibody to the Toledo region gene product(s).

The invention also provides a method of treating or preventing CMV infection, the method comprising administering to an individual an efficacious dose of a polypeptide which is substantially identical to the deduced amino acid sequence of UL148. In a variation, the polypeptide is a truncated variant, mutein, or analog of the deduced amino acid sequence of UL148, wherein the polypeptide is soluble.

A further understanding of the nature and advantages of the invention will become apparent by reference to the remaining portions of the specification and drawings.

BRIEF DESCRIPTION OF THE DRAWINGS

FIGS. 1A-1R. Nucleotide sequence of Toledo genome region isolated from Toledo strain of HCMV) (SEQ ID NO: 1).

FIGS. 2A-2H. Deduced amino acid sequences of open reading frames UL130, and UL132 through UL151 (SEQ ID NOs:2-22, respectively). Conventional single letter abbreviations are used.

FIG. 7. Southern blot showing that a variety of clinical isolates of CMV contain sequences homologous to the Toledo $U_L$/b' region. The Towne lane contains genomic DNA from Aviron's highly-passaged Towne strain (Towne AV).

FIG. 8. Southern blot showing that previous variants of the Towne strain hybridize to the Toledo $U_L$/b' region. Twn•Merck indicates Towne strain from the Merck clinical trial. Twn•MA, Twn•MA#5 and Twn•MA#8 are variants of Towne obtained from Microbiological Associates. Twn•Aviron is highly-passaged Towne obtained at Aviron.

FIG. 9. Schematic depiction of generation of chimeric CMV virus genomes by cotransfection of cosmids containing portions of Towne and Toledo genomes.

DEFINITIONS

Figure 3:
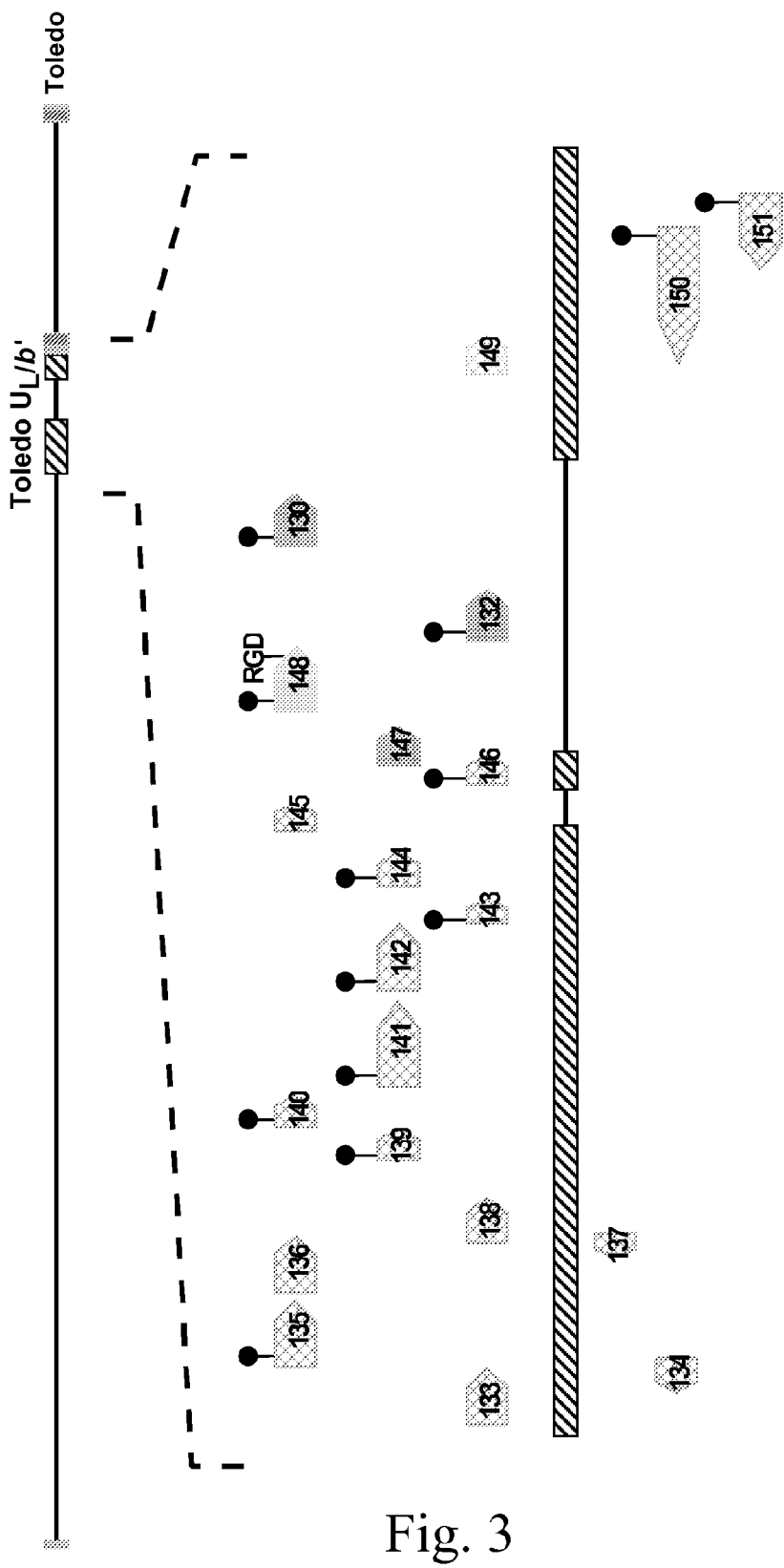
FIG. 3. Schematic representation of open reading frames and their location in Toledo genome region. Top line schematically portrays entire Toledo genome with $U_L/b'$ region identified. Bottom line shows enlarged view of $U_L/b'$ region. Arrows indicate polarity and length of open reading frame. Solid circles indicate potential glycosylation sites.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991)). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATAT".

The following terms are used to describe the sequence relationships between two or more polynucleotides: "reference sequence", "comparison window", "sequence identity", "percentage of sequence identity", and substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1A-1R (SEQ ID NO. 1), or may comprise a complete cDNA or gene sequence. A full-length cDNA or gene sequence is defined as a polynucleotide containing the sequence(s) necessary to encode a complete protein product, including a translation initiation codon and a translation termination codon, unless linked to another encoding sequence in a format for production as a fusion protein. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisions between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (U.S.A.)* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25 50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of an open reading frame shown in FIG. 1A-1R.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "analog", "mutein" or "mutant" as used herein refers to polypeptides which are comprised of a segment of at least 10 amino acids that has substantial identity to a portion of the naturally occurring protein The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described herein below. Agents are evaluated for potential activity as specific protein interaction inhibitors (i.e., an agent which selectively inhibits a binding interaction between two predetermined polypeptides but which does not substantially interfere with cell viability) by inclusion in screening assays.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3$H, $^{14}$C, $^{35}$S, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single-stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15-25 or more nucleotides, although it may contain fewer nucleotides. Short primer molecules generally require cooler temperatures to form sufficiently stable hybrid complexes with template. In some embodiments, the primers can be large polynucleotides, such as from about 200 nucleotides to several kilobases or more. The primers herein are selected to be substantially complementary to the different strands of each specific sequence to be amplified. The primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

The term "recombinant" used herein refers to macromolecules produced by recombinant DNA techniques wherein the gene coding for a polypeptide is cloned by known recombinant DNA technology. For example, an amplified or assembled product polynucleotide may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, *Aspergillus* and insect cells. One preferred embodiment employs bacterial cells as the host. Alternatively, the product polynucleotide may serve a non-coding function (e.g., promoter, origin of replication, ribosome-binding site, etc.).

DETAILED DESCRIPTION

Commonly-assigned U.S. patent application U.S. Ser. No. 08/414,926 filed 31 Mar. 1995 is incorporated herein by reference.

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. *Molecular Cloning: A Laboratory Manual,* 2d ed. (1989) Cold Spring Harbor Laboratory Press, Cold Spring Harbor, N.Y.).

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Stockton Press, New York, N.Y. (1989); *PCR Protocols: A Guide to Methods and Applications,* eds. Innis, Gelfland, Snisky, and White, Academic Press, San Diego, Calif. (1990); Mattila et al. (1991) *Nucleic Acids Res.* 19:4967; Eckert, K. A. and Kunkel, T. A. (1991) *PCR Methods and Applications* 1:17; and U.S. Pat. Nos. 4,683,202 and 4,965,188, each of which are incorporated herein by reference) and exemplified hereinbelow.

It is evident that optimal PCR and hybridization conditions will vary depending upon the sequence composition and length(s) of the targeting polynucleotide(s) and target(s), and the experimental method selected by the practitioner. Various guidelines may be used to select appropriate primer sequences and hybridization conditions (see, Maniatis et al., *Molecular Cloning: A Laboratory Manual* (1989), 2nd Ed., Cold Spring Harbor, N.Y.; Berger and Kimmel, *Methods in Enzymology,* Volume 152*, Guide to Molecular Cloning Techniques* (1987), Academic Press, Inc., San Diego, Calif.; *PCR Protocols: A Guide to Methods and Applications,* eds. Innis, Gelfland, Snisky, and White, Academic Press, San Diego, Calif. (1990); Benton W D and Davis R W (1977) *Science* 196:180; Goodspeed et al. (1989) *Gene* 76: 1; Dunn et al. (1989) *J. Biol. Chem.* 264:13057 which are incorporated herein by reference.

A basis of the invention is the unexpected discovery that there are significant genomic differences between clinical isolates of CMV and highly-passaged CMV strains, including differences between low-passage Towne and high-passage Towne, as well as differences as compared to Toledo strain; the identification of these genomic differences, including definition of novel genomic region(s); and the phenotypic significance and biological function of said genomic differences and specific ORFs within said novel genomic regions. Based, in part, on these unexpected discoveries, it is possible to construct and use chimeric CMV viruses which have predetermined genome compositions comprising at least a portion of a genome of a first CMV isolate or strain and at least a portion of a genome of a second (or subsequent) CMV isolate or strain, so as to form a complete, replicable recombinant chimeric CMV genome, with and the resultant chimeric CMV genome being capable of replication in a suitable host replication system and being useful for a variety of uses, such as human or veterinary vaccines, commercial reagents for laboratory use (e.g., as restriction enzymes are sold), use in screening systems to identify novel candidate drugs to inhibit replication or pathogenesis (e.g., virulence, tropism, host range, etc.) of pathogenic, clinically relevant CMV virus types, and other uses such as diagnostic reagents, gene expression vectors, anti-tumor agents, heterologous gene expression systems, and the like.

Overview An approach of the invention starts with identification of DNA sequences which confer virulence on human cytomegalovirus (HCMV). These sequences can be manipulated to produce a new, more efficacious HCMV vaccine strain with predicted characteristics. Introduction of the virulence genes into an overattenuated strain can improve its immunogenicity and deletion of the virulence genes from a virulent strain can render it safe in humans by decreasing its virulence. Specifically, deletion of genetic information from a clinical isolate called Toledo is used to attenuate an HCMV virus, and in one embodiment, a segment from a laboratory strain called Towne, especially a highly-passaged Towne variant, is transferred to the deleted region of Toledo to act as a "spacer". Deleting genetic information has utility in improving a clinical isolate such as Toledo as an immunizing composition. Removing these sequences from Toledo, which has been shown to cause disease in people, can result in an attenuated virus which may be a safe vaccine candidate.

The Towne strain of HCMV has been used as a vaccine in humans. In some clinical settings, Towne has been used to prevent the disease consequences associated with infection by HCMV (reviewed by Marshall and Plotkin In: *The Human Herpesviruses B*. Roizman, R. J. Whitley, & C. Lopez Eds. Raven Press, New York). The Towne strain is believed to be overattenuated as a vaccine candidate and consequently, is poorly immunogenic. This loss of immunogenicity may have been the result of an extensive passage history in tissue culture. Genetic information in the virulence region may have been lost during passage, particularly after about Passage 40. Variation in DNA content among isolated strains does exist based on crude hybridization experiments. Other investigators have reported minor regions of sequence heterogeneity between two so-called laboratory strains of HCMV, the Towne and AD169 strains. Heterogeneities can exist within HCMV strains depending upon the extent of passages in their culture history.

The public health impact of HCMV infections have not been well controlled by current treatment strategies or available antiviral chemotherapies. Preventive vaccine strategies are likely to prove efficacious because of the observations that seropositive renal allograft recipients are protected from severe HCMV disease and maternal immunity protects the fetus from disease after intrauterine infection. HCMV (Towne) was developed as a vaccine strain by serial passage 125 times in WI38 human diploid fibroblasts (Towne 125). It has been administered to humans without significant adverse reactions. However, in one study, vaccines were directly challenged by wild-type virus and found to resist only low challenge doses of 10 plaque-forming units or less. The consensus view is that the Towne strain may be overly attenuated. One positive feature of the Towne strain is that it has never been shown to reactivate.

One important obstacle to the development of a vaccine for HCMV is the lack of an animal model system that can be used to test the safety and efficacy of vaccine candidates. Therefore, cell culture systems or surrogate animal models such as the SCID-hu (thy/liv) mouse have to be developed to test vaccine strains. Replicative differences in HCMV strains have been described in a variety of cell types and in the SCID-hu mouse model. These differences correlate to the virulence and passage history of the virus. Thus, low passage, virulent clinical isolates, such as Toledo, can replicate better in the human implant of SCID-hu (thy/liv) mice and in cultures of human endothelial cells than cell culture adapted, highly-passaged avirulent laboratory strains such as Towne or AD169 (Brown et al. 1995; Waldman et al., 1991). This observation can be exploited to measure the "virulence" of a strain by assessing its growth characteristics in the SCID-hu mouse, in vivo in humans, or by other means. Recombinant vaccine candidates such as the ones described here which have deleted or incorporated DNA sequences are believed to replicate less well than the virulent parent in a suitable virulence assay. This observation would be indicative of an attenuated vaccine candidate. Deletion of the Toledo $U_L$/b' region from the low passage, virulent HCMV Toledo genome results in a virus with reduced replicative ability in the SCID-hu mouse. This recombinant virus should have a concomitantly reduced virulence which allows administration of the virus without causing the undesired clinical manifestations exhibited by the Toledo virus in humans.

The invention identifies, maps, and sequences differences between the virulent Toledo strain and the avirulent highly passaged Towne strain, for the purpose of transferring novel genetic information to Towne to restore its immunogenicity or, alternatively, to remove information from Toledo to render it safe as a vaccine candidate. One major region of difference mapped to the internal portion of the L component. This large 13 kbp region present in Toledo but not highly passaged Towne is located at the border between the unique long (UL) and the inverted repeats bordering the UL region termed IRL or b'. We have deduced the coding information resident in the Toledo sequences and have extensively compared the information resident in AD169, highly passaged Towne and Toledo. We have made recombinant viruses which have either inserted the $U_L$/b' region from the virulent Toledo strain, into the corresponding region of Towne, and have also deleted this region from Toledo and replaced it with a selectable marker and reporter gene or with the corresponding $U_L$/b' region from Towne. Deletion of the virulence genes from Toledo decreased the ability of the recombinant to replicate within the SCID-hu (thy/liv) mouse, a model for CMV virulence. The new recombinant viruses exhibit growth properties in the SCID-hu mouse that indicate that vaccine candidates with attenuated virulence can be generated by deleting the $U_L$/b' region from the Toledo virus. We have also demonstrated that we can add the Toledo region to the Towne virus which will presumably result in increased immunogenicity for the highly passaged Towne virus while retaining its safe profile for humans.

FIG. 1A-1R show the nucleotide sequence of Toledo genome region isolated from Toledo strain of HCMV (SEQ ID NO. 1). FIGS. 2A-2H show the deduced amino acid sequences of open reading frames UL130, and UL132 through UL151 (SEQ ID NOS 2-22, respectively).

A basis of the present invention is the surprising and unexpected finding that: (1) clinical isolates of pathogenic CMV variants contain a genomic region which typically is not present in CMV strains which have undergone extensive laboratory passaging of the virus in cell culture, and (2) functional disruption (e.g., deletion or insertional inactivation and the like) of genes in this genomic region produces a substantial attenuation of CMV virulence and pathogenicity in vivo. The genomic region is conveniently termed the "Toledo genomic region" herein, although equivalent (e.g., homologous) regions or subsequences thereof are present in other clinical isolates of CMV besides the Toledo strain of CMV; the term "Toledo genomic region" encompasses these homologous regions in other clinical CMV isolates and non-isolated pathogenic CMV variants which have a genomic region of at least 500 bp having at least 80 percent sequence identity to the Toledo genomic region of the Toledo strain having the sequences disclosed herein and in WO96/30387, incorporated herein by reference. The Toledo genomic region which is present in pathogenic CMV isolates and which is typically substantially absent in laboratory passaged CMV strains (e.g., AD169, Towne) has been sequenced and several open-reading frames have been identified. Functional disruption of these open reading frames, either singly or in combination, has been unexpectedly found to substantially reduce virulence of the resultant CMV mutant(s) in vivo. Thus, in part, the invention provides methods and compositions for suppressing or inactivating expression of genes of the Toledo genomic region and its homolog regions in other CMV variants, and thereby reducing virulence and pathogenicity of clinically important CMV variants. The invention is, in part, further based on the heretofore unrecognized finding that pathogenic clinical isolates of CMV have a distinct genome as compared to the commonly used laboratory-passaged strains of human CMV (e.g., AD169, Towne), and that the genomic region which is present in the clinical isolates and which is substantially absent in laboratory-passaged strains confers enhanced virulence in vivo. Most common approaches to development of CMV therapies and vaccines have heretofore relied on laboratory-passaged strains which lack the Toledo genomic region and the genes encoded therein which have been unexpectedly found to confer enhanced in vivo virulence and are believed to contribute to clinical pathology and CMV-related disease.

The invention provides a method for attenuating virulence of CMV comprising functionally inactivating at least one open reading frame in a genomic region of a CMV genome having substantial identity to at least 300 bp, typically at least 500 bp, of an approximately 15 kb sequence present in the genome of the Toledo strain of CMV and absent from the genome of the AD169 strain of CMV. In an aspect, the method functionally inactivates at least one open reading frame present in a genomic region of a CMV genome having substantial identity to at least 300 bp of a 13 kb sequence present in the genome of the Toledo strain of CMV and absent from the genome of the highly-passaged Towne strain of CMV. In an embodiment, the method functionally inactivates at least one open reading frame present in a genomic region of a CMV genome having substantial identity to at least 500 bp of the sequence shown in FIGS. 1A through 1R (SEQ ID NO: 1). In an embodiment, the method functionally inactivates at least the open reading frame corresponding to UL 148 as identified herein. In a variation, the method functionally inactivates open reading frames in the region spanning UL138 to UL 148. In an embodiment, the method functionally inactivates UL138, UL139, UL140, UL141, UL142, UL143, UL144, UL145, UL146, UL147, and/or UL148. In a variation, UL148 is inactivated singly or in combination with other open reading frames of the Toledo genomic region. In a specific embodiment, UL148 is inactivated in combination with UL141 and/or UL144. Inactivation is typically accomplished by genetic engineering and involves predetermined mutations (which may include additions, transpositions, or deletions), generally of the specific type which are not known to occur naturally in CMV strains even after extensive passaging.

In an aspect, the method of attenuating virulence comprises functional inactivation of open reading frames by structural mutation (e.g., deletion, insertion, missense or nonsense mutation, and the like) of at least one open reading frame, or a mutation of a transcriptional control sequence that controls transcription of the open reading frame, or mutation of a splicing signal sequence or the like necessary for efficient expression of the encoded gene product of the open reading frame. In an embodiment, a selectable marker gene is introduced into an open reading frame, often in the portion of the open reading frame believed to encode the amino-terminal two-thirds of the gene product, to structurally disrupt the open reading frame and result in the inactivation of the open reading frame's capacity to encode its functional gene product. In a variation, open reading frame UL148 is structurally disrupted by predetermined mutation, often produced by site-directed mutagenesis or in vitro recombination; in one embodiment the structural disruption results from insertion of a selectable and/or screenable marker gene (e.g., gpt/lacZ). In an embodiment, a selectable marker gene is used to replace all or part of at least one open reading frame, such as by replacement of a deleted region of the Toledo genomic region with a selectable marker gene. In a variation, a region spanning open reading frame UL138 to UL148 is structurally disrupted by predetermined mutation; in one embodiment the structural disruption results from deletion of the UL138-UL148 region and replacement with a selectable and/or screenable marker gene (e.g., gpt/lacZ).

In an aspect, the functional inactivation of a Toledo genomic region gene is provided by transcriptional and/or translational suppression with an antisense polynucleotide having a sequence of at least 15 nucleotides, typically at least 25 nucleotides, that are substantially complementary to a Toledo genomic region, most usually the antisense polynucleotide is substantially complementary to an open reading frame sequence of a Toledo genomic region open reading frame. In an embodiment, the antisense polynucleotide is substantially complementary to at least 25 nucleotides of UL148. In an embodiment, the antisense polynucleotide is complementary to UL148 and further comprises additional 5' and/or 3' nucleotide(s) which are not substantially complementary to UL148. In variations, the antisense polynucleotides comprise non-natural chemical modifications, and can include, for instance, methylphosphonates, phosphorothioates, phosphoramidites, phosphorodithioates, phosphorotriesters, and boranophosphates. In a variation the antisense molecules can comprise non-phosphodiester polynucleotide analogs wherein the phosphodiester backbone is replaced by a structural mimic linkage include: alkanes, ethers, thioethers, amines, ketones, formacetals, thioformacetals, amides, carbamates, ureas, hydroxylamines, sulfamates, sulfamides, sulfones, and glycinylamides. In a variation, the invention provides peptide nucleic acids (PNAs) having a nucleobase sequence which is substantially complementary to a Toledo genomic region sequence, such as an open reading frame (e.g., UL148, UL141, UL142, etc.).

The invention also provides attenuated live virus CMV vaccines wherein at least one open reading frame of a Toledo genomic region is structurally disrupted by predetermined mutation. Typically, the UL148 open reading frame is structurally disrupted, either singly or in combination with other Toledo region open reading frames (e.g., UL141, UL144, and the like). Often the disruption of the open reading frame is an insertion, deletion, or replacement mutation which confers the property of reduced virulence as determined by a suitable in vivo virulence assay (e.g., see Experimental Examples). Toledo genomic region mutants which exhibit at least one log reduction, preferably two logs or more reduction, in virulence as determined by in vivo virulence assay, or other equivalent virulence measure, are attenuated CMV vaccines. Such attenuated CMV vaccines are used to immunize individuals to confer protective immunity, typically antibody-mediated and/or cell-mediated immunity, to prevent or reduce the severity of subsequent CMV infection following a suitable immunization period.

In an aspect, the invention also provides attenuated live virus CMV vaccines wherein at least one open reading frame of a Toledo genomic region is replaced by a segment of Towne genome which is not present in AD169. The highly-passaged Towne genome comprises a region not present in AD169; the region contains open reading frame designated UL147, UL152, UL153, and UL154 and generally is spanned by nucleotides 178221 to 180029 of the Towne genome according to the AD169 (EMBL accession number X17403) numbering convention. An attenuated virus of the invention can, in one embodiment, comprise a Toledo genome wherein the Toledo genome region spanning open reading frames UL133 to UL151 are replaced with a Towne genome region spanning UL147, UL152, UL153, and UL154; this engineered CMV virus variant is an attenuated Toledo virus which comprises desirable features of Towne while reducing undesirable virulence of the Toledo genome region. The invention provides other variations of this basic method, whereby a segment of the Toledo genome region comprising at least one open reading frame is deleted or otherwise structurally disrupted in a CMV variant having a Toledo genome region or its homolog, and a segment of a Towne genome region comprising at least one open reading frame in inserted in the CMV variant. In an embodiment, the engineered CMV variant comprises: (1) Toledo DNA (DNA substantially identical to a Toledo strain, preferably identical to it) from about nucleotides 1 to about 168,000 corresponding to (i.e., according to) the AD169 (EMBL accession number X17403) nucleotide numbering convention, operably linked to (2) Towne DNA (DNA substantially identical to a Towne strain, preferably identical to it) from about nucleotides 143,824 to 189,466 according to the AD169 (EMBL accession number X17403) nucleotide numbering convention, operably linked to (3) Toledo DNA (DNA substantially identical to a Toledo strain, preferably identical to it) from about nucleotides 189,466 to about 209, 514 corresponding to (i.e., according to) the AD169 (EMBL accession number X17403) nucleotide numbering convention, operably linked to (4) Towne DNA (DNA substantially identical to a Towne strain, preferably identical to it) from about nucleotides 200,080 to 229,354 according to the AD169 (EMBL accession number X17403) nucleotide numbering convention. The invention also provides vaccine compositions and formulations of such attenuated CMV viruses, which can include adjuvants, delivery vehicles, liposomal formulations, and the like. The invention also provides the use of such attenuated CMV variants for prevention of CMV disease and infection; in one aspect this use includes administration of such vaccine to human subjects.

In a variation, the functional inactivation of a Toledo genomic region gene is provided by suppressing function of a gene product encoded by a Toledo region open reading frame by contacting or administering an antibody which is specifically reactive with said gene product. In an embodiment, the Toledo genomic region gene is UL148, UL141, and/or UL144, typically at least UL148, although other Toledo open reading frames can be used. The antibody binds to a gene product encoded by a Toledo region open reading frame with an affinity of at least about $1 \times 10^7$ M.$^{-1}$, typically at least about $1 \times 10^8$ M.$^{-1}$, frequently at least $1 \times 19$ M.$^{-1}$ to $1 \times 10$ M.$^{-1}$ or more. In some aspects, the antibody is substantially monospecific. In an embodiment, the antibody is a human antibody raised by immunizing an individual with an immunogenic dose of a gene product of a Toledo region open reading frame. In an embodiment, the human antibody is a monoclonal antibody, or collection of human monoclonal antibodies which bind to the Toledo region gene product(s). In an embodiment, the antibody is a humanized antibody comprising complementarity-determining regions substantially obtained from a non-human species immunoglobulin reactive with the Toledo region gene product, and further comprising substantially human sequence framework and constant regions. The invention also comprises pharmaceutical formulations of such antibodies and the use of such antibodies to treat or prevent CMV diseases, such as by passive immunization or the like.

In an aspect, the invention provides a composite CMV variant comprising a Towne genome and at least one open reading frame of a Toledo genome region, typically present in or adjacent to the $U_L$/b' region of the composite CMV. In an aspect, the composite CMV is a Towne genome further comprising a Toledo UL148, UL141, and/or UL144. In an embodiment, the composite CMV is a highly-passaged Towne genome with a complete Toledo genome region; in a variation said Toledo genome region has at least one open reading frame functionally inactivated to further attenuate the virulence of the composite CMV.

In a variation, the invention provides a diagnostic method for identifying a virulent CMV strain in a sample by detecting the presence of unique Toledo genome region polynucleotide sequences and/or by detecting the presence of a polypeptide encoded by an open reading frame of the Toledo genomic region. Detection of polynucleotide sequences can be by any suitable method, including but not limited to PCR amplification using suitable primers, LCR, hybridization of a labeled polynucleotide probe, and the like. Detection of polypeptide species is typically done by immunoassay using a specific antibody to the Toledo region gene product(s).

The invention also provides a method of treating or preventing CMV infection, the method comprising administering to an individual an efficacious dose of a polypeptide which is substantially identical to the deduced amino acid sequence of UL148. In a variation, the polypeptide is a truncated variant, mutein, or analog of the deduced amino acid sequence of UL148, wherein the polypeptide is soluble.

EXPERIMENTAL EXAMPLES

Overview

The growth advantage of Toledo in the SCID-hu mouse model resides in the genetic information encoded by the additional sequences (Toledo genomic region) we have identified. One gene in particular, UL148, has been mutagenized in Toledo by insertion of a selectable marker (gptILacZ) and the Toledo-based recombinant has been shown to replicate less well than Toledo in the SCID-hu assay. The genetic information of the corresponding region of the avirulent Towne virus has been deduced by nucleotide sequence analysis and demonstrated to lack an open reading frame in Towne. UL148 can be considered to be representative of a "virulence determinant" for Toledo. The new Toledo sequence identified at the inverted repeats has been analyzed to reveal novel genes in Toledo. Deletion of genes encompassing UL138 to UL148 in recombinant viruses have been tested for growth properties in the SCID-hu (thy/liv) mouse. These recombinants have been shown to replicate to levels similar to the Towne virus and represent attenuated vaccine candidates, since Towne has been shown to be safe and avirulent in humans. Such recombinants should show increased immunogenicity owing to their greater similarity to low passage virulent strains over that shown by highly-passaged Towne in humans. In addition, these strains should not exhibit the fully virulent phenotype shown by unmodified Toledo in humans due to the alterations we have introduced into their genomes.

This invention describes new recombinant HCMV viruses not previously described which are attenuated in virulence relative to low passage, virulent isolates by virtue of deletion of sequences shown to be present in low passage, virulent isolates but which are lacking in laboratory strains. The identification of these sequences was essential in order to prepare transfer vectors capable of shuttling deletions (or insertions such as selectable markers) resulting in an effective removal of coding information. Knowledge of the ORF usage on these DNAs permits deletion or insertion of one DNA into the other to specifically disrupt existing coding information. In addition, this invention identifies sequences which can be used as "spacer" DNA for substitution into deleted regions of HCMV clinical isolates for purposes of attenuation.

Cosmid Subclones of Towne and Toledo

Cosmid subclones of the CMV(Towne) and CMV(Toledo) genomes were constructed according to the method of Kemble et al. (1996) *J. Virol.* 70:2044, incorporated herein by reference. Human foreskin fibroblast (HF) cells were infected with either Towne or Toledo and following the development of extensive CPE, DNA was isolated from nucleocapsids by a procedure similar to that used for the preparation of HSV nucleocapsids (Denniston et al. (1981) *Gene* 15:365, incorporated herein by reference). The DNA was partially digested with Sau3AI, fractionated by agarose gel electrophoresis, and ligated to the BamHI site of BamHI, XbaI digested arms of the SuperCos•A1 cosmid vector. SuperCos•A1 was derived from SuperCos-1 (Stratagene, San Diego, Calif.) by the insertion of an oligonucleotide incorporating SrfI and PacI recognition sequences flanking a unique BamHI site. The position of the cosmid subclones relative to the viral genome was identified by Southern and DNA sequence analyses.

Overlapping Cosmids for Virus Regeneration

Mapping the extent of the viral insert within the cosmid subclones was used as a basis to form specific Towne/Toledo chimeric viruses by choosing the appropriate cosmids from each virus. The ends of adjacent cosmids should overlap (~200 bp or more) such that homologous recombination is permitted in eucaryotic cells.

Figure 5:
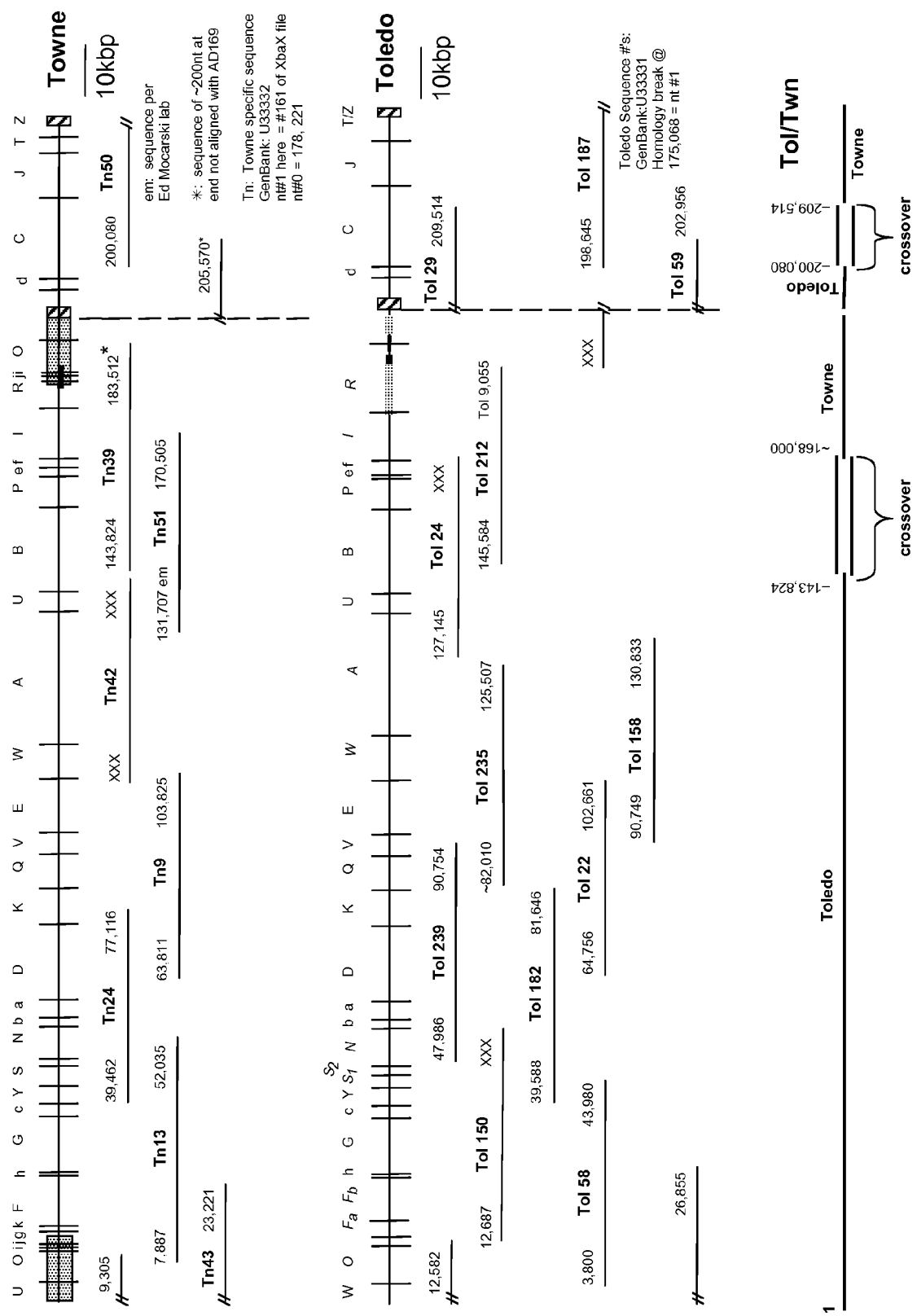
FIG. 5. CMV Towne and Toledo cosmids used to regenerate specific chimeric CMV viruses. The location of the cosmid insert are indicated beneath the appropriate viral genome. The numbers at the end of the insert denote the endpoints determined by DNA sequence analysis; the numbers correspond to AD169 genomic sequence in GenBank (EMBL accession number X17403). "XXX" denotes an end which was refractory to DNA sequence analysis. These ends were mapped by restriction enzyme and Southern blot analyses. The vertical dashed line represents the location of the internal "a" sequence of the virus. The lower line depicts the structure of the Tol/Twn 39/50 genome. The thick gray line denotes sequences derived from Toledo and the thin black line depicts sequences contributed from highly-passaged Towne strain. Regions of overlap could be derived from either virus and are represented by a region of a thick gray and a thin black line together. The Tol/Twn 39/50 genome does not contain the Toledo genomic region.

To construct a Toledo based virus which lacked the Toledo $U_L/b'$ region and in its place contained the Towne $U_L/b'$ region, the following set of cosmids was used: Tol29, Tol58, Tol182, Tol22, Tol158, Tol124, Tn39, and Tn50. The resulting virus was designated Tol/Twn 39/50 (see FIG. 5). Other viruses were regenerated by cosmid cotransfection which lacked portions of the Toledo $U_L/b'$ region. Toledo based viruses were generated by the cotransfection of the Toledo cosmids, Tol29, Tol58, Tol182, Tol22, Tol158, Tol24, Tol 212, Tol187 OR Tol59, Tol150, Tol239, Tol235, Tol158, Tol24, Tol212, Tol187. Towne/Toledo chimeras lacking portions of the Toledo $U_L/b'$ region were regenerated by cotransfection of Tn43, Tn13, Tn24, Tn9, Tn42, Tn51, Tol212, Tol187. Because Tol 212 and Tol187 did not overlap, deletions resulted in the viruses regenerated from these cosmid sets which lacked varying portions of the Toledo $U_L/b'$ region.

Preparation of Cosmids for Cotransfection

A set of overlapping cosmid clones constituting the appropriate viral genome were individually digested with PacI to release the intact viral insert from the cosmid vector. The restriction enzyme was inactivated by heating at 65° C. for 20 minutes, the cosmids were combined and the DNA precipitated with ethanol. A $CaPO_4$ precipitate was formed from approximately 8 to 16 µg of this mixture and transfected using general transfection methods. The DNA was transfected into approximately $1 \times 10^6$ low passage (<15 passes) HF, LF (human embryonic lung fibroblast) or IFIE1.3 (a gift of Ed Mocarski; these cells are immortalized HF cells that express the CMV major immediate early protein) cells. All these cells are permissive for CMV replication.

For HF and LF cells, approximately $1 \times 10^6$ cells were plated onto a 25 cm² flask 3 to 5 hours prior to the addition of the $DNA-CaPO_4$ precipitate. At this point, the precipitate was adsorbed directly to the cell monolayer for 30 minutes prior to the addition of media. 2 ml of media was added and incubation continued for 4 hours at 37° C.

For IFIE1.3 cells, the cells were trypsinized approximately 16 hours prior to the addition of the $DNA-CaPO_4$ precipitate and seeded at a 1:2 density. At the appropriate time post seeding, the $DNA-CaPO_4$ precipitate was added in addition to 2 ml of media and incubated at 37° C. for 4 hours.

Following the 4 hour incubation, the DNA-CaPO.sub.4 precipitate was removed, the cells incubated at 37° C. for 3 min in 15% glycerol in Hepes buffered saline, rinsed one time with media and fed with 5 ml of media. The media on the cells was changed every 3 to 4 days and plaques appeared in 10 to 21 days.

Construction of Recombinant CMV by Insertion of a gpt/LacZ Marker

Figure 4:
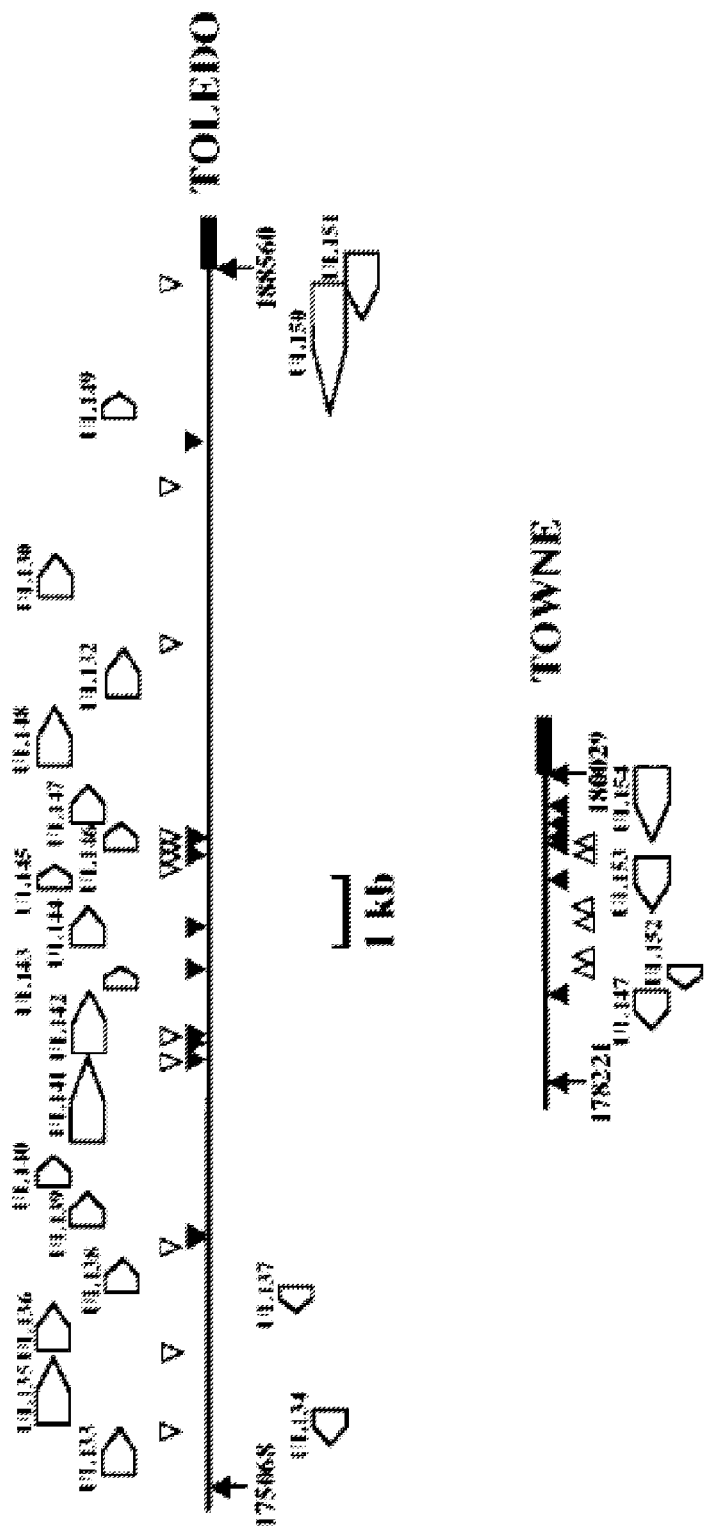
FIG. 4. Schematic comparison of the novel genome regions of Toledo and highly-passaged Towne as compared to AD169.

Two plasmids encompassing the Toledo $U_L/b'$ region and derivatives thereof were constructed which contained a marker gene. A segment of DNA encompassing AD169 bases 156251 174483 was removed from pON2601 (Cha et al. (1996) J. Virol. 70:78, incorporated herein by reference) and a PacI linker was introduced at AD169 base 174484 to yield a subclone of pON2601. FIGS. 3 and 4 show a schematic drawing of the open reading frames in the Toledo $U_L/b'$ region using sequence numbering from the Toledo $U_L/b'$ region DNA insert. A 4.8 kb DNA fragment containing the *E. coli* gpt and lacZ genes driven by the HSV thymindine kinase and β actin promoters (Prichard et al. (1996) *J. Virol.* 70:3018, incorporated herein by reference), respectively, was then inserted into the NsiI site in Toledo UL148 within the pON2601 subclone. The resulting plasmid containing the gpt and lacZ insert in UL148 was designated pGD6. Toledo open reading frames UL138 to UL148 were removed from pGD6 by a BamHI collapse to produce the plasmid pGD7. Toledo recombinant viruses Tol pGD6 and Tol pGD7 were constructed using plasmids pGD6 and pGD7, respectively, as described (Prichard et al. (1996) op.cit.).

Analysis of Recombinant CMV in SCID-hu (thy/liv) Mice

SCID-hu (thy/liv) mice were derived by implanting human fetal thymus and liver beneath the kidney capsule of a female C.B.-17 scid/scid IcrTac mouse (McCune et al. (1988) *Science* 241:1632, incorporated herein by reference). The SCID-hu (thy/liv) mouse model serves as an animal model that can distinguish virulent from avirulent strains of CMV based on their replication levels within the human implant (Mocarski et al. (1993) *Proc. Natl. Acad. Sci.* (U.S.A.) 90:104 and Brown et al. (1995) *J. Infect. Dis.* 171:1599, each incorporated herein by reference). Several weeks following implantation, the human implant on the murine kidney was surgically exposed and an inoculum of $10^4$ PFU of the appropriate virus was injected directly into the human tissue in a volume of 10-25 µl. The murine kidney/human implant was placed back into the animal in its natural position and the animal was recovered. 2 weeks following infection of the human tissue, the animal was sacrificed and the implant was removed and added to 2 ml of 4.5% skim milk/50% media.

The excised implant was homogenized with an automated Dounce apparatus (Glas-Col, Terre Haute, Ind.) and the suspension was stored at −80° C. until the titers were determined. The suspension was thawed at 37° C., sonicated on ice by three cycles of 10 sec on/10 sec off and centrifuged to remove the debris. The supernatant was recovered and the titer of CMV present was determined on confluent monolayers of HF cells. 7 to 10 days after plating the virus, the monolayers were fixed and stained with Giemsa and plaques enumerated.

Figure 6:
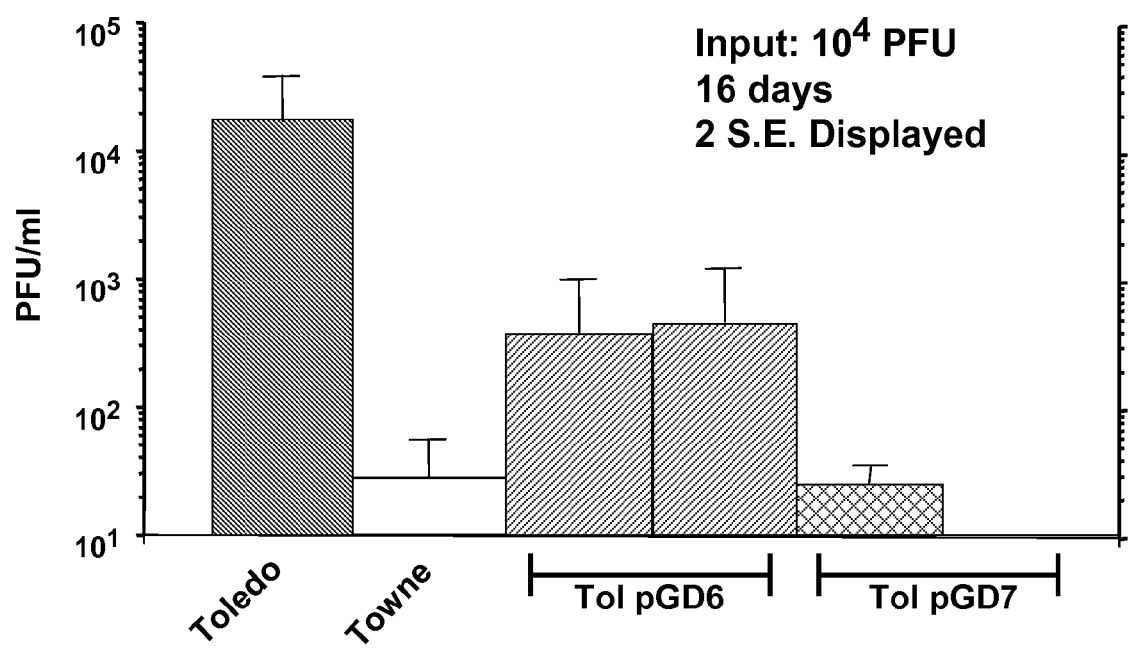
FIG. 6. Analysis of the gpt/LacZ recombinant viruses in the SCID-hu (thy/liv) model. Two independent isolates of Tol pGD6 and Tol pGD7 were tested in the model. 3 mice were used per group and the mean of the data is displayed. Error bars representing 2 standard errors from the mean are also displayed.
Figure 10:
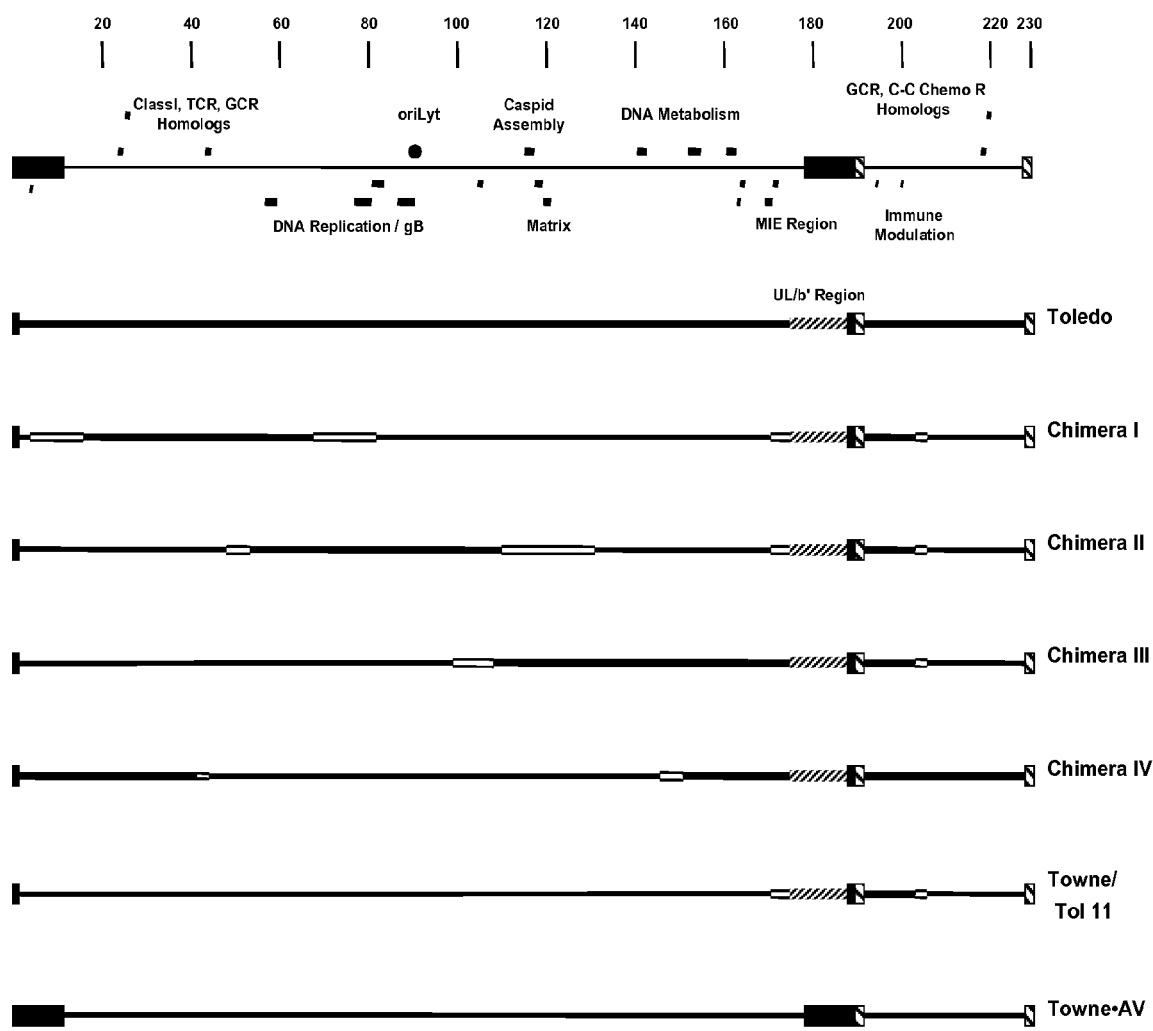
FIG. 10. Schematic depiction of the specific exemplary embodiments denoted Chimera I, Chimera II, Chimera III, Chimera IV, and Towne/Tol 11. Toledo genome is depicted as "Toledo"; highly-passaged Towne genome is depicted as "Towne•AV"; selected reading frames of importance, proposed function/homologues of selected ORFs, and scale (in kbp) is shown on the top line.

FIG. 6 shows results from this experiment. The virulence of the Toledo strain CMV is attenuated by functional disruption of Toledo genome region open reading frames.

Figure 11:
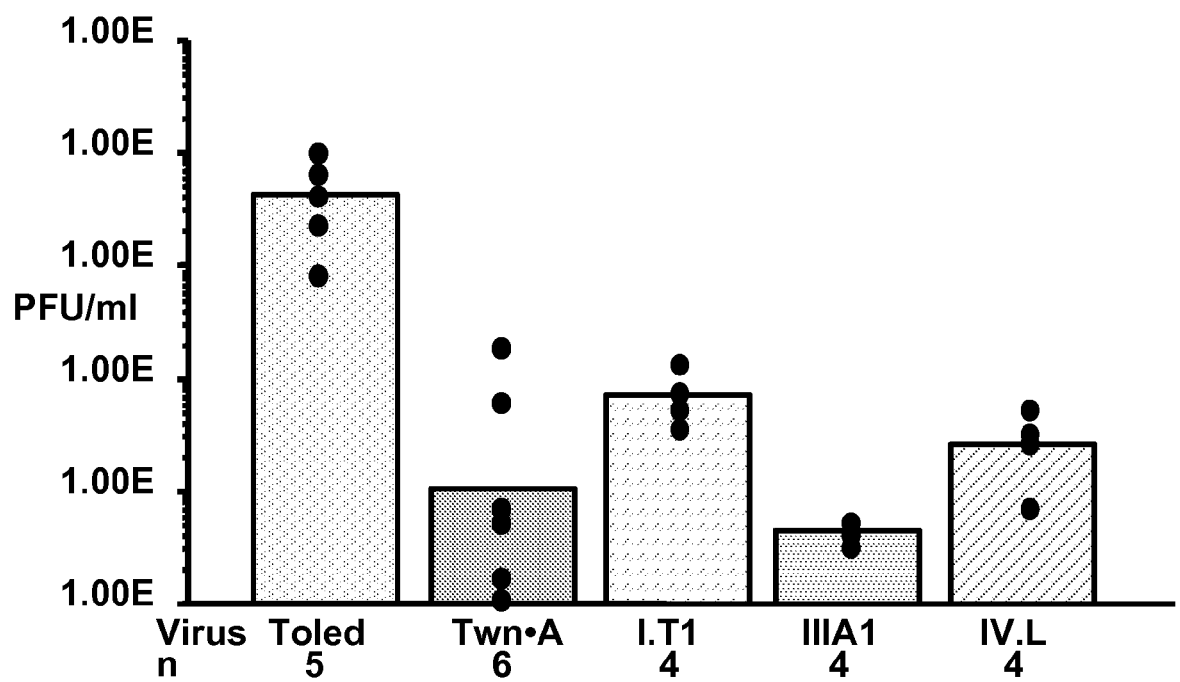
FIG. 11. Replication of Toledo, highly passaged Towne, and Chimeras I, III, and IV (in order, respectively) in SCID-hu mice having a thymus/liver implant.
Figure 12:
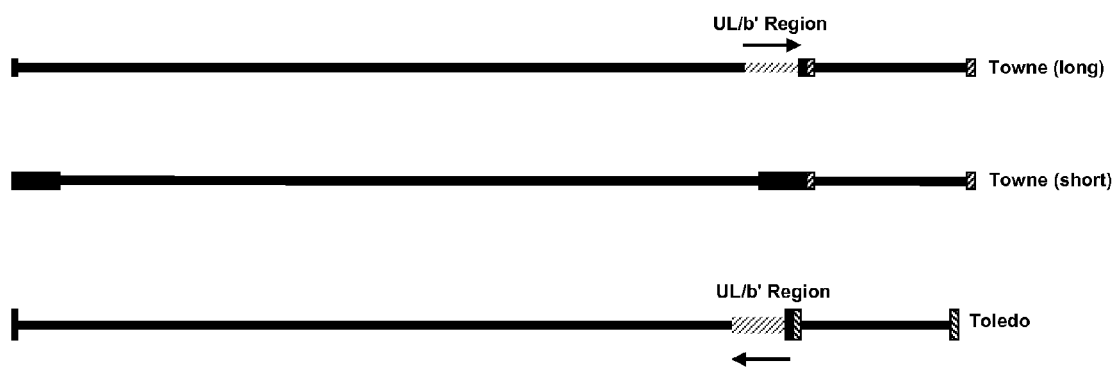
FIG. 12. Schematic comparison of low-passage (long) Towne genome and high-passage (short) Towne genome.

The difference in virulence between the Towne and Toledo strains appears to have resulted from genetic differences generated during the adaptation of Towne to growth in dipoid fibroblasts in culture. Both Towne and Toledo were originally isolated from the urine of a congenitally infected infant. Towne was subsequently passaged over 125 times in culture resulting in genetic alterations in the viral genome and an avirulent virus. The virulent Toledo virus, in contrast, was passaged approximately 5 times in diploid fibroblasts in order to produce material that could cause disease in humans.

These linked genetic and biological differences can be used to create a live, attenuated HCMV vaccine. The rationale for tissue culture adaptation of Towne was to generate a live, attenuated vaccine strain. Towne has been shown to be safe and somewhat immunogenic. Towne, however, is overattenuated. The immune response induced by inoculation with Towne does not protect against subsequent HCMV infection as effectively as that generated by natural infection. Vaccine candidates can be generated by replacing genetic elements of the overattenuated Towne strain with homologous portions of the virulent Toledo strain. Through the analysis of these "chimeric" viruses, a skilled artisan can select those that have the level of desirable characteristics of Towne and be attenuated to a more efficacious degree.

Our first four chimeric viruses, as a set, will contain the entire Toledo genome introduced into the Towne genetic background. Each individual chimera of the set will contain approximately 40 55% of the Toledo genome; the remainder will be derived from Towne. Each of these chimeras will contain the $U_L$/b' region derived from Toledo. Genes within this region of the Toledo genome can affect cell tropism of HCMV. The viruses, designated chimera I, II, III, and IV were constructed from the cosmids listed in Table 1 (see also FIGS. 9 and 10).

TABLE 1

Cosmids used to generate specific chimeras.

| Viruses | | | |
|---|---|---|---|
| I | II | III | IV |
| Tn46a | Tn46 | Tn46 | Tol29 |
| Tol58b | Tn45 | Tn45 | Tol58 |
| Tol182 | Tol239 | Tn23 | Tn23 |
| Tn47 | Tol22 | Tn47 | Tn47 |
| Tn44 | Tol158 | Tol184 | Tn44 |
| Tn26 | Tn26 | Tol24 | Tn26 |
| Tn20 | Tn20 | Tol212 | Tol212 |
| Tol11 | Tol11 | Tol11 | Tol122 |

Large quantities of each cosmid were prepared by purification of the *E. coli* produced material over a Qiagen column as described by the manufacturer. 10 micrograms of each cosmid was digested with the restriction enzyme Pac I (New England Biolabs) to physically separate cosmid vector from viral sequences. Following digestion, the enzyme was inactivated by incubation at 65° C. for 20 minutes and the appropriate cosmids were combined, precipitated with ethanol in the presence of 0.3M sodium acetate, rinsed in 70% ethanol, and air-dried briefly. The resulting DNA was solubilized in approximately 100 microliters of 10 mM Tris pH 7.5/1 mM EDTA. Various amounts of the cosmid mix was transfected by the calcium phosphate technique into permissive fibroblast cells, specifically human lung fibroblasts (LF, prepared in our laboratory), human neonatal foreskin fibroblast (HF, a gift of Dr. Ed Mocarski, Stanford University), MRC-5 (ATCC) or IFIE 1.3 cells (a gift of Ed Mocarski, Stanford University). The IFIE1.3 cell line constitutively expresses the HCMV ie1 gene product and has been transformed with the human papilloma virus E6 and E7 genes transduced by a retrovirus vector. 3 to 5 hours after transfection the cells were shocked by incubation in 15% glycerol/Hepes buffered saline for 3 minutes at 37° C. and fed with DME/10% fetal bovine serum. 7 to 10 days after transfection plaques with distinct HCMV CPE were evident.

Plaques derived from the chimeras were allowed to grow until 100% of the monolayer exhibited CPE. At this point, DNA was extracted from the supernatent and cellular fractions and analyzed by restriction enzyme digestion. The structures of the viruses can be deduced by the cosmids used for construction of the chimera and confirmed by comparing the EcoRI digestion pattern to the maps derived for Towne and Toledo (see FIG. 10). Table 2 describes the composition of each of the chimeras, the nucleotide limits are derived from sequence analysis of the end of each cosmid insert and its homology to the AD169 strain of HCMV, which has been sequenced in its entirety (EMBL accession number X17403). All of the chimeras had restriction enzyme patterns consistent with the proposed structures.

TABLE 2

Genetic composition of the chimeras.

| Chimera | Towne DNA | Toledo DNA | Crossover Region |
|---|---|---|---|
| I | 1-3799 | 15750-67568 | 3800-15749 (SEQ ID NO.: 23)) |
| | 81647-170499 | 175069-203136 | 67569-81646 (SEQ ID NO.: 24) |
| | 205803 to S term. | | 170500-175068 (SEQ ID NO.: 25) |
| II | 1-47985 | 53244-~10000 | 47986-53243 (SEQ ID NO.: 27) |
| | 138834-170499 | 175069-203136 | ~110000-130833 (SEQ ID NO.: 28) |
| | 205803 to S term. | | 170500-175068 (SEQ ID NO.: 25) |
| | | | 203137-205802 (SEQ ID NO.: 26) |
| III | 1-~99000* | 108094-203136 | ~99000-108093 (SEQ ID NO.: 29) |
| | 205803 to S term. | | 203137-205802 (SEQ ID NO.: 26) |
| IV | 43981-145583 | 1-41356 | 41357-43980 (SEQ ID NO.: 30) |
| | | 150754-S term | 145584-150753 (SEQ ID NO.: 31) |

*Sequence at end of cosmid was undefinable. Nucleotide number is not exact crossover region is the region of cosmid overlap. The contribution of each virus to this region has yet to be defined.

Two other chimeras are constructed based on an observation derived from the sequence analysis of several different members of the beta-herpesvirus family including HCMV, human herpesvirus 6 (the causative agent of roseola) and murine cytomegalovirus. Representative members of each of these viruses have been sequenced in their entirety and a "core" set of genes corresponding to HCMV UL23 to UL122 are conserved among these evolutionarily divergent entities (Chee, et al. 1990; Gompels, et al. 1995; Rawlinson, et al. 1996, incorporated herein by reference). These core genes contribute to DNA replication, virion structure, and other basic features of the virus. Genes outside this core region are involved in virus-host and virus-immune system interaction and may determine specific properties of virus biology. Replication of the Chimeras was tested in SCID-hu mice having a thy/liv sandwich under the kidney capsule; representative data is shown in FIG. 11.

Two additional chimeras are constructed: one which has the core derived from Toledo with the remainder of the genes derived from Towne and an inverse construct in which the core is derived from Towne and the remainder of the genes are from Toledo. These viruses are constructed through the use of overlapping cosmids and derivatives of the cosmids. Table 3 outlines the constructs that can be used to generate these two chimeric viruses.

TABLE 3

Construction of chimeras containing conserved core regions.

| Towne Core/Tol Noncore | Tol Core/Towne Noncore |
|---|---|
| Tol29 | Tn43 |
| Tol58 nts: 3800-27862 | Tn45 nts: 7854-27862 |
| Tn45 nts: 27500-53243 | Tol58: 27500-43980 |
| Tn23 | Tol182 |
| Tn47 | Tol22 |
| Tn44 | Tol158 |
| Tn26 | Tol24 |
| Tn20 | Tol212 nts: 145584-17200 |
| Tol11 nts: 170852-188890 | Tn39 nts: 170852-183512 |
| Tol122 | Tn15 |

All of these viruses are used to inoculate healthy adult human volunteers. These individuals are assessed for symptoms of HCMV disease, including fever, malaise, and abnormal liver enzyme levels. Hallmarks of viral infection are also assessed by measuring HCMV specific antibody titers before and after inoculation as well as viral culture for the isolation of infectious virus from bodily fluids. A successful vaccine candidate is identified as a strain that maintains the safety profile of Towne while stimulating a greater immune response to the virus.

FIG. 12 shows schematic depiction of the Toledo genome in comparison with highly passaged Towne (short genome) and low-passage Towne (long genome).

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

The invention claimed is:

1. A chimeric cytomegalovirus (CMV) virus which comprises: (a) the polynucleotide sequence of a high-passage Towne genome from nucleotides 1 to 99000; (b) the polynucleotide sequence of a Toledo genome from nucleotides 108094 to 203136; (c) the polynucleotide sequence of a high passage Towne genome from nucleotides 205803 to S-term, wherein the high-passage Towne genome has been passaged at least 50 times and wherein the nucleotide number of the Towne and Toledo genomes is according to the numbering convention of the AD169 genome.

2. A chimeric CMV virus which comprises: (a) the polynucleotide sequence of a high-passage Towne genome from nucleotides 1 to 99000; (b) a crossover region comprising SEQ ID NO.: 29; (c) the polynucleotide sequence of a Toledo genome from nucleotides 108094 to 203136; (d) a crossover region comprising SEQ ID NO.: 26; (e) the polynucleotide sequence of a high passage Towne genome from nucleotides 205803 to S-term, wherein the high-passage Towne genome has been passaged at least 50 times and wherein the nucleotide number of the Towne and Toledo genomes is according to the numbering convention of the AD169 genome.

3. An immunogenic composition comprising the chimeric virus of claim 1.

4. An immunogenic composition comprising the chimeric virus of claim 1.

5. A method of inducing an immune response comprising administering to a human an immunological composition of claim 3 in an amount sufficient to stimulate an immune response in said human.

6. A method of inducing an immune response comprising administering to a human an immunological composition of claim 4 in an amount sufficient to stimulate an immune response in said human.

* * * * *

SEQUENCE LISTING

```
<160> NUMBER OF SEQ ID NOS: 31

<210> SEQ ID NO 1
<211> LENGTH: 18318
<212> TYPE: DNA
<213> ORGANISM: Human cytomegalovirus
<220> FEATURE:
<221> NAME/KEY: misc_feature
<222> LOCATION: (17955)..(17955)
<223> OTHER INFORMATION: n is a, c, g, or t
<220> FEATURE:
<221> NAME/KEY: misc_feature
<222> LOCATION: (18105)..(18105)
<223> OTHER INFORMATION: n is a, c, g, or t
<220> FEATURE:
<221> NAME/KEY: misc_feature
<222> LOCATION: (18154)..(18154)
<223> OTHER INFORMATION: n is a, c, g, or t
<220> FEATURE:
<221> NAME/KEY: misc_feature
<222> LOCATION: (18160)..(18160)
<223> OTHER INFORMATION: n is a, c, g, or t

<400> SEQUENCE: 1
cgctgtaggg ataaatagtg cgatggcgtt tgtgggagaa cgcagtagcg atgggttgcg     60
acgtgcacga tccttcgtgg caatgccaat ggggcgttcc cacgattatc gtggcctgga    120
taacatgcgc ggctttagga atttggtgtt tggcgggatc gtcggcggat gtctcttcgg    180
gacccggcat cgcagccgta gtcggctgtt ctgttttcat gattttcctc tgcgcgtatc    240
tcatccgtta ccgggaattc ttcaaagact ccgtaatcga cctccttacc tgccgatggg    300
ttcgctactg cagctgcagc tgtaagtgca gctgcaaatg catctcgggc ccctgtagcc    360
gctgctgttc agcgtgttac aaggagacga tgatttacga catggtccaa tacggtcatc    420
gacggcgtcc cggacacggc gacgatcccg acagggtgat ctgcgagata gtcgagagtc    480
ccccggtttc ggcgccgacg gtgtccgtcc ccccgccgtc ggaggagtcc caccagcccg    540
```

-continued

| | |
|---|---|
| tcatcccacc gcagccgcca gcaccgacat cggaacccaa accgaagaaa ggtagggcga | 600 |
| aagataaacc gaagggtaga ccgaaagaca aacctccgtg cgaaccgacg gtgagttcac | 660 |
| aaccaccgtc gcagccgacg gcaatgcccg gcggtccgcc cgacgcgcct cccccgcca | 720 |
| tgccgcagat gccacccggc gtggccgagg cggtacaagc tgccgtgcag gcggccgtgg | 780 |
| ccgcggctct acaacaacag cagcagcatc agaccggaac gtaacccgcc cccggtgcga | 840 |
| taaggaattt tccgacttgg cgcacatctc cttcctcaat gtttggacaa taaacacatt | 900 |
| ccttgccaaa aaatgacgtt tccagaaatc caaggcataa atgtccgtac accggccctt | 960 |
| cccaacacgg agtttgagat tccaagcagg agagaagatc atggtgtgga tatggctcgg | 1020 |
| catcgggctc ctcggcggta ccggactggc ttccctggtc ctggccattt ccttatttac | 1080 |
| ccagcgccga ggccgcaagc gatccgacga gacttcgtcg cgaggccggc tcccgggtgc | 1140 |
| tgcttctgat aagcgtggtg cctgcgcgtg ctgctatcga aatccgaaag aagacgtcgt | 1200 |
| cgagccgctg gatctggaac tggggctcat gcgggtggac acccacccgc cgacgccgca | 1260 |
| ggtgccgcgg tgtacgtcgc tctacatagg agaggatggt ctgccgatag ataaacccga | 1320 |
| gtttcctccg cgcggttcg agatcccga cgtatccacg ccgggaacgc cgaccagcat | 1380 |
| cggccgatct ccgtcgcatt gctcctcgtc gagctctttg tcgtcctcga ccagcgtcga | 1440 |
| cacggtgctg tatcagccgc cgccatcctg gaagccacct ccgccgcccg ggcgcaagaa | 1500 |
| gcggccgcct acgccgccgg tccgggcccc caccacgcgg ctgtcgtcgc acagacccc | 1560 |
| gacgccgata cccgcgccgc gtaagaacct gagcacgccg cccaccaaga aaacgccgcc | 1620 |
| gcccacgaaa cccaagccgg tcggctggac accgccggtg acacccaggc ccttcccgaa | 1680 |
| aacgccgacg ccacaaaagc cgccgcggaa tccgagacta ccgcgcaccg tcggtctgga | 1740 |
| gaatctctcg aaggtgggac tctcgtgtcc ctgtccccga ccccgcacgc cgacggagcc | 1800 |
| gaccacgctg cctatcgtgt cggtttccga gctagccccg cctcctcgat ggtcggacat | 1860 |
| cgaggaactc ttggaacagg cggtgcagag cgtcatgaag gacgccgagt cgatgcagat | 1920 |
| gacctgagac cgaaagagcg agcgcgtccg ttgtacagtt gtatagcagc acacgccttc | 1980 |
| cctcttttc accgcagcta agagagagaa agagagtatg tcagtcaagg gcgtggagat | 2040 |
| gccagaaatg acgtgggact tggacgttag aaataaatgg cggcgtcgaa aggccctgag | 2100 |
| tcgcattcac cggttctggg aatgtcggct acgggtgtgg tggctgagtg acgccggcgt | 2160 |
| aagagaaacc gacccaccgc gtccccgacg ccgcccgact tggatgaccg cggtgtttca | 2220 |
| cgttatctgt gccgttttgc ttacgcttat gattatggcc atcggcgcgc tcatcgcgta | 2280 |
| cttaagatat taccaccagg acagttggcg agacatgctc cacgatctat tttgcggctg | 2340 |
| tcattatccc gagaagtgcc gtcggcacca cgagcggcag agaaggagac ggcaagccat | 2400 |
| ggatgtgccc gacccggaac tcggcgaccc ggcccgccgg ccgttgaacg gagctatgta | 2460 |
| ctacggcagc ggctgtcgct tcgacacggt ggaaatggtg gacgagacga gacccgcgcc | 2520 |
| gccggcgctg tcatcgcccg aaaccggcga cgatagcaac gacgacgcgg ttgccggcgg | 2580 |
| aggtgctggc ggggtaacat cacccgcgac tcgtacgacg tcgccgaacg cactgctgcc | 2640 |
| agaatggatg gatgcggtgc atgtggcggt ccaagccgcc gttcaagcga ccgtgcaagt | 2700 |
| aagtggcccg cgggagaacg ccgtatctcc cgctacgtaa gagggttgag ggggccgttc | 2760 |
| ccgcgcgagt gctgtacaaa agagagagac tgggacgtag atccggacag aggacggtca | 2820 |
| ccatggacga tctgccgctg aatgtcgggt tacccatcat cggcgtgatg ctcgtgctga | 2880 |
| tcgtggccat cctctgctat ctggcttacc actggcacga caccttcaaa ctggtgcgca | 2940 |

```
tgtttctgag ctaccgctgg ctgatccgct gttgcgagct gtacggggag tacgagcgcc   3000
ggttcgcgga cctgtcgtct ctgggcctcg cgccgtacg gcgggagtcg acagacgat    3060 accgtttctc cgaacggccc gacgagatct tggtccgttg ggaggaagtg tcttcccagt   3120
gcagctacgc gtcgtcgcgg ataacagacc gccgtgtggg ttcatcgtct tcgtcgtcgg   3180
tccacgtcgc tagccagaga aacagcgtgc ctccgccgga catggcggtg acggcgccgc   3240
tgaccgacgt cgatctgttg aaacccgtga cgggatccgc gacgcagttc accaccgtag   3300
ccatggtaca ttatcatcaa gagtacacgt gaatgagaaa agaaaaaag aggggagcgg    3360 atcgcgataa tgtcgctttg acattctctg ctcgatctac tcagcgtctg cacgaaacgg   3420
catccgcacg gaggcgagcc caagcgtatc tgcagcaagc ggttcttcc ctcggtgatg    3480 gtggcagcat cggtggcggg agcttgttcg gacgatggac ggtgaggagt ccctggcgat   3540
caggcggctc ccgggtgtgg agttcaacgg gtggtaatgg tggcggtgat cggtgttaga   3600
aaacggtggc cctggcaaac atatatctac tgtaaaccct ctgctctgtt aataaaagc    3660 acactttttca catgagttcg taattttatt gtgtagtgga aattttacg tcattgggaa    3720 accccagaat gaaagagtat aatgtgcata tcaccggggg ttccctgtca gtacgaatgt   3780
acacaacgcg ggttacatta cgataaactt tccggtaaaa cgatgccgat acagcgtgta   3840
taacgctgat tgttacgaca aacgagttgg tatatccatt atatagtaac gaacatgctg   3900
tggatattag ttttatttgc actcgccgca tcggcgagtg aaaccactac aggtaccagc   3960
tctaattcca gtcaatctac tagtgctacc gccaacacga ccgtatcgac atgtattaat   4020
gcctctaacg gcagtagctg gacagtacca cagctcgcgc tgcttgccgc tagcggctgg   4080
acattatctg gactccttct cttatttacc tgctgctttt gctgctttg gctagtacgt     4140 aaaatctgca gctgctgcgg caactcctcc gagtcagaga gcaaaacaac ccacgcgtac   4200
accaatgccg cattcacttc ttccgacgca acgttaccca tgggcactac agggtcgtac   4260
actcccccac aggacggctc atttccacct ccgcctcggt gacgtaggct aaaccgaaac   4320
ccacgttgaa cctaacgcgg tttcggaagg cctgagacgt cactttcaca atgacgtccg   4380
tatacacgtt catcataaaa caccgtagag gctaaggctt cggtagggag agacctcaac   4440
tgttcctgat gagcacccgt gctctcatct cttcagactt gtcatgaccc ccgctcagac   4500
taacgcgact accaccgtgc acccgcacga cgcaaaaaac ggcagcggcg gtagtgccct   4560
gccgaccctc gtcgtttttcg gctttatcgt tacgctactt ttctttctct ttatgctcta   4620
cttttggaac aacgacgtgt tccgtaagct gctccgtgcg cttggatcca gcgctgttgc   4680
gaccgcttcg acgcgtggca agacgaggtc atctaccgtc gtccatcacg tcgttcccag   4740
agcgacgacg agagtcgtac taacagcgtg tcatcgtacg ttctttttatc acccgcgtcc   4800 gatgcggtt ttgacaaccc ggcactgaca gaggccgtcg acagcgtgga cgactgggcg    4860
accacctcgg ttttctacgc cacgtccgac gaaacggcgg acgccgagcg ccgagactcg   4920
cagcaactgc tcatcgagct tccgccggag ccgctcccgc cgacgtggt ggcggccatg    4980 cagaaagcag tgaaacgcgc tgtacagaac gcactacgac acagccacga ctcttggcag   5040
cttcatcaga ccctgtgacg ccagatgaac gttccttctt aaacatccga ggtagcaatg   5100
agacaggtcg cgtaccgccg cgacgcgag agttcctgcg cggtgctggt ccaccacgtc    5160
ggccgcgacg cgacggcga gggggaggca gcaaaaaaga cctgcaaaaa aaccggacgc    5220
tcagttgcgg gcatcccggg cgagaagctg cgtcgcacgg tggtcaccac cacgccggcc   5280
```

-continued

```
cgacgtttga gcggccgaca cacggagcag gagcaggcgg gcatgcgtct ctgtgaaaaa    5340
gggaagaaaa gaatcatcat gtgccgccgg gagtcgctcc gaactctgcc gtggctgttc    5400
tgggtgctgt tgagctgccc gcgactcctc gaatattctt cctcttcgtt cccttcgcc     5460
accgctgaca ttgccgaaaa gatgtgggcc gagaattatg agaccacgtc gccggcgccg    5520
gtgttggtcg ccgagggaga gcaagttacc atcccctgca cggtcatgac acactcctgg    5580
cccatggtct ccattcgcgc acgtttctgt cgttcccacg acggcagcga cgagctcatc    5640
ctggacgccg tcaaaggcca tcggctgatg aacggactcc agtaccgcct gccgtacgcc    5700
acttggaatt tctcgcaatt gcatctcggc caaatattct cgcttacttt taacgtatcg    5760
atggacacag ccggcatgta cgaatgcgtg ctacgcaact acagccacgg cctcatcatg    5820
caacgcttcg taattctcac gcagctggag acgctcagcc ggcccgacga accttgctgc    5880
acaccggcgt taggtcgcta ctcgctggga gaccagatct ggtcgccgac gccctggcgt    5940
ctacggaatc acgactgcgg aacgtaccgc ggctttcaac gcaactactt ctatatcggc    6000
cgcgccgacg ccgaggattg ctggaaaccc gcatgtccgg acgaggaacc cgaccgctgt    6060
tggacagtga tacagcgtta ccggctcccc ggcgactgct accgttcgca gccacacccg    6120
ccgaaatttt taccggtgac gccagcaccg ccggccgaca tagacaccgg gatgtctccc    6180
tgggccactc ggggaatcgc ggcgtttttg gggttttgga gtattttttac cgtatgtttc   6240
ctatgctacc tgtgttatct gcagtgttgt ggacgctggt gtcccacgcc gggaagggga    6300
cgacgaggcg gtgagggcta tcgacgccta ccgacttacg atagttaccc cggtgttaga    6360
aagatgaaga ggtgagaaca cgtataaaat aaaaaaataa tatgttaaaa aatgcagtgt    6420
gtgaagtgtg aatagtgtga ttaaaatatg cggattgaat gggtgtggtg gttattcgga    6480
tactttgtgt catccgttgg gagcgaacgg tcattatcct atcgttacca cttggaatct    6540
aattcatcta ccaacgtggt ttgcaacgga aacatttccg tgtttgtaaa cggcacccta    6600
ggtgtgcggt ataacattac ggtaggaatc agttcgtctt tattaatagg acaccttact    6660
atacaagtat tggaatcatg gttcacaccc tgggtccaaa ataaaagtta caacaaacaa    6720
cccctaggtg acactgaaac gctttataat atagatagcg aaaacattca tcgcgtatct    6780
caatattttc acacaagatg gataaaatct ctgcaagaga atcacacttg cgacctcaca    6840
aacagtacac ctacctatac atatcaagta aacgtgaaca acacgaatta cctaacacta    6900
acatcctcgg gatggcaaga ccgtctaaat tacaccgtca taaatagtac acactttaac    6960
ctcacagaat cgaacataac cagcattcaa aaatatctca acactacctg catagaaaga    7020
ctccgtaact acaccttgga gtccgtatac accacaactg tgcctcaaaa cataacaaca    7080
tctcaacacg caacaaccac tatgcacaca atacctccaa atacaataac aattcaaaat    7140
acaactcaaa gccatactgt acagacgccg tcttttaacg acacacataa cgtgacgaaa    7200
cacacgttaa acataagcta cgtttatca caaaaaacga ataacacaac atcaccgtgg     7260
atatatgcca tacctatggg cgctacagcc acaataggcg ccggtttata tatcgggaaa    7320
cactttacgc cggttaagtt cgtatacgag gtatggcgcg gtcagtaaag acgattcgga    7380
ttcaacacat atactcccca cgatcctcga acaccttaca gcatatgagc aaaaaacaag    7440
aaagtatagc cacaatcaca tttgggcgaa taacatgctg tcatccacta gcgtctatta    7500
atctaatgtt taacgggagc tgtactgtca ccgttaaaat atccatggga atcaacgggt    7560
caaccaacgt ccatcagctt gtgattgtgc tccatctggg taaccgctgt cagccttggc    7620
gacaggtgta atcacagctg tcacataact cacgaagcct ccaatcacag cagcacacat    7680
```

```
agtcctaacg ccattggcgt gtataaaagt tcggaaaact tgacggttgt acggcacgac   7740
aaatcgatgt agtggtatgt ttttccagca gagaccgtgt gcggtctctt aggttcgcta   7800
tactgtggct ggaaactggt tacctgtgaa gatggctaac tatcctgttc tgtcctggaa   7860
aaacttttgg cgtcgtaggt ggactttgca gtatgcgggt tagtgaagtt atgtcattta   7920
tttacgttta cgatctcgta ttacaaaccg cggagaggat gataccgttc ggccccatga   7980
gttattttta ttcttccggt aggaggcatg aagcctctga taatgctcat ctgctttgct   8040
gtgatattat tgcagcttgg agtgactaaa gtgtgtcagc ataatgaagt gcaactgggc   8100
aatgagtgct gccctccgtg tggttcggga caaagagtta ctaaagtatg cacggattat   8160
accagtgtaa cgtgtacccc ttgccccaac ggcacgtatg tatcgggact ttacaactgt   8220
accgattgca ctcaatgtaa cgtcactcag gtcatgattc gtaactgcac ttccaccaat   8280
aataccgtat gcgcacctaa gaaccatacg tactttttcca ctccaggcgt ccaacatcac   8340
aaacaacgac agcaaaatca taccgcacat ataaccgtca acaaggaaa aagcggtcgt    8400
catactctag cctggttgtc tctctttatc tttcttgtgg gtatcatact tttaattctc   8460
tatcttatag ccgcctatcg gagtgagaga tgccaacagt gttgctcaat cggcaaaatt   8520
ttctaccgca ccctgtaagc ttcctgttgt tgttttttaca tcacggtacg atgaagtcac   8580
acagataatt acagatgagc tgttcatatt tttattatt ttttccaatt cctgcactaa    8640
aaaaagaagc actttacgga accgtgtctg agtatctgtg gggaatttag gtactttttg   8700
ccgacgtcag gaaaaataag tgtcgcctac ataagagccc ggtgctatcg tgctgtcact   8760
ctttcttgtt gccttcgatg tacggcgtcc tggctcatta ctactccttc atcagtagcc   8820
ccagcgttat ggttaatttt aagcatcata acgccgtgca gctgttatgt gcacggaccc   8880
gagacgcact gccggatggg aacgtttaac ccatcatgcg tcgtatcacg cgaactacgg   8940
ggcatacgcc gtgttgatgg ctacatcgca aagaaagtcc ctagtgttac atcgatacag   9000
tgccgtgaca gccgtggccc tgcagctcat gcctgttgag atcgtccgca agctagatca   9060
gtcggactgg gtgcggggtg cctggatcgt gtcagagact tttccaacta gcgaccccaa   9120
aggagtttgg agcgacgatg actcctcgat gggtggaagt gatgattgat gatgagaacc   9180
tgacaagaaa gacgagagag aaatttagag ctgtcattgt agaattagtc tagattcctg   9240
ataataaaca gtatcgattt tgaaacctaa ttgacgtgtg atcgattttt aaacctctgt   9300
gttgtgtgat tgattggtat gtgggggggat ccgatttcaa aggggggtac ttatcgggaa   9360
ttgatgtgtc atggacgcag ttttgagcga ttttccggga ataccggata ttacgaatta   9420
ctggtagtga cgtagataat aaaattataa tgcgattaat ttttggtgcg ttgattattt   9480
ttttagcata tgtgtatcat tatgaggtga atggaacaga attacgctgc agatgtcttc   9540
atagaaaatg gccgcctaat aaaattatat tgggtaatta ttggcttcat cgcgatccca   9600
gagggcccgg atgcgataaa aatgaacatt tattgtatcc agacggaagg aaaccgcctg   9660
gacctggagt atgtttatcg cccgatcacc tcttctcaaa atggttagac aaacacaacg   9720
ataataggtg gtataatgtt aacataacga aatcaccagg accgagacga ataaatataa   9780
ccttgatagg tgttagagga taatatttaa tgtatgtttt caaacagaca agttcgttaa   9840
aacaaaatat tacagtatgt gtttaatatg gtgctaacat ggttgcacca tccggtttca   9900
aactcgcata tcaatctgtt atcggtacga cacctgtcat taatcgcata tatgttactt   9960
accatatgtc cctagccgt ccatgttta gaactagaag attacgacag gcgctgccgt    10020
```

```
tgcaacaacc aaattctgtt gaatacccctg ccggtcggaa ccgaattgct taagccaatc   10080
gcagcgagcg aaagctgcaa tcgtcaggaa gtgctggcta ttttaaagga caagggaacc   10140
aagtgtctca atcctaacgc gcaagccgtg cgtcgtcaca tcaaccggct attttttcgg   10200
ttaatcttag acgaggaaca acgcatttac gacgtagtgt ctaccaatat tgagttcggt   10260
gcctggccag tccctacggc ctacaaagcc tttctttgga aatacgccaa gagactgaac   10320
taccaccact tcagactgcg ctggtgatca tgtccctatt ttaccgtgcg gtagctctgg   10380
gcacgctaag cgctttggtg tggtacagca ctagcatcct cgcagagatt aacgaaaatt   10440
cctgctcctc atcttctgcg gatcacgaag actgcgagga accggacgag atcgttcgcg   10500
aagagcaaga ctatcgggct ctgctggcct tttccctagt gatttgcggt acgctcctcg   10560
tcacttgtgt gatctgagac gtcatgctgg tagcgtttat gagtcgggcg gtggccgaca   10620
cgccgcattt cctaacccgc gcagcatgtt gcgcttgctg ttcacgctcg tcctgctggc   10680
cctccacggg cagtctgtcg gcgctagccg cgactatgtg catgttcggc tactgagcta   10740
ccgaggcgac cccctggtct tcaagcacac tttctcgggt gtgcgtcgac ccttcaccga   10800
gctaggctgg gctgcgtgtc gcgactggga cagtatgcat tgcacaccct tctggtctac   10860
cgatctggag cagatgaccg actcggtgcg gcgttacagc acggtgagcc ccggcaagga   10920
agtgacgctt cagcttcacg ggaaccaaac cgtacagccg tcgtttctaa gctttacgtg   10980
ccgcctgcag ctagaacccg tggtggaaaa tgttggcctc tacgtggcct acgtggtcaa   11040
cgacggcgaa cgcccacaac agttttttac accgcaggta gacgtggtac gctttgctct   11100
atatctagaa acactctccc ggatcgtgga accgttagaa tcaggtcgcc tggcagtgga   11160
atttgatacg cctgacctag ctctggcgcc cgatttagta agcagcctct tcgtggccgg   11220
acacggcgag accgactttt acatgaactg gacgctgcgt cgcagtcaga cccactacct   11280
ggaggagatg gccttacagg tggagattct aaaaccccgc ggcgtacgtc accgcgctat   11340
tatccaccat ccgaagctac agccgggcgt tggcctgtgg atagatttct gcgtgtaccg   11400
ctacaacgcg cgcctgaccc gcggctacgt acgatacacc ctgtcaccga aagcgcgctt   11460
gcccgcaaaa gcagagggtt ggctggtgtc actagacaga ttcatcgtgc agtacctcaa   11520
cacattgctg attacaatga tggcggcgat atgggctcgc gttttgataa cctacctggt   11580
gtcgcggcgt cggtagaggc ttgcggaaac cacgtcctcg tcacacgtcg ttcgcggaca   11640
tagcaagaaa tccacgtcgc cacatctcga gaatgccggc cttgcggggt ccccttcgcg   11700
caacattcct ggccctggtc gcgttcgggt tgctgcttca gatagacctc agcgacgcta   11760
cgaatgtgac cagcagcaca aaagtcccta ctagcaccag caacagaaat aacgtcgaca   11820
acgccacgag tagcggaccc acaaccggga tcaaacatgac caccacccac gagtcttccg   11880
ttcacaacgt gcgcaataac gagatcatga aagtgctggc tatcctcttc tacatcgtga   11940
caggcacctc cattttcagc ttcatagcgg tactgatcgg ggtagtttac tcctcgtgtt   12000
gcaagcaccc gggccgcttt cgtttcgccg acgaagaggc cgtcaacctg ttggacgaca   12060
cggacgacag tggcggcagc agcccgtttg gcagcggttc ccgacgaggt tctcagatcc   12120
ccgccggatt ttgttcctcg agcccttatc agcggttgga aactcgggac tgggacgagg   12180
aggaggaggc gtccgcggcc cgcgagcgca tgaaacatga tcctgagaac gtcatctatt   12240
tcagaaagga tggcaacttg gacacgtcgt tcgtgaatcc caattatggg agaggctcgc   12300
cttttgacca tcgaatctcac ctctcggaca atgaggagga ccccatcagg tactacgttt   12360
cggtgtacga tgaactgacc gcctcggaaa tggaagaacc ttcgaacagc accagctggc   12420
```

```
agattcccaa actaatgaaa gttgccatgc aacccgtctc gctcagagat cccgagtacg   12480
actaggcttt ttttttttgtc tttcggttcc aactcttttcc ccgccccatc acctcgcctg   12540
tactatgtgt atgatgtctc ataataaagc tttctttctc agtctgcaac atgcagctgt   12600
gtcgggtgtg gctgtctgtt tgtctgtgcg ccgtggtgct gggtcagtgc cagcgggaaa   12660
ccgcggaaaa aaacgattat taccgagtac cgcattactg ggacgcgtgc tctcgcgcgc   12720
tgcccgacca aacccgttac aagtatgtgg aacagctcgt ggacctcacg ttgaactacc   12780
actacgatgc gagccacggc ttggacaact ttgacgtgct caagaggtga gggtacgcgc   12840
taaaggtgca tgacaacggg aaggtaaggg cgaacgggta acggctaagt aaccgcatgg   12900
ggtatgaaat gacgtttgga acctgtgctt gcagaatcaa cgtgaccgag gtgtcgttgc   12960
tcatcagcga ctttagacgt cagaaccgtc gcggcggcac caacaaaagg accacgttca   13020
acgccgccgg ttcgctggcg ccacacgccc ggagcctcga gttcagcgtg cggctctttg   13080
ccaactagcc tgcgtcacgg gaaataatat gctgcggctt ctgcttcgtc accactttca   13140
ctgcctgctt ctgtgcgcgg tttgggcaac gccctgtctg gcgtctccgt ggtcgacgct   13200
aacggcaaac cagaatccgt ccccgccatg gtctaaactg acgtattcca aaccgcatga   13260
cgcggcgacg ttttactgtc cttttctcta tccctcgccc ccacggtccc ccttgcaatt   13320
ctcggggttc cagcaggtat caacgggtcc cgagtgtcgc aacgagaccc tgtatctgct   13380
gtacaaccgg gaaggccaga ccttggtgga gagaagctcc acctgggtga aaaaggtgat   13440
ctggtatctg agcggtcgca accagaccat cctccaacgg atgccccaaa cggcttcgaa   13500
accgagcgac ggaaacgtgc agatcagcgt ggaagacgcc aagatttttg gagcgcacat   13560
ggtgcccaag cagaccaagc tgctacgctt cgtcgtcaac gatggcacgc gttatcagat   13620
gtgtgtgatg aagctggaga gctgggccca cgtcttccgg gactacagcg tgtcttttca   13680
ggtgcgattg acgttcaccg aggccaataa ccagacttac accttctgta cccatccccaa   13740 tctcatcatt tgagcccgtc gcgcgcgcag ggaattttga aaaccgcgcg tcatgagtcc   13800
caaagacctg acgccgttct tgacgacgtt gtggctgcta ttgggtcaca gccgcgtgcc   13860
gcgggtgcgc gcagaagaat gttgcgaatt cataaacgtc aaccaccgcc cggaacgctg   13920
ttacgatttc aaaatgtgca atcgcttcac cgtcgcgtac gtattttcat gattgtctgc   13980
gttctgtggt gcgtctggat ttgtctctcg acgtttctga tagccatgtt ccatcgacga   14040
tcctcgggaa tgccagagta gattttcatg aatccacagg ctgcggtgtc cggacggcga   14100
agtctgctac agtcccgaga aaacggctga gattcgcggg atcgtcacca ccatgaccca   14160
ttcattgaca cgccaggtcg tacacaacaa actgacgagc tgcaactaca atccgtaagt   14220
ctcttcctcg agggccttac agcctatggg agagtaagac agagagggac aaaacatcat   14280
taaaaaaaaa agtctaattt cacgttttgt acccccttc ccctccgtgt tgtagcccat   14340
cggccgcggc gatctcctag taacactcgt ccgacacttc caccatctcc agctcggccg   14400
gcggttcggc atcctctacc agcggcgtcg tctcatcttt gccgcagcag cggacgcaca   14460
ccttctccag gcagaacgcc accagctgcc gccgaacgta ccacaggtac acgtgcagac   14520
ctgcgaacag gactacggag gtcatgacca ccacgacgca cacgggaatc cagggatcga   14580
gattgttgct ggaactcatg gctatcgcca ccgacgtgcc cgcgtctgtc tcaccgccgc   14640
tcgcccgatg tcgcgcggct tgttatacgc tagcccgtcg ccgcctcggg gcacggtgcc   14700
ctcctaccca cgtaacttcc tccgtgactt aaagtcgcgt gtggtagatc tcctgctccg   14760
```

```
tggacgaacc gtccggcagg atagcggtta aggattcggt gctaaggccg tgtcgccaac    14820
gtcgaatgct acgttgcaac agcttcgacg gacggccatc ccctctctca tcgcaataat    14880
aaaacaccag cagcgcgcac gacgcgatca cggtgacacc catgattaga cccacgcaga    14940
tagccagccc cgctagcgta tctagcgcca tcccgttcgc tcccgttgtc tcctgagcga    15000
agcaacttct cggtccccgt tttcaacagt ttttgtttcc ttctccgcga ctagatgtta    15060
acgcccgcgg tctttccggc cgtgctctac ctcctggcgc ttgtcgtctg ggttgagatg    15120
ttctgcctcg tcgccgtagc cgtcgtcgag cgcgagatcg cctgggcgct gctgctgcgg    15180
atgctggtcg ttggcctgat ggtggaagtc ggcgccgccg ccgcttggac cttcgtgcgt    15240
tgtcttgcct atcagcgctc cttccccgtg cttacggcct tccctgaaa cccacgttaa     15300
ccgaccgtcc caaaaacgcc ggtgttaaca caggaaaaaa agaaaccacg caggaaccgc    15360
gcaggaacca cgcggaacat gggacactat ctggaaatcc tgttcaacgt catcgtcttc    15420
actctgctgc tcggcgtcat ggtcagtatc gtcgcttggt acttcacgtg aaccaccgtc    15480
gtcccggttt aaaaaccatc atcgacggcc gttataaagc cacccggaca cgcgccgcgg    15540
cacttgccta cggcgctgct tcagggaaac tcctcttcct tctgctcttc ctccttcacc    15600
gcagggatcg tttccctcga ccagggactc gccgaagcaa ccgccggagc aacctggagg    15660
agtcgcggca tgacgcgcc caagtgtgtc accaccagta cttatctggt caagaccaag     15720
gaacagccct ggtggcccga caacgccatc aggagatggt ggatcagtgt tgctatcgtc    15780
atcttcatcg gagtctgtct ggtggccctg atgtacttta cgcagcagca ggcacgcagc    15840
gggagcagca gcggctagac aagtctctgg cggctacagc tccaagcgcc gtagccgggc    15900
cgcctgccga tcgcgacgtc gtggaccatc gaacagagac tcacgcgtac gagaccccga    15960
ggtacgccac gcggtgccta acgcggtata ccacacccgt acggtctgca gtgcggcgta    16020
caacgtgtgg aaaacgcgtt gcgtcgcaga gtccgccacg ttcctgtctt gtcgctcccc    16080
aatcgtctcc cgcacacccc ccgcgacacc cagagggcgg gtgagccaag tattcttaag    16140
gccgttcttt gttccatagc ccataaattg ttgattccgg agctcgttgg cgcggaaata    16200
gccggataag gggagcaaca accgttggcg aaagccgtcc cgctcattca gtccgggttt    16260
cgcgtccagt cggacgtgtg accgttgggc aacggaacgg cgtttcactg ccaaaatcgt    16320
atcgggtagt gtacgagacg tcggcggtgc agaatgcgac tcgcggcgta gctcgccgtc    16380
gctatgcggc tcgtcgccgt gtggcgcggc ctggccggct gtctgcgtcc agatctgttg    16440
gccttttggt tcctctggct gctgctgcgt gtgtgctttg gtagacgcgg tggcagtttg    16500
cggtctgcgg taagtgagga gtgtcgccga gcaaacgcact tgcggcgcgt gggcggcacg    16560
cgtgtcattg taggttcgtt gccagatggc aagtgctgtc aacagcaggc gttgtgggcg    16620
gtcggtgtat ttttgtgggt tgcggtgaga gtcggcactc ggtgttttgt gagtcatctc    16680
aactatctgt gttgctttga gcagcgtcca gaacagcgac gcgactttgg ggatggcctc    16740
gtgctcacct ccgcggagag cgccgccgga cctgctcgtc agcagcgagc tacgcagacg    16800
gaatatctgt aggagagtta cgtgtgtcac aggagagcgc gggtctccgg cggtaacgac    16860
ggcggtgtcg tcgacacgtg tgcggcctgt tgtgctctgc ggaaaagtgc cggtctcgga    16920
gaccgtggac gaaaaagaga acgcagcagc taccgctggc ggcggcggcg ttaatgcagc    16980
cgttgatgtt cgacgttgtg agcactcgga aacagcggtg aggcagaagg tcgattctcc    17040
agggaacgac agtcgatgcg tggtagccgc agcaggtgag gttggggcgg acaacgtgtt    17100
gcggattgtg gcgagaacgt cgtcctcccc ttcttcaccg ccccacccac cctcggttgg    17160
```

-continued

```
tgtttcttttt tcttgtgtc ctgcagatag ttccacggac agcgacggca agtccataat    17220
cagcggtgtg caagtggtgg aacacgacga agatatcatc gcgccgcaga gtttgtggtg    17280
cacggcgttc aaggaagccc tctgggatgt ggctctgttg gaagtgccgc gttgggcgtg    17340
gcagggctgg aagaggtggc gcaacagcga ggccgggcgt cgatggagtg ctgggtctgc    17400
gtcggcttcc agcttgtctg acttggcggg cgaggccgtt ggagaattgg tgggatcggt    17460
cgtcgcgtac gtgatccttg aacgtctgtg gttggcagcc agaggttggg tgtgcgaaac    17520
aggtgtggaa gccgaggagg ccatgtcgcg cggcgacag cgcatgctgt ggcgtattgt     17580
tctctcgtgg aggcgacggc gaatgcagca gacggtgttc gatggagatg gcgtgcgggg    17640
aagaaagcgc cgtgttgtga gcagacgacg taggatgcgg gacgtcggag cacatgggcc    17700
atgtgtggtg gcagatggcg gtgtccgctg gtgtctgctg cggcagtgca tagacgaagc    17760
aacatgtcgc tgtgaagaga tagagtgtga gcatagctgc atgcagcgtt gcgtgtataa    17820
gcggggggga ttaagacgtt aataaagaat agcggcggtt ctgatagggc gaccgctgaa    17880
gtgagctgcg tgtgcgtgtg gtttgtggag tccccgccgc ccccggtccc gtgtccgccg    17940
gcaaagcccc ccggntccgc acactcctgg ccgcgcaacc ctcgtcgctg caaaagcccc    18000
ccgtccccgc acaccccgc gaccgccggt cccgcgagtc cccgtccccg ccgcaaaagg      18060
cccccgtcct cgccgcaaac accccgtca ccccgtccc tcagnccggg tccgcgagtc      18120
cccgttccca gcgtaatccc cgtacccgca acgnccccggn cccaccgtcg tcccgcacac    18180 ccccccgtccc ccagcccggt gcccagcgtg cgaaaaaagc tccgtccctc acacccgcag    18240
aaagatccct cagcgcggtg aaaccccgtc cccagcgccg tgccgctgac aaagaccatg    18300
ggacgacacg cacaggca                                                   18318
```

<210> SEQ ID NO 2
<211> LENGTH: 214
<212> TYPE: PRT
<213> ORGANISM: Human cytomegalovirus

<400> SEQUENCE: 2

```
Met Leu Arg Leu Leu Arg His His Phe His Cys Leu Leu Leu Cys
1               5                   10                  15

Ala Val Trp Ala Thr Pro Cys Leu Ala Ser Pro Trp Ser Thr Leu Thr
                20                  25                  30

Ala Asn Gln Asn Pro Ser Pro Pro Trp Ser Lys Leu Thr Tyr Ser Lys
                35                  40                  45

Pro His Asp Ala Ala Thr Phe Tyr Cys Pro Phe Leu Tyr Pro Ser Pro
        50                  55                  60

Pro Arg Ser Pro Leu Gln Phe Ser Gly Phe Gln Gln Val Ser Thr Gly
65                  70                  75                  80

Pro Glu Cys Arg Asn Glu Thr Leu Tyr Leu Leu Tyr Asn Arg Glu Gly
                85                  90                  95

Gln Thr Leu Val Glu Arg Ser Ser Thr Trp Val Lys Lys Val Ile Trp
            100                 105                 110

Tyr Leu Ser Gly Arg Asn Gln Thr Ile Leu Gln Arg Met Pro Gln Thr
        115                 120                 125

Ala Ser Lys Pro Ser Asp Gly Asn Val Gln Ile Ser Val Glu Asp Ala
    130                 135                 140

Lys Ile Phe Gly Ala His Met Val Pro Lys Gln Thr Lys Leu Leu Arg
145                 150                 155                 160
```

```
Phe Val Val Asn Asp Gly Thr Arg Tyr Gln Met Cys Val Met Lys Leu
                165                 170                 175

Glu Ser Trp Ala His Val Phe Arg Asp Tyr Ser Val Ser Phe Gln Val
            180                 185                 190

Arg Leu Thr Phe Thr Glu Ala Asn Asn Gln Thr Tyr Thr Phe Cys Thr
        195                 200                 205

His Pro Asn Leu Ile Ile
    210

<210> SEQ ID NO 3
<211> LENGTH: 270
<212> TYPE: PRT
<213> ORGANISM: Human cytomegalovirus

<400> SEQUENCE: 3

Met Pro Ala Leu Arg Gly Pro Leu Arg Ala Thr Phe Leu Ala Leu Val
1               5                   10                  15

Ala Phe Gly Leu Leu Leu Gln Ile Asp Leu Ser Asp Ala Thr Asn Val
            20                  25                  30

Thr Ser Ser Thr Lys Val Pro Thr Ser Thr Ser Asn Arg Asn Asn Val
        35                  40                  45

Asp Asn Ala Thr Ser Ser Gly Pro Thr Thr Gly Ile Asn Met Thr Thr
50                  55                  60

Thr His Glu Ser Ser Val His Asn Val Arg Asn Asn Glu Ile Met Lys
65                  70                  75                  80

Val Leu Ala Ile Leu Phe Tyr Ile Val Thr Gly Thr Ser Ile Phe Ser
                85                  90                  95

Phe Ile Ala Val Leu Ile Ala Val Val Tyr Ser Ser Cys Cys Lys His
            100                 105                 110

Pro Gly Arg Phe Arg Phe Ala Asp Glu Glu Ala Val Asn Leu Leu Asp
        115                 120                 125

Asp Thr Asp Asp Ser Gly Gly Ser Ser Pro Phe Gly Ser Gly Ser Arg
    130                 135                 140

Arg Gly Ser Gln Ile Pro Ala Gly Phe Cys Ser Ser Ser Pro Tyr Gln
145                 150                 155                 160

Arg Leu Glu Thr Arg Asp Trp Asp Glu Glu Glu Ala Ser Ala Ala
                165                 170                 175

Arg Glu Arg Met Lys His Asp Pro Glu Asn Val Ile Tyr Phe Arg Lys
            180                 185                 190

Asp Gly Asn Leu Asp Thr Ser Phe Val Asn Pro Asn Tyr Gly Arg Gly
        195                 200                 205

Ser Pro Leu Thr Ile Glu Ser His Leu Ser Asp Asn Glu Glu Asp Pro
    210                 215                 220

Ile Arg Tyr Tyr Val Ser Val Tyr Asp Glu Leu Thr Ala Ser Glu Met
225                 230                 235                 240

Glu Glu Pro Ser Asn Ser Thr Ser Trp Gln Ile Pro Lys Leu Met Lys
                245                 250                 255

Val Ala Met Gln Pro Val Ser Leu Arg Asp Pro Glu Tyr Asp
            260                 265                 270

<210> SEQ ID NO 4
<211> LENGTH: 257
<212> TYPE: PRT
<213> ORGANISM: Human cytomegalovirus

<400> SEQUENCE: 4
```

```
Met Gly Cys Asp Val His Asp Pro Ser Trp Gln Cys Gln Trp Gly Val
1               5                  10                 15

Pro Thr Ile Ile Val Ala Trp Ile Thr Cys Ala Ala Leu Gly Ile Trp
            20                 25                 30

Cys Leu Ala Gly Ser Ser Ala Asp Val Ser Ser Gly Pro Gly Ile Ala
             35                 40                 45

Ala Val Val Gly Cys Ser Val Phe Met Ile Phe Leu Cys Ala Tyr Leu
         50                 55                 60

Ile Arg Tyr Arg Glu Phe Phe Lys Asp Ser Val Ile Asp Leu Leu Thr
65                  70                 75                 80

Cys Arg Trp Val Arg Tyr Cys Ser Cys Ser Cys Lys Cys Ser Cys Lys
                85                 90                 95

Cys Ile Ser Gly Pro Cys Ser Arg Cys Cys Ser Ala Cys Tyr Lys Glu
             100                105                110

Thr Met Ile Tyr Asp Met Val Gln Tyr Gly His Arg Arg Arg Pro Gly
         115                120                125

His Gly Asp Asp Pro Asp Arg Val Ile Cys Glu Ile Val Glu Ser Pro
     130                135                140

Pro Val Ser Ala Pro Thr Val Ser Val Pro Pro Ser Glu Glu Ser
145                 150                155                160

His Gln Pro Val Ile Pro Pro Gln Pro Ala Pro Thr Ser Glu Pro
                165                170                175

Lys Pro Lys Lys Gly Arg Ala Lys Asp Lys Pro Lys Gly Arg Pro Lys
                180                185                190

Asp Lys Pro Pro Cys Glu Pro Thr Val Ser Ser Gln Pro Ser Gln
             195                200                205

Pro Thr Ala Met Pro Gly Gly Pro Pro Asp Ala Pro Pro Ala Met
         210                215                220

Pro Gln Met Pro Pro Gly Val Ala Glu Ala Val Gln Ala Ala Val Gln
225                 230                235                240

Ala Ala Val Ala Ala Ala Leu Gln Gln Gln Gln His Gln Thr Gly
                245                250                255

Thr

<210> SEQ ID NO 5
<211> LENGTH: 175
<212> TYPE: PRT
<213> ORGANISM: Human cytomegalovirus

<400> SEQUENCE: 5

Met Ala Arg Thr Arg Glu Ala Ser Pro Val Pro Pro Arg Ser Pro Met
1               5                  10                 15

Pro Ser His Ile His Thr Met Ile Phe Ser Pro Ala Trp Asn Leu Lys
            20                 25                 30

Leu Arg Val Gly Lys Gly Arg Cys Thr Asp Ile Tyr Ala Leu Asp Phe
             35                 40                 45

Trp Lys Arg His Phe Leu Ala Arg Asn Val Phe Ile Val Gln Thr Leu
         50                 55                 60

Arg Lys Glu Met Cys Ala Lys Ser Glu Asn Ser Leu Ser His Arg Gly
65                  70                 75                 80

Arg Val Thr Phe Arg Ser Asp Ala Ala Ala Val Val Glu Pro Arg
                85                 90                 95

Pro Arg Pro Pro Ala Arg Gln Leu Val Pro Arg Pro Arg Arg Val
         100                105                110
```

```
Ala Ser Ala Ala Trp Arg Gly Glu Ala Arg Arg Ala Asp Arg Arg Ala
        115                 120                 125

Leu Pro Ser Ala Ala Thr Val Val Asn Ser Pro Ser Val Arg Thr
130                 135                 140

Glu Val Cys Leu Ser Val Tyr Pro Ser Val Tyr Leu Ser Pro Tyr Leu
145                 150                 155                 160

Ser Ser Val Trp Val Pro Met Ser Val Leu Ala Ala Val Gly
                165                 170                 175

<210> SEQ ID NO 6
<211> LENGTH: 328
<212> TYPE: PRT
<213> ORGANISM: Human cytomegalovirus

<400> SEQUENCE: 6

Met Ser Val His Arg Pro Phe Pro Thr Arg Ser Leu Arg Phe Gln Ala
1               5                   10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
        35                  40                  45

Arg Arg Gly Arg Lys Arg Ser Asp Glu Thr Ser Ser Arg Gly Arg Leu
    50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
                85                  90                  95

Met Arg Val Asp Thr His Pro Thr Pro Gln Val Pro Arg Cys Thr
            100                 105                 110

Ser Leu Tyr Ile Gly Glu Asp Gly Leu Pro Ile Asp Lys Pro Glu Phe
        115                 120                 125

Pro Pro Ala Arg Phe Glu Ile Pro Asp Val Ser Thr Pro Gly Thr Pro
    130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Ser
                165                 170                 175

Trp Lys Pro Pro Pro Pro Gly Arg Lys Lys Arg Pro Pro Thr Pro
            180                 185                 190

Pro Val Arg Ala Pro Thr Thr Arg Leu Ser Ser His Arg Pro Pro Thr
    195                 200                 205

Pro Ile Pro Ala Pro Arg Lys Asn Leu Ser Thr Pro Thr Lys Lys
210                 215                 220

Thr Pro Pro Pro Thr Lys Pro Lys Pro Val Gly Trp Thr Pro Pro Val
225                 230                 235                 240

Thr Pro Arg Pro Phe Pro Lys Thr Pro Thr Pro Gln Lys Pro Pro Arg
                245                 250                 255

Asn Pro Arg Leu Pro Arg Thr Val Gly Leu Glu Asn Leu Ser Lys Val
            260                 265                 270

Gly Leu Ser Cys Pro Cys Pro Arg Pro Arg Thr Pro Thr Glu Pro Thr
        275                 280                 285

Thr Leu Pro Ile Val Ser Val Ser Glu Leu Ala Pro Pro Arg Trp
    290                 295                 300

Ser Asp Ile Glu Glu Leu Leu Glu Gln Ala Val Gln Ser Val Met Lys
305                 310                 315                 320
```

Asp Ala Glu Ser Met Gln Met Thr
            325

<210> SEQ ID NO 7
<211> LENGTH: 240
<212> TYPE: PRT
<213> ORGANISM: Human cytomegalovirus

<400> SEQUENCE: 7

Met Ser Val Lys Gly Val Glu Met Pro Glu Met Thr Trp Asp Leu Asp
1               5                   10                  15

Val Arg Asn Lys Trp Arg Arg Lys Ala Leu Ser Arg Ile His Arg
                20                  25                  30

Phe Trp Glu Cys Arg Leu Arg Val Trp Trp Leu Ser Asp Ala Gly Val
            35                  40                  45

Arg Glu Thr Asp Pro Pro Arg Pro Arg Arg Pro Thr Trp Met Thr
        50                  55                  60

Ala Val Phe His Val Ile Cys Ala Val Leu Leu Thr Leu Met Ile Met
65                  70                  75                  80

Ala Ile Gly Ala Leu Ile Ala Tyr Leu Arg Tyr Tyr His Gln Asp Ser
                85                  90                  95

Trp Arg Asp Met Leu His Asp Leu Phe Cys Gly Cys His Tyr Pro Glu
            100                 105                 110

Lys Cys Arg Arg His His Glu Arg Gln Arg Arg Arg Gln Ala Met
        115                 120                 125

Asp Val Pro Asp Pro Glu Leu Gly Asp Pro Ala Arg Arg Pro Leu Asn
130                 135                 140

Gly Ala Met Tyr Tyr Gly Ser Gly Cys Arg Phe Asp Thr Val Glu Met
145                 150                 155                 160

Val Asp Glu Thr Arg Pro Ala Pro Pro Ala Leu Ser Ser Pro Glu Thr
                165                 170                 175

Gly Asp Asp Ser Asn Asp Asp Ala Val Ala Gly Gly Ala Gly Gly
            180                 185                 190

Val Thr Ser Pro Ala Thr Arg Thr Thr Ser Pro Asn Ala Leu Leu Pro
        195                 200                 205

Glu Trp Met Asp Ala Val His Val Ala Val Gln Ala Ala Val Gln Ala
    210                 215                 220

Thr Val Gln Val Ser Gly Pro Arg Glu Asn Ala Val Ser Pro Ala Thr
225                 230                 235                 240

<210> SEQ ID NO 8
<211> LENGTH: 96
<212> TYPE: PRT
<213> ORGANISM: Human cytomegalovirus

<400> SEQUENCE: 8

Met Ala Thr Ile Ser Thr Ser Ile Thr Pro Met Met Gly Asn Pro Thr
1               5                   10                  15

Phe Ser Gly Arg Ser Ser Met Val Thr Val Leu Cys Pro Asp Leu Arg
                20                  25                  30

Pro Ser Leu Ser Leu Leu Tyr Ser Thr Arg Ala Gly Thr Ala Pro Ser
            35                  40                  45

Thr Leu Leu Arg Ser Gly Arg Tyr Gly Val Leu Pro Arg Ala Thr Tyr
        50                  55                  60

Leu His Gly Arg Leu Asn Gly Gly Leu Asp Arg His Met His Arg Ile
65                  70                  75                  80

```
His Pro Phe Trp Gln Gln Cys Val Arg Arg Arg Thr Ser Arg Gly
                85                  90                  95

<210> SEQ ID NO 9
<211> LENGTH: 169
<212> TYPE: PRT
<213> ORGANISM: Human cytomegalovirus

<400> SEQUENCE: 9

Met Asp Asp Leu Pro Leu Asn Val Gly Leu Pro Ile Ile Gly Val Met
1               5                   10                  15

Leu Val Leu Ile Val Ala Ile Leu Cys Tyr Leu Ala Tyr His Trp His
                20                  25                  30

Asp Thr Phe Lys Leu Val Arg Met Phe Leu Ser Tyr Arg Trp Leu Ile
            35                  40                  45

Arg Cys Cys Glu Leu Tyr Gly Glu Tyr Glu Arg Arg Phe Ala Asp Leu
        50                  55                  60

Ser Ser Leu Gly Leu Gly Ala Val Arg Arg Glu Ser Asp Arg Arg Tyr
65                  70                  75                  80

Arg Phe Ser Glu Arg Pro Asp Glu Ile Leu Val Arg Trp Glu Glu Val
                85                  90                  95

Ser Ser Gln Cys Ser Tyr Ala Ser Ser Arg Ile Thr Asp Arg Arg Val
                100                 105                 110

Gly Ser Ser Ser Ser Ser Val His Val Ala Ser Gln Arg Asn Ser
            115                 120                 125

Val Pro Pro Asp Met Ala Val Thr Ala Pro Leu Thr Asp Val Asp
        130                 135                 140

Leu Leu Lys Pro Val Thr Gly Ser Ala Thr Gln Phe Thr Thr Val Ala
145                 150                 155                 160

Met Val His Tyr His Gln Glu Tyr Thr
                165

<210> SEQ ID NO 10
<211> LENGTH: 135
<212> TYPE: PRT
<213> ORGANISM: Human cytomegalovirus

<400> SEQUENCE: 10

Met Leu Trp Ile Leu Val Leu Phe Ala Leu Ala Ala Ser Ala Ser Glu
1               5                   10                  15

Thr Thr Thr Gly Thr Ser Ser Asn Ser Ser Gln Ser Thr Ser Ala Thr
                20                  25                  30

Ala Asn Thr Thr Val Ser Thr Cys Ile Asn Ala Ser Asn Gly Ser Ser
            35                  40                  45

Trp Thr Val Pro Gln Leu Ala Leu Leu Ala Ala Ser Gly Trp Thr Leu
        50                  55                  60

Ser Gly Leu Leu Leu Leu Phe Thr Cys Cys Phe Cys Cys Phe Trp Leu
65                  70                  75                  80

Val Arg Lys Ile Cys Ser Cys Cys Gly Asn Ser Ser Glu Ser Glu Ser
                85                  90                  95

Lys Thr Thr His Ala Tyr Thr Asn Ala Ala Phe Thr Ser Ser Asp Ala
                100                 105                 110

Thr Leu Pro Met Gly Thr Thr Gly Ser Tyr Thr Pro Gln Asp Gly
            115                 120                 125

Ser Phe Pro Pro Pro Arg
        130                 135
```

-continued

<210> SEQ ID NO 11
<211> LENGTH: 114
<212> TYPE: PRT
<213> ORGANISM: Human cytomegalovirus

<400> SEQUENCE: 11

```
Met Thr Pro Ala Gln Thr Asn Ala Thr Thr Val His Pro His Asp
1               5                   10                  15

Ala Lys Asn Gly Ser Gly Gly Ser Ala Leu Pro Thr Leu Val Val Phe
            20                  25                  30

Gly Phe Ile Val Thr Leu Leu Phe Leu Phe Met Leu Tyr Phe Trp
            35                  40                  45

Asn Asn Asp Val Phe Arg Lys Leu Leu Arg Ala Leu Gly Ser Ser Ala
        50                  55                  60

Val Ala Thr Ala Ser Thr Arg Gly Lys Thr Arg Ser Ser Thr Val Val
65                  70                  75                  80

His His Val Val Pro Arg Ala Thr Thr Arg Val Val Leu Thr Ala Cys
                85                  90                  95

His Arg Thr Phe Phe Tyr His Pro Arg Pro Met Ala Val Leu Thr Thr
            100                 105                 110

Arg His
```

<210> SEQ ID NO 12
<211> LENGTH: 425
<212> TYPE: PRT
<213> ORGANISM: Human cytomegalovirus

<400> SEQUENCE: 12

```
Met Arg Gln Val Ala Tyr Arg Arg Arg Glu Ser Ser Cys Ala Val
1               5                   10                  15

Leu Val His His Val Gly Arg Asp Gly Asp Gly Glu Gly Glu Ala Ala
            20                  25                  30

Lys Lys Thr Cys Lys Lys Thr Gly Arg Ser Val Ala Gly Ile Pro Gly
            35                  40                  45

Glu Lys Leu Arg Arg Thr Val Val Thr Thr Thr Pro Ala Arg Arg Leu
        50                  55                  60

Ser Gly Arg His Thr Glu Gln Glu Gln Ala Gly Met Arg Leu Cys Glu
65                  70                  75                  80

Lys Gly Lys Lys Arg Ile Ile Met Cys Arg Arg Glu Ser Leu Arg Thr
                85                  90                  95

Leu Pro Trp Leu Phe Trp Val Leu Leu Ser Cys Pro Arg Leu Leu Glu
            100                 105                 110

Tyr Ser Ser Ser Ser Phe Pro Phe Ala Thr Ala Asp Ile Ala Glu Lys
            115                 120                 125

Met Trp Ala Glu Asn Tyr Glu Thr Thr Ser Pro Ala Pro Val Leu Val
        130                 135                 140

Ala Glu Gly Glu Gln Val Thr Ile Pro Cys Thr Val Met Thr His Ser
145                 150                 155                 160

Trp Pro Met Val Ser Ile Arg Ala Arg Phe Cys Arg Ser His Asp Gly
                165                 170                 175

Ser Asp Glu Leu Ile Leu Asp Ala Val Lys Gly His Arg Leu Met Asn
            180                 185                 190

Gly Leu Gln Tyr Arg Leu Pro Tyr Ala Thr Trp Asn Phe Ser Gln Leu
            195                 200                 205
```

```
His Leu Gly Gln Ile Phe Ser Leu Thr Phe Asn Val Ser Met Asp Thr
    210                 215                 220

Ala Gly Met Tyr Glu Cys Val Leu Arg Asn Tyr Ser His Gly Leu Ile
225                 230                 235                 240

Met Gln Arg Phe Val Ile Leu Thr Gln Leu Glu Thr Leu Ser Arg Pro
                245                 250                 255

Asp Glu Pro Cys Cys Thr Pro Ala Leu Gly Arg Tyr Ser Leu Gly Asp
            260                 265                 270

Gln Ile Trp Ser Pro Thr Pro Trp Arg Leu Arg Asn His Asp Cys Gly
        275                 280                 285

Thr Tyr Arg Gly Phe Gln Arg Asn Tyr Phe Tyr Ile Gly Arg Ala Asp
    290                 295                 300

Ala Glu Asp Cys Trp Lys Pro Ala Cys Pro Asp Glu Glu Pro Asp Arg
305                 310                 315                 320

Cys Trp Thr Val Ile Gln Arg Tyr Arg Leu Pro Gly Asp Cys Tyr Arg
                325                 330                 335

Ser Gln Pro His Pro Pro Lys Phe Leu Pro Val Thr Pro Ala Pro Pro
            340                 345                 350

Ala Asp Ile Asp Thr Gly Met Ser Pro Trp Ala Thr Gly Ile Ala
        355                 360                 365

Ala Phe Leu Gly Phe Trp Ser Ile Phe Thr Val Cys Phe Leu Cys Tyr
    370                 375                 380

Leu Cys Tyr Leu Gln Cys Cys Gly Arg Trp Cys Pro Thr Pro Gly Arg
385                 390                 395                 400

Gly Arg Arg Gly Gly Glu Gly Tyr Arg Leu Pro Thr Tyr Asp Ser
                405                 410                 415

Tyr Pro Gly Val Arg Lys Met Lys Arg
            420                 425

<210> SEQ ID NO 13
<211> LENGTH: 306
<212> TYPE: PRT
<213> ORGANISM: Human cytomegalovirus

<400> SEQUENCE: 13

Met Arg Ile Glu Trp Val Trp Trp Leu Phe Gly Tyr Phe Val Ser Ser
1               5                   10                  15

Val Gly Ser Glu Arg Ser Leu Ser Tyr Arg Tyr His Leu Glu Ser Asn
                20                  25                  30

Ser Ser Thr Asn Val Val Cys Asn Gly Asn Ile Ser Val Phe Val Asn
            35                  40                  45

Gly Thr Leu Gly Val Arg Tyr Asn Ile Thr Val Gly Ile Ser Ser Ser
        50                  55                  60

Leu Leu Ile Gly His Leu Thr Ile Gln Val Leu Glu Ser Trp Phe Thr
65                  70                  75                  80

Pro Trp Val Gln Asn Lys Ser Tyr Asn Lys Gln Pro Leu Gly Asp Thr
                85                  90                  95

Glu Thr Leu Tyr Asn Ile Asp Ser Glu Asn Ile His Arg Val Ser Gln
            100                 105                 110

Tyr Phe His Thr Arg Trp Ile Lys Ser Leu Gln Glu Asn His Thr Cys
        115                 120                 125

Asp Leu Thr Asn Ser Thr Pro Thr Tyr Thr Tyr Gln Val Asn Val Asn
    130                 135                 140

Asn Thr Asn Tyr Leu Thr Leu Ser Ser Gly Trp Gln Asp Arg Leu
145                 150                 155                 160
```

```
Asn Tyr Thr Val Ile Asn Ser Thr His Phe Asn Leu Thr Glu Ser Asn
                165                 170                 175

Ile Thr Ser Ile Gln Lys Tyr Leu Asn Thr Thr Cys Ile Glu Arg Leu
            180                 185                 190

Arg Asn Tyr Thr Leu Glu Ser Val Tyr Thr Thr Val Pro Gln Asn
        195                 200                 205

Ile Thr Thr Ser Gln His Ala Thr Thr Thr Met His Thr Ile Pro Pro
    210                 215                 220

Asn Thr Ile Thr Ile Gln Asn Thr Thr Gln Ser His Thr Val Gln Thr
225                 230                 235                 240

Pro Ser Phe Asn Asp Thr His Asn Val Thr Lys His Thr Leu Asn Ile
                245                 250                 255

Ser Tyr Val Leu Ser Gln Lys Thr Asn Asn Thr Thr Ser Pro Trp Ile
            260                 265                 270

Tyr Ala Ile Pro Met Gly Ala Thr Ala Thr Ile Gly Ala Gly Leu Tyr
        275                 280                 285

Ile Gly Lys His Phe Thr Pro Val Lys Phe Val Tyr Glu Val Trp Arg
    290                 295                 300

Gly Gln
305

<210> SEQ ID NO 14
<211> LENGTH: 92
<212> TYPE: PRT
<213> ORGANISM: Human cytomegalovirus

<400> SEQUENCE: 14

Met Ala Arg Ser Val Lys Thr Ile Arg Ile Gln His Ile Tyr Ser Pro
1               5                   10                  15

Arg Ser Ser Asn Thr Leu Gln His Met Ser Lys Lys Gln Glu Ser Ile
            20                  25                  30

Ala Thr Ile Thr Phe Gly Arg Ile Thr Cys Cys His Pro Leu Ala Ser
        35                  40                  45

Ile Asn Leu Met Phe Asn Gly Ser Cys Thr Val Thr Val Lys Ile Ser
    50                  55                  60

Met Gly Ile Asn Gly Ser Thr Asn Val His Gln Leu Val Ile Val Leu
65                  70                  75                  80

His Leu Gly Asn Arg Cys Gln Pro Trp Arg Gln Val
                85                  90

<210> SEQ ID NO 15
<211> LENGTH: 176
<212> TYPE: PRT
<213> ORGANISM: Human cytomegalovirus

<400> SEQUENCE: 15

Met Lys Pro Leu Ile Met Leu Ile Cys Phe Ala Val Ile Leu Leu Gln
1               5                   10                  15

Leu Gly Val Thr Lys Val Cys Gln His Asn Glu Val Gln Leu Gly Asn
            20                  25                  30

Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
    50                  55                  60

Val Ser Gly Leu Tyr Asn Cys Thr Asp Cys Thr Gln Cys Asn Val Thr
65                  70                  75                  80
```

```
Gln Val Met Ile Arg Asn Cys Thr Ser Thr Asn Asn Thr Val Cys Ala
                85                  90                  95

Pro Lys Asn His Thr Tyr Phe Ser Thr Pro Gly Val Gln His His Lys
            100                 105                 110

Gln Arg Gln Gln Asn His Thr Ala His Ile Thr Val Lys Gln Gly Lys
        115                 120                 125

Ser Gly Arg His Thr Leu Ala Trp Leu Ser Leu Phe Ile Phe Leu Val
    130                 135                 140

Gly Ile Ile Leu Leu Ile Leu Tyr Leu Ala Ala Tyr Arg Ser Glu
145                 150                 155                 160

Arg Cys Gln Gln Cys Cys Ser Ile Gly Lys Ile Phe Tyr Arg Thr Leu
            165                 170                 175

<210> SEQ ID NO 16
<211> LENGTH: 100
<212> TYPE: PRT
<213> ORGANISM: Human cytomegalovirus

<400> SEQUENCE: 16

Met Cys Thr Asp Pro Arg Arg Thr Ala Gly Trp Glu Arg Leu Thr His
1               5                   10                  15

His Ala Ser Tyr His Ala Asn Tyr Gly Ala Tyr Ala Val Leu Met Ala
            20                  25                  30

Thr Ser Gln Arg Lys Ser Leu Val Leu His Arg Tyr Ser Ala Val Thr
        35                  40                  45

Ala Val Ala Leu Gln Leu Met Pro Val Glu Ile Val Arg Lys Leu Asp
    50                  55                  60

Gln Ser Asp Trp Val Arg Gly Ala Trp Ile Val Ser Glu Thr Phe Pro
65                  70                  75                  80

Thr Ser Asp Pro Lys Gly Val Trp Ser Asp Asp Ser Ser Met Gly
                85                  90                  95

Gly Ser Asp Asp
            100

<210> SEQ ID NO 17
<211> LENGTH: 117
<212> TYPE: PRT
<213> ORGANISM: Human cytomegalovirus

<400> SEQUENCE: 17

Met Arg Leu Ile Phe Gly Ala Leu Ile Ile Phe Leu Ala Tyr Val Tyr
1               5                   10                  15

His Tyr Glu Val Asn Gly Thr Glu Leu Arg Cys Arg Cys Leu His Arg
            20                  25                  30

Lys Trp Pro Pro Asn Lys Ile Ile Leu Gly Asn Tyr Trp Leu His Arg
        35                  40                  45

Asp Pro Arg Gly Pro Gly Cys Asp Lys Asn Glu His Leu Leu Tyr Pro
    50                  55                  60

Asp Gly Arg Lys Pro Pro Gly Pro Gly Val Cys Leu Ser Pro Asp His
65                  70                  75                  80

Leu Phe Ser Lys Trp Leu Asp Lys His Asn Asp Asn Arg Trp Tyr Asn
                85                  90                  95

Val Asn Ile Thr Lys Ser Pro Gly Pro Arg Arg Ile Asn Ile Thr Leu
            100                 105                 110

Ile Gly Val Arg Gly
            115
```

<210> SEQ ID NO 18
<211> LENGTH: 159
<212> TYPE: PRT
<213> ORGANISM: Human cytomegalovirus

<400> SEQUENCE: 18

```
Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
            20                  25                  30

Ile Cys Pro Leu Ala Val His Val Leu Glu Leu Glu Asp Tyr Asp Arg
        35                  40                  45

Arg Cys Arg Cys Asn Asn Gln Ile Leu Leu Asn Thr Leu Pro Val Gly
    50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Arg Leu Asn Tyr His His Phe Arg Leu Arg Trp
145                 150                 155
```

<210> SEQ ID NO 19
<211> LENGTH: 316
<212> TYPE: PRT
<213> ORGANISM: Human cytomegalovirus

<400> SEQUENCE: 19

```
Met Leu Arg Leu Leu Phe Thr Leu Val Leu Leu Ala Leu His Gly Gln
1               5                   10                  15

Ser Val Gly Ala Ser Arg Asp Tyr Val His Val Arg Leu Leu Ser Tyr
            20                  25                  30

Arg Gly Asp Pro Leu Val Phe Lys His Thr Phe Ser Gly Val Arg Arg
        35                  40                  45

Pro Phe Thr Glu Leu Gly Trp Ala Ala Cys Arg Asp Trp Asp Ser Met
    50                  55                  60

His Cys Thr Pro Phe Trp Ser Thr Asp Leu Glu Gln Met Thr Asp Ser
65                  70                  75                  80

Val Arg Arg Tyr Ser Thr Val Ser Pro Gly Lys Glu Val Thr Leu Gln
                85                  90                  95

Leu His Gly Asn Gln Thr Val Gln Pro Ser Phe Leu Ser Phe Thr Cys
            100                 105                 110

Arg Leu Gln Leu Glu Pro Val Val Glu Asn Val Gly Leu Tyr Val Ala
        115                 120                 125

Tyr Val Val Asn Asp Gly Glu Arg Pro Gln Gln Phe Phe Thr Pro Gln
    130                 135                 140

Val Asp Val Val Arg Phe Ala Leu Tyr Leu Glu Thr Leu Ser Arg Ile
145                 150                 155                 160

Val Glu Pro Leu Glu Ser Gly Arg Leu Ala Val Glu Phe Asp Thr Pro
                165                 170                 175
```

```
Asp Leu Ala Leu Ala Pro Asp Leu Val Ser Ser Leu Phe Val Ala Gly
            180                 185                 190

His Gly Glu Thr Asp Phe Tyr Met Asn Trp Thr Leu Arg Arg Ser Gln
        195                 200                 205

Thr His Tyr Leu Glu Glu Met Ala Leu Gln Val Glu Ile Leu Lys Pro
    210                 215                 220

Arg Gly Val Arg His Arg Ala Ile Ile His Pro Lys Leu Gln Pro
225                 230                 235                 240

Gly Val Gly Leu Trp Ile Asp Phe Cys Val Tyr Arg Tyr Asn Ala Arg
                245                 250                 255

Leu Thr Arg Gly Tyr Val Arg Tyr Thr Leu Ser Pro Lys Ala Arg Leu
            260                 265                 270

Pro Ala Lys Ala Glu Gly Trp Leu Val Ser Leu Asp Arg Phe Ile Val
        275                 280                 285

Gln Tyr Leu Asn Thr Leu Leu Ile Thr Met Met Ala Ala Ile Trp Ala
    290                 295                 300

Arg Val Leu Ile Thr Tyr Leu Val Ser Arg Arg
305                 310                 315

<210> SEQ ID NO 20
<211> LENGTH: 122
<212> TYPE: PRT
<213> ORGANISM: Human cytomegalovirus

<400> SEQUENCE: 20

Met Val Asp Gln Cys Cys Tyr Arg His Leu His Arg Ser Leu Ser Gly
1               5                   10                  15

Gly Pro Asp Val Leu Tyr Ala Ala Ala Gly Thr Gln Arg Glu Gln Gln
            20                  25                  30

Arg Leu Asp Lys Ser Leu Ala Ala Thr Ala Pro Ser Ala Val Ala Gly
        35                  40                  45

Pro Pro Ala Asp Arg Asp Val Val Asp His Arg Thr Glu Thr His Ala
50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
                85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
        115                 120

<210> SEQ ID NO 21
<211> LENGTH: 642
<212> TYPE: PRT
<213> ORGANISM: Human cytomegalovirus

<400> SEQUENCE: 21

Met Gln Leu Cys Ser His Ser Ile Ser Ser Gln Arg His Val Ala Ser
1               5                   10                  15

Ser Met His Cys Arg Ser Arg His Gln Arg Thr Pro Pro Ser Ala Thr
            20                  25                  30

Thr His Gly Pro Cys Ala Pro Thr Ser Arg Ile Leu Arg Arg Leu Leu
        35                  40                  45

Thr Thr Arg Arg Phe Leu Pro Arg Thr Pro Ser Pro Ser Asn Thr Val
        50                  55                  60
```

-continued

```
Cys Cys Ile Arg Arg Arg Leu His Glu Arg Thr Ile Arg His Ser Met
65                  70                  75                  80

Arg Cys Arg Arg Arg Asp Met Ala Ser Ser Ala Ser Thr Pro Val Ser
                85                  90                  95

His Thr Gln Pro Leu Ala Ala Asn His Arg Arg Ser Arg Ile Thr Tyr
            100                 105                 110

Ala Thr Thr Asp Pro Thr Asn Ser Pro Thr Ala Ser Pro Ala Lys Ser
        115                 120                 125

Asp Lys Leu Glu Ala Asp Ala Asp Pro Ala Leu His Arg Arg Pro Ala
    130                 135                 140

Ser Leu Leu Arg His Leu Phe Gln Pro Cys His Ala Gln Arg Gly Thr
145                 150                 155                 160

Ser Asn Arg Ala Thr Ser Gln Arg Ala Ser Leu Asn Ala Val His His
                165                 170                 175

Lys Leu Cys Gly Ala Met Ile Ser Ser Ser Cys Ser Thr Thr Cys Thr
            180                 185                 190

Pro Leu Ile Met Asp Leu Pro Ser Leu Ser Val Glu Leu Ser Ala Gly
        195                 200                 205

His Lys Lys Lys Glu Thr Pro Thr Glu Gly Gly Trp Gly Gly Glu Glu
    210                 215                 220

Gly Glu Asp Asp Val Leu Ala Thr Ile Arg Asn Thr Leu Ser Ala Pro
225                 230                 235                 240

Thr Ser Pro Ala Ala Ala Thr Thr His Arg Leu Ser Phe Pro Gly Glu
                245                 250                 255

Ser Thr Phe Cys Leu Thr Ala Val Ser Glu Cys Ser Gln Arg Arg Thr
            260                 265                 270

Ser Thr Ala Ala Leu Thr Pro Pro Pro Ala Val Ala Ala Ala Phe
        275                 280                 285

Ser Phe Ser Ser Thr Val Ser Glu Thr Gly Thr Phe Pro Gln Ser Thr
290                 295                 300

Thr Gly Arg Thr Arg Val Asp Asp Thr Ala Val Val Thr Ala Gly Asp
305                 310                 315                 320

Pro Arg Ser Pro Val Thr His Val Thr Leu Leu Gln Ile Phe Arg Leu
                325                 330                 335

Arg Ser Ser Leu Leu Thr Ser Arg Ser Gly Ala Leu Arg Gly Gly
            340                 345                 350

Glu His Glu Ala Ile Pro Lys Val Ala Ser Leu Phe Trp Thr Leu Leu
        355                 360                 365

Lys Ala Thr Gln Ile Val Glu Met Thr His Lys Thr Pro Ser Ala Asp
    370                 375                 380

Ser His Arg Asn Pro Gln Lys Tyr Thr Asp Arg Pro Gln Arg Leu Leu
385                 390                 395                 400

Leu Thr Ala Leu Ala Ile Trp Gln Arg Thr Tyr Asn Asp Thr Arg Ala
                405                 410                 415

Ala His Ala Pro Gln Val Arg Leu Leu Gly Asp Ile Leu Thr Tyr Arg
            420                 425                 430

Arg Pro Gln Thr Ala Thr Ala Ser Thr Lys Ala His Thr Gln Gln Gln
        435                 440                 445

Pro Glu Glu Pro Lys Gly Gln Gln Ile Trp Thr Gln Thr Ala Gly Gln
    450                 455                 460

Ala Ala Pro His Gly Asp Glu Pro His Ser Asp Gly Glu Leu Arg Arg
465                 470                 475                 480
```

```
Glu Ser His Ser Ala Pro Pro Thr Ser Arg Thr Leu Pro Asp Thr Ile
            485                 490                 495

Leu Ala Val Lys Arg Arg Ser Val Ala Gln Arg Ser His Val Arg Leu
            500                 505                 510

Asp Ala Lys Pro Gly Leu Asn Glu Arg Asp Gly Phe Arg Gln Arg Leu
            515                 520                 525

Leu Leu Pro Leu Ser Gly Tyr Phe Arg Ala Asn Glu Leu Arg Asn Gln
        530                 535                 540

Gln Phe Met Gly Tyr Gly Thr Lys Asn Gly Leu Lys Asn Thr Trp Leu
545                 550                 555                 560

Thr Arg Pro Leu Gly Val Ala Gly Gly Val Arg Glu Thr Ile Gly Glu
                565                 570                 575

Arg Gln Asp Arg Asn Val Ala Asp Ser Ala Thr Gln Arg Val Phe His
                580                 585                 590

Thr Leu Tyr Ala Ala Leu Gln Thr Val Arg Val Trp Tyr Thr Ala Leu
        595                 600                 605

Gly Thr Ala Trp Arg Thr Ser Gly Ser Arg Thr Arg Glu Ser Leu Phe
610                 615                 620

Asp Gly Pro Arg Arg Arg Asp Arg Gln Ala Ala Arg Leu Arg Arg Leu
625                 630                 635                 640

Glu Leu

<210> SEQ ID NO 22
<211> LENGTH: 336
<212> TYPE: PRT
<213> ORGANISM: Human cytomegalovirus
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 22

Met Val Phe Val Ser Gly Thr Ala Leu Gly Thr Gly Phe His Arg Ala
1               5                   10                  15

Glu Gly Ser Phe Cys Gly Cys Glu Gly Arg Ser Phe Phe Arg Thr Leu
                20                  25                  30

Gly Thr Gly Leu Gly Asp Gly Gly Cys Ala Gly Arg Arg Trp Xaa Arg
            35                  40                  45

Xaa Val Ala Gly Thr Gly Ile Thr Leu Gly Thr Gly Thr Arg Gly Pro
    50                  55                  60

Gly Leu Arg Asp Gly Gly Asp Gly Gly Val Cys Gly Glu Asp Gly Gly
65                  70                  75                  80

Leu Leu Arg Arg Gly Arg Gly Leu Ala Gly Pro Ala Val Ala Gly Val
                85                  90                  95

Cys Gly Asp Gly Gly Leu Leu Gln Arg Arg Gly Leu Arg Gly Gln Glu
            100                 105                 110

Cys Ala Xaa Pro Gly Gly Phe Ala Gly Gly His Gly Thr Gly Gly Gly
        115                 120                 125

Gly Asp Ser Thr Asn His Thr His Thr Gln Leu Thr Ser Ala Val Ala
130                 135                 140
```

```
Leu Ser Glu Pro Pro Leu Phe Phe Ile Asn Val Leu Ile Pro Pro Ala
145                 150                 155                 160

Tyr Thr Arg Asn Ala Ala Cys Ser Tyr Ala His Thr Leu Ser Leu His
            165                 170                 175

Ser Asp Met Leu Leu Arg Leu Cys Thr Ala Ala Ala Asp Thr Ser Gly
        180                 185                 190

His Arg His Leu Pro Pro His Met Ala His Val Leu Arg Arg Pro Ala
        195                 200                 205

Ser Tyr Val Val Cys Ser Gln His Gly Ala Phe Phe Pro Ala Arg His
        210                 215                 220

Leu His Arg Thr Pro Ser Ala Ala Phe Ala Val Ala Ser Thr Arg Glu
225                 230                 235                 240

Gln Tyr Ala Thr Ala Cys Ala Val Ala Ala Ala Thr Trp Pro Arg
                245                 250                 255

Leu Pro His Leu Phe Arg Thr Pro Asn Leu Trp Leu Pro Thr Thr Asp
            260                 265                 270

Val Gln Gly Ser Arg Thr Arg Arg Pro Ile Pro Ile Leu Gln Arg
                275                 280                 285

Pro Arg Pro Pro Ser Gln Thr Ser Trp Lys Pro Thr Gln Thr Gln His
            290                 295                 300

Ser Ile Asp Ala Arg Pro Arg Cys Cys Ala Thr Ser Ser Ser Pro Ala
305                 310                 315                 320

Thr Pro Asn Ala Ala Leu Pro Thr Glu Pro His Pro Arg Gly Leu Pro
                325                 330                 335

<210> SEQ ID NO 23
<211> LENGTH: 11950
<212> TYPE: DNA
<213> ORGANISM: Human cytomegalovirus

<400> SEQUENCE: 23
cctcgccatg aggatcgcga caggcgcgtc gaggggcag gaacacccctt gcggattgac    60 attcttggtg gtgtttcgtt gttgtcggta gttgttgttg acgatgagga taaataaaaa   120
tgaccttgtt tttgttctgt tttctcttgt tgggaatcgt cgactttgaa ttcttcgagt   180
tatcggaaag ctgaggtacc caaatgtctg tagctttttt cttttttaccc tcttgtttat   240 catctgcgat tcgtggtagg taggagaggg aaatgataat ccgagattaa ggaaaggaga   300
agataaaaaa taaaaaaaaa taataaaaca gaagccgacc ggccgccgac ccgttcccca   360
ggaccagcct acgaggaacg ataacgcgg tggcgacggc agcggtggtg cgctgggggg   420
tggcggcagt ggtactgctg atggtagtcg ggacggagga gaggcgatgc atacatacac   480
gcgtgcatgc tgcatgggtg gatggtacgg ccgggagacg cggaagagaa actcacataa   540
aaaggtgaca aaagagcgg ttgaaaaaag aaacaagat tcgaccagac agaagagaag    600
gaccggggct tggcgaccct tccacgactg ctgttgtcat ctcggctcct ccgtcttctc   660
ccggccacgg gcggctaagt caccgccgtt ctccccatcc gtccgagcgc cgaccgacca   720
gccggccgat tcgcccgccg gggcttctgg agaacgccgg ggcagcagcg atctggggaa   780
gctgctaaac ccctgcgttt ttatatggta gctctgccga gcgcgggctg acgcgttggg   840
taagcggaaa gacgtgtgtg acgaaaaggg gtcccatgg atttcacgtg acgatgagga   900
gatacggttt ggagcacata cggtttagaa aaagggagtt gtcgtgacaa gggctgaggg   960
acctctgtct ccatgtgtgt ataaaaagca aggcacgttc ataatgtaaa aagaacacg   1020 ttgtaaacaa gctattgctg tatcattcgg ctgactatgc ttcattcgga ctgattttct  1080
```

-continued

```
tttcctaacg gcgtaactta aagtgattaa cgtatgatat ttgttcccca gagttatact    1140
atagtcatca tcctaaaatt cagatataaa tgaacacatg tcgtatggga ttattaagaa    1200
accgaaactc tccacagttc accatcttct tcgtcattca accgatgacc cactccgtac    1260
aacgaatcag tctgctgcgt catattgcaa agcacaagcg acgtatgcga acaacttgaa    1320
acacaggctt tgtattgac gaccgttgta ccattattag tcaccaccgt tatcccatgt    1380
ttcccacccg atggaaaacc gtcttctatc atcaactgtg gtaagatttc gaccctgcga    1440
ggtattcagt ttcctcatat ccataacctg gattttatca ttaaacccca atattaaaca    1500
cttttttagt acccccacc caccaaaaaa tgtgactgga ccggttccta gcagctctgg    1560
gagccatgtt caggttgaac cacagctaca gcgaaaccga gtccagtgac cggtaaccac    1620
gtccagcccc tgcgtatgta ccagtccaag cacgtccggt cattgttcta cacaggaaat    1680
ctaactaggt caacgcaatt ttattccacc gttacgcaga atactaacaa aaaaacacac    1740
aaatttaacg aattacacgt agtttattac atgaaaactg taagaacacc aattcactaa    1800
gcgatacaac atttagctga cttccaagtg ccacacatca ccactgtatt catccatgtt    1860
ttcaccgaac caacgagaca gatcgaagaa gccagaatct cccgacttta aattacataa    1920
atccaacgta ttatgaccac agctcgacac acaaatagtt gcgttactat tcacagtagc    1980
attacctata cccgtaacgt tgcacaacca ctgatcacca ttgttaccaa aaacggtttt    2040
ccacttagtt gtcaacggat cttttcctatg cgtaatggta aaattactac cagtcgtcgc    2100
ttttagctca ttacgagtat tatccgcatc cacatatatc aacgtcatag ctaggcacgc    2160
tataagtacc cccccccac aatggaatgt tgccaaaccg gttctttccc gttatagcca    2220
tagcgttccc aggcaaaagc aaacgccaaa cctaatgcag tgaaaagcgc ttgcagccag    2280
aaccagctta tgtaccagcc acaatcacat ccggttattg tttccacagg aaatcctacc    2340
aggcaaagcc ccgcttgttt tgttcctatc ttgtttagca attcgtaaac tgtcagccta    2400
gcgacgtccg tttagatcaa aagtcacgta tatagcgacg ctgtttccat ccgtttcccc    2460
gtcccgccgt ttccgaacaa cccacccggg ttcagacaac cgaccaccaa cagaaatata    2520
cacacagacc actgggagtt cagttaaaga tttcatcagg tttattttgg ctgctgctag    2580
tcttttgctt cttagaaaaa aaatacccat atagagaaat aatgatagtt tgacaacaca    2640
tatggcaggg atttcttctt catcaataag atatgcaatt ccccaggga gagactttca    2700
acaattgaat ttacaaaaac aaaattacat caggagaaag agaggataca ttaataaata    2760
tattatatct ggtgtatata ctgaatgctg ctggttcata aggtaacgat gctacttttt    2820
ttaattccaa gatggttttt cttttgttagt cttttgttga cttgctggtt cctaaaagtt    2880
cgcaaaaacg attgtgtgaa gattttatga cgttggttga ctagttcatg agattctgct    2940
gtacgtgtga tggttattcg ctggttcgtt ctaagatgag tatcgtactg tgtctgcgat    3000
ggtcgtctct tactggcatt ctctcggctg cctcttgctt tcatgattga aaaggaaaaa    3060
aggactccga gggcgcggtc atcttttact tttcggtttt ctcgttggcg ggtcagaggt    3120
agtcagatca tgagactgtc gtggtcgatg aaactgtgtc tgctcaagtg acgtccattt    3180
cttgtacgga gaaaaagtc atcgggataa ataaggctat acaaggcgtt gtcaagcgtg    3240
cggctctaaa caaattaagc gatacaaaat tacagtaata cgaataataa attaccccc    3300
tccccctgtg gtccccgag acgagagcca cccatcgtgt actctcgcac cacccacgac    3360
cacagaggga gacgggacga agagacgacg cacagcgcca tctcctcctg gaggccggcg    3420
```

```
acgttaactg ctacagctgc ggcggcgaag acagctgcga tttgtcggcc gacatgccga    3480
tggtatgggc ggcggcggca atggccgcgg cagcggggag gagaggagag agaagaggag    3540
cggggcgtcc gaaggcgagg atggcatggt ctcgccggag cgcccggctt ttatggaaca    3600
ctcgcgtccg gttgggtatc acccacagga agatgagtca caacttccaa accatcttga    3660
gacccgagta acggtttaca ggtcgcacgc cagtcagcta aaaacagcgg acagtcccac    3720
gctgtttctg ttgtggctct ctccagtttc ctcatcaccg tcccggtctc cgtcgtcatc    3780
ggaagaatac cacccgctct catgcggcag tcgatcggcc tcgacgaacg agacgcggcg    3840
acgcctctcc acgccgact ggttgtggtg gtgaaagaag agcaccagca atcccaggag     3900
gagcaacaag ccctcacatg tccaggaggt cggggagagg cctgtcgga tggccgtg      3960
aggcatcacg tacggcagct gaggagaaac ggagaagaaa ggaaaattac cgtcaggggc    4020
cggggttctt attagagaaa cagcacgtag gtcaggatcc agatgctaat ggcaatcatg    4080
atgacgatga tcatgcaggc caagacgcgg cgcaccaatg ccgaatccaa tagccgccgt    4140
gcctccggtt ggtggccggc ggcatctaga gacatgattt ggggggggacc ggcggcgcaa    4200
aaagacaggg agatggacag tgtcacggtg ttttgttata attaggacat ggggaccgga    4260
agccgagaca gagtactaca gggtgttgaa gggtaacgtg agggagatca tgtcatgggc    4320
gggctgaaga ccgtgcgggg aggattgacg tgtgcggtgc ttgtggaaca cggtgtttta    4380
atatgtatcc gcgtgtaatg cacgcggtgt gctttctggc actcagcttg gtaagctatg    4440
tggccgtctg cgccgaaacc aaagtcgcca ccaactgtct cgtgaaatca gaagatacc     4500
atttgacgtg caagtgcagt ccgaataaca catcatctaa taccggcaat ggcagcaagt    4560
gccacgcgat gtgcaaatgc cggatacag aacccattac catgctaggc gcatactcgg     4620
cctggggcgc gggctcgttc gtggctacgc tgatagtcct gctggtggtc ttctttgtaa    4680
tttacgcgcg cgaggaggag aaaaacaaca cgggcaccga ggtagatcaa tgtctggcct    4740
atcggagcct gacacgcaaa aagctggaac aacacgcggc taaaaagcag aacatctacg    4800
aacggattcc ataccgaccc tccagacaga aagataactc cccgttgatc gaaccgacgg    4860
gcacagacga cgaagaggac gaggacgaca acgtctgata aggaaggcga gaacgtgttt    4920
tgcaccatgc agacctacag cacccccctc acgcttgtca tagtcacgtc gctgttttg     4980
ttcacaactc agggaagttc atcgaacgcc gtcgaaccaa ccaaaaaacc cctaaagctc    5040
gccaactacc gtgccacctg cgaggaccgt acacgcacgc tggttaccag gcttaacact    5100
agccatcaca gcgtagtctg gcagcgttat gatatctaca gcagatacat gcgtcgtatg    5160
ccgccacttt gtatcattac agacgcctat aaagaaacca cgcgtcaggg cggtgcggcg    5220
ttcgcgtgca cgcgccaaaa tctgacgctg tacaatctca cggttaaaga tacgggagtc    5280
tacctcctgc aggatcagta taccggcgat gtcgaggctt tctacctcat catccaccca    5340
cgtagcttct gccgagcctt ggaaacgcgt cgatgctttt atccgggacc agggagagtt    5400
gtggttacgg attcccaaga ggcagaccgg gcaattatct cggatttaaa acgccagtgg    5460
tccgccctct cactccattg cgcctgggtt tcgggaatga tgatctttgt tggcgcgctg    5520
gtcatctgct tcctgcgatc gcaacgaatc ggggaacagg acgctgaaca tctgcggacg    5580
gacctagata cggaaccttt gttgttgacg gtggacgggg atttacagta aaagatgcgt    5640
gtcgcctgcc gaagacctca ccatctcacg tacaggcata cggcgtatac aatcataata    5700
ttctatattc tgcatagagt tacatgcaac agtactacta ccaatactgc atccatcaca    5760
tcacccaaca ctgcttctac caccttttgtg accagcgtat tttctactcc gaataacaac    5820
```

```
acatcaacga cgccacacac atctgtcacc tcacaagcgt caaccattgg caacatcacc    5880
aacgttacct ccgacttgag tactttcaca accgtatatt ctacattcaa tacatcatat    5940
gctaatatat ccaatacggc tgccactaca gaattgattt caacaaatac caacactata    6000
ttatctttta ccaacgtaac agcaaacgct acatcatctt ataacacaac aatcaccgta    6060
actatcacgt cagatgaaac ttcgcacaac gtatccacta atactgcact tataagcacg    6120
ccatggctta caaattgcag cgccacaacg tacaccacgt acaaccgtac taactcttcc    6180
aacgcttgtc acacagagac aacaatcata cgtttcaaag aaactaatac aacaggaata    6240
gaagggagta atgtcaccat aaaaggtaat tctacgtggg attgtctttc agtcgcctgg    6300
atacgacatt acaatcgatc cacacacgga catcatctag gtcatcgtaa gaacgcacat    6360
acccaatctt ggtattggtt acgcatcctt acctctcata ctgtatgtca ttctcaacat    6420
gaaagacctt cactgtacca tgacttatgt cgttcgtgca acaacacaga actacatctg    6480
tacgatctaa atatcaccaa ttccggcagg tacagcagac gttgttttaa agaaaattac    6540
ttcacaggac atcacgaaga tgaaaatttc tacctattag taacaccaaa aaatcatact    6600
gaagctatta atgctacttt cgtttgccct agatacaaca ccgatatcga aaatgaagat    6660
agagagaaag gaagtcaaca tactaacaat acacatcacc acaaacgtaa tctctatcat    6720
agctcgcaaa gaagccgcac cgtatggacc atcgtgttgg tttgtatggc ctgcatagtt    6780 ctgtttttg cacgacgagc ctttaacaaa aagtaccata tgttgcaaga caccgtcagt    6840
gaatcagaat tcattgttcg atatcacaca gaacatgaag attgagctac gtttccgggc    6900
agacatctta tgaagctgaa caataaacta aacattctg taaggctcag cgttcaaagg    6960
aatattaatg cccattgagc gagaactaat attgcaatgg actggcgatt tacggttatg    7020
tggacgatac taatatccgc gttatcagaa agctgcaatc aaacctgttc ctgtcaatgt    7080
ccctgtagta ctaccgttaa ctattccact agtactgaga cagccacatc aacatacagt    7140
acaacagtta tcagcaataa aagcacttca gaatctataa attgctctac tgcaactgca    7200
ccagcaacca ccgtttctac aaaaccgtcg aaaacaacca cacagatatc cacaacgaca    7260
aatacaaacg ttgagactac cacatgtacc aacaccacca cgaccgttac ttgtgatggt    7320
ttcaattata cagtccataa aagatgcgac cgcagttacg aggtaatcaa cgtaacagga    7380
tacgttggtg gcaacataac tctaaaaaat gcaatcagac tgagaaatgg cacaatgtag    7440
actggattca ttatgagtac cccacgcata aaatgtgcga attaggcaac tatcaccaaa    7500
caacaccacg gcacgacata tgttttgact gcaacgacac ctccctaact atctacaact    7560
taaccacaag aaacgctgga aaatatacca ggcatcaccg tgataacggt caagaagaaa    7620
attactacgt aacggtgtta attggagaca caacgttatc cactcttggc acatgccctg    7680
taagatataa agaatctagg aacactgaaa acaccattgg aagtaacatc ataaaaacca    7740
ttgagaaagc taacattccc ctgggaattc atgctgtatg ggcaggcgta gtggtatcag    7800
tggcgcttat agcgttgtac atgggtagcc atcgcattcc caaaaaaccg cattacacca    7860
aacttcccaa atatgatcca gatgaatttt ggactaaggc ttaacatgca catcaataaa    7920 cttttttaa ccaataacat gtctctgttt ttttttgtta acaacctatg atataaagcg    7980
gtatattcaa tcattactaa acaaaaaaac atgggcatgc aatgcaacac taaattgtta    8040
ttgccagtcg cactaatacc ggttgtaatc atcctaattg gtactctagt gcccatactt    8100
ttacatgaac aaaaaaaggc gttttactgg cgacttttc tgcaaagtca acatgtagaa    8160
```

```
gcacccatta cagtaacgca gggagacaca gtctacctag atgctagcaa taatccctgt   8220
aattattcca gcttttggta ccacggtaat tgcgaacttt gtggatggaa cggatatcta   8280
cgcaatgtta cacattacta cacaaacaca tcgtgttccc cgcaattcat gtgcataaac   8340
gaaactaaag gtctgcagtt atataatgta acattaaacg attcaggtgc ttatactgaa   8400
cacgtttacg aatgtgatct ttcatgtaac attactactt ataacgaata tgaaatactc   8460
aattacttcg ataactgtaa ctacaccata aatagcacca agcatattat caccgtggtg   8520
tcttcacgtc attctaaaca aacaaattcc cacgtatcca ctcacgctgg ttgggcagcc   8580
gccgtggtga cggtaattat gatctacgtt ttgatccact ttaacgttcc ggcaactctg   8640
agacacaaac tacgaactag aaacaacgta atcgcatag cgtgattaca agtatcgac    8700 actaatttat ccaagataaa atttgattac tccgtgcggt tctcaaaaac tgtaaggtcc   8760
cgcttttcta ctccatcatg aaggatcgca atagaatact gctatgtatc atctttattt   8820
gcatcatgtg cctcatttgt atttacttta aacgtcgttg tgttcttact ccgtctccag   8880
acaaagcgga tctgcgagtg gaatttccct cgttaccccc gtgtatcggc atacaatgtg   8940
ctgcatgaga acacgcgtga cacatagcgt acccctggac ggtacagttt atgataacgt   9000
cattcagggg aagtatacat tactatcgac gtgttatcac agaacacaca gattttctgc   9060
gtgttttata aaagagcgtc tcgaagcagc ttgagccaca ctacggtcca gatgacgagc   9120
gtaatcaaaa atatgccgcg cagtagtcga aagccgtact gagcgtgcga ggcgggtagg   9180
gtgccgaacg acggatatgc gtcgttgtca tcttcgacta taaggatcgc gaccgagtct   9240
tcggccatgg taaacgtcac cctgtgtggc tggtatgtag cgtatccggt ttggaattgt   9300
tctgctccag ctcgggggat agtgaggaat tctcaaggga tacgggaccc aatgactgga   9360
taagagaagg gttttttcccc gtaagatgat cctcgtatca catgaggtct ggatatgtat   9420
aaatgaagag tgaaataggc acagggaatc agatgccagc ctcgtgatgc agccgctggt   9480
tctctcggcg aagaaattgt cgtctctgtt ggcttgcaaa tacatcccac cttaagcgat   9540
gagtccataa agcaccgttg tccgggtacg gtgaaagtga ctcggattgt agcacgtccc   9600 tttttttttgt ttttgtatcg cttatcgcca ctgacagtgc aatattttga tcgtgaggct   9660
gagtatggtt atgatgctta gaacgtggag attattacca atggtactac ttgccgcgta   9720
ctgttattgt gttttggga cttgttcaat cggcacgacg actgctcccg tggaatggaa    9780
gtctcccgac cgtcagattc ctaagaatat tacttgcgct aactactcag ggaccatcaa   9840
cggcaacgtt acatttcgag gtcttcagaa caaaacggaa gactttttgc actggttgtt   9900 agggtgggt cataagtcca tctgttcgtt cttcccgaaa ctccagggca actataacga    9960
acaacattac agatatgaag tagcgaacct gacgtataac tgcacctata accgcttgac  10020
gttgctaaat ctgacgacgg aaaacagcgg aaagtactat tttaaaaggg aagatgcgaa  10080 tttcacccttt tattactctt gttacaacct gaccgtgtcc taaagaacgc acgtgaagtt  10140
ccacagagcc gcgtggctgt agctattgtg tttacgttgc ttttgaaatg ttaagcgtcc  10200
ctacggcgct aacatgtttc taggctactc tgactgtgta gatcccggcc ttgctgtgta  10260
tcgtgtatct agatcacgct taaagctcgt gttgtctttt gtgtggttgg tcggtttgcg  10320
tctccatgat tgtgccgcgt tcgagtcctg ctgttacgac atcaccgagg cggagagtaa  10380
caaggctata tcaagggaca aagcagcatt cacctccagc gtgagcaccc gtacaccgtc  10440
cctggcgatc gcgcctcctc ctgatcgatc gatgctgttg tcgcgggagg aagaactcgt  10500
tccgtggagt cgtctcatca tcactaagca gttctacgga ggcctgattt tccacaccac  10560
```

```
ctgggtcacc ggcttcgtct tactaggact tttgacgctt ttcgccagcc tgtttcgcgt    10620
accgcaatcc atctgtcgtt tctgcataga ccgtctccgg gacatcgccc gtcctctgaa    10680
ataccgctat caacgtctcg tcgctaccgt gtagctagtt agccagctgt gtatagtttg    10740
ttgtgttttg cttttgcata tttgttttca gtcagagagt ctgaaacggg gtgggaggga    10800
cttttacggg taatgcatgc taagatgaac gggtgggctg gggtgcgctt ggtaactcac    10860
tgtttgaata cgcgctcacg cacatatgta gcactcaaca tgttagcttt tgcccgcacg    10920
ccccggggcg tgccgagctg ccttttaat aaagtctggg tttccagata cgcgctggtt    10980
ctgattttga tggtttgtgc ctctgaaagc tctacgagct gggccgtgac atccaatcga    11040
ctgcctaact gtagcacgat aactacaaca gcgggtcaag acgctgaatt gcacggtccg    11100
gcaccgttaa gctgtaatgt gacccagtgg ggacgttacg agaatggaag cacacccgta    11160
ttatggtgca ctttatgggg atcacgcacg cgagtctcat taggacaccg tgtagcgttt    11220
ggctgttctt ggaaaacatt ttttatttat aacgtttctg aaagtagtgg tggcacttat    11280
tatcaaaaag gttacaactg caccgacaaa catataacac tatcttgttt caacctaacg    11340
gtggttcctc gagcggttca aagcacaacc accgtaatga cacccacggt ggttacaaac    11400
tccacattca gtgtgtcact tgttgcgtcg agactgacga caaattccag cgcgtttaga    11460
cacgctagtt atcaacggca acagcgtgtc ggaaacggga cgttatccaa gaacataact    11520
aacttggcat tcacctacgg cagctggggc gtcgcgatgc tgctgttcgc cgccgtgatg    11580
gtgctcgttg atttgggttt gcctcaatcg gcttggcgac gctggcgaag ccacgtggac    11640
gatgaagaac gtggtttgtt aatgtaggaa ataaaaggca ctgtttgagc atgactgttt    11700
ccaaaccgta acgtggtaaa taaatcatgg cttccgacgt gagctcccat cttctaacgg    11760
ttacacaatc ccgttggaca atacatcata tgtacaataa actgttgatt ttggcgttgt    11820 ttaccccgt gattctggaa tccatcatct acgtgtctgg gccacaggga gggaacgtta    11880
ccctggtatc caacttcact tcaaacatca gcgcacggtg gtttcgctgg gacggcaacg    11940
atagtcatct                                                          11950

<210> SEQ ID NO 24
<211> LENGTH: 14078
<212> TYPE: DNA
<213> ORGANISM: Human cytomegalovirus

<400> SEQUENCE: 24
cggtctggca gcgactggaa cccggacgcg tagccggcgg cgccgcgcgt catcaaaaag     60
tgcaggaact gttgcagcgc ttgggtcaga cgctaggcga cctagaactg caggaaacgt    120
tggcgacgga atactttgcg ctgttacacg gaatccagac cttcagctac gggctggact    180
ttcggtcgca gttggaaaag atccgcgatc tgcggactcg ttttgcggaa ctggccaagc    240
gacgcggcac gcgtctctcc aacgagggag tcctgcccaa ccccggaaa ccgcaggcga    300 cgacttcact gggcgccttt acacgcgggt tgaacgcgct ggaacgacac gtccagctgg    360
gtcaccagta tctgctcaac aagctcaacg gctcatcgct agtctatagg ctggaagaca    420
ttcctagcgt gcttccggca acacacgaga ccgaccccgc gctgataatg cgcgaccgcc    480
tgcgtcgcct atgcttcgcg cgtcaccacg acaccttcct tgaagtggta gacgtcttcg    540
gcatgcggca aatcgtcacg caggccggcg aacccattca cctggtcacc gattatggca    600
acgtagcctt taagtacttg gcgctgcgag acgatggtcg gccccctggca tggcggcgcc    660
```

```
gctgtagcgg cggaggactc aagaacgtcg tcaccacacg ttataaagcc atcacggtag      720
ccgtggccgt ctgtcagaca ttgcgcactt tctggccaca gatctcgcag tacgacctac      780
gaccctacct cacgcagcat cagagccaca cgcaccccgc ggagactcac acgttgcata      840
accttaagct cttttgttat ctggtgagca ccgcctggcc ccagcgcatc gacacgcagc      900
aggagctgac ggccgccgat cgcgtaggca gcggcgaggg tggtgacgta ggggaacaga      960
gacccgggccg cggtaccgtg ctgcgcctga gtctgcaaga gttttgtgta ctcatagcgg     1020
ctctgtaccc cgagtacatc tacaccgtcc tcaaataccc ggtgcagatg tcactaccct     1080
ccctcacagc tcacctacat caggatgtga tacacgcggt agtcaataac acacacaaaa     1140
tgcccccccga ccacctcccc gaacaggtca aggccttctg tatcaccccc acccaatggc    1200
ccgccatgca gctcaataaa ctgttttggg aaaataaact ggtacagcaa ctgtgccagg     1260
taggcccgca aaaaagcaca ccgcccttag gcaagctatg gctctacgcc atggccacgc     1320
tggtctttcc acaagacatg ctgcagtgtc tgtggctaga actgaaaccc cagtacgccg     1380
agacatacgc ctcggtgtcc gaattggtac agacgttgtt tcagattttc acgcaacaat     1440
gcgaaatggt gaccgagggg tacacgcaac cgcagctccc caccggagag ccggtgcttc     1500
agatgatccg cgtgccacgt caggacacaa ccaccacaga cacaaacacg accacggagc     1560
cgggactttt agatgttttt attcaaacag aaaccgccct agactacgcg ctgggctcct     1620
ggcttttcgg catacccgtg tgtctcggcg tgcatgtagc cgacctgctg aaaggccaac     1680
gtatactagt agcgcgccac ctcgaataca cgtcgcgaga ccgcgacttc ctccgcatcc     1740
aacgctcccg ggatctcaat ctcagtcaac tgctccagga cacgtggacc gaaacgccgc     1800
tggagcactg ctggctacaa gcccaaatca gacggctacg cgattacctg cgtttcccca     1860
cccgcttaga gtttattccc ctagtcattt acaacgcaca ggaccacacc gtcgtacgcg     1920
tgctgcgacc gccctccacg ttcgaacagg accacagtcg gctggtgttg gacgaggcct     1980
tccccacctt cccgctgtat gaccaagatg ataactcatc cgcggacaac atcgctgcgt     2040
ctggcgccgc tccaacaccg ccggtaccct tcaaccgcgt gccagtcaat attcagtttc     2100
tgcgtgaaaa cccgccaccc atcgcgcgag ttcagcagcc gccgcgccga catcgtcatc     2160
gagcggccgc ggccgcagac gacgacggac agatagatca cgtacaagac gatacatcaa     2220
ggacagccga ctctgcatta gtctctaccg cctttggcgg gtccgtcttt caagaaaacc     2280
gattgggaga acaccacta tgccgagatg aacttgtggc cgtggcgccc ggcgccgcca     2340
gcaccagttt cgcctcgccg cctatcacgg tgcttacgca gaacgtcctc agtgctctag     2400
aaatactgcg gctagtgcga ttggacctgc gacaactggc gcaatccgta caggacacta     2460
ttcaacacat gcggtttctc tatctttgt aaccgacact gacagtagcg ggtaataaaa      2520
acaataggat ttttatcgtt tttttatgtt acaaaacaac gtatcacttt cacggtgatt     2580
tattcttgct attccttttc cccttgggct gtcagcgccg ggtgcgcgac acggctacca     2640
tgcgcaacag gtccagctta aaggcgcact tgtcattaaa caggctggac atgcgcgtgt     2700
acttgctcag catggtggcc aacaccgggt gggtggcctc tgatatctcg gtcggcagct     2760
ccaaaacgac gttaacgacg tgacggtgtt tttcgtcccg cttgttggcc accgtgggtc     2820
ccggcgcggt gttagacatg gggcaggccg tggggggagg acgaagagga agccgctgct     2880
aaaccgccgc gcgcctgctg cacaatgtgg ccgccgacgt ggcaggcggt ctgtttaacc     2940
agcgcgcagc cccgacacag cggggcgccg tcctcgcttt ccaaacagct gtcgcggtac     3000
tcgcccgtct gacagcgcgc gcacagcagg ccgtgcccgt gcgaagtgag gcgcaggaga     3060
```

```
cgcgggaccg tcacgtcgcg taccaccaca gtggagtcgc aggtgcgtgc cgcgcagggc    3120
agaatgacgt cgaaagccag ccggtgatcg tacacggcac aagccgcgtt gaggcccagc    3180
acggctttcc agcccacgcg tacgcagcgc tgtccaaaga gcgtctcgga gacgagctcg    3240
tagacgcgct gccgcaccac ccgctgactg ccgcagagcg agcagtgcac gagctcggcg    3300
tgcgtgttga agatgacgct cttttcttga cggtcccgat aatagaacat cgagttgagc    3360
ggaaagtttt gctggcagtg tagcttttcc ttacccaggt tgaggcagtg tccgcactgc    3420
cgacagacca cggccaccag cgagcgcgcg tccagatggc gctcgcactt gagtcgacac    3480
agacaccaga gcggcaggtc gatgacgctg ccgatgaggc cgccgcgcag cgcggcgctg    3540
agtgcaaaga ggacgatctt ggtgggctct acgtgacgcg cctgctgtcc ggcgcccgcg    3600
tgtcctaccg ccgcagctgc cgccgtcgag cctcctccgc gcgtctcgtc gtgcagaccc    3660
agtgcccgca acggcaccag gtatcgcgga cacgtgtcgc aaaacgtctg caccgcttgt    3720
cgggccagta cgtagagcgg gtttccgcag ggtaccttcc cggcgtaccg gcgcaaggct    3780
gcgatgaggc cccgcaactg cggcgaccgc ggctgccgtt ggtgacacca ctggttacgg    3840
tggtatacgg ccaaatcagc gcgggcgtcg aagcgcttgg cgcgtagtaa tgctaggcac    3900
ggcgagctgg tggggtgaag cacgggcagc cgaaggtcca ccccgaaaag gaaacggtga    3960
aggtcaccta gcagcgaggc ggtgacaccg tccaacaacg cgtgcagccg ctcgggcggg    4020
tagagccgca gacggcgcag caggtagtcg gtgtcgtagc gttcgaaacg cagaaaggcc    4080
atcgtgcgga cggccacggt gtgcagacag tccatgctgt agacgtaagc gagaaacaca    4140
aagtagggct tggtcataac catacgctga agagcgccg tcaccgcctc ccgctcggct     4200
tgccgacaca ccagccattc gcgcaggaag cgttggtaga gacggtcgcc cagctcgcga    4260
ttcagaaagc gcttatccgt cacgaagaga tgaaggacgc aagaacgtgg cacgtgatgc    4320
accagctgct gctggaggac cgccgacgtc tgcgccgcaa actgcgccgg tggctgcgac    4380
gtttctaccg ccgcttcctc cggctgcagc gcaccgcggc cgatcaccag ctgcacatgg    4440
aaatggtcct cgtgaacgca gagggcgcg aagagacggc gcagagcctg gtggaactca     4500
tcagtcgcgg tgtgcggagc gtgtcggaga cgacgactgg ccatgaccgc gccacagcag    4560
agccagcacc agcagaagag ccagcaccag cgggcccaga gtcgcaaagc gcgcgggcag    4620
ccacggccca gactgcggtc gcgatggccc ggagcgcgct cgccaccacg atgacggtgc    4680
ccaacgataa ccagtccgct ccaaggacgg cgcgcacggc ggagacggcg gatgacggtg    4740
atgggtcgac accccctcgcc gacgactcac gtgctcctcc agaggccgac gcgcggaccc    4800
tccgacgtcc tggcccgccg ctgccgctgc cgccttccct tctcccgcca gagccagcaa    4860
ctcctcctcc tcttcatcag cgtctccctc gcttgcgcat ccgcatcgtc ccatacaggc    4920
ctcacaacga cacagccgcc acgacccgc cgccatgggt ggcggcggcg ccgaggccc      4980 ggcagcggcg ccgccagcgg cgaccatggt gggagagcaa ctcggatgac gaggaggagg    5040
agggggagat gcggtccgag aggaccgctt cccgccgtt cgcgtaagcg cggccgacat     5100
gcgggcgcgc cacagggacg gaccgctgcc gctgtgactg cttacggtga cgtggttccg    5160
gaccgccaac gacgtcgacg cggctttctt ggcgtacagc tcgcgcagca gattctcgta    5220
ctcgccctcg ttttcgggtc cgaaggcgat gagctcgatg ttgaagaccg acgccgaatt    5280
ggatttgcgc accacgcact tcgtcagcac tccgtaggcc gagggcttga tctcctcgat    5340
gtccttgagc gtgacgatga gcgactcgtt caccttaagc acattgaact cacctacgtg    5400
```

```
gcgcgccggc gaaacgagct tgacgggcgc tcgtacaaaa cagcagaggg agacggcgca    5460
gccagtgttt ttaaagataa acaaggcac gtggtctgtg cggctctccc agtagctgag    5520
tagatactcg acacaataga ccgtgtctgt cttgagcatg gcgtcgcaca ccgagtaatt    5580 ggggtttttta cagatgaggc cggcatcggt gacgcgcagc tcgctgggac ccaacttgag    5640
gatacgccgc gtggcctgca ccagatcctg atggagaacc ttgttcatct ccatcgcacc    5700
gacgccaccg ccgatttatt tacccggcgc cgactcgtct tttccctcca ggattccgtt    5760
aatgtccatg agcttgctga cgatcgccgt taatagttgc gtcttctcac ggaggatctc    5820
tccgtgactg caggtcgcgc agtcgccgtg cacgtacttg aggaaggcgg cgtacttctg    5880
acccgcgttc acgaaattta agcgcgcgtc cagagagggc agcaacagat cgtagacgcg    5940
cggcagcatc ggctcgaact gtaatagcag atcgtcgtca agatcgggta gcgcgtgtcc    6000
gtcttcaccg tcctcgtcgt caccacctcc ccctcgagc ccaccgctcg taccagccgc    6060
gggctccgcg tcctcgtcga tcaccagcgg tcgcgtcggc accggagaat ccacgtcatc    6120
ctgcacgtcg ttttcctcct ctccgtcgtc atcgtccaga aacggcaccc gctgcttagc    6180
ccaggacatt cttttttccg cgtcctcaat cagcggcgcc gatcgccatg aatccgagta    6240
cccacgtgag cagtaacggc ccaacgactc cccctcacgg gccccacacc acgtttcttc    6300
ccccgaccag cccggccccg tccaccagct ccgtcgccgc cgctaccttg tgcagtccgc    6360
aacgacaggc cgtttcgcgt tacagcggct ggagcaccga gtacacccag tggcactcgg    6420
acttgacaac tgagctgcta tggcacgcgc acccgcgtca agtacctatg gacgaagcgc    6480
tggccgccgc ggcggccgcc tcataccagg taaatcctca acaccccgcc aaccgttacc    6540
gtcattacga attccagacg ctcagcctcg gcacctcgga ggtagacgaa ctgctcaact    6600
gttgtgcgga agaaaccacg tgcggcggca cgcaatccac cgtactcacc aatgcgacca    6660
acaccactag ctgcggcgga gccgtcgccg gcagtagcaa cgtaggaccc gccggcgctt    6720
cggccgcctg cgacctagat gcagaactgg ccggcctcga aacctcggcg gccgactttg    6780
aacaactgcg gcgactgtgc gcgccgctgg ccatcgacac gcgctgtaac ctatgcgcca    6840
tcatcagcat ctgcctcaaa caggactgcg accagagctg gctcctcgag tacagcttgc    6900
tgtgcttcaa atgcagttac gcgccccgtg cggcgctcag cacgctcatc atcatgtccg    6960
agtttacgca tctgctgcag cagcactttt ccgatctgcg catcgacgac ctgttccgac    7020
accacgttct cacggtcttc gatttccacc tgcactttt catcaatcgt tgctttgaaa    7080
aacaagtggg cgacgcggtt gataacgaga atgtcaccct gaaccatctg gccgtggtgc    7140
gggccatggt catgggtgaa gacacggtgc cttacaacaa gcctcggcgc cacccgcaac    7200
agaagcaaaa aaacaaccct tatcacgtcg aagtgccgca agaactgatc gacaactttc    7260
tagaacacag ctcacctagc cgcgaccgct tcgtgcagct gcttttctat atgtgggccg    7320
gcaccggcgt catgagcacc acgccactca cggaactcac gcacactaag ttcgcgcgac    7380
tagacgcgtt atccacggcc tcggaaagag aagacgcaag gatgatgata aagaagagg    7440 aggatgaaga aggaggagaa aaaggaggag acgatccggg ccgtcacaac ggcggtggca    7500
ccagcggggg gttcagcgag agcacgctaa aaaaaaacgt gggtcccatt tacctatgtc    7560
ccgtacccgc ttttttttacc aagaaccaaa ccagtaccgt gtgtctgctg tgcgaactca    7620
tggcctgctc ctattacgat aacgtcgtcc tgcgcgagct gtaccgccgc gtcgtctcgt    7680
attgtcagaa caatgtgaag atggtggacc gcattcagct ggtattggcc gatctgttgc    7740
gcgaatgcac gtcgccgctc ggcgcggcac acgaggacgt ggcgcgctgt ggactcgaag    7800
```

```
cacccacctc gcccggaggc gactcggact accacggcct gagcggcgtc gacggcgcac   7860
tggcgcgacc cgacccggta ttttgccacg tcctgcgtca ggcaggcgtc acgggcatct   7920
acaagcactt tttctgcgac ccgcagtgcg ccggcaacat ccgcgtcacc aacgaggccg   7980
tgctcttcgg acgcctgcac ccccaccacg tccaggaggt gaaactggcc atctgtcacg   8040
acaattacta tataagtcga cttccgcgac gtgtgtggct ctgcatcaca ctcttcaagg   8100
cctttcagat tacaaaacgc acctacaaag gcaaagtgca cctggcggac tttatgcgcg   8160
atttcacgca gctgttggag agttgcgaca tcaagctggt ggaccccacg tacgtgatag   8220
acaagtatgt ctagcgtgag cggcgtgcgc acgccgcgcg aacgacgctc ggccttgcgc   8280
tccctgctcc gcaagcgccg ccaacgcgag ctggccagca agtggcgtc gacggtgaac   8340
ggcgctacgt cggccaacaa ccacggcgaa ccgccgtcgc cggccgacgc gcgcccgcgc   8400
ctcacgctgc acgacctgca cgacatcttc cgcgagcacc ccgaactgga gctcaagtac   8460
cttaacatga tgaagatggc catcacgggc aaagagtcca tctgcttacc cttcaatttc   8520
cactcgcacc ggcagcacac ctgcctcgac atctcgccgt acggcaacga gcaggtctcg   8580
cgcatcgcct gcacctcgtg cgaggacaac cgcatcctgc ccaccgcctc cgacgccatg   8640
gtggccttca tcaatcagac gtccaacatc atgaaaaata gaaacttttaa ttacgggttc   8700
tgtaagagca gcgagctact caagctctcc accaaccagc cgcccatctt ccaaatttat   8760
tacctgctgc acgccgccaa ccacgacatc gtgcccttta tgcacgccga ggacggccgg   8820
ttgcacatgc acgtcatctt cgaaaacccc gacgtgcaca tccctgcga ctgcatcacg   8880
cagatgctca cggcggcgcg cgaagactac agcgtcacgc tcaacatcgt gcgcgaccac   8940
gtcgttatca gcgtgctgtg tcacgccgtc tcggccagca gcgtcaagat cgacgtgact   9000
attttgcaac gcaagattga cgagatggac attcccaacg acgtgagcga gtcctttgag   9060
cgctacaaag agctcattca ggagctgtgt cagtccagcg gcaacaacct atacgaggag   9120
gccacgtcgt cctacgcgat acggtctccc ttaaccgcgt cgccgttgca cgtagtttcc   9180
accaacggct gcggccctc ctcctcgtcc cagtccacgc cgcctcatct ccaccccgccg   9240
tcgcaggcga cgcagcccca ccactactct caccaccagt ctcagtctca gcagcatcat   9300
caccgtcccc agtcaccacc gccgccgctg tttctcaaca gcattcgtgc gccttgacac   9360
tgtacggcag aaaagccggc tccaagtgca agcgccgcgg cagcaccatg tgcaaaaact   9420
tgtccttgcg cgcggtttcg ccgccgggaa agacgggcga cagcacgtta gttacagcct   9480
tgagaacctg ctcaaagtac ttgtcggcgt gaatgggcac gccgtgctcg cgcacgtagc   9540
tcggatcttc ggctacctcg tagttgcaca cggccgacgg tggtttccgc gccctcttct   9600
ttgccggctc tcctcctctc ctgttgctct cctctacccc gccgccgtca gcgtcgtcgt   9660
ccgtgccatc aatcgcgtcc gacccgggaaa ccacgccggc ggttacagaa tcaccgttgt   9720
cggaggaacc ctgcggcgcc gtccggacac cgggcgccgt cagaacgtaa aagacccgat   9780
ccccgaccga gggtagctcc tcagaacggg ccgccaatcg cttaatgacg gcaatgtgcg   9840
gcaggttaga ttgacggtac agcgagatgt ccttagagag caccgacgaa agcaccaggt   9900
cctcgacacg cacacggtgc aggtacagat cgtcgcgggc ctgcaccaag cggcgtaaga   9960
tacgccagaa accgcgtggc acgccgtact tcttgacttc atcgagtgag aggcgcgaca  10020
ggcgcacggc tgcttccgag acctcgcgat cctcaaagag cagcgagagg acgtcacgcg  10080
tgacgcccctt gacgaactcg caggccgtct tgcgcaccag atccacgccc ttcatgctca  10140
```

```
gacccgaggc gccctccact ttgccgatgt aacgtttctt gcagatcatc ataagagaga    10200
cgaagacctt ttcaaactcc agcttgacgg gctccacaaa aagacaggcc gtcacgtagt    10260
gcgccaggct gggcccacgc gccaccagag cctgcggcgt caggccacga aagcggacaa    10320
acacgctgtc cgtgtccccg tagatgaccc gcgcctccac ccgccgttcg ttcgagcccc    10380
ctgacgatgt ttcgagcccc tccggtaacg cgctgctctc ctccgaatcc ccctcccgcg    10440
ttcccactac atagtcttcc tgattaaaaa aattgtgcaa aaaacacggc tctgaaaagt    10500
tgtctttgat gaaccgcgcc gtgcgctcta gcatgtcgcg accgatgcgc gtgatgctgg    10560
cggcgatggg cagacacggc atcataccgt tgaccacgcc ggtaaaaccg tagaaagcgt    10620
tgcacgttac tttgagcgcc atctgttcct tgtcgagcag catacggcgc acagggtctt    10680
gacactcgcg catgcattcg cgcacggcac gccgctgcga acccacttg ttgagcagtt    10740 ccgagagcac cgagacgcgc accgaagcac gcacaaagcg gtgggtcacg ccgttctcta    10800
gcgtgacgct gtatacgtcg gcggggtcca cagggtactc gccacccggc accagcaggg    10860
tggagtagca gaggttgtgg gccatgatga tggaagggta gaggctggca aagtcgaaca    10920
cggccacggg gtcgttgtag taacccacct cgggctcaaa caccgtggcg ccctggtacg    10980
aaaccgccgc agtaccgccg gcgccgtgat tgtcgttgga aacgccgacg ccgccactac    11040
tgccggagcc gacgctgaaa acgccgacgc tgctactact gttactgccg gagccgggtg    11100
aaacgccgtc ctgactggac ggcgcagatt gcaagggcgg cgacatctga acatagccg    11160 ccacagaacc cgcgtcgccg ggcacagcgg cggtagagat gatagcagcg ttaggtgaca    11220
cagcaacgct attcgtttcg ggcaccgtcg tacctttgct gtagtggttg ggcaggataa    11280
aatcgcggca ggcgcactcg tccagcagcg aggtgtagat acggatctgc tgtccgtcaa    11340
agatgacacg ccgcaacgga attttagcca gccgcgcgat ggccccggcc tcgtagtgaa    11400
aattaatggt gttgaacaga tcgcgcacca atacggcgtc ctgcagacag taacggccta    11460
cctgggcgcg gccctcggca ttagccacga aacaacgcgg gatgtccttg taagacaggt    11520
catccttgcg ttgccgcagg taaagctcgg ccatagtgtt gagcttatag ttgggcgagt    11580
tagtcttggc catgcataca gggtacatgt cgataaccac cgaacccgca atatacacct    11640
tggtggcggc cgtgctggcc ggattgttgt gagaagccga gggaaaagcg gcggcgtact    11700
gccgcttaaa acccacggcg gggctgtgta aaaagaaacg gccgccctgc gccgtaggca    11760
acttgcagaa gcgctgcgag tccaccttat acaggtactc gagacgcgtg aggatgtact    11820
tcaagtcaaa agagttgatg ttgtaaccgg tcacaaaggc cggcgcgtac cgttgaaaga    11880
aaagcataaa gcccagcagc agctcgtatt cggaagggaa ctcgtagacg tccacgtctg    11940
ggcccacctg cccgcaggtg ccgatcgtaa agagatgaag acccgagtgc ccaaagatca    12000
caccctccga agtgcagccc cgaccatcgt tcccgtttgg gatcccctga tccacggcgg    12060
tgtttccccc cgtctcgtag cacacgcacg agatctgaat gacaatgtca tcggacttct    12120
cggcgcaggg aaaaccaccc tcgccgctca tgcactcgat atcgaaggac aggcatcgat    12180
agcgcggcca cgagctgtcg tcgggcacag ccaccaggtc agagacatcg cagtctacct    12240
cgatatcaca agtcgacgcg cgaccctgct gccgccagtc gtaacgattc acggagcacc    12300
agccgaacgt ggtgatccgc cgatcgatga ccaaacgcgt cagcggatcc acacggacct    12360
cgtacacggg aaaaccctgc tccagcagat actcgccgat ttttctggcc atggtccagt    12420
tgctgataga cacacactgc aaatcgggca cgggtcgcgt cccgtaccca tagatggagg    12480
tcttggtggc cggcgtgaca gacacggcgt atggcgtccg cggttcgggc actagttcgc    12540
```

| | |
|---|---:|
| ccacgctggc aatgacctca cgcagcctat cggtgtcgct gtactcacag taaaagtagc | 12600 |
| tgcgctgccc gaaaacgttg acgcagatac tgtagccgtg ttctgtggcc ccgaagaaac | 12660 |
| gcaacacgtt ccccgaaggc accagatgct gacgatagcg cggcgacacg ttttcgggcg | 12720 |
| agtcgaagaa gagcacggcg tccgtctgat cgtaggtgtg aaaacgaata ggtcccacca | 12780 |
| cgcgacccac cagggtctcg cgccaaggac acggccaaac catgtcatga ctcaacaaat | 12840 |
| gtttaatctc tcgatagaac atgagaggca gccgtcccgt cttatgcttg atcaaccccg | 12900 |
| tctgaccgtc gaacatgaca cctcgcggca cgatctgcaa aaactgtttc tgtggcggcc | 12960 |
| gcttgcccga gccctgcgcg gagccgggct gcgaacgctg acgccggcca cccgcgaccg | 13020 |
| caccgccggt cacgccgccg ctcagatacg ggttgaaaaa catagcggac cgtgagaggc | 13080 |
| tgacagctta cgaagcaaaa tcacaaagaa aatacacatg cagcacctag atatccagtt | 13140 |
| taacccgta tatcacaagt ctctgtgtca atatttttg tctagttttt ttttcctcct | 13200 |
| ggttcagacg ttctcttctt cgtcggagtc tttcaagtgt ctgtagccgt ttttgcgatg | 13260 |
| tcgcagccgg tctagcaggt taggcttctg tcccttgtcc tgcgtgccag tctgtccgtc | 13320 |
| caaagaatct gtaccgttct gctgcgctcg ctgctctgcg tccagacggg ccagggccag | 13380 |
| aagcatctgg taagcctgct cgttggtgta aggcggagcc gccgtggatg catcagacga | 13440 |
| cggtggtccc ggtcctttgc gaccagaatt ataaacactt tcctcgtagg aaggcggagc | 13500 |
| ctgtaacgac gtgtctttgg tgctgcccga cgtcacggtg gtcccgtcgg cggacaccag | 13560 |
| atagggaaag aggttctgca gcggctgcgt gcacagacgc cgctgtcgag tatagatcaa | 13620 |
| ataagtgata atgactacgg ctatggccac gaggatgatg gtgaaggctc cgaagggggtt | 13680 |
| tttgaggaag gtggcaacgc cttcgaccac ggaggccacc gcgccaccca cggcccaat | 13740 |
| ggctacgcca acggcctttc ccgcggcgcc caggccgctc atgaggtcgt ccagacccctt | 13800 |
| gaggtagggc ggtagcgggt cgactacctt gtcctccacg tactttaccc gctgcttgta | 13860 |
| cgagttgaat tcgcgcatga tctcttcgag gtcaaaaacg ttgctggaac gcagctcttt | 13920 |
| ctgcgagtaa agttccagta ccctgaagtc ggtattttcc agcgggtcga tatccagggc | 13980 |
| gatcatgctg tcgacggtgg agatactgct gaggtcaatc atgcgtttga agaggtagtc | 14040 |
| cacgtactcg taggccgagt tcccggcgat gaagatct | 14078 |

<210> SEQ ID NO 25
<211> LENGTH: 4569
<212> TYPE: DNA
<213> ORGANISM: Human cytomegalovirus

<400> SEQUENCE: 25

| | |
|---|---:|
| agatcacgat acagccggcg gtatcgataa tcttgttgcg gtactggatg gtaaagtcgg | 60 |
| gctcgggctt gatgtcttcc tgtttgatga gggcagcat gataggcgcg ggaggcacgg | 120 |
| gcggtttaat aatcaccttg aaaggacgcg tggttttgcg cggtttctta cgcgggctga | 180 |
| gctcgggagt agcggatgcc ccggggagag gagtgttagt aaccgcgacg ctggtggggg | 240 |
| tcggcttgtt aagaggggcg ctgctaacgc tgcaagagtg ggttgtcagc gtggggccgg | 300 |
| tgctactgga atcgataccg gcatgattga cagcctgggc gaggatgtca cctgatggtg | 360 |
| ataagaagac acgggagact tagtacggtt tcacaggcgt gacacgttta ttgagtagga | 420 |
| ttacagagta taacatagag tataatatag agtatacaat agtgacgtgg gatccataac | 480 |
| agtaactgat atatatatac aatagtttac tggtcagcct tgcttctagt caccataggg | 540 |

```
tgggtgctct tgcctccaga ggcggtgggt tcctcagcac catcctcctc ttcctctggg    600
gcaacttcct ctatctcaga cactggctca gacttgacag acacagtgtc ctcccgctcc    660
tcctgagcac cctcctcctc ttcctcatca ctctgctcac tttcttcctg atcactgttc    720
tcagccacaa ttactgagga cagagggata gtcgcgggta caggggactc tgggggtgac    780
accagagaat cagaggagct gacaccagcg gtggccaaag tgtaggctac aatagcctct    840
tcctcatctg actcctcggc gatggcccgt aggtcatcca cactaggaga gcagactctc    900
agaggatcgg cccccagaat gtactgggca aagaccttca tgcagatctc ctcaatgcgg    960
cgcttcatta cactgataac ctcaggcttg gttatcagag gccgcttggc cagcatcaca   1020
ctagtctcct ctaagacata gcagcacagc acccgacaga actcacttaa gagagagatg   1080
cccccgtaca tggtcatcat acaagcgtca ctagtgacct tgtactcatt acacattgtt   1140
tccacacatg tagtgaggat atccataaat atgtgatcaa tgtgcgtgag caccttgtct   1200
ctctcctcat ccaaaatctt aaatattttc tgggcataag ccataatctc atcaggggag   1260
cactgaggca agttctgcag tgccgccatg gcctgactgc agccattggt ggtcttaggg   1320
aaggctgagt tcttggtaaa gaactctata ttcctgtagc acatatacat catctttctc   1380
ctaagttcat cctttttagc acgggcctta gcctgcagtg cacccccaa cttgttagcg   1440 gcgcccttgc tcacatcatg cagctcctta atacaagcca tccacatctc ccgcttatcc   1500
tcaggtacaa tgtagttctc atacatgctc tgcatagtta gcccaataca cttcatctcc   1560
tcgaaaggct catgaacctt atctaagata tctaaggcat tctgcaaaca tcctcccatc   1620
atattaaagg cgccagtgaa tttctcttcc gtctgggtat atttttttcag catgtgctcc   1680 ttgattctat gccgcaccat gtccactcga accttaatct gtttgactgt agaggaggat   1740
aacaacacat ataagtatcc gtcctcctga ctcatttatc gctatctcga tgccccgctc   1800
acatgcaaga gttaatcttt actctatctg acatacacaa gtaaatccac gtcccatgca   1860
ggttagtata catcacatac atgtcaacag acttaccgag ttctgccagg acatctttct   1920
cggggttctc gttgcaatcc tcggtcactt gttcaaaagt tttgagggat tcttcggcca   1980
actctggaaa cagcgggtct cccagactca gctgactgtt aacctccttc ctcaacatag   2040
tctgcaggaa cgtcgtggcc ttggtcacgg gtgtctcggg cctaaacaca tgagaaatag   2100
agtcataagc acatgggtca catacaggag atatgtatat aacattaata caattttatt   2160
aaaaaaaaag ggggggcaca aaccccgaca cgtaccgtgg caccttggag gaagggccct   2220
cgtcaggatt atcagggtcc atctttctct tggcagagga ctccatcgtg tcaaggacgg   2280
tgactgcaga aaagacccat ggaaaggaac agtctgttag tctgtcagct attatgtctg   2340
gtggcgcgcg cggcagcaac gagtactgct cagactacac tgccctccac cgttaacagc   2400
accgcaacgg gagttacctc tgactcttat cagaacacaa caactcagct gcctgcatct   2460
tcttctgccg ctgccttaag tcttccaaat gcgtcagcgg tgcaagcccg ctccccgagc   2520 tcatttttcag acacataccc taccgccacg gccttgtgcg gcacactggt ggtggtgggc   2580
atcgtgctgt gcctaagtct ggcctccact gttaggagca aggagctgcc gagcgaccat   2640
gagtcgctgg aggcatggga gcagggctcg gatgtagaag ctccgccgct accggagaag   2700
agcccatgtc cggaacacgt acccgagatt cgcgtggaga tccacgttta tgtttaataa   2760
aaactgcggg cactggggac ggtggtgttg tatatgtgaa tttgtaaata ataaatgaga   2820
ccccatcctg taaaaataca gagtccgtgt cagtctctga aggacagtgt attggcatat   2880
agccaataaa gagagttgtg gcaaagagcc atgttatgga ttagtaatgg aaagtatcgt   2940
```

-continued

```
caccaatagg ggagtggtca ataatggtca ataacccaca cctataggct aagctatacc      3000
atcacctata acatgaggaa gcggggtgt atagacccca agccaaaaac agtatagcat      3060
gcataagaag ccaaggggt gggcctatag actctatagg cggtacttac gtcactcttg      3120
gcacggggaa tccgcgttcc aatgcaccgt tcccggccgc ggaggctgga tcggtcccgg      3180
tgtcttctat ggaggtcaaa acagcgtgga tggcgtctcc aggcgatctg acggttcact      3240
aaacgagctc tgcttatata gacctcccac cgtacacgcc taccgcccat ttgcgtcaat      3300
ggggcggagt tgttacgaca ttttggaaag tcccgttgat tttggtgcca aaacaaactc      3360
ccattgacgt caatggggtg gagacttgga atccccgtg agtcaaaccg ctatccacgc      3420
ccattgatgt actgccaaaa ccgcatcacc atggtaatag cgatgactaa tacgtagatg      3480
tactgccaag taggaaagtc ccataaggtc atgtactggg cataatgcca ggcgggccat      3540
ttaccgtcat tgacgtcaat aggggcgta cttggcatat gatacacttg atgtactgcc      3600
aagtgggcag tttaccgtaa atactccacc cattgacgtc aatggaaagt ccctattggc      3660
gttactatgg gaacatacgt cattattgac gtcaatgggc gggggtcgtt gggcggtcag      3720 ccagcgggc catttaccgt aagttatgta acgcggaact ccatatatgg gctatgaact      3780 aatgacccg taattgatta ctattaataa ctagtcaata atcaatgtca acatggcggt      3840
aatgttggac atgagccaat ataaatgtac atattatgat atggatacaa cgtatgcaat      3900
ggccaatagc caatattgat ttatgctata taaccaatga ataatatggc taatggccaa      3960
tattgattca atgtatagat cgatatgcat tggccatgtg ccagcttgat gtcgcctcta      4020
tcggcgatat agcctcatat cgtctgtcac ctatatcgaa actgcgatat ttgcgacaca      4080 cagatcgcc caagtcacca aagtcgtcta tcgccatccc ccgtaaacga taagcgct      4140 atcgccagat atcgcgtatg cccaaaaatc acttttggaa aaatggcgat atcagttaca      4200
cagaaactca catcggcgac attttcaata tgccatattt tcaaatatcg atttttccaa      4260
tatcgccatc tctatcggcg ataaacacca ctatcgcgcg acatgaattt agtcggcgac      4320
agaaatctca aaacgcgtat ttcggacaaa cacacatttt attattcact gcagcatata      4380
gcccatttta gcgcggcaca catccagccg tttgtgtttt ttaacgctct ccaggtactg      4440
atccaggccc acgatccggg ttatcttgtc gtattccagg ttgatccatc gatagggaac      4500
gctgccagcg gcgcccagca ggtactgcgc cttgtcgttc actttgccgc agcgtattcg      4560
cccgtcagc                                                            4569
```

<210> SEQ ID NO 26
<211> LENGTH: 2666
<212> TYPE: DNA
<213> ORGANISM: Human cytomegalovirus

<400> SEQUENCE: 26

```
agatcgtgct tccctcttcc aaggatcgga aagtagcgtc cgtcgtttcc gcggacgcgg        60
cttccctggt acgctccgtt tccgacgacg cggtttcccg ctgcgtggaa actgtctcca       120
tgtcgggacc gcagcgcccg gcggcgtatc cgcaaggtct cgaagctaca gcttgtcaga       180
ggaaaagtag gtttgcaaaa aggtgcgcag ggtcatgatt tcagcaccca tcagcagagt       240
gaaaaccaga ctgagaaaca ccttgacggc cgccaaaagc gcgcgttcca gcggcgtctc       300
gtagcgtaca gccagggccg cttcgtggaa atgcgagacg gctagacagg taatgagcac       360
gctgaaggac aagacgatct taagcaccg ggaccaacca cgcctcaaga tgaccaccac       420
```

```
gattgccgtg aaggtcaacg tgatcaaagc atggacgacc acgatctgac ggcggacggt    480
acgttcggga gccaacaacg ctacgccggt gcagctgaga aaggccagta aggtgaacaa    540
cgcggccgag atgaccaacg taccgtccag gcagagacat atcacgatca acggcggcac    600
gtgaagcagc gtgtaaaaga gcagaacgcc gatattgctg ggatgcgatg tttcgtaaca    660
gtgaatgaag atcactgacg tgacgggtat gacaaagacg aggctgggcg aggactccgt    720
gagacacaga cgagaatggt gaaaccacgt cgcgggcgcc gcgtagcaga aggcgctcaa    780
caacgcggtc aagccggcca gctgccaacc cacggcgcca taggtgtgca gcgccacgcg    840
gcaacagtcg acccaagcca gactgcgggt cgccagccgg gtctcttgga tcccgggggg    900
cacgtagatg accgtgccat cggtgggtac ttgaaaccct tttctcttc tcatggtgcg     960 ctgcgttctc tggaaacggc tgctctgtcc gaaaaccagt tccgaacgaa aatctagggc   1020
gagagggtgg acaacggcgt cgacgacgaa gcatgggaca ggtcgttcgg cgttaacgtc   1080
atcgcgtcgg acgacggtag ttctaagaga cgtagatcgc tcagcaggtc ctgacagttg   1140
cggattcgca agatcagaaa aaaaagggaa atgaacgtaa taaagagctg tagcgacgta   1200
tgcgccacat cgcgtggcat aagaacgtga cggacgaaaa ggacctgctg cgaaaagtga   1260
ccggcgaaga taaggcccac cgtgctgtag aagcccaaaa gcagccgcag gggccaagtc   1320
cagggccgcg tgaagacgat gagaacgttg accagaaaga ccacgaccca gacgccgttg   1380
atgagggtaa attgatcgga cagggtgcag ttgtcgcgac agatgaagac tacttccgcg   1440
cagagcaagg tgatgaccaa cgtgagcaca acgacgtca acacctcgcg gggctcctgg    1500
caggcacacg tgacacctag cgccgggatg tgcgccagga ggccggcgag taatagcacc   1560
agctgtcgga acgacgacg gcagcgcggg tgccggtttc gctgagcgag aaccggtcgc    1620
tcatagcgga aatacacgaa gagcgcggag gccacaggcc caggaggag cacctcgggc    1680 gcccagacaa cgtgacaagg aaagcccgga cgcgacttga gagtcgctgt agggaagacc   1740
agagagaagc tacccaagac ggccaccgcc gcggagattt ggaagaggag caagccggcg   1800
attcggacga caacctcgaa gcgatgcacc cagcccagca cggccaccac ggccgcttca   1860
tcatagtcgt cgttgttgcc gctgtcgaac agccgccgaa acacgatctg tcgctgggtc   1920
gcggtgggaa agcgcagacc catgacagcc ggaggctata tgaccgcgcg tctaagacgc   1980
gagatccgtg gggggacttt tagatgtttg ggcggcccgc ggttctaaca ggcttgattg   2040
gtggagacgg ccggcgcggc gggtggggga aacgacgagt ttttccgtta cgccatggtt   2100
cgcgtgaggt ttctctgtac ctcccgcaaa aggtcacagc ccgaaatgga ggccgcgttg   2160
gtggccccgg tggcgcgtga cgataaccag gtcatccaag cgatgagttt gtctaatgag   2220
tcctcggtgg tgaagaggat gagaatgagc aggtacaggt acaccaggtt ctcatagaga   2280
cacaaggtga gcaggtcagc ctcggaccac gcgatctcaa acaggcgcgt ggtgtcaaag   2340
accgtgacga ccagcatgaa gctgagcgcc atggcgtaat agcccaaaaa agtttgtgc   2400 cccaacggta cgggctgcag gtaaagtgcg atcaagaacg cgataacgcc gatcacaaac   2460
agcgtgacga tgacctgcca tcgacggtga ttatggccgg ctagaccgt gacgcagctg    2520 cagaggctaa aaagcacgca agccaagagg cccgagaagg tcactagcgt agaggaggag   2580
caggcgctgg ccacgatcac cgaaagcgtc gtgagcacgc tataaatggt gagcaggcca   2640
gggctcggtg gcgacgtgaa cgatcc                                       2666

<210> SEQ ID NO 27
<211> LENGTH: 5258
```

```
<212> TYPE: DNA
<213> ORGANISM: Human cytomegalovirus

<400> SEQUENCE: 27
gatctggccg aaaacctacg gcatctctga aagcggtttt tcctcttttt ctacgtgtct      60
gtctcaagat gagacgtcga tatcaataaa ataccgtcg acgtggtttt tttaacagtg     120
tggttttctt tattgactag cgaagtacac agtttacgag tagaaaagac agggaaaggt     180
tatataaaat gctgtattat atacaaaaac atgcacataa acaaacggga ccatcgtgct     240
catcatcccc tccttgatca gttgttcatg taaacgtgtg gcggggtgag gggcggcatg     300
ccgttggcgg cgccgggaat aatgtgccgt cgaccgacgt cgcacacctt gaaacgccgt     360
cggcgcacgc agcggtcgca ggacgggata tcccagagga agcccatgta ggtctcgggg     420
tcctcgtcgt gaaagcggta ggagagttca aagtggtgca acgagcccgt ccgagctcgc     480
agcttctggc gaacaccctc cacgtcatcg gtgcacagcg acagtgctgg gctgtcacac     540
agggcctgaa gctcctgcgg ccacaggtgc gtggccaggg gcgagtccgt cgtcaccagt     600
ttgacgcagt gcatcaggtt ctcggtgatg gcgtcgtaca ggcgactctc agcctcctcg     660
tgcgtcatca cgtttcgagg cagcgacagc tcgtcgtcgt catcctcgtc aaacatgatc     720
atggggtcag gggtttttttt gggatgttga caggtgggtg tcttttccag acgcacgatg     780
gcctcacgcc ggccgctgaa acggtggttt cggtgtccct tctttcccat gacgcaggtg     840
aacataacca cgtcctcggc caaacggtag acggcgtcca tggcggggtc gtagccgtag     900
acgacgccga aagtgtccac caagacgtac tggcgtacga ggaactcttt gcgttctggc     960
acctcgtggc ccagcgcgcc caacaactgg tggtaacagg tgatgcgcgg cacggtacgg    1020
atcatgagct ccatggtctg gatgctgccg cccgcgcgca cgacgctgaa ggatgtttcc    1080
ttgaacttca taacctctgt gttgtgggtc cagaaggcga aatgggtgtc gggacactca    1140
tcgaaagggt cgtcgatggt gtaggaagcg tagcctcgct tggtcacctc ggccgacagg    1200
ctctccacgt caccgcggta gagcatgacg gcgttccagt agtcgtcgta ctgcaccatg    1260
ggccgctggt agtcgcgcat agtgtggaag tggtcgcggt gacgaaagcc gttccgcaga    1320
aagtccttca tggtgggtgc cagctcgtag acgcagtcgc gcaggtcatc gtagcagtag    1380
atgccgccgc gctgcccgat gagcacgatg agttggtagc gcataaagcc cggaccctcg    1440
acgaagccaa aggggtgcag gtactcctga cagcagacgt aagcacctgg tagagaatag    1500
aaaaaatcca cgcacgttga aaacacctgg aaagaacgtg cccgagcgaa cgtcctcttt    1560
ccaggtgtct tcaacgacgt ggggcttacc ttgcgaacag acggtgccca tcttgcccac    1620
gaagggcccc agggcgctgc gcgaacggag ctggatgaag cagcgttcgg gccaggccac    1680
gtgcagccgg gtgccgcatt cctgctccag aaagtcgttg agaccgttaa agtccccggc    1740
tcggatggcg atgcagccgt aggccatcag cgtgtcccgt aggtcgtcca tgacggactc    1800
ctctaccttc gctcgccgac gctgcgcttc tccagccacc gctgcggtcg acagactcct    1860
ccgtccgcct tcggagaact acggcgcggc ggcacggcct ttatagacac tatcagcgtt    1920
gacgtcagac gatccgatga acgtcgtttt ttgtgctgga acttccctcg tcccgacaaa    1980
tgtagcggaa atcttcaagc aaatcgcgac gaagtccgat gaggaggatg caaaagaggc    2040
tgagcaacgc gatgctgccc gccgccacag tacatatgct caacaacgcc cagtgtccca    2100
aggcgcgact tttggctcgg aggagagccg aacggcggtt tctccacatg acggacaacg    2160
tggtccagta cgtccatcct ttgcattccg gtgtccagac gggaagcgtt gtcatgttat    2220
```

-continued

```
ttcccgtaac tgtcacgtta tgttttgttt tgtttctcgt gagcttaacg gtcctcttga    2280
gaaatcgcgg gcacatgtct tgtagaaaga tataatcact ttccgcgtat ttcgtcagtg    2340
ttgacatcac ggtggtagtg ttttctgaag aagtagcgtt gtcagtgacg tttgtttctt    2400
cccaacgtac gtatgattcg aacggactcg tgtgcgctat tgcccgcaac acgtagctgt    2460
ggccggtgaa gttgagcgtc agttgtccca cggtcacgtt cgtgtcattc ctaaaacatg    2520
ctacttctcc gtgaacttcc gtgacgttta tctcacgact ctcgttcaag acacgcaggg    2580
gaaaccagcc ttccaggtga tactgaaaac caaatttaag catgacgctg tgccatttcc    2640
gtcgtgattg attaaacgtt acattcaagg gcagtctggc ttcggtcccg agacaggggc    2700
cgttgtagat ttgcgtgtga ttgcgtgtgc agtttaggtg gcagttcatg ctcgtggtgt    2760
tggaagtgcg attaacgtcc gtaccgtggt acgtacatcg gaccgaaaca ccgtgtcccg    2820
tgctccaaag cagcgtcaac aacagccaca cagaaaccta cgtggagacg cacgggact    2880 ttttattgac ggagactcac gtttctaccc tccccttccc cgtaggtaaa acccacgtt    2940 tatcacacac gttgttttta cctgaaaccc gcgcagcccg tggacgcgac aaaaaaccgc    3000
ggcactagaa agaaaatgaa acaagtatgt ttattaagca gcatgtgggg ctaataggg    3060 ggataactga ggtatagcaa ctatgaaaaa atactacaaa aaaaaaagct gaacatggtc    3120
atctagcagc aaagttctcc ttctagacca cgaccaccat ctgtaccacg tcgccctccc    3180
cggccgtgta cacgacatcc ttcaccacga ccggcggcag cggcggcgac gaggacaact    3240
cgctctcgac ggaggccggg acgacagagg acgggggggt ggtggcggcg gaggacgaag    3300
gggtggcggc ggcagcggga tcttcttccg acacgggcaa cggcaggctc ggcggcgcgg    3360
acagcacccg ttgcgccggg gcgtgagaag gctgagcccc ggtggcctgg atgtgggcca    3420
acgaattggc tcgcagcgag tcgcgatcca cgaaggtcat aggaattttc ccttcgcgga    3480
tccgccgctc agattccagg atggcgcgca cgtagctgtt caccgacttg gcaaaagtgc    3540
gcggcccctc cgtattcttg tcgcgacgcg cttccagcac ctgcttttcg tagtccagct    3600
ggtggaagac catcaccagg tcgtccatag tgtgcgcgtg ctgacggacg tgggagcgca    3660
cctccaccgg gaacaaagcg ttccaatact ccagcacgat agcaccgtgc cagaactgcg    3720
ccatgctggg cgccaggaaa aacaggatac cggagtcgta ggcgaacacg tcccacttgg    3780
gcgtcatgaa caacaccagc tgacgcgtgg gccgcaccga agcttcctcc caggcctcga    3840
tgaccccgaa catgatgagc tcctggtcca acgggggca gtgtcgctcc agccaactga    3900
tcttgctcag gttcatctgc agaaactcgt acgaagggtc gcagatgcac acgtagagac    3960
ccgagtcgtg ccgcagcctg gctccgcgct tcatcagttt cctcaccgcg tagcgaagcg    4020
ccaccttgcc caacgccgac gcctggatca gtcccccac gtccatctgc gtctgtcgcc    4080
actcggcctc gtccagcagg ctcatgatag cggcagtgct atgcgtggtc gtagtcatcc    4140
tttctatcct tctctatgaa tagcagcaat agcggtaaag tcccttctta tactatcccg    4200
gagtctgtgg tttttttgtt taccctgct tactggtgag actgctgggg gccgttgtgc    4260
tgcagcatcc gagctcgttg ccgccgttgc cacaggaacc ggtgtctccg cagggccttt    4320
ttgagggctt cgcaggcttc tcgcgcaagt cctgagaggc cctcggcgtc gatgggttc    4380 acctcggggcg tccgagcctc gttttcttct tcttcatcct cccttcctc ctccgtgtcc    4440 tcccgctctg tgtcctccgt tacgctctcc tccccggcct cggccaagag cgcggccacc    4500
aagtccacgg accgctcggt ctccgagttc tcaccgtcaa ttacgccatg ttggcggcgt    4560
aaccggtgcc gagaacgccg ggtgagcgca catgcttttt tctttcttaa ccaaggcggg    4620
```

```
agaggatctt caaggcgttt tcgctggatc cagcggtagc taaagtacca aaaggccagc      4680
aggcccacgc tacctaacag attcacgtag actggagaca taattaaaga aagaagtgaa      4740
acccgcgtgt gggtctcacg tcgtcttgaa acaccgtctt atatacatga agatgccgga      4800
catgacgcgc ccaagacacg tggggttttc cccttaggcg acccggtttc ttaagatgtt      4860
tttcatcttc gcacgcgatg tactacatca aagggtcggc tgaccgaccg cattgacgca      4920
cagtttccga gtacgcgcgt ctcggagcac ctgacggtga gccacccaac tcacgcggat      4980
aggggacaac actgacgtga ggggcgattc acgtcactga cgggaataag acgggtgagg      5040
gatttccacc ttttcttaa gtgtgactct ctttacggta aatcgcacct gtgacctctt       5100
aacccctcct ccctggtacc cgataaccgt gaaaaacaca caccacacgt cacgacaccg      5160
atcgattttc tttattctta gtgtgatgat aggtaagggc actcgtgagg atgtgcaatt      5220
atcattatca agccttttc aaggcgtagt gatgatcg                              5258
```

<210> SEQ ID NO 28
<211> LENGTH: 20834
<212> TYPE: DNA
<213> ORGANISM: Human cytomegalovirus

<400> SEQUENCE: 28

```
tgttgagtag taggtgaaat gcgtgagggt ccagcgcttc ggatgcggcg tccgcgccat        60
atcgttgcga aggtaggtga ctgaggaggt agacggtgaa gacagtgagg taggggggga      120
ggccgggccg catagcgcgg ctgcgccgct gggttcagcg gcgtgatcca ggtggtggtt      180
ggcgttacac ccgagagaag gagagaaagg atcccaggaa ggggcaccog ggtgtggcgc      240 tacgggttac aaaagtcgcg tctctgtcta tttaatacga tgtcattggc cgctgcgaag      300
gaagaagagg ggacacgcgg gtaagccatg ccgtccgggc gtggggacga cgctgattcg      360
acggggaacg ctctgcggag attgcctcac gtgcgtaagc ggatcggtaa gcgtaagcac      420
ctggacatct accgtcgcct gttgcgggtc tttccctcgt tgtggccct caaccgcctg       480 ttgggaggcc ttttcccacc cgagctgcaa aagtaccgtc gccgtctttt catcgaagta      540
cgattaagtc ggcggattcc cgactgcgtg ttggtgtttt taccgccgga ctctgggtcg      600
cgcggcatcg tgtattgcta cgtgattgag ttcaaaacta cgtactcaga cgccgacgat      660
cagtccgtgc ggtggcacgc cacccacagc ctgcagtacg ccgagggcct gcgccagctc      720
aagggcgcct tggtggactt tgattttctg cgtctgccgc gcggtggcgg tcaagtctgg      780
agcgtagtgc ccagtctggt ttttttcag caaaaggccg atcgcccatc tttttaccgg       840
gcttttcgtt cgggccgttt cgacttgtgt accgattctg tcctggacta tctgggacgg      900
cgtcaggatg agtctgttgc acaccttttg gcggctaccc gtcgccgtct tcttcgaacc      960
gcacgaggaa aacgtgctgc gctgccccga gcgcgtgctt cggcggttgc tggaggacgc     1020
ggcggtgaca atgcgcggcg ggggctggcg cgaggacgtg ctcatggacc gggtgcgcaa     1080
acggtatctg cgtcaggagc tcagggatct gggtcacagg gtgcagactt actgcgagga     1140
tctcgaaggg cgcgtgtccg aggcggaggc gctgttgaac cagcagtgcg agctcgacga     1200
aggaccgtcg ccgcggacgc tgctacaacc accgtcgtcgt ccgcgttctt cgtccccagg    1260
gaccggcgtg gcaggagctt ctgccgtccc acacggtctt tatagtcggc acgatgccat     1320
cacgggaccc gccgccgccc cgtctgacgt ggtcgccccg tctgacgcgg tcgccgcgtc     1380
agcggccgcc ggtgcttctt ctacctggct ggcgcagtgc gccgagcggc cgttgcccgg     1440
```

```
gaacgtacct agctactttg gaatcacgca gaacgatccc tttatccgct ttcacaccga    1500
ttttcgcggc gaggtggtca acaccatgtt cgagaatgcc tctacttgga ctttctcctt    1560
tggtatctgg tactatcggc tcaagcgggg gttgtacacg caaccacggt ggaaacgagt    1620
gtaccatctg gcgcagatgg acaacttttc catttcgcag gagctgctgc tcggcgtggt    1680
caacgctttg gaaaacgtga cggtgtatcc gacgtacgac tgtgtactct ccgatttgga    1740
agccgccgcc tgtctgctgg ccgcctacgg acatgcgctt tgggagggcc gcgatccgcc    1800
ggactccgtg gcgacggtgt tgggtgagct ccctcagctg ttgccgcgtc tggccgacga    1860
cgtgagtcgt gagattgccg cttgggaagg ccccgtcgcc gcgggtaaca actattacgc    1920
gtatcgcgac tcgcccgatc tacgctacta catgcccta agcggtggtc gtcactatca     1980
cccgggcact tttgatcgtc acgtgctggt gcggcttttc cacaaacgcg cgttattca     2040
gcatttgccg ggctacggga cgataacgga ggagctggtg caagagcgtc tgtcgggcca    2100
ggtgcgcgac gacgtgcttt ctctctggag tcgacgtctg ctggtcggca agctgggtcg    2160
cgacgtgccc gtctttgtgc acgaacagca atatctgcgt tcgggcctga cctgcctggc    2220
tggcctgctg ttgttgtgga aggtgaccaa cgcggatagc gtcttcgctc cgcgcacggg    2280
caaatttacg ttggccgacc tgctgggttc ggatgccgta gccggcggcg ggttgcccgg    2340
ggggcgcgcg ggcggcgaag aggagggcta cggggacgg cacggcggg tacgtaactt       2400
tgagtttctg gtacggtact acatcgggcc gtggtacgcg cgcgaccccg cggtcacgct    2460
gtcgcagctc tttcccggcc tggctctgtt ggccgtgacc gagagcgtgc gcagcggctg    2520
ggatccctca cgtcgcgagg acagcgccgg aggtggcgac ggcggcggcg ccgtgctcat    2580
gcagctcagc aagagcaacc ccgtggccga ctacatgttc gcgcagagct ccaaacagta    2640
cggcgattta cgtcgcttag aggtacacga tgccctgctc tttcactacg aacacgggct    2700
agggcggctg ttgtcagtga ccctgccgcg tcaccgtgtg tccactctgg gctcgtccct    2760
ctttaacgtc aacgatattt acgaactgtt gtactttta gtgttggggt tcttccgag      2820
cgtggcggtg ttgtaatttc caccacgtgt cgctcgctgc ataaagggcg aacgtcctcg    2880
gagagggtat attcgttcgg cgagagcggg cggcggtggt gggtatgtcc ccttctgtgg    2940
aggagactac ctcagtcacc gagtccatca tgttcgctat tgtgagtttc aaacacatgg    3000
gcccgttcga aggctactct atgtcggccg atcgcgccgc ctcggatcta ctcatcggca    3060
tgttcggctc cgttagcctg gtcaacctgc tgactatcat cggttgcctc tgggtgttgc    3120
gtgttacgcg gccgcccgtg tccgtgatga ttttacttg gaatctggta cttagtcagt     3180
ttttttccat cctggccacc atgttgtcca agggtatcat gctgcgtggc gctctaaatc    3240
tcagcctctg tcgcttagtg ctctttgtcg acgacgtggg cctatattcg acggcgttgt    3300
ttttcctctt tctgatactg gatcgtctgt cggccatatc ttacggccgt gatctctggc    3360
atcatgagac gcgcgaaaac gccggcgtgg cgctctacgc ggtcgccttt gcctgggttc    3420
tttccatcgt agccgctgtg cccaccgccg ctacgggttc actggactac cgttggctag    3480
gctgtcagat ccctatacag tatgccgcgg tggacctcac catcaagatg tggttttgc     3540
tgggggcgcc catgatcgcc gtactggcta acgtggtaga gttggcctac agcgatcggc    3600
gcgaccacgt ctggtcctac gtgggtcgtg tctgcacctt ctacgtgacg tgtctcatgc    3660
tgttgtgcc ctactactgc ttcagagtcc tacgcggtgt actgcagccc gctagcgcgg      3720
ccggcaccgg tttcggcatt atggattacg tggaattggc tacgcgtacc cttctcacca    3780
tgcgtcttgg cattctgccg ctctttatca ttgcgttctt ctcccgcgag cccaccaagg    3840
```

```
atctggatga ctcctttgat tatctggtcg agagatgtca gcaaagctgc cacggtcatt   3900
tcgtacgtcg gttggtgcag gcgttgaagc gggctatgta tagcgtggag ctggccgtgt   3960
gttacttttc tacgtccgtc cgagacgtcg ccgaggcgt  gaaaaagtcc tccagccgtt   4020
gttacgccga cgcgacgtcg gcggccgttg tggtaacgac aaccacgtcg gagaaagcca   4080
cgttggtgga gcacgcggaa ggcatggctt ccgaaatgtg tcctgggact acgatcgatg   4140
tttcggccga aagttcctcc gtcctctgca ccgacggcga aaacaccgtc gcgtcggacg   4200
cgacggtgac ggcattatga gcggcggcgc tgtacggcag cggggagaaa agtggcagat   4260
aaatcacgtc aggttcacac gtcgttagcc agcgtcggca tatgaagggc gcgggcggcc   4320
agtacggcct ctgggctgag acaggacgag gcagggtgag aaagaggagg atgggggga   4380
ccggggtggt ggtgctgctg ctgttgtggg tgcggacggt gcgggtgccg ggacagcgtg   4440
ccggcgaacg ttctgtaatc ttccataata aaagtaaaaa tgcccgtctc gtgtcgactc   4500
cgctggatct cgaaggcgtc gggggtaatg cgcatcttgc cggtgccgat gagataaaag   4560
taccacattt tttgacagat gatgcgaatc aagggttcgt acgcttcggc accccagtgg   4620
cgcgtgaaga aggccgccag acgaaacaag cggtgtccgt agagcgtgcc tagggagaag   4680
aggatgttgc cgttgcgcgc caggtcttcg gggaaaacga ccggcaggcc ggtgtggcgc   4740
tgcacaaagc gcgtcagcag tccgccgctc aagcgcgggt gacacaggcg ctggctgaga   4800
cgggcggcgc gcgtttcatc gaacacggcc gcctcaaagt ccagcccgg  gaaggcctgg   4860
cgcagttcgc ggtacagatg aggccagtag ggttgcggcg tcttgcgact aagcacggcg   4920
tggtccgaga cacccaggtt gttcatggtt tcgcgcagta gcagcgtttc gagaccgcgg   4980
tgaaagagga ggacgcagat gaggcgtacg atcttgagtt cttccaaacg cagcgagctc   5040
agcggctgtc cgcgcgacat cttctcgcta atctgtaata ttagatgatt ggcgcaagta   5100
aaggagaatt tgcccgtgcg gacccgcggg acggcggggt tctcttcgtc gcgggccatc   5160
atcgttcgct cggtgagcgg gtagcgacgg tgacgacaat gacgatggac gagcagcagt   5220
cgcaggctgt ggcgccggtc tacgtgggcg gctttctcgc ccgctacgac cagtctccgg   5280
acgaggccga attgctgttg ccgcgggacg tagtggagca ctggttgcac gcgcagggcc   5340
agggacagcc ttcgttgtcg gtcgcgctcc cgctcaacat caaccacgac gacacggccg   5400
ttgtaggaca cgttgcggcg atgcagagcg tccgcgacgg tctttttgc  ctgggctgcg   5460
tcacttcgcc caggttttctg gagattgtac gccgcgcttc ggaaaagtcc gagctggttt   5520
cgcgcgggcc cgtcagtccg ctgcagccag acaaggtggt ggagtttctc agcggcagct   5580
acgccggcct ctcgctctcc agccggcgct gcgacgacgt ggaggccgcg acgtcgcttt   5640
cgggctcgga aaccacgccg ttcaaacacg tggctttgtg cagcgtgggt cggcgtcgcg   5700
gtacgttggc cgtgtacggg cgcgatcccg agtgggtcac acagcggttt ccagacctca   5760
cggcggccga ccgtgacggg ctacgtgcac agtggcagcg ctgcggcagc actgctgtcg   5820
acgcgtcggg cgatcccttt cgctcagaca gctacggcct gttgggcaac agcgtggacg   5880
cgctctacat ccgtgagcga ctgcccaagc tgcgctacga caagcaacta gtcggcgtga   5940
cggagcgcga gtcatacgtc aaggcgagcg tttcgcctga ggcggcgtgc gatattaaag   6000
gcggcgtccg cgagcgttcg ggcgacagcc gcagtcaggc cgccacgccg gcggctgggg   6060
cgcgcgttcc ctcttcgtcc ccgtcgcctc cagtcgaacc gccatctcct gtacagccgc   6120
ctgcgcttcc agcgtcgccg tccgttcttc ccgcggaatc accgccgtcg ctttctccct   6180
```

-continued

```
cggagccggc agaggcggcg tccatgtcgc accctctgag tgctgcggtt cccgccgcta    6240
cggctcctcc aggtgctacc gtggcaggtg cgtcgccggc tgtgtcgtct ctagcgtggc    6300
ctcacgacgg agtttattta cccaaagacg cttttttctc gctacttggg gccagtcgct    6360
cggcagtgcc cgtcatgtat cccggcgccg tagcggcccc tccttctgct tcgccagcac    6420
cgctgccttt gccgtcttat cccgcgtcct acggcgcccc cgtcgtgggt tacgaccagt    6480
tggcggcacg tcactttgcg gactacgtgg atccccatta tcccgggtgg ggtcggcgtt    6540
acgagcccgc gccgtctttg catccgtctt atcccgtgcc gccgccacca tcaccggcct    6600
attaccgtcg gcgcgactct ccgggcggta tggatgaacc accgtccgga tgggagcgtt    6660
acgacggtgg tcaccgtggt cagtcgcaga agcagcaccg tcacggggc agcggcggac     6720
acaacaaacg ccgtaaggaa accgcggcgg cgtcgtcgtc gtcctcggac gaagacttga    6780
gtttcccagg cgaggccgag cacggccggg cacgaaagcg tctaaaaagt cacgtcaata    6840
gcgacggtgg aagtggcggg cacgcgggtt ccaatcagca gcagcaacaa cgttacgatg    6900
aactgcggga tgccattcac gagctgaaac gcgatctgtt tgctgcgcgg cagagttcta    6960
cgttactttc ggcggctctt ccctctgcgg cctcttcctc cccaactact actaccgtgt    7020
gtactcccac cggcgagctg acgagtggcg gaggagaaac acccacggca cttctatccg    7080
gaggtgccaa ggtagctgag cgcgctcagg ccggcgtggt gaacgccagt tgccgcctcg    7140
ctaccgcgtc gggttctgag gcggcaacgg ccgggccctc gacggcaggt tcttcttcct    7200
gcccggctag tgtcgtgtta gccgccgctg ctgcccaagc cgccgcagct tcccagagcc    7260
cgcccaaaga catggtagat ctgaatcggc ggattttgt ggctgcgctc aataagctcg     7320
agtaagagag acgctatatt tagggcttcc ctctctttt tttctacacc gtgatacccc     7380
aataaagcac accgcggtta ttatcaacgt ctctgtgttt ttattattta gaaataaata    7440
cagggaatgg gaaaaacacg cggggaaaa acaaagaagt ctctctctag atgcggggtc     7500
gactgcgtgg ggtgctggaa gtggaagcgg tgctgatggg tgagggtcgt ggcgcgggca    7560
cggaccgcaa cgtgctgctg atgtctgccg cggtacgcac gtcgccgtcc atgtcgctgc    7620
gcagataaga ggtaggtcgt agtgcggcgt gctgcacgct caccgttaat ggtaccaagt    7680
cgtcaaggct cgcaaagacg tgccacgagg ggatgacgag cgtgagagcc ccgttgttac    7740
cgcttcgacg tctttgtccg gtcaggatca gtgccgggga cagtccggct tgggtgtccg    7800
agtcctcgtc gccgctggct tcctcgaagc cggcaaacat ggcttcggac aggggggtcg    7860
gcgtcggtgt ggaggagagg tcatcttcgt cgtcctcttc ctcttcttcc tcctcttcct    7920
cggtgggtgg taatccgggg gactgcggga gaaactcgga gacggcgccg cgcatgacgt    7980
tgctccgtgg aaagagaccg gcgcgcagct gcacctgggg acgcttgatt ttgtccggtt    8040
taccgggtgt gagagtccaa aacccacggc ggaaaaagtg gatgcggcct agcggctgtc    8100
ggtgttccaa atgaacggcc tgatcgccgg tcagcgtgac gcggagggtg attcgcacac    8160
gatcgggtag cgggccggct tctatggaga cgcccgggat gttttccggg aaaaagatgg    8220
tgtcgtgagt ctgattggtc tcgaaagcat tctggatctg cacgatgtac tcgggatgta    8280
tgcgcgtcag cgtaaaactt tgggaatca acagctggaa gccgttgtcc ggcaagcgtc      8340
gtaggtgcgg gtacgattg tgtcgcgcca ccacctcggc gcgatgcgtg taaaccgaaa      8400
agtgcagaaa cacgctggtc ggcgggtgcg gtgagtcgtg atgcagaaac agcatgatcc    8460
attggcctcg ttcgtccgtc tccgtttgt ggatgtacgt gttagggtcc gaacaggcca      8520
gctgctccag ggcgtctacc agcgtcagcg ggatggcgcc ggcgcgaaag gcgaactggc    8580
```

```
tgacaaagat ctgccctgcc tccaaactgc tgtcggttct gcggcgccag ttcggcgtta    8640
cggtcagtcg cacggcccag tggtgagccg tgcggcggat gatggcgcgc gcttccattc    8700
gcggccgatt ttcttcgccg ccgcgccgct ggctctgaaa gaggtgcagt ccgctaacgg    8760
gcacgcggtc cagcggcagc gcaaaggcca gtaccgagac cgtgttgttt tctgagcctg    8820
gcgtcaggcg tcgtgggcca aagttgttga ggtccaccag cagtcggtcc tgttcgccca    8880
ccacgcagcg gcccttgatg tttaagtcgg tcaggtctac ggtgtcgtgc ggagatttgt    8940
tctcctgaaa acagcagaga accgagggcc ggctcacctc tatgttggta cgcaggtcca    9000
ggagtcgcag acgaccggct ccagcgagc cgccttccac gttggtgatg agccgaagca    9060
cctggcagtg caggcgacca aagcttccgc tggcggcttc ggcctcgctg atcgcggccg    9120
cttccgacga gggtccctca ccgggcgagg acgatgcctg agacattgcg aaggcgggat    9180
ggggggaggg tcaggggatg cgcaaaggtg aacgggtctt cgtgggaggt cgggaagggt    9240
tccggcaact gtcgcaaata tagcagcggt gacaggtgtg gcggccaaaa gttgcgtgtc    9300
tgagtggacg tgggtttta tagagtcgtc ctaagcgcgt gcggcgggtg gctcaacctc    9360
ggtgcttttt gggcgtcgag gcgatgcatg gcccgggcaa ggcgtcttgc cggtggcggc    9420
gacgtttggg ttgcgcagcg ggctgccata cgccttccaa ttcggcgaag atgcggtaga    9480
tgtcgttggc gtcccagaag aattcctggt acttcagatt ctgaccctga accgtagcca    9540
ccatgggcac caggttgcgg gccaggatgc cggcctgcca gggcggccag gtgaacacgg    9600
ccggattgtg gatttcgttg tcggaatcct cgtcggtgtc ctcttcggc gcgacggtgg    9660
actcggcctt aaggcggccg cgtgtcataa cgcccgacgt gcacgccgtc gccgaggatg    9720
ctgatttgcg tttgcggccc gcggaagtgg aggcgcccgc catggcgccg ccgccggtga    9780
cgcggggcgt cttgcgctcg gtggttacga gttcttcgtc ggagtccgat ccgctggtcc    9840
agacgtcgtc gtcgccctgg gcggcaccct cgtcgtgccg gtcccaggtg tgtcggtact    9900
caagcttgcc ctggatgcga tactggctgg tgaaggtggg gtgctcgctg tactgaggcc    9960
cgcgctgcag cagcaagtcg atatcgaaaa agaagagcgc agccacggga tcgtactgac   10020
gcagttccac ggtctcgcgt atggcttgta cctccaggaa gatctgctgc ccgttcatca   10080
acaggttacc tgagatgctc aggcccggga tgctcttggg acacagcagc ccaaaatgct   10140
cgtgtgaggt aaaagccaca tccagcatga tgtgcgagat cttgcccggt tgattatca    10200
tattttggg acacaacacc gtaaagccgt tgcgctcgtg ggggcgcatg aagggttgcg   10260
ggttgcgggt catcgtcagg tcctcttcca cgtcagagcc cagcgtgacg tgcataaaga   10320
gcttgccgga gggcacgtcc tcgcagaagg actccaggta caccttgacg tactggtcac   10380
ctatcacctg catcttggtt gcgcgcgtgt tctccatgga gcaaaccagc tcgtgcgcgc   10440
acaccacgtg ccgcagtgcc acgtccttgg tgggaaacac gaacgctgac gtgtagtaga   10500
cgtcgggctc tttccactgg ttctgctgac gcgtccaggc cagtcccgag accgtgagac   10560
gcgcctgcca catctgcttg cccgacgcgt gaatcacagc gtcagctacg ggcaggtgtc   10620
ggtgtttgcg ctcggccgcc gacgggtagt ggtgcacgtt gatgctgggg atgttcagca   10680
tcttgagcgg cagcgcgtac acatagatcg acatgggctc ctggctgggg cagatgcttc   10740
ggcccgtggg gttgtgcacg ttgaccgaca cgttctccac ctcgctgccc gtaaagtacg   10800
tgtgctgcac ctgcagctga ttgtcgccgc ggtggcatgg cgtcgagtcg ggcgtgtact   10860
gcgataccaa gatcagcgag ggctggctca cgcgtacgtg gatacccgtc tgcaggagtc   10920
```

-continued

```
gcgtctcgtg cggcagcacc ggcgtatcgc cgcgactaaa cacggctttc agcacgtgcc    10980
ccgaaatggg acccagtacg gatatcattt cgggacaacg gcgaccgcgc gactccatgc    11040
tgcctgcgcg tacgggtgta ggcgactgag cggcgcgccc tctgcggccg ccgccttaca    11100
taggcaggcg accaaacgcg gaacccgaaa taaaaacgtt ctacacagag acaaccgcgg    11160
attattgagt gtcttttttt attacaaaaa aagaggcga agccccaccg tcaccacacc    11220
ccatcacaca ccaccaccga ttttttttg ttttaatccc gtatggcgcg gacgcctagt    11280
gtccgtttcc cattatcagg gtcctctgtt tagagatcgc cgcagaccat ggctaaagtg    11340
acaggactcg tcttctctgt cgtatttttcc gtaagcttac agtcttgcgg ttccgtctcc    11400
ggggacgcca gtcgcatggg cagcaggtcc tccagcgcga tggaagcgcc cagcaccgag    11460
agctgctgtt gcgacggcga atgggatgtg gaccgcgagt gtagcgtgga tttgacttgg    11520
tgcgtcattg ctgacaggca accccgattc agcgtatgct ttgacgagat aaaatagagg    11580
cgccccagga gcgcgtcccg tgggaacgtg gcgccgttct cgtcgctcac cagtacggtt    11640
aattccaacc aggagcgcgg tagccagacc gtaacgggca ttttgagtcc ctgacggttg    11700
tgtggtacaa aaacacccag ataaggcccg taaaagcggc ggtagatacg taacgtgtgc    11760
gagttcttca gcgtcaattc gtaagggacg cgcacctcca gtccctcgtc cgccgcgccg    11820
gagcgtggcg gtacaaagta aggcagtggc gcgtccgaaa agaagggtcg tcgcaccgtt    11880
tcgcgtcgca gccgcaggcg aaacgccact gggtcggctg gcgcctcggt gcggtcgcag    11940
gtcacgttga aacgtaatat gccgtcttgg tatagcgtga gtgacgacag cgtcaggtcc    12000
ggcggtgatt cgttcgggtc tagctccaat cgtccaaaga cggagggtcc caatgtcttg    12060
gccgtggttt ccgagaggcg cgccgagata cggctggtga gtccacgcgg ccccgagatg    12120
ccgccttcca ctcgatgcca gcacagcgcg tgtcgtacgc gcaccgtcag cgtgggcgtc    12180
agatccgcgt ccgttgattc cgcggtatca gcgacggaag ccgcgttctc cgttacgttg    12240
tttatatcca gcgtcggctc gaacgtgagt tctggcagat gcagcgccag acagtcgtgt    12300
aacgccgtgt gatgcgcggc tttacgtcgt agcggtagcc gtttcaacag cggcgtgatg    12360
atacggagcg cgaagagatt gagtgatagg cgcacgatgg ccatgcgcgt cagttgttgg    12420
tcaattaccg agcgcaggat atggcagcct gggcgtgcgg gaaagagaga gaaggccggg    12480
cgcacgtcag aatcctcgtt agagaccacg catagaatgc cgcgttcacg atcgtcgttg    12540
cggtcatcct cgtcctcttc tttcttctct tgttttttcct ttttttttctc gggctcgtgg    12600 gaagccgccg tttcttcttc ttgcaacgtc gcggggggcg tttgagactc gtcgttcgct    12660
tcccccaatt gcagcggcgt agagagcaga atctggaagg gatcccgcaa ttcttcgggt    12720
cggaggtcga ggtgcaactg gatcagatgg taggtgccgc ggtgcacccg aggctgacgg    12780
atgtcgtgtt tatccgtcag tgtgaggatg gtctgcggcg agccgctgta cttgtccagc    12840
tcgtccggcg ttttcaggag gagactgtcg tcgtcggtac tggcgacgcc catcatggtc    12900
gtggtggtag tggtggcgag gaaagtgagc ggcggcgccg acagagctcg gcgttggcgg    12960
cggcattttc cgctgtgtcg gctgctattg ctgccaacgc caccgccgcc gcctcgtctg    13020
gctcgtggcc ggcgggcccg attccgaagg ttggggtcga cgcgtggcat gcttggtgtc    13080
tgcgggcgca gagggccgg ctcagccttt aaatatgcag gtcgcggatt tgttatcggg    13140
tgaaacgtca cacaccgtga agacgacctg ttcgcggatg aggtcatcca gctgtcgcag    13200
catgacgaaa agcgccgaca gccgcgcgat ctcgtcgtcg ggcgacacgt gctgcggccg    13260
cgcgggcgtg cgcggctcgc cgacgctgcg ctcgcggtcc agccgcatca gcagctcctg    13320
```

```
gcacttgacg agcagcatgg agctgtcctc tagcgccaac ttgcgcacgt aggtcatggt   13380
cagctccgag gctaggttgg ccaccatgga catggagagg caggcggtct tcatgtcgat   13440
cagcaggtgc tggtcgatga ccggatcggg gatggtgaag gtggcgtcgc gaaaagtaat   13500
ggtctgcagc tgctgcacgg cagcctttac ctcctcgtac gaacggtcga gcgagaagag   13560
gcccatgatg agtagtcgct ggttgatttc cagcgccagt ggcatgggta cgatccaggg   13620
cagcaccagc tcccactggc ccagcgtcag caggttctcg cgcgccagcg gtccgtggaa   13680
gagcggcgga agcacgcata gcgcgtcgcc cttctcccaa gtcacgggtc ccgtgttgag   13740
gacggtgtag agcagtccgt gcgtgggtac gtgtaggagg atctggttgc cttctacgcg   13800
ccgcatcaac gtcagcgtca tattgcgcag caggccgcgc agtcgtacgt agccgcgggt   13860
gtgatctacg aactggtgta ggcccagctg gtagtgcttg atgagatgta gacgttgcgg   13920
aatgggcaca acgccgcta ctagcttggt cagtttgcct acgtcggcga tgctgagctt   13980
gtggtcgaaa gtgcagaaga tgttggcctc catggccgcc atagcggcgg tgaaatcctg   14040
gccgcgacgg aggagaggca gagacgaaca acgtctgcac cgggcgcggc gtcagagcga   14100
gcgtggcgcg tccgggcccg cgtttgcgtc taggtgactc gccgctaacc tgcggtcgtc   14160
gccgtcctcc tcaccggacg gcctcacgag ttaaataaca tggattgctg cagcgggatg   14220
atttcgccta cgacgtagtt accaaagtgc gtttcggacg tagcaaaagc cccggcgcca   14280
cccttgagtt tggtctccat cagcgccagc gtggtggtgc tgaggatcgg tagcgcttcc   14340
tgcgtcagac ggcacgggtt ttcgatgagt tgttccgtgc cttcgacgca gacgtactgc   14400
gtgtccgtgt cgccgcggat gcagtccttg gcgcgtagca ggtactcgtc gatggttttg   14460
aagagcgttt tgttggccgc gataatctct tctgtgttaa agtactgcgc gcaagggctg   14520
tagaatttgg agttgtagcc tagacgttcg cgatgtcggg tgttgtagag tacgtcgctc   14580
agacagccgg cttgcgaggc ccaggggttg tgtgtggccg cgaaagtctg tgcgtccgct   14640
tcgcgatggt cgtagatggc cttggtggcg gcctccgtgt cgtacggatc gacggccagc   14700
atgcaggagg cacgcccgcg cgggttgttg gggatcttaa agtaattaac gtccatcgtc   14760
accggcgtaa ggattagttc gcacgcggcc ttttgtccgt gcaccgtggc ggcggcattg   14820
cgctcggaca tgctgccgaa cgtcagcata gagatggtct ccgtgtctaa cagttgcggc   14880
cgttctacgc cggccgcgtg ccggatccag cggtccacct cgtcgtgccg gtacacgttc   14940
atagggaaga cgcgaaagag gtcctgcacg cggacgccca tgtcggttcg cacgcggttt   15000
acgtaggcta cgcaggtatt tgacgtgtaa cccagaccca tgtctacggt gttaatgttc   15060
tgcgtgacgt ggtacgtagt gctgatgtcg cgttcctcct tggtcacgat agggttgttg   15120
atgataactg acgtgcatga tttgccgctg tagagcagca tgtccacctc gaaggtgtcg   15180
gtgcgtacgg ccgtgagtgc gaatcccggg tggatgtgcg ccttggtctg cagcaccagt   15240
gaaactggtg agattttgta taacatggcg gccagcgtca tgactgagtg caacacgttg   15300
ggacaggtgg ccgagtaacg cgaaaagggc gagcgcagcc agttgtggta ctcgtgcgcg   15360
aaggctgtgg gtagcgggaa accaccgtcg tgacggtgat agtgcgggaa ctcggtcacg   15420
tagcgtttaa tgtcgtcgct caacgccgcg cagatggtgg ggtttgagta gaaacggtgg   15480
aaaggtacgg gtaggctgta ctcgatcaac gtcttaggcg ccgtcacgac gcagcagccg   15540
ttgtaaagca cgtgctgacg tgagataaag tccggcaggc cctgacgctg cgcgtggtcc   15600
agaggcgcgc gcacttcgag caccttgacg tgctcgccca cgaattgcac ggccaaaaac   15660
```

```
agttcacgac aggcctgcag cagcggcgta tgtgcgtcgg tggcgacgtc ctccaccagc    15720
tcggtcagca tctcgcctac ggcttgacgt tgcgccgcta tcgagtcttc gggggtgaca    15780
ccgcttgtgc tctctttcga cgtcgtacct gacgtggaga ccgcggtggc ggccggcatc    15840
aggagaaacg ccggtcggta aaagaggtct actagcagcg tcttgaggtt gagtcccagg    15900
ccgcaggccc ggttgttggt catggcgggc atgaggcaga gataaaagac cttttgtaac    15960
gtccattcgt cgtcggtggc acggtaatcg tccacaaaca gcggctcgtc ggcatccatg    16020
gcgcccaaac gcggtacgtc cgaaacgccg tggtgtcgcg cctcgatgtt ggccgggttc    16080
aacggttgcc ggtcggccac tacctgtacg ccttccatgt tacgcggcag gtgcgtaacg    16140
aaggggggcc acagccggtg gtcgtgcagc gcgttcacgt aagccgatag cggttcctca    16200
gccagttgac cgttgttaag tcccggcagc gctgagatgc gcgttaccag acgcagcacg    16260
gcgaccagat tgcggtagtg aaagagcaac tgcggtggta gggcgccatc agccaggtgt    16320
tcggcgatca acgtcaccag cgcgtagctg tgcgcaaaaa ccagcagctg acgtgtgtga    16380
aacatgttga cgatacaacg tgctacgaaa gtgcggatta gcaaaaagc gtcgacgttg     16440
ccgtgtacca gcacgtcgac caggtagcaa agctcggggt aattgggggct tgtcacggtg   16500
gttttgaaaa gtcgcaacgt ctcttcgtag tcgggtggtg gccgcagtcg catgtgttcc    16560
atgatctccc aggtgcgcag ttcgtggaag gggcccggtg ccagtccatc tggcaaatta    16620
ccgatgacga tacgcggtgt acacagcgcc accgtttcgc tgttttcctg gcagtgcgta    16680
aagtcgaaga aggggtgcag ctcggtgtag agcgtgatgt tgcccacctt gtagaagtcg    16740
gtgaccacaa agtcctgctt catttcgttc accgtgcgcg ggacctcgcg tcgtacgcgg    16800
taaaaatgcg gtatgcggcg cgccgcaccg cccatgggtt cctgctgaaa acgacactcg    16860
agcagtcgtt gcatggcggg ttccgagggc ggtccgcgtt ccgtgaaggt ctgtagacag    16920
ggcgcgggct cgtgcagcac cgggtggcac agcgtcttga gcgcgtccac aaagtctatt    16980
ttttgtacgg cacggtcccg gtttagcagg taggccgtgg tgggcaacgc gttgcgaacg    17040
gtgtcgttaa gcttaacttt gctttccacc gtggtgtaac cgcgatcctc gggcagatac    17100
agccctacgg ggaagaaaaa cgtcaggtcc acgttacgtt ctagcggatc tttggtatcg    17160
gtgttttgt agacgcgccg caagtttcc ataatcaccg ttttttcgcc cagtcggatc      17220
acgtccatgc tcagcggcgt taagctgtgc gccccggcct gcgaaagcga gtcgttgggc    17280
aaatgcggtt ggcccgaagt cagatgagcc ttgtacgagt tgaaatcggc caggatcgag    17340
tgataggata tggcagtgac ggcattttcg ggactgagta caaaattgcc gtaggtggcc    17400
ggcgccgaga ccgtttcttt ggtgatgtgg cttgagagca gcgacatgat gatctgcata    17460
acgttggccg tgcttaccat cacgccgctg atcttggccc ccgagctcgt ggtgtacgtg    17520
gtggggttgt ctaggatgct atcggtggcc gcttcggcca gacgcgtgag gaacttgagc    17580
acatagtcgc gatcgcgcgt gcgattcagc aaaaagagcg tggccagcat tttggccttg    17640
aagctctgca agatgttgct tcgctggatg cggttcagtg cctgtcgcgc cagtgtggcg    17700
ttttctacca gcgtctgcac cacaaagtac ggcggcgcct tgcgtagcag tgtctgtaaa    17760
aagctgtgaa tcaagccgcg ctccatggcg tcggccgtgt tttaagcgc gcgcagcacc     17820
gtgtgcatgg cttccacgtt gaggatcttg tccaagatgt tgccctcgaa tgtctcgcgc    17880
agatacgtga ggcaggctgc gctgagctcg aaggggatgg tgatggggga ttttcactg     17940
tatttggtga ccataatggt ggtctgacga ctagtgggca aaccggcgcc gctgccacca    18000
cgcggcacct gcacgtggaa cagcattttg cccgtagtca gtttattgag gtcgtggaac    18060
```

```
ttgatggcgt gcgccgccgc ggccaagccg ctggtcaaaa aataaaccca ttccaggcga   18120
ttgcagaagg tgccgaagat ggcttcgaag tgaatattgt aacgctcggg gtcatcgccg   18180
tagtagatgc gtaaggcctc aaacatctcc tcgccggcgc tggtcttgac gtgcgtcaga   18240
aagtcagtgg gaatgcctac tttaggcagg agctcgagcg ccgaccagtt ctccatcgcg   18300
gcggcggcgt gagcgcgagg cgtcggagct cggggaaagc agcgcgaccc ggagaatggc   18360
cggcgctgcg ccgcgccgcc tcggctgtga cgctctaata gtcgttggcg gctccgctat   18420
gccgcgccgg gttttacacg tccccgtgca cgttcgcgcc tgcaacctca cccaagagct   18480
atcgacgggc gaggacgccc gcttttgtcg tccgcgaccc gttaacgtcg aacgggtgcg   18540
cgctgttttt gcggctctct accgtgcctg tccgatacac gtgaggaccg agcccgagcg   18600
tgtcaagctg gtactgggtc gtctgttact gggacccgtg gccgtaccct gttttttgcga  18660
cggtgaagtg gagggccacg tgaacatct ggtacctacg acgcagtttt gtcgcgggcc   18720
gctgctctac gtgcaccgac gttgttgttg cggatccgtg accgccgggc gcgcgctgtc   18780
ctaccacgtt ctcgaaaacc acgtggccac gcatgtgcta cgcggattgc tctcgctgac   18840
ggaatggaat cgagaattgc cgagcctctt ttgcgactgt cctggcggcg gtggcgcctc   18900
gggaaccgag gaacgctacg ctatggcctg cctgccgcgc gacctcagcc tgcacctgga   18960
cgactatcct tacctgatgg tggaaatcgg acgcgtactc agtgtcagcg aggtagacga   19020
ctacgtaacc gccgtctccg gctacctggg cgaggccgcg gcgccgcgca tccaggttca   19080
ctacaagctg ctctttggac tcaacgtgcg tccgcaagcg ccgtgcgcgt tggacgctac   19140
acgcgacttt tttctgctgg agctgcaaaa gctttggctg ggcgttgaat atcaccacga   19200
agtcacgtcg gagttttttcg gtcgcgtact ggctcagctg catcgcgacc cgcgcccgcgt  19260
catgatggcg cttcgcttgc ccgagcagac ggtgtgccac ctgagcacct tcgttctcag   19320
tcgcttcaag cgacaggtac tgtacttcaa gctacaggtg agctacggca agtgccggac   19380
tggtcacgct gacagaagtg ggggaggggg gaacggtgga aatcagggac accacaacct   19440
actgtgttat cgacgcctta gcgtcacatt tgccgacaca gacacggtgt ggagaaacct   19500
tttctacgtt tattacgaac tagctcggga tctggggtcc catgggacgg aggaccgacc   19560
cgtaagccgc ggttacggtg tttcttgcgc ttcgaggacg tcgcgactgt caccgtcaga   19620
atcgacggtg gtttcggcga acggacacgc gctgtcttcc accgcgctcc cgacgacgag   19680
cgcgggtcac aagctgtcac tgccgcgcga cccggccgca gatcgcgttc gacgttacgt   19740
atgcattatc tcgcgtctca tgtacgctcg gtacggggag agatggcgta aacactgtca   19800
acggcggtcg gagacgggag aagaggagga ggaagagacg ctggaatcgg gggagactga   19860
cgccacgccg ccatttgact ttacggggca gcagctgcgc cgggcctatc aggaacaccg   19920
acgtcgtaaa catctagccg tgcagcgtta cgcgccgtgc cgtcgtaagc tcatcggcgg   19980
gatggagttt gccgaggtga cgggcgtgag tctagaccgc atcgccgtca acgctttcaa   20040
caccaaccgc gttatcaata tgaaggctgc gctctcgtcc atcgccgcgt cgggtctcgg   20100
cgtacgcgcg ccgcggcttc ccaagaacat gacccacagt tttgtgatgt acaagcacac   20160
ctttaaggag cccgcttgca ccgtcagcac ttttgtttcc aacgacgccg tctacatcaa   20220
ctcgctcaac gtcaatattc gcggttccta ccccgagttt ctgtactcgc tgggcgtgta   20280
ccggctgcac gttaatatcg atcactttttt tctgccggcc gtggtgtgca acagcaactc   20340
ctcgctggac gtgcatgggc tggaggacca ggcggtgatt cgctcggagc gcagcaaggt   20400
```

```
gtactggacc accaactttc cgtgcatgat ctcgcatact aacaacgtca acgtgggctg    20460
gttcaaagcg gctacggcca ttgtgccgcg cgtctcgggc gccgacctgg aagccattct    20520
gctcaaagaa ctctcgtgca tcaagaacat gcgcgacgtg tgcatcgatt acggtctgca    20580
ccgtgttttc acgcaactag agctgcgcaa ttcgtaccag atccccttcc tggccaagca    20640
gttagtgctg tttctgcgtg cttgcctgct caagctgcac ggtcgagaga gcggctgca    20700 gttggaccgc ctagtatttg aggcggcaca gcggggtctc tttgactaca gcaagaacct    20760
cacggcgcac accaagatca agcacacttg tgcgctcatc ggcagtcgtc tagccaacaa    20820
cgtgcccaag atcc                                                      20834

<210> SEQ ID NO 29
<211> LENGTH: 9094
<212> TYPE: DNA
<213> ORGANISM: Human cytomegalovirus

<400> SEQUENCE: 29
gtaggtaccc atggcgttgt tagtatcgaa ctggtcaaaa aattggggcg taccggtgac      60
ttgcaacgcg cgacggcgta gcgagacggc cacgcgcgag aaagagcaca cataggccat     120
ggcgcggtgc atgggttgcg agaaggtctc gggcggacgc ttctgcagat cgcagacgtc     180
gtcgcgtagc caggcgctca tttgaccggg cttcttgact agccgtttga gcgtgctgca     240
atggtcgccc cagccgtcct ggtggtccag gatgcagccc aggtccaggt tgttgagttt     300
gttgaagagt agctgacgca tgccgcccac cgtctccaga tagggatcgt gcgggttgac     360
gggtagcccg tgcaggtggt ggtacttcat gtagctgagc gtttcgtcga tgatggccag     420
caacgtgtgc aagttgggag cgttgtacac ggcgaagatc ttttccacca ccagcttgcg     480
cagcaacggt tcctccagcc aatcgaactg ttgacgaatg tgcaacaggt agtcggtgtg     540
catgagctcg tcgtgtgaca gcaggatgcg accgcgcggc tgatgatctt gcgggaaggc     600
ggtggggacc ttgagatcgg cggggtaggg tgccagacgt agactctcgg ccgtgtagcg     660
ctgaaggtcg taaacgggcg aggtagaact cggtgaggta cccgacgagg cggcgccgcg     720
ctgcagacgc gctctttttt tcttttcgat caaacggctg agttgctgta gttcgtcctc     780
gtccatggcg tccagttcgt cgtcaataag cgccagcatc tgttgttgtt gcggtccggc     840
ggacgatccg tgatgattat tggctgagga ggggtgagaa gaaccgaaag tcgtaggaca     900
actgggaact cggcgacgaa gatgcgtcga atcgccgccg tgatggtgcg gttcgccgtc     960
atcgttgtcg taagacttac cgtagtgggg gttaaggggc accgaggcgg acgcggccac    1020
gcgtcgcttg aaagaggagg acgccctatg tccgccacgg aagcccgcgg tgcccatgat    1080
gatgtgtccc ccggtgcccc cgagtgcgtg gcgggaggag ggtggaaggg gaggaggata    1140
gtggtccgga tcgccttcgg tatcatcgtc tttgctgtag cggggtcgtc gtgcggggac    1200
gcagggtcgt tgatgatgcg aggcggcgcc gacggtatct ccgcgagat ggtgttcgct     1260 ggcggctgct ccgttccgtg tcgacggcga ggttggactt cgctcgcgtc ggaacttccg    1320
tggcacgggt tcgtaatcca gacagaagcg ccgtgcgcga cgggcgcggc gttcgcgctc    1380
gctcagggaa gataacgacg gagcgtcgtg acggccgcgt gagtgcagct ccatggccgc    1440
cgtcgctagg aaggtcacgt tcgggcacgc tgatgtatat atagatgaga ccgctgccgg    1500
ggggcgggtc accggcgccg tggaaagtga ggctcagacg gcgtcgccg gcggcacggg     1560 cgcgtcgggc ggtctgattt tgatggaaat gtggacgttt ttggcgttgg agtgacactt    1620
tttggtgaaa cagcggctcc agaggctggc ccagagcgcg tagctgtgct cggtgcgcag    1680
```

```
gtcgatgaac acctgcacgg tctcttgcgg gttgcggtgc gtgtagttga gacagcgaaa    1740
atcccgcgtg cgcgcgccgt cgcgccgctt gacggccacg cagcaggcgc cgtggggctg    1800
aaagaggagg acgtggggcg cggtaaactg ctcgctgacg tgcggttcgt agtgttgcgt    1860
gaggtgctcg agcagcggcg gccacacgcg ggtgacgacg agccgctgca agtccgtgtc    1920
ggaaatcgca gcggcagtgg cgccgtcgcc accgtacagg tgataggcga gcacctcggt    1980
gagaccgcgg cgtcgataac gcgtcacgtt aagcgagcgc gtctcgataa agttggcttc    2040
ggtcgagggg cagattttgt cgcgtacgct gagaatgacg cgtggcggcg gcgacagggg    2100
caacgcgggc aggtcgtgcg gcgggtggtg gtgaagcagg ttacgcagat ccagttgggc    2160
gcgcacaaag cctagcgggt gttcgcggta ggcgtcgggc acgatgaaca gcggcaacag    2220
acggcgatgc atgaaatagc cgtcgtcttg gtccattttta tacatgtagg gcagacgtac    2280
agagcgtcca tggtggtaga tgcctgtgtc taggctgctc tcgggatgcg agatggggtc    2340
cagcagcgtg tgcagttcgg cgtcgagaca gacggcgtga ttgagcacct gcgccacggc    2400
gcgtaaaacg ctggggtgta cggcgacggt gcaggcgggg aacggcgtga tgatgcgcag    2460
ccccagtttg cccttgcagc ggcagtaagg gggtgacgtg tcaacggagg acgttgtttt    2520
ttggaaaacg ccgttatccg ggacgttatt tttatcctct ttcccgtctt cgtcttcctc    2580
tgtgtcgcgc tcgtcccggt aatcgagata gtcgtcgtca tcgaaaggcg cgccggccgc    2640
gtccacgggc acgctgttgg gtgggcacgc gcttttgaag aaatagaccg ggtgccggtc    2700
ggggtgcgtg tagccaaaga ggctcgccca tacggtcatc cagacgcgtc gtagtccgcg    2760
acatagctca aagacggtgt gtcgcgccag accggagacg ccgtcgcgca gccgtaaatc    2820
aaagtcggcc acaaaattga agacgggcag acgttcgttg aagacttcgt gtcgcgtgta    2880
gtagaactgt gtctcggggc tggtgctggc cacgtcgtcg tcgtgtagcc acacggtctc    2940
ggtcagggcc tcgtccgaga aacgctgtc gggtacgtga cggagcaggt cacgcggaaa    3000
gaggctgcga tgccaggttt cggaggccac ggcgcagaag acgtgctggt cattgggcag    3060
gtgtacgcgg tagacgggca gcggtcgctc cagcagcggt gccagcgcgg gctcgggtag    3120
caggtagcga cgttgcgagt aacgcgttag cgtgccggtg gtgtaagtct gggctgtgcg    3180
tagcgaggcg catagacgta acaagccgga cagggagcgt tccagcgggg agaagacaga    3240
ctcggaaagc gtgttgatgc gttcgagctg gcgcgccagc tgcgtggagg tgccgaagaa    3300
gcccgccagg tgcgtgccgt cgatgcggcc gccgtagccg gccagcccca agccgtgcgg    3360
gctggtcgcc gagtgggggg attcgtcgag acgcagtagg tgcgtctcca cgtagtcgtg    3420
tagaaagttg tcgagcgaga agtatttttg catgacgtcc agcagctcgg tggaaagccg    3480
gcggcccaga aaacccggtt cgcgcgtgca ctgcgcttcg ggcgccgcgt cagcgtcgta    3540
agccaccacg cgccggtact cgagcaaccg cgcgcgtgcc agcgccgtgc ggtaggccag    3600
gtagacgtag tgcacgcaga ccgtgtcggg cagacgcgca cgttcgcgga acgcgttgat    3660
ctgcgtgtcc acctgctcta gctcggtgta gtcgcggcgg ttgcgcgcga cggcgtacgc    3720
cacgaaagcg gacacgcgct gacggaaggg cgagcccagt agcagacgcg cgaactcgcc    3780
catggaggcg tgcgtgggga tgatggtgcc caggtcgcgc gtgcagaagc tgcgcacgta    3840
ctcctccacg gtggagatgg tgctgtactg gccctcgaat aggtagtagg ccatggtcag    3900
cagcacctgg ccctcggtgt gcccgaagac gctgatgaac cacgagggcg aggtggggca    3960
gaggaagacc tggttgagat gacgtagcac ggccgcgtgg tgaaagtaca ccaggtgctt    4020
```

```
gaattcgcgc acctcgccgc cgtgttcggg cgagagcacg ggcgtgcgga aaagatgccg    4080
gtagagcggt tgcgtctcgg cctcgtccag actggcgatg agcgccgaga gggggatggg    4140
ctggcgcgcg gccaggtagc gcgagagctg cagcgtttcg ttgttcacgg cgaagacggg    4200
cgccacccgc cgcgagtccg agcacttttg cgtctgtagg cagaagtaaa cacgtcgcga    4260
gacctggtgt ttgaccagca gggggaagac gcagtggtcc gtcggtgtct gcgagagtac    4320
gttggcgact atatgagcag aatcatactc tgttgcgaac agaacgagcg tcatcgtcgc    4380
gccggcacga tgcagctggc ccagcgcctg tgcgagctgc tgatgtgccg tcgcaaagcc    4440
gcgcctgtgg ccgattacgt gctgctgcag cctagcgagg acgtggagct gcgcgagctg    4500
caggcgtttc tggacgagaa ctttaagcag ctggagatca ccccggccga cctgcgaacc    4560
ttttctcgcg acacggacgt ggtgaaccac ctgctgaagc tgctgccgct ctataggcaa    4620
tgccagagca agtgcgcgtt cctcaagggc tatctctcgg agggctgttt gcctcacacg    4680
cggccggcgg ccgaggtgga gtgcaagaaa tcgcagcgta tcctagaggc cctggacatt    4740
ctcatcctca aactggtggt gggcgagttt gccatgtccg aggccgacag cctggagatg    4800
ttgctggaca agttctccac ggatcaggcc tcgctggtgg aggtgcagcg cgttatgggc    4860
ctggtggaca tggactgcga gaaaagcgcg tacatgctcg aggccggcgc ggctgcgacg    4920
gttgcgccac tgacgccacc ggcggtcgtt caggggaaa gcggcgtccg cgaggacggg    4980
gaaacggttg ccgccgtgtc ggcctttgcc tgtccctcgg tttcggactc gctgatcccc    5040
gaggaaacgg gggtcacgcg tcctatgatg agtttggctc acattaacac cgtctcctgt    5100
cctaccgtta tgaggttcga ccagcggctg ctggaagagg gcgacgagga ggatgaagtg    5160
accgtgatgt cgccgtcacc cgagcccgtg caacagcagc cgccggtcga gcccgtgcag    5220
cagcagcccc agggacgcgg gtctcaccgt cggcgctaca aggagtcggc gccgcaagag    5280
acgctgccta cgaatcacga acgcgagatt ttggatctca tgcgacacag ccccgacgtg    5340
cctcgggagg cggtgatgtc accgaccatg gtcaccatac ctcctcccca gatacccttt    5400
gtgggttccg cgcgtgaact caggggcgtg aagaaaaaga aacccacggc ggcggccttg    5460
ctgtcctccg cgtgaacagc ctggcacgtt ttggaaaacg tacgtgatca cggacacgac    5520
gagtacgggg tttctcatag acgtacttta ttaggtcagg gatgacgggg aggtttcggg    5580
ccgacgtcaa aaataacgtc attcgtgttg acagggcttt ctgcgtcgga gctcttttca    5640
tcttcttctg tctcgtcgac gtcatcgtct accggcgagg gtgtccgttg cagcaacgcg    5700
tgctcgggcg tgtgggtgaa accgatgtcg ggggtgggcg gcacgatcat ctgtcctagg    5760
gggtgactgc ccaccggcag ataggtaaag cggtgggtgg taaaaaccgc tttggctacg    5820
gtggtgtgtg gggagatgca gacggtggtg tgcgaagtgt tgaccaccgt cacgccggcc    5880
gcggtacccg ggagccagat ggtgggtcgg atgatgagat ccgattgact aaactggcgc    5940
acgcccacta tgagggcgca gataccgggc gcgtgcacgt aggccgcgtc aaaatagacg    6000
gtttgcgtgt gacccggacc gatcaccagc gtctgacggg tacgtaacga aaagaaacgg    6060
tgttcgttgg gcggcggcaa gttcatgagc tgccagggtt ctggtacaaa acaggggaaa    6120
acgccgatat cgccttcgat ggtgcccgga agatggact gaaaagtgtc gttgaggttg    6180
acgacatcca actgcgggac ttgcagcctg gattccagca gctcgggcat gcaaacgaat    6240
tgcgcgtcca ggcatttgta aaaggtaatg ccgaaaaaac cttcggggat atagaggctg    6300
acgcccagcg aggtgggcac tttgcgctcg cgtgatagcc aaatgatgtg tttattgtaa    6360
aaggccagct gcgtgtggca ttgtttgacg atgaaactgg aaggcatcca cttgtaagga    6420
```

```
actttgagcg gtgacggtaa tggcgacgac gcttcatcct ctcccggatg ctgctctttg   6480
tcgtatttct cctcggtcga ttggggcagc gtaaatgtgg tttgaaaatc gctatcgcta   6540
gcgaaacgca cgcagtaacg catgttgacg gatttctcgg ctaggatgat ggagcctgat   6600
gacgatgcgg actcttcctt cattattaac gtaggggtct cccagaatcg ctgaaaacgg   6660
gagcgcggca gccgcgacag taccagttga gagtcgattc ggtcggtcaa catcgtaagc   6720
atcgtggcgg tggtgtgatg gagtggaaca cactagtatt aggtctttta gttttatcgg   6780
tagtggcaga gagttctggt aacaattcat ccacgtcaac ctctgcaact acatcaaagt   6840
cttctgctag cgtatcaact accaaactaa caacagttgc aacaacttct gcaacaacta   6900
cgacgactac gaccttatcg acaactagca ctaaactcag ttctaccacc cacgatccta   6960
atgtgatgag acgacatgcg aacgatgatt tttacaaggc gcattgcaca tcgcatatgt   7020
atgagctctc actgtccagc tttgcggcct ggtggactat gcttaatgct ctaattctca   7080
tgggagcttt ttgtattgta ctacgacatt gctgcttcca gaactttact gcaaccacca   7140
ccaaaggcta ttgagggtgg acagatttac agcccggcgg tgttccggcg gggtaaggtt   7200
tacatacgtg ggtgaccgga ggctaaagtt acgaatctca tctagaaaca gcagcgagtc   7260
tagatagtcc cacaggggat ctataaatgt tctctgaaac cccattgatg gtgacgtagg   7320
tgtagttttg ttactatcgg aagctgtttt gttttccacg aacatggttt cgttgtaata   7380
taaggagctc atgtcgagag taccgtaaat agtgtacggc gtttcgttac ggattagtac   7440
gtgcgtgttt ttcataaatt ctgacacggc ggttcggttg cggcttggtt cacaaaaagg   7500
attttgccgg taacgtagag tggtatacac ccacgttgct aggtccctta actgtgtggc   7560
cataatggac ttcataaagc tgctatcagg acgataagca attgtagacg tggaaacccg   7620
ccttgcggcg gtagtaatac tataagtcac gttagtagtg acgttgagag cggcagacgt   7680
tgtataggaa aagtatggcg tagtagtact ctgagttttc ttagcttttt tttcgaattg   7740
ttccttaacg ggcgcttgtt tacgttttag ttttcgcata gtgtttttta acttggtgcc   7800
gttaatatac ttggggacgc gaaatagatt ccggctcatg gcgttaacca ggtagaaact   7860
gtgtgtacag ttgcgttgtg cgtaacgtaa aagcagggcg gttaaaccta gaaaataaat   7920
cgtttgacta tctacgttaa ccttagtcgg acccacgtac aatttggtgt tccaacgcgg   7980
tacattgaaa acatgggggt tgaacgtggt gaaattaccg caaccttgtt cgccagtatc   8040
attacgtttg gaaacgttta gcatttcgga aagacaagtc atggaaggca cagtaccaca   8100
aggtgggggt ctgaatgtta tcgttttagc cgtatgattg tactgtgagt aaacgtattt   8160
tgcgggtttt ctaagctggg tactataaaa atcaaaccac agataggtta tactataatt   8220
ctgaatgggg cccgctaaaa tgtagtattg tggaaactct gtcatgttca tagtgagatt   8280
tttaaccggt tgtttactta cattgtattt tgtagaaata gtcgtttcta gttgtctcaa   8340
aatttctaac ttaagctgat ctaatttata tttgcctatc ttagacagta ccaagcccct   8400
ccaaggacga ttataaagcg cttttgacat aactttacag tttatgaaag aaacaagcaa   8460
gaaagatata gatattagaa acaccatctt agggacgtct ctcaccatca tctctttttct   8520 ccccatgaca gaggaggaga ccccgcaccg tccgtctgcc ttgtggtttg gcttgcctgc   8580
gtgtactcac tgctgattct ggtcgttttg ctgctcatct accgttgttg catcggcttc   8640
caagacgacc tagtctcccg caccttggct gtgtaccaag cttgtatcca gggcccgata   8700
tgtaaccaga cccataacag tacctcgtaa ataaagacgc acagacctca cgcatatagt   8760
```

```
accatcacac cgtgtggcgt gtactttatt acaacgagca agagtgcccc taagtattgg      8820
ggcccgtacc gttttagaag attttgtgtg aatgtcttta acttttctgt ccctttttctc     8880 ataaactgtc aggttctaca gtcagcatgt cttgagcatg cggtagagca gatagatgcc     8940
gatgatggcc gatagcgcgt agacggacat catgaggaga cgactgtcgg tggcgtccac     9000
gacgacgtca gttacttcta ggaccgtacc gtttttcaaa agcatgaggt agtgagttcg     9060
cggagatgag accaccactt cgttgtaggg atcc                                 9094

<210> SEQ ID NO 30
<211> LENGTH: 2624
<212> TYPE: DNA
<213> ORGANISM: Human cytomegalovirus

<400> SEQUENCE: 30
ggatcttgac ggttgggggg atagccatcc gagctgtcgg aatcctcgtc gcccgagaaa       60
agatcccctc tggtctccgt gagcggcctc acgtcccacg cgctgtcccg acggacccctt     120 cccgggctgg ccttggtcac ctgcggggag acgagactga aagccgcgtg acgctgttgt      180
tgttgcggga tgttcaaggg accgctggtc ggtttctgac tgcccgagga taacaggccg      240
ctgaaaatgc tggaaacacc gccaccacta gcggcgccct tgccgctagt tcccggtttc      300
ttgatgggcg taaagatgtt tttctcgtca tcatcatcgt cgtcgtcctc atcggcactg      360
gagccaaaga gcctccggga ggcgctcggt ttacgtgccg ggggcggtgg ttgctgctga      420
cgttgctgca ggttctgctg cctctcctcc caagccttca gctgctgttt ctcacgctgc      480
accacctcgt cgtccacccg tttctgccgc tcgcgacgct tttcctcttc gtcgtaatag      540 ccgacgccg ccgaacgggc agcgtgggct cggcggccg gtgccagaga accatgggcc        600
tcgaagcgga acggtttgtg tcccttccag ggactggcga tccagctcca gccgtccagc      660
ggctgcgtgg ggacatgttt cttgggtacc gacgagaagg ccgaaccgcc gccgagcgag      720
aggagattgg cgtcatcgtc aaactccaac gacggcgagc gcgcgcccaa aaacgtgtgc      780
gccgactgtg ggaagctgtc cacgtagata tcaaagtcct cgatgagcag ctccaacagc      840
gtgtcggccg agtcgccgtt tccacggcg tgcttgagga tattgcgaca gtagttggaa       900
tcaaaggaaa ggcacatgcg cagctccttg accagcagct tgcagcgctc ctgaatgcgc      960
gccagacatt tgcgctccag ctcctcccaa gacctgcgca cgttcatgat gagacggccc     1020
gtgtacacga gcttgttgac ggcgttgacc agcgccgtgt tggcgtgccg gtccaggtta     1080
aggtcgagcg gttttcacgca gaacatgtta cggcgcacac cctccaggtt ttcttcaatg   1140
cgctgcacct ccgtatcctt gaggtgcaca aaggcgatgg gttccgtctg gccgatggct    1200
gtgaccagcg tctcgcgcac cgacatcttg gccagaatga ccgcgcttac gagcgcgcgt    1260
tccacgatct cggcatcgtg gcgcacgtcc gtatcgaatt cggtacggtc tagcacagcc    1320
aggtggtcac gcgccttacc acgatcaccg aacgggtaag tgtagccgcg acgcgccacg   1380
gccacgcaac gcacctcgaa ctcctcgagc actgaggaga ggtcgggggtt gtgaaaacgc    1440 agctcgcggt agtatcccaa ccaaagcatg agctcgttga acagcaccgt acgccggtgc    1500
aggcgttttt cgccacattt tttcaggatc ttggggtgtg cctcgagatc cacgtcgggc    1560
ttttgcgtga gatggcgcag aaagttgacc agggctacca catcgcgccg ctgtagaccg    1620
ataaactgca aactcatgct ggcttttctc cagaacccgg aagcgtcgtc gccccggact   1680 gcgcccgcg tctgctattc gcccacgatg gacaccatca tccacaactc ggtgagcgcc    1740
ccacctagag ggaggggggg tagtttaata gcggaggcgg atacgcggtt ttcttttaag    1800
```

```
cgccgctgac ttgtttcttc tgttttttcg ccccgtgtgc tgttccgccc agacccgcaa    1860
caacactcct ccgcacatca atgacacttg caacatgaca gggccgctat tcgccattcg    1920
aaccaccgaa gccgtactca acacattcat catcttcgtg ggcggtccac ttaacgccat    1980
agtgttgatc acgcagctgc tcacgaatcg cgtgcttggc tattcgacgc ccaccattta    2040
catgaccaac ctctactcta ctaatttttct cacgcttact gtgctaccct ttatcgtact    2100
cagcaaccag tggctgttgc cggccggcgt ggcctcgtgt aaatttctat cggtgatcta    2160
ctactcaagc tgcacagtgg gctttgccac cgtagctctg atcgccgccg atcgttatcg    2220
cgtccttcat aaacgaacat acgcacgcca atcataccgt tcaacctata tgattttgct    2280
attgacatgg ctcgctggac taattttttc cgtgcccgca gctgtttaca ccacggtggt    2340
gatgcatcac gatgccaacg ataccaataa tactaatggg cacgccacct gtgtactgta    2400
cttcgtagct gaagaagtgc acacagtgct gctttcgtgg aaagtgctgc tgacgatggt    2460
atggggtgcc gcacccgtga taatgatgac gtggttctac gcattcttct actcaaccgt    2520
acagcgcacg tcacagaaac aaaggagtcg taccttaacc tttgttagcg tgctactcat    2580
ctccttcgtg gcgctacaaa ctccctacgt ctctctcatg atct                     2624

<210> SEQ ID NO 31
<211> LENGTH: 5170
<212> TYPE: DNA
<213> ORGANISM: Human cytomegalovirus

<400> SEQUENCE: 31
agtaaaaagt agatgatgga gatgatagcg tagaccacga agacggctaa caccatgtgg      60
cctgtacgca cgaaaaagtt gtttccgaag ccgtagcaca gggccatggc taccacggtg     120
gtgttgaaac caagcgctac ctctaccagg ttgacgatga gcgtgcggaa ctgcaccgta     180
cctttgagct tggggtgcag acgcgagaag aaaaagagtg agcgtttgta gctgcggtac     240
tgcgtgacca tgctcacgtt gaaaatggtc aggcagaaaa agtgcacggc ggccatgaag     300
gcgatcatgc tgggcagccg aaatgacatg gtcagtgtga atagttggaa cgtgtccatg     360
ctgagaatga agaggaaggc tgtgaggctg tcgcccatgt acgaaatgtc gcgtgtcgac     420
tggtttaggc tcatgccttt gtccttgcgc atgctgatct tgatccagca taccaggtag     480
tagatggtca cggctaaaaa gacgagctgc atgaacacgg cgtagcacac caactgcacc     540
gagtctaaga aaagcatagg cgtgtgcagg tgcattacgt tgtaggccga catgttgagc     600 cttttcaaagt ccacgacgtg atagtagacg caggggtagc ccaggtgcgg aaaattgctc     660
agcactagat gcacgctgac gttgacaaaa gtcagcacca tgaaaacgat agaagcgctc     720
catgtccgtg tattcacctt atccacgtgc gagggggcca tggcgatagc ggcggcccgc     780
tcgctcggga ggcgatgggg gcgcgccgat gacgacaggc tcgcgggtcg ttaaatacta     840
cgatgggagc cgccgcggct cacgacgcgg tttgagcacg tccggggcggt cggtgaaaaa     900 agaccccgcg ggccttcgcg actctcttct gtccgaggat gaccgctcag ccgccgctgc     960
accaccgcca ccacccgtac accctgttcg ggaccagctg tcatctcagc tggtacggcc    1020
ttctagaggc ctcggtgcct atcgtacaat gtctgttttt ggatctgggt ggcggccgtg    1080
ccgagccgcg gcttcacacg ttcgtggtgc gcggtgaccg tctaccgccg gctgaggtgc    1140
gtgctgtgca tcgcgccagc tagggtgcgc tggcctcggc cgtgactacg gacgccgatg    1200
agcgtcggcg cggcctagag cagcgtagcg ccgtgttggc gcgcgtgttg ctagaaggca    1260
```

```
gcgcgttaat ccgcgtgttg gcgcgcacct tcacgccggt gcagattcag acggacgcta      1320
gtggcgtgga gattttggag gccgcaccgg cactgggcgt ggaaaccgca gcgctgtcga      1380
acgcgcttag tcttttccac gtagccaagc tagtggtcat cggctcgtat cccgaagtgc      1440
acgagccgcg tgtggtcacg cataccgcgg aacgcgtctc cgaagagtat ggcacccacg      1500
cgcacaaaaa attgcgtcgc ggttactacg cctacgattt ggccatgtcg tttcgcgtcg      1560
gcactcacaa gtatgtgctg gagcgcgacg acgaggccgc cctggcacgc ctctttgagg      1620
tgcgcgaggt gtgttttttg cgcacctgtc tgcgtctggt cacgcctgtc ggtttcgtgg      1680
ccgtggcagt gaccgacgag cagtgttgtt tattgctgca gtcggcctgg actcacctttt     1740 acgacgtgct tttccgtggt ttcgctgggc agccgccgct acgcgactac ctggggccgg      1800
acctctttga gacgggcgcc gcccgttctt tcttttttcc cggtttcccg cccgtgcccg      1860
tctacgcggt ccacggtctg cacacgttaa tgcgcgagac ggcgttggac gcggcggctg      1920
aggtgctctc gtggtgcggc ctgcccgaca tcgtgggctc ggccggcaag ctggaggtgg      1980
aaccctgcgc gctctcgctc ggcgtgcccg aggatgagtg gcaggtcttc ggtaccgagg      2040
ccggcggcgg cgccgtgcgt ctcaatgcca cggcttttcg cgagcgaccg gccggcggcg      2100
atcgtcgctg gctgttgccg ccgctgccac gtgacgacgg cgacggtgaa acaacgtcg      2160 tggaagtcag cagcagcacc ggcggtgcgc accgccgag cgacgacgcc actttcaccg      2220
tgcacgttcg cgacgccacg ctacatcgag tgctcatcgt ggatttggtc gagcgcgtgc      2280
tggccaagtg tgtacgcgcg cgcgacttca atccctacgt gcgttatagt catcgactcc      2340
acacttatgc ggtttgtgaa aagtttattg agaatctgcg ttttcgctcg cgacgcgctt      2400
tctggcagat ccagagtctg ctgggctaca tctccgagca cgttacgtca gcctgcgctt      2460
cggccggcct tttgtgggtt ctgtcgcgcg gccaccgcga gttttatgtc tacgacggct      2520
attcgggtca cggacccgtc tcggccgaag tgtgcgtgcg gactgtggtc gactgttatt      2580
ggcgcaaact ttttggcggc gacgatccgg gtcccacctg tcgtgttcaa gagagcgcgc      2640
ccggcgtgct gttggtctgg ggcgacgagc ggttggtggg tcccttcaac ttcttctacg      2700
gcaacggcgg cgccggtggt agtccgctcc acggggtggt gggtggtttc gcggcgggac      2760
attgcggtgg cgcttgttgc gcgggctgcg tcgtcactca ccgccattct agcggcggcg      2820
gtggtagtgg cgtgggcgac gcggaccacg cgagtggcgg cggtctagat gccgctgccg      2880
ggagtggtca taacggcggt agtgatcggg tttctccctc cacgccgccc gcggcgttag      2940
gtggctgttg ctgcgcagcc ggtggcgact ggctctcggc cgtgggtcat gtcctgggcc      3000
ggctgccggc gctgttacgg gagcgcgtga gcgtgtccga gctggaagcc gtgtaccgcg      3060
agatcctctt tcgtttcgtg gctcgccgca acgacgtgga ctttttggtta ctgcgcttcc      3120 agcccggtga aaacgaagta aggccgcacg ctggggtgat tgactgcgcg cccttccacg      3180
gcgtgtgggc cgagcagggc cagatcatcg tacagtcacg cgatacgcg ttgcggccg       3240 atatcggcta cggcgtctat gtggacaagg cctttgccat gctcacggct tgcgtggagg      3300
tctgggcgcg agagttattg tcgtcctcca ccgcttccac caccgcttgt tcttcttctt      3360
ccgttctctc ctccgccttg ccgtccgtca cttcgtcctc ttcgggcacg gcgacggtgt      3420
ctcctccgtc ttgttcttct tcgtcggcga cttggctcga ggagcgcgac gagtgggtgc      3480
gctcgctggc ggttgacgcg caacacgctg ctaagcgggt ggcttccgag ggcctgcggt      3540
ttttccggct caacgcttaa cgagtcacgt aggggaacta cgtgggtaag tgacgtggat      3600
actagtaaaa aaagtgcgtc aaagctctta gcgtgtgacg tggatactag taaaagggac      3660
```

```
-continued gtcaaagctc actacgtgtt gcgtgttttt ttttttttcta tgatatgcgt gtctagttcg    3720
cttctcactc ttcctctcct cgttcccagc gcggcggcag cttgggggt gagggcaaat      3780
tggggtagtt ggcgttgagc acgtctagca ggcccaggcc cacgggccaa ccgtccacgg     3840
tcttgcgctc ggtcagcttg aggctgaacg agtgtgcctc gtcctgaccg gtaaggcgga    3900
aaaagaagcg tgctaccagc tgcaggcagg tatgccgcgt ctgctggaag agcacgaagg    3960
tagcgggcac gtactgcaca atgtgcggct cttttcctc aaagagcagg tagagcgcgc     4020
tgcagatcag ccgcctggcg ctgtggtgca gcagccggcc gaagctttcg cgcacgttca    4080
ccgcgtccag gtactggagc aggtcgtgca ggcacttgcg cgttaagttg caattttcca    4140
cgcacgaaat aacggtacag agcgcgaagt gcagcaggtt gtcggctttg acgatgccgc    4200
agcggtgttt gagccgcaga tccgagagcc tcacctgcgt gacggcgtct tcggtctcga    4260
gcaaaaacac ggcggagtag cctagaaagg ccgaggtgca cagcaactcg ctgcggtact    4320
cggccatgga gaccagcagc ccgtgctccg tgtgcagcca cagcttgtcg ccgcgcaccg    4380
taaagtcgag cacttgcggc tccatgatca tcacattctg tctagtgaaa tccgtatgga    4440
cctccagcac gccgcggatc atcagggcct ccatttcgaa atcggccgac acgctctggg    4500
ccgcgccgct cctcgtctgc cgtgatcaag cggcgcggcg cggacctttc aagtgttcct    4560
gggccgccgc tcgaggcagt tccccttct ggcactccgc ccgccgcttc gcggctcatt     4620
tggcgccgac gcgccttctc gcggctgcaa atcagctcca cgtatcggca aaacttgctg    4680
tcgtcgtagg cggcggccac gatctcgccg aaggagagct gcaggtaggc ctcgggtacg    4740
gggtccagcg tgcccagcgc caggatgtga cacagatagg gcagggtcac gcgctctacc    4800
gtgtaattgg agtagacgat ggcctcttcg gcccccttgat gcgtgaccag acgccgtagg   4860
cgaaaggtac ggaaatactc gttttcccac aactgcgtga ggaagcgttc cagcgactcg   4920
gtgccgggca cgaactgcga gaagaagctg ttggccacca ggcggttgtc ttccaccgcc   4980
agcggacgga agggcgccgc gtcgcgcgcc ttgcgcacgg cctccaacac gggcaggtgg   5040
tagagttcgg cgtcgcgcgc gcccaggctc atggagtcct cgcgccgcga ggcgtagcgc   5100
gtgagcaggt cgcgcagttc gcgcacgcga ttctcccagg tctggttaag cgtgcgcagg   5160
tcctggatct                                                          5170
```